US012642606B2

(12) United States Patent
Post et al.

(10) Patent No.: US 12,642,606 B2
(45) Date of Patent: Jun. 2, 2026

(54) SYSTEMS AND METHODS FOR GUIDING MOVEMENT OF A HANDHELD MEDICAL ROBOTIC INSTRUMENT

(71) Applicant: MAKO Surgical Corp., Weston, FL (US)

(72) Inventors: Nicholas Jon Post, Kalamazoo, MI (US); Michael Dale Dozeman, Portage, MI (US); Richard Thomas DeLuca, Kalamazoo, MI (US); Timothy J. Bozung, Belding, MI (US)

(73) Assignee: MAKO Surgical Corp., Weston, FL (US)

( * ) Notice: Subject to any disclaimer, the term of this patent is extended or adjusted under 35 U.S.C. 154(b) by 662 days.

(21) Appl. No.: 18/011,641

(22) PCT Filed: Sep. 8, 2021

(86) PCT No.: PCT/US2021/049440
§ 371 (c)(1),
(2) Date: Dec. 20, 2022

(87) PCT Pub. No.: WO2022/055980
PCT Pub. Date: Mar. 17, 2022

(65) Prior Publication Data
US 2023/0255701 A1     Aug. 17, 2023

Related U.S. Application Data

(60) Provisional application No. 63/085,651, filed on Sep. 30, 2020, provisional application No. 63/075,615, filed on Sep. 8, 2020.

(51) Int. Cl.
*A61B 34/30*      (2016.01)
*A61B 17/00*      (2006.01)
*A61B 17/14*      (2006.01)

(52) U.S. Cl.
CPC ............ *A61B 34/30* (2016.02); *A61B 17/142* (2016.11); *A61B 2017/00982* (2013.01)

(58) Field of Classification Search
CPC .................. A61B 34/30; A61B 17/142; A61B 2017/00982
See application file for complete search history.

(56) References Cited

U.S. PATENT DOCUMENTS 7,035,716 B2    4/2006  Harris et al.
7,206,626 B2    4/2007  Quaid, III
(Continued)

FOREIGN PATENT DOCUMENTS

CN        110430836 A      11/2019
JP        2017528255 A      9/2017
(Continued)

OTHER PUBLICATIONS

English language abstract for JP 2017-528255 A extracted from espacenet.com database on Apr. 25, 2025, 2 pages.
(Continued)

*Primary Examiner* — Kevin T Truong
*Assistant Examiner* — Diana Jones
(74) *Attorney, Agent, or Firm* — Howard & Howard Attorneys PLLC

(57) ABSTRACT

The present teachings provide for a hand-held robotic system for use with a saw blade or other surgical tool. The hand-held robotic system also includes an instrument with a hand-held portion, a blade support coupled to the hand-held portion by a plurality of actuators, the actuators configured to move the blade support or tool support in a plurality of degrees of freedom relative to the hand-held portion. The system includes a localizer and a control system coupled to the localizer and the plurality of actuators. The control
(Continued)

system is configured to control each of the plurality of actuators and/or the tool drive motor.

19 Claims, 34 Drawing Sheets

(56) References Cited

U.S. PATENT DOCUMENTS

| | | | |
|---|---|---|---|
| 7,206,627 | B2 | 4/2007 | Abovitz et al. |
| 7,422,582 | B2 | 9/2008 | Malackowski et al. |
| 7,747,311 | B2 | 6/2010 | Quaid, III |
| 7,831,292 | B2 | 11/2010 | Quaid et al. |
| 7,984,663 | B2 | 7/2011 | Dent |
| 7,998,157 | B2 | 8/2011 | Culp et al. |
| 8,010,180 | B2 | 8/2011 | Quaid et al. |
| 8,095,200 | B2 | 1/2012 | Quaid, III |
| 8,303,575 | B2 | 11/2012 | Rodriguez Y Baena |
| 8,391,954 | B2 | 3/2013 | Quaid, III |
| 8,498,744 | B2 | 7/2013 | Odermatt et al. |
| 8,571,628 | B2 | 10/2013 | Kang et al. |
| 8,617,174 | B2 | 12/2013 | Axelson, Jr. et al. |
| 8,753,346 | B2 | 6/2014 | Suarez et al. |
| 8,898,043 | B2 | 11/2014 | Ashby et al. |
| 8,911,499 | B2 | 12/2014 | Quaid et al. |
| 8,992,542 | B2 | 3/2015 | Hagag et al. |
| 8,996,169 | B2 | 3/2015 | Lightcap et al. |
| 9,002,426 | B2 | 4/2015 | Quaid et al. |
| 9,008,757 | B2 | 4/2015 | Wu |
| 9,060,794 | B2 | 6/2015 | Kang et al. |
| 9,119,655 | B2 | 9/2015 | Bowling et al. |
| 9,161,760 | B2 | 10/2015 | Suarez et al. |
| 9,399,298 | B2 | 7/2016 | Kang |
| 9,566,122 | B2 | 2/2017 | Bowling et al. |
| 9,597,157 | B2 | 3/2017 | Hagag et al. |
| 9,636,185 | B2 | 5/2017 | Quaid et al. |
| 9,707,043 | B2 | 7/2017 | Bozung |
| 9,724,167 | B2 | 8/2017 | Ziaei et al. |
| 9,770,306 | B2 | 9/2017 | Hagag et al. |
| 9,775,681 | B2 | 10/2017 | Quaid et al. |
| 9,801,686 | B2 | 10/2017 | Lightcap et al. |
| 9,812,035 | B2 | 11/2017 | Stuart et al. |
| 9,820,753 | B2 * | 11/2017 | Walen .................... A61B 34/20 |
| 9,820,818 | B2 | 11/2017 | Malackowski et al. |
| 9,937,014 | B2 | 4/2018 | Bowling et al. |
| 10,052,166 | B2 | 8/2018 | Ziaei et al. |
| 10,098,704 | B2 | 10/2018 | Bowling et al. |
| 10,117,713 | B2 | 11/2018 | Moctezuma de la Barrera et al. |
| 10,206,750 | B2 | 2/2019 | Hagag et al. |
| 10,231,790 | B2 | 3/2019 | Quaid et al. |
| 10,231,792 | B2 | 3/2019 | Shiels et al. |
| 10,314,661 | B2 * | 6/2019 | Bowling ................ A61B 34/70 |
| 10,327,849 | B2 | 6/2019 | Post |
| 10,369,708 | B2 | 8/2019 | Kang |
| 10,410,746 | B2 | 9/2019 | Moctezuma de la Barrera et al. |
| 10,492,875 | B2 | 12/2019 | Janik et al. |
| 10,603,119 | B2 | 3/2020 | Ross et al. |
| 10,660,711 | B2 | 5/2020 | Moctezuma de la Barrera et al. |
| 10,660,715 | B2 | 5/2020 | Dozeman |
| 10,687,823 | B2 | 6/2020 | Mac an Tuile et al. |
| 10,863,981 | B2 | 12/2020 | Overmyer et al. |
| 10,864,047 | B2 | 12/2020 | Hagag et al. |
| 10,967,525 | B2 | 4/2021 | Kang |
| 11,076,918 | B2 | 8/2021 | Quaid, III |
| 11,123,881 | B2 | 9/2021 | Kang |
| 11,253,329 | B2 | 2/2022 | Bowling |
| 11,278,363 | B2 | 3/2022 | Ross et al. |
| 11,284,946 | B2 | 3/2022 | Shalayev et al. |
| 11,369,438 | B2 | 6/2022 | Malackowski et al. |
| 11,701,188 | B2 * | 7/2023 | Kang .................... A61B 34/76 |
| | | | 606/130 |
| 11,998,283 | B2 | 6/2024 | Lavallee et al. |
| 12,161,429 | B2 | 12/2024 | Bonny et al. |
| 2011/0196377 | A1 | 8/2011 | Hodorek et al. |
| 2011/0315413 | A1 | 12/2011 | Fisher et al. |
| 2016/0120610 | A1 | 5/2016 | Wu |
| 2017/0156799 | A1 | 6/2017 | Bozung |
| 2018/0333207 | A1 | 11/2018 | Moctezuma de la Barrera |
| 2018/0344409 | A1 * | 12/2018 | Bonny ................ A61B 17/157 |
| 2019/0070731 | A1 | 3/2019 | Bowling et al. |
| 2019/0269476 | A1 * | 9/2019 | Bowling ................ A61B 34/20 |
| 2020/0170651 | A1 | 6/2020 | Otto et al. |
| 2020/0275943 | A1 | 9/2020 | Keppler et al. |
| 2020/0281676 | A1 | 9/2020 | Rohs et al. |
| 2020/0323540 | A1 | 10/2020 | Kang et al. |
| 2021/0029846 | A1 | 1/2021 | Revankar et al. |
| 2021/0059656 | A1 | 3/2021 | Otto et al. |
| 2021/0059771 | A1 | 3/2021 | Hagag et al. |
| 2021/0093400 | A1 | 4/2021 | Quaid et al. |
| 2021/0186632 | A1 | 6/2021 | Quaid et al. |
| 2022/0022986 | A1 | 1/2022 | Gilhooley et al. |
| 2022/0233251 | A1 | 7/2022 | Bowling et al. |

FOREIGN PATENT DOCUMENTS

| | | |
|---|---|---|
| JP | 2019501677 A | 1/2019 |
| WO | 2018104439 A1 | 6/2018 |
| WO | 2019219348 A1 | 11/2019 |
| WO | 2021011646 A2 | 1/2021 |
| WO | 2021067438 A1 | 4/2021 |
| WO | 2021158367 A1 | 8/2021 |

OTHER PUBLICATIONS

English language abstract for JP 2019-501677 A extracted from espacenet.com database on Apr. 25, 2025, 2 pages.

U.S. Appl. No. 18/072,715, filed Dec. 2, 2022.

Tamis, Marijn et al., "Constrain Based Physics Solver", Version 1.02, http://www.mft-spirit.nl/files/MTamis_ConstraintBasedPhysics-Solver.pdf, Jun. 15, 2015, 31 pages.

Tamis, Marijn, "Comparison Between Projected Gauss-Seidel and Sequential Impulse Solvers for Real-Time Physics Simulations," Version 1.01, http://www.mft-spirit.nl/files/MTamis_PGS_SI_Comparison.pdf, Jul. 1, 2015, 11 pages.

Vossel, Manuel et al., "MINARD HD: Control and Evaluation of a Handheld, Highly Dynamic Surgical Robot", International Journal of Computer Assisted Radiology and Surgery, Jan. 23, 2021, 8 pages.

Becker, Brian C. et al., "Vision-Based Control of a Handheld Surgical Micromanipulator With Virtual Fixtures", IEEE Transactions on Robotics, vol. 29, No. 1, Jun. 2013, pp. 674-683.

Payne, Christopher J. et al., "An Ungrounded Hand-Held Surgical Device Incorporating Active Constraints with Force-Feedback", IEEE/RSJ International Conference on Intelligent Robots and Systems (IROS), November 307, 2013, Tokyo, Japan, pp. 2559-2565.

* cited by examiner

Contraint Equation

Calculate force for each constraint ($F_{p_i}$) in constraint space by solving
system of n linear equations ($Ax = b \rightarrow x = A^{-1}b = F = (M^{-1})^{-1}a$)

$$F_p = \left(J_p M^{-1} J_p^{T} + \frac{C}{\Delta t}\right)^{-1} \left(\frac{v_{p2}}{\Delta t} - \frac{J_p v_{cg1}}{\Delta t} - \frac{\varepsilon \Delta d}{\Delta t^2}\right) - \left(J_p M^{-1} + \frac{C}{\Delta t} J_p^{-T}\right)\left(F_{inertial} + F_{damping} + F_{cgext}\right) \geq 0$$

FIG. 25

Forward Dynamics Algorithm

Configuration Parameters:

Mass matrix, $M_{6DOF}$ [6x6] combination of Mass and Inertia [3x3] matrices

Velocity Limits, $V_{max}$, $\omega_{max}$

Inputs:

initial pose, $_n^0 T(t_0)$ initial velocity, $^n v(t_0)$ total force applied at CG, $^n F_{total}$ time interval, dT Outputs:

final pose, $_n^0 T(T_0 + dT)$ final velocity, $^n v(t_0 + dT)$

FIG. 26

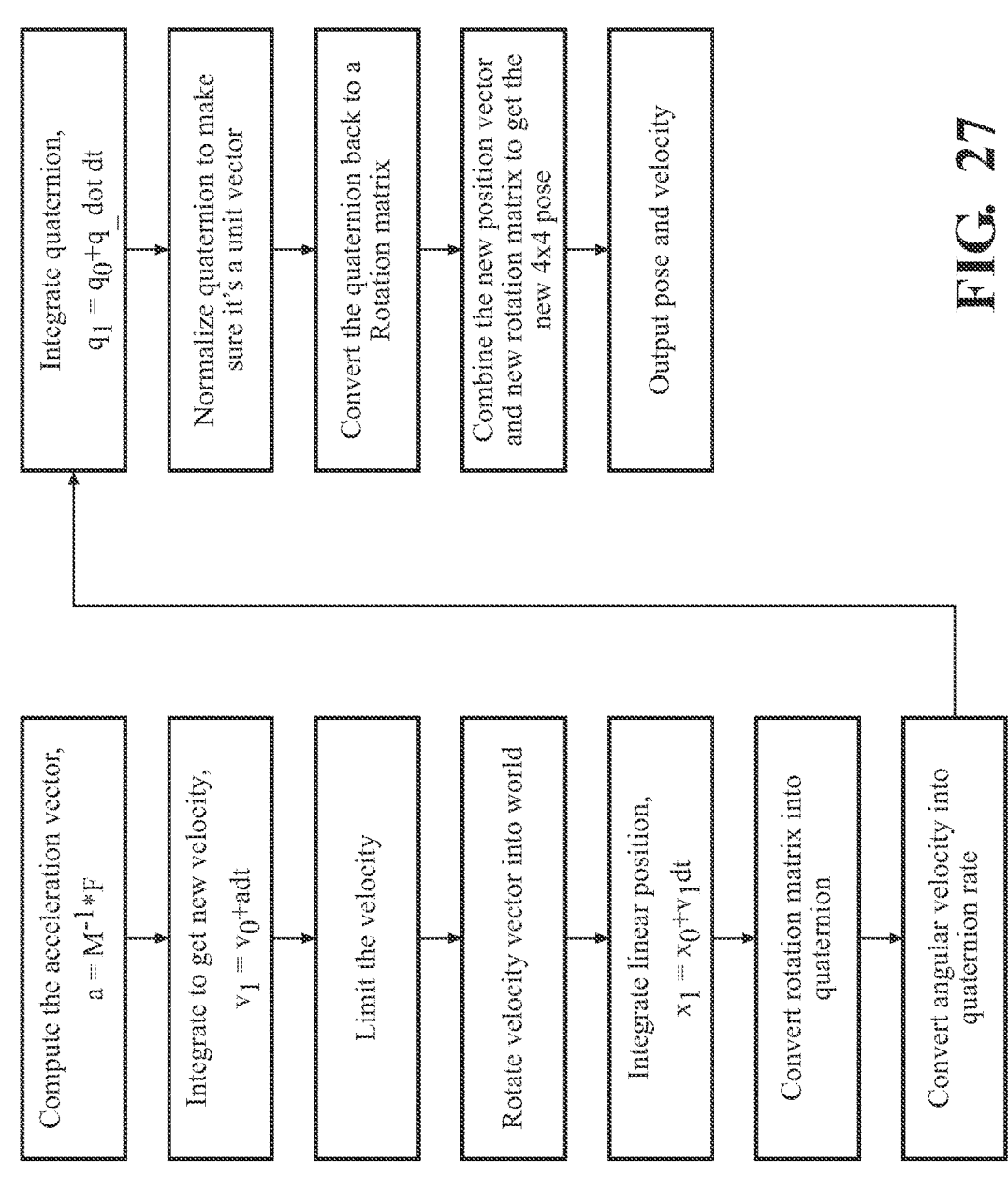

Forward Dynamics Algorithm

Compute the acceleration vector,
$a = M^{-1} * F$

Integrate to get new velocity,
$v_1 = v_0 + a dt$

Limit the velocity

Rotate velocity vector into world

Integrate linear position,
$x_1 = x_0 + v_1 dt$

Convert rotation matrix into quaternion

Convert angular velocity into quaternion rate

Integrate quaternion,
$q_1 = q_0 + \dot{q} \, dt$

Normalize quaternion to make sure it's a unit vector

Convert the quaternion back to a Rotation matrix

Combine the new position vector and new rotation matrix to get the new 4x4 pose

Output pose and velocity

FIG. 27

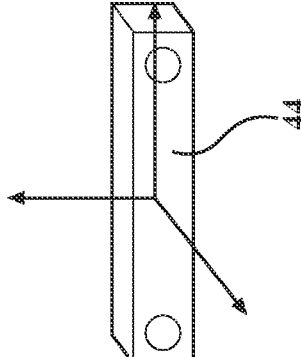
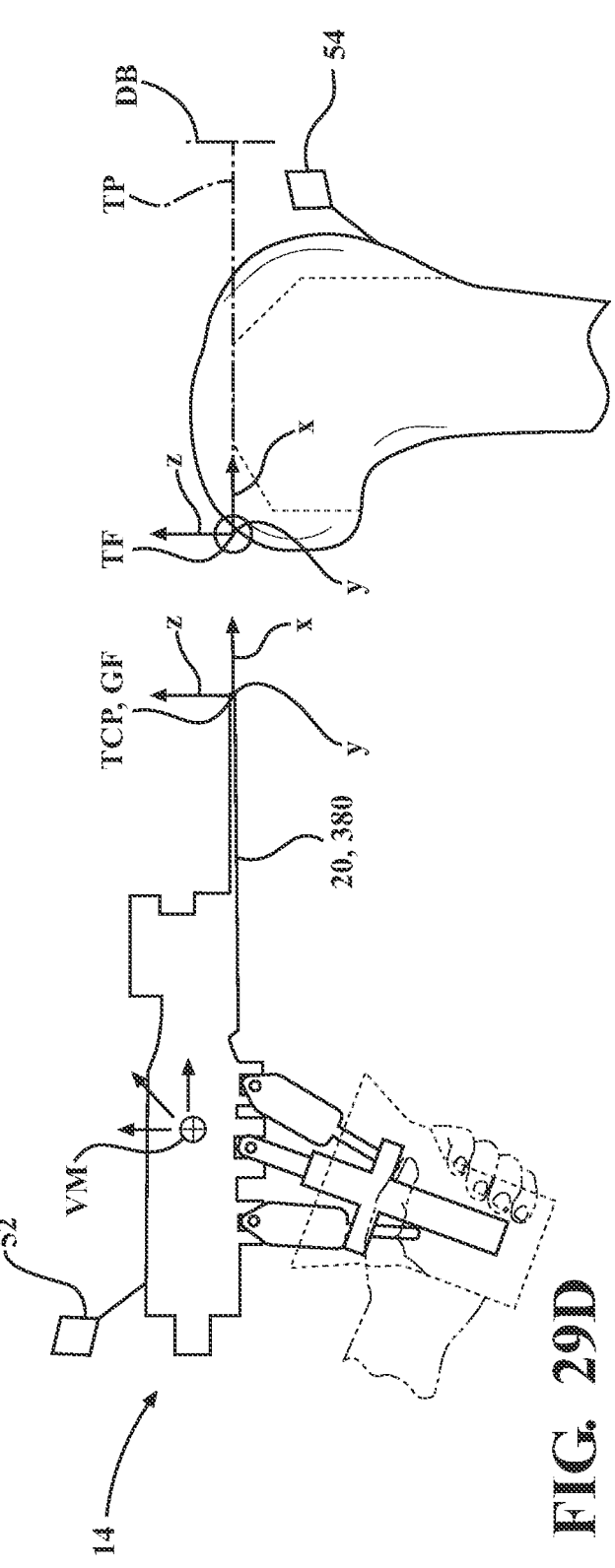
FIG. 29D

SYSTEMS AND METHODS FOR GUIDING MOVEMENT OF A HANDHELD MEDICAL ROBOTIC INSTRUMENT

BACKGROUND

Physical cutting guides are used to constrain surgical tools when resecting tissue from a patient. In some cases, physical cutting guides constrain such surgical tools for the purpose of preparing joints to accept replacement implants. The time required to position and secure a physical cutting guide to the patient can represent a significant portion of the overall time required to perform a surgical procedure.

Navigation systems (also referred to as tracking systems) can be used to properly align and secure jigs, as well as track a position and/or orientation of a surgical tool used to resect tissue from a patient. Tracking systems typically employ one or more trackers associated with the tool and the tissue being resected. A display can then be viewed by a user to determine a current position of the tool relative to a desired cut path of tissue to be removed. The display may be arranged in a manner that requires the user to look away from the tissue and surgical site to visualize the tool's progress. This can distract the user from focusing on the surgical site. Also, it may be difficult for the user to place the tool in a desired manner.

Robotically assisted surgery typically relies on large robots with robotic arms that can move in six degrees of freedom (DOF). These large robots may be cumbersome to operate and maneuver in the operating room.

There is a need for systems and methods to address one or more of these challenges.

SUMMARY

One aspect of the present teachings provides for a hand-held medical robotic system for use with a tool, the system comprising: an instrument. The instrument comprises; a hand-held portion to be held by a user; a tool support coupled to the hand-held portion to support the tool, the tool support comprising a tool drive motor; an actuator assembly having a plurality of actuators operatively interconnecting the tool support and the hand-held portion to move the tool support in a plurality of degrees of freedom relative to the hand-held portion to place the tool on to a desired plane. The system further includes a localizer and a control system coupled to the plurality of actuators, the localizer, and the tool drive motor. The control system is configured to: determine, in a known coordinate system, a target pose of the tool, a state of the tool, and determine a position and/or orientation of a reference coordinate system relative to the known coordinate system. The control system is also configured to determine a state of a first constraint based on a relationship between the state of the tool and the reference coordinate system, a state of a second constraint based on a relationship between the state of the tool and the reference coordinate system, with the first constraint being different than the second constraint. The control system further comprising: a constraint solver to calculate a constraint force adapted to move a virtual tool towards the target pose based on the state of the first constraint and based on the second constraint; a virtual simulator to simulate dynamics of the virtual tool in a virtual simulation based on the constraint force and to output a commanded pose; and the control system further configured to control each of the actuators based on the commanded pose.

In some implementations the control system of the hand-held medical robotic system determines a first constraint and a second constraint are guide constraints. In some implementations, the first constraint and second constraint are joint centering constraints. In some implementations, the first constraint and the second constraint are workspace limit constraints. In some implementations, the first constraint and the second constraint are boundary constraints. In some implementations, the control system determines a first constraint to be one of a guide constraint, a joint centering constraint, a joint limit constraint, a workspace constraint, a boundary constraint, and a second constraint to be a different constraint a guide constraint, a joint centering constraint, a joint limit constraint, a workspace constraint, a boundary constraint. In some implementations, the first constraint and the second constraint are the same type of constraint with different values. In some implementations, the first constraint and the second constraint are different types of constraints.

In some implementations the control system of the hand-held medical robotic system determines a plurality of first constraints and a plurality of second constraints. In some implementations the plurality of first constraints correspond with a first pose of the tool and are two or more of a guide constraint, a joint centering constraint, a joint limit constraint, a workspace constraint, and a boundary constraint. In some implementations, the plurality of second constraints correspond with a second pose of the tool and are two or more of a guide constraint, a joint centering constraint, a joint limit constraint, a workspace constraint, and a boundary constraint.

One aspect of the present teachings provides that the hand-held robotic system controls the plurality of actuators through determining the pose of the tool support of the instrument. In some implementations, the hand-held robotic system determines the pose of the saw blade. In some implementations, the hand-held robotic system controls the plurality of actuators through determining the pose of a combination of one or more of the hand-held portion of the instrument, the tool support of the instrument, and the tool, or one or more components interconnecting the hand-held portion, the tool, and the tool support.

One aspect of the present teachings provides the methods for controlling the hand-held robotic system comprises at least one step of determining a pose of a portion of the instrument. In some implementations, the at least one step of determining the pose of a portion of the instrument includes determining the pose of the tool support. In some implementations, the at least one step of determining the pose of a portion of the instrument includes determining the pose of the saw blade. In some implementations, the at least one step of determining the pose of a portion of the instrument includes determining the pose of one or more of the hand-held portion, the tool support, and the tool.

One aspect of the present teachings provides the hand-held robotic system configured to be used with surgical tools other than surgical saws. In some implementations, the hand-held robotic system is configured to be used with a drill bit, a driver, a bur, an ultrasonic cutting tool, a tap or other rotary cutting tools.

One aspect of the present teachings provides for the control systems of the hand-held robotic system to control the plurality of actuators to place the tool support and tool relative to a virtual object other than a plane, such as a virtual axis. The virtual axis may be derived from a surgical plan, such as a planned trajectory or a planned screw trajectory or planned hole trajectory.

One aspect of the present teachings provides for the control systems of the hand-held robotic system to determine a target plane or a target trajectory or target virtual object without identifying a planned pose of a surgical implant.

One aspect of the present teachings provides for the methods of controlling the hand-held robotic system are used with alternative actuator assemblies. In some implementations, the control systems of the robotic hand-held system are used with a plurality of actuators that arranged in series relative to the other actuators.

The present teachings may include corresponding computer systems, apparatus, and computer programs recorded on one or more computer storage devices, each configured to perform the actions of the devices and methods.

BRIEF DESCRIPTION OF THE DRAWINGS

Advantages of the present disclosure will be readily appreciated as the same becomes better understood by reference to the following detailed description when considered in connection with the accompanying drawings.

FIG. 25 shows a sample constraint equation.

FIGS. 26 and 27 show a sample forward dynamics algorithm for carrying out a virtual simulation.

FIGS. 29A-29D illustrate movements of the tool in response to application of guide constraints to attract the tool to a target position and target orientation

DETAILED DESCRIPTION

Overview

Figure 1:
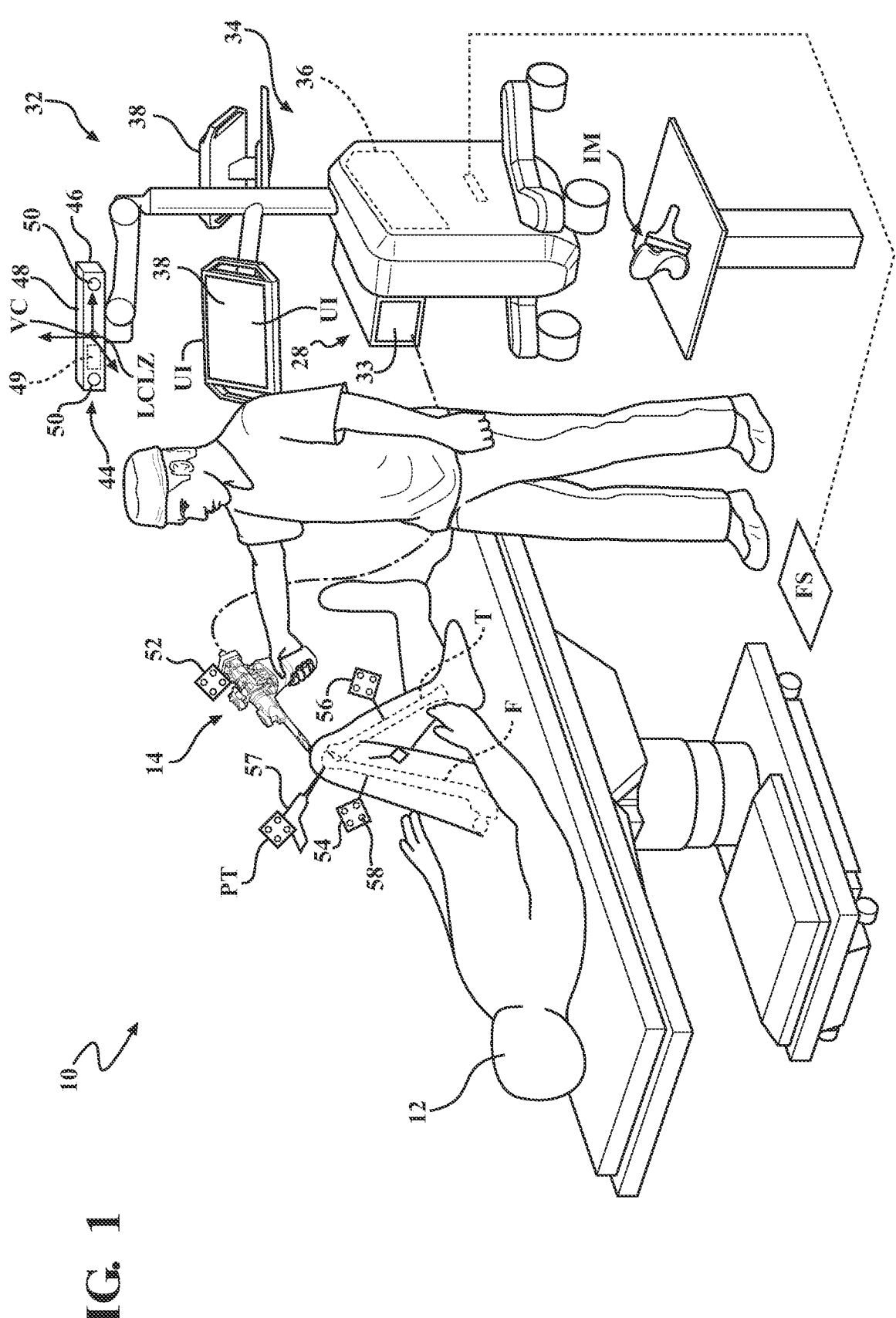
FIG. 1 is a perspective view of a robotic system.

Referring to FIG. 1, a robotic system 10 is illustrated. The robotic system 10 is shown performing a total knee procedure on a patient 12 to resect portions of a femur F and tibia T of the patient 12 so that the patient 12 can receive a total knee implant IM. The robotic system 10 may be used to perform other types of surgical procedures, including procedures that involve hard/soft tissue removal, or other forms of treatment. For example, treatment may include cutting tissue, drilling holes, coagulating tissue, inserting implants, ablating tissue, stapling tissue, suturing tissue, or the like. In some examples, the surgical procedure involves knee surgery, hip surgery, shoulder surgery, spine surgery, and/or ankle surgery, and may involve removing tissue to be replaced by surgical implants, such as knee implants, hip implants, shoulder implants, spine implants, and/or ankle implants. The robotic system 10 and techniques disclosed herein may be used to perform other procedures, surgical or non-surgical, and may be used in industrial applications or other applications where robotic systems are utilized.

Figure 2:
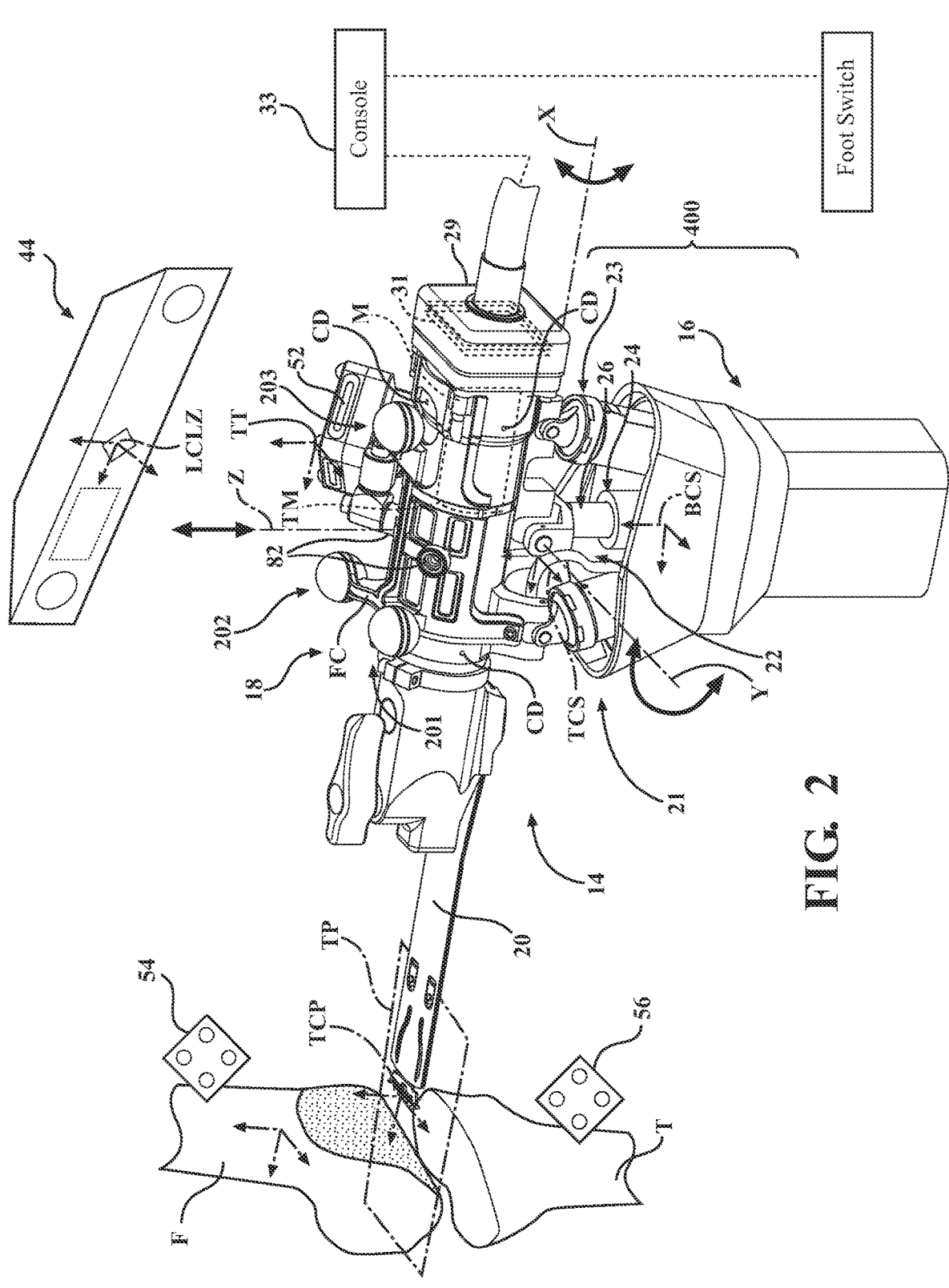
FIG. 2 is a perspective view of a robotic instrument being used to cut one or more planes on a femur and a tibia to receive a total knee implant.

Referring to FIGS. 1 and 2, the robotic system 10 includes an instrument 14. In some examples, a user manually holds and supports the instrument 14 (as shown in FIG. 1). In some other examples, the user may manually hold the instrument 14 while the instrument is being at least partially, or fully, supported by an assistive device, such as a passive arm (e.g., linkage arm with locking joints, weight-balancing arm), an active arm, and/or the like. As best shown in FIGS. 1 and 2, the instrument 14 comprises a hand-held portion 16 for being supported by the user.

The instrument 14 may be freely moved and supported by a user without the aid of a guide arm/assistive device, e.g., configured to be held by a human user while effecting physical removal of material or cutting of material such that the weight of the tool is supported solely by a hand or hands of the user during the procedure. Put another way, the instrument 14 may be configured to be held such that the user's hand is supporting the instrument 14 against the force of gravity. The instrument 14 may weigh 8 lbs. or less, 6 lbs.

or less, 5 lbs. or less, or even 3 lbs. or less. The instrument 14 may have a weight corresponding to ANSI/AAMI HE75: 2009.

In implementations where the weight of the instrument configured to be supported by the user without the aid of a guide arm or assistive device, the hand-held portion has no rigid reference to earth and moves relative to earth during control of the actuator assembly. This can be contrasted with robotic arms that feature bases that are coupled to tables, carts, imagers, or other components that remain static during a procedure. Because the hand-held portion of the instrument may move relative to earth, the pose of the hand-held portion is dynamic and may need to be accounted for during control of the hand-held robotic instrument to achieve optimal performance, including to achieve optimal range of motion, optimal balance and center of gravity relative to the user's hands, and optimal feel to a user to avoid providing sensations that may distract the user from positioning the hand-held portion in an ideal manner to complete the procedure. This is due to the fact that the control system of the instrument cannot assume that the base aka hand-held portion is in a fixed location when calculating the navigation transforms between the various moving/conformable components of the system, including but not limited the tool, the tool platform, the actuator assembly, and/or the hand-held portion.

Another complexity introduced for hand-held medical robotic instruments that are configured to have their weight supported by a user without use of a guide arm or assistive device is that reaction forces transmitted through the kinematic chain of the instrument are ultimately transmitted solely to the user's hand(s), as opposed to be being transmitted, at least in part, to the guide arm/assistive device. Because the user has to bear the reaction forces in a hand-held robotic system, the control system for a hand-held robotic instrument needs to carefully control the actuator assembly so as to ensure that these reactive forces do not compromise the usability of the system. If the control system results in significant reactive forces being applied to the user's hands at undesirable times and/or in undesirable directions, these reactive forces can influence the user's behavior and cause them to move their hand(s), and hence the robotic instrument, to undesirable positions, orientations, and/or poses. For example, if there is a discrepancy between the virtual world and the real world with respect to the bone, the tool, the tool support, and/or the hand-held portion, the discrepancy may lead to the control system controlling the actuator assembly in a way that applies reactive forces to the user's hands.

The instrument 14 also comprises a tool support 18 for receiving a tool 20. In some examples, when the tool 20 is a saw blade 380, the tool support 18 may be referred to as a blade support. The method for operating the instrument 14 may include a user suspending the weight of the instrument 14 without any assistance from a passive arm or robotic arm. Alternately, the weight of the instrument 14 may be supported through use of a counter-balanced passive arm, assistive device, or active robotic arm, such that the user does not have to support the entire weight of the instrument. In such cases, the user may still grasp the hand-held portion 16 in order to interact with and/or guide the instrument 14. The passive arm and the contents of U.S. Pat. No. 9,060,794 to Kang et al. are incorporated herein by reference. Furthermore, the robotic system 10, in some examples, may be free from a robot arm having more than one joint in series.

The tool 20 couples to the tool support 18 to interact with the anatomy in certain operations of the robotic system 10 described further below. The tool 20 may also be referred to as an end effector. The tool 20 may be removable from the tool support 18 such that new/different tools 20 can be attached when needed. The tool 20 may also be permanently fixed to the tool support 18. The tool 20 may comprise an energy applicator designed to contact the tissue of the patient 12. In some examples, the tool 20 may be a saw blade, as shown in FIGS. 1 and 2, or other type of cutting accessory. In such instances, the tool support may be referred to as a blade support. It should be appreciated that in any instance where blade support is referred to, it may be substituted for the term 'tool support' and vice-versa. However, other tools may be contemplated, such as the contents of U.S. Pat. No. 9,707,043 to Bozung, which is hereby incorporated herein by reference. In some examples, the tool 20 may be a twist drill bit, a screw driver, a tap, an ultrasonic vibrating tip, a bur, a stapler, a rotary cutting tool, or the like. The tool 20 may comprise the blade assembly and drive motor to cause oscillatory motion of the blade as shown in U.S. Pat. No. 9,820,753 to Walen et al. or U.S. Pat. No. 10,687,823, hereby incorporated herein by reference. Such driving components may comprise a transmission TM coupled to the drive motor M to convert rotary motion from the drive motor M into oscillating motion of the tool 20.

The system and methods described in PCT/US2020/ 042128, entitled "Robotic Handheld Surgical Instrument Systems and Methods", filed on Jul. 15, 2020, are also hereby incorporated by reference.

Figure 6:
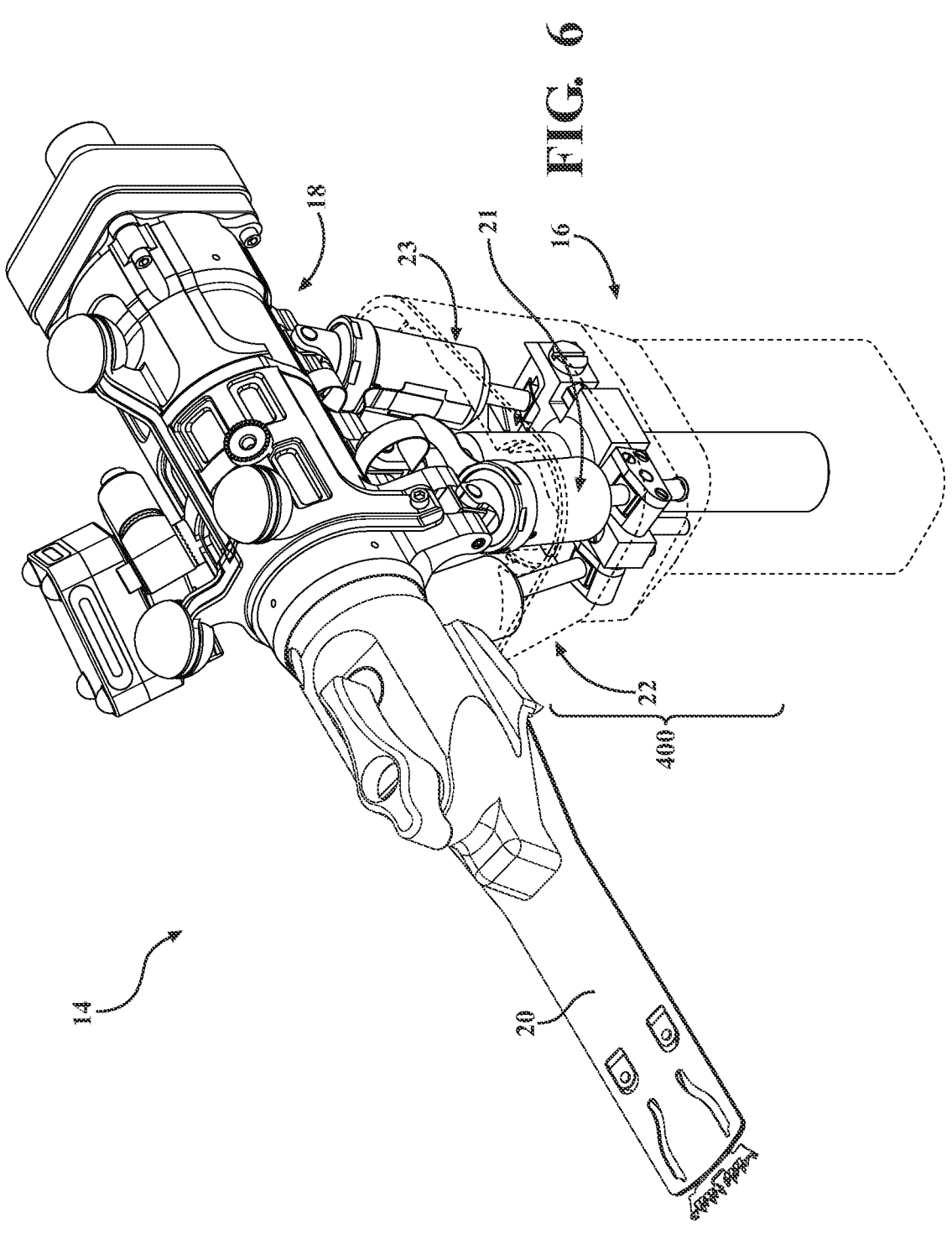
FIG. 6 is a front perspective view of the robotic instrument illustrating one particular pose of a tool support relative to a hand-held portion.

An actuator assembly 400 comprising one or more actuators 21, 22, 23 move the tool support 18 in three degrees of freedom relative to the hand-held portion 16 to provide robotic motion that assists in placing the tool 20 at a desired position and/or orientation (e.g., at a desired pose relative to the femur F and/or tibia T during resection), while the user holds the hand-held portion 16. The actuator assembly 400 may comprise actuators 21, 22, 23 that are arranged in parallel, in series, or a combination thereof. In some examples, the actuators 21, 22, 23 move the tool support 18 in three or more degrees of freedom relative to the hand-held portion 16. In some examples, the actuator assembly 400 is configured to move the tool support 18 relative to the hand-held portion 16 in at least two degrees of freedom, such as pitch and z-axis translation. In some examples, such as shown herein, the actuators 21, 22, 23 move the tool support 18 and its associated tool support coordinate system TCS in only three degrees of freedom relative to the hand-held portion 16 and its associated base coordinate system BCS. For example, the tool support 18 and its tool support coordinate system TCS may: rotate about its y-axis to provide pitch motion; rotate about its x-axis to provide roll motion; and translate along an axis Z coincident with a z-axis of the base coordinate system BCS to provide z-axis translation motion. The allowed motions in pitch, roll, and z-axis translation are shown by arrows in FIG. 2 and in the schematic illustrations of FIGS. 3A-3C, 4A-4C, and 5A-5C, respectively. FIG. 6 provides one example of a pose of the tool support 18 and a pose of the hand-held portion 16 within the range of motion of the instrument 14. In some examples, not shown in the figures, actuators may move the tool support 18 in four or more degrees of freedom relative to the hand-held portion 16.

The actuator assembly 400 may be arranged as a parallel manipulator configuration. The parallel manipulator configuration, as shown throughout the present application, uses the actuators 21, 22, 23 to support a single platform (i.e. the tool support 18), the actuators 21, 22, 23 controlled and manipulated by the control system 28. The actuators 21, 22,

23, are separate and independent linkages working simultaneously, directly connecting the tool support 18 and the hand-held portion 16. In some examples, such as shown throughout the present application, there is no geometric parallelism required to be a parallel manipulator. Other actuator assembly arrangements are contemplated, such as described in U.S. Pat. No. 9,707,043, entitled "Surgical instrument including housing, a cutting accessory that extends from the housing and actuators that establish the position of the cutting accessory relative to the housing" which is incorporated by reference.

Referring back to FIG. 2, a constraint assembly 24 having a passive linkage 26 may be used to constrain movement of the tool support 18 relative to the hand-held portion 16 in the remaining three degrees of freedom. The constraint assembly 24 may comprise any suitable linkage (e.g., one or more links having any suitable shape or configuration) to constrain motion as described herein. In the example shown in FIG. 2, the constraint assembly 24 operates to limit motion of the tool support coordinate system TCS by: constraining rotation about the z-axis of the base coordinate system BCS to constrain yaw motion; constraining translation in the x-axis direction of the base coordinate system BCS to constrain x-axis translation; and constraining translation in the y-axis direction of the base coordinate system BCS to constrain y-axis translation. The actuators 21, 22, 23 and constraint assembly 24, in certain situations described further below, are controlled to effectively mimic the function of a physical cutting guide, such as a physical saw cutting guide.

Figure 7:
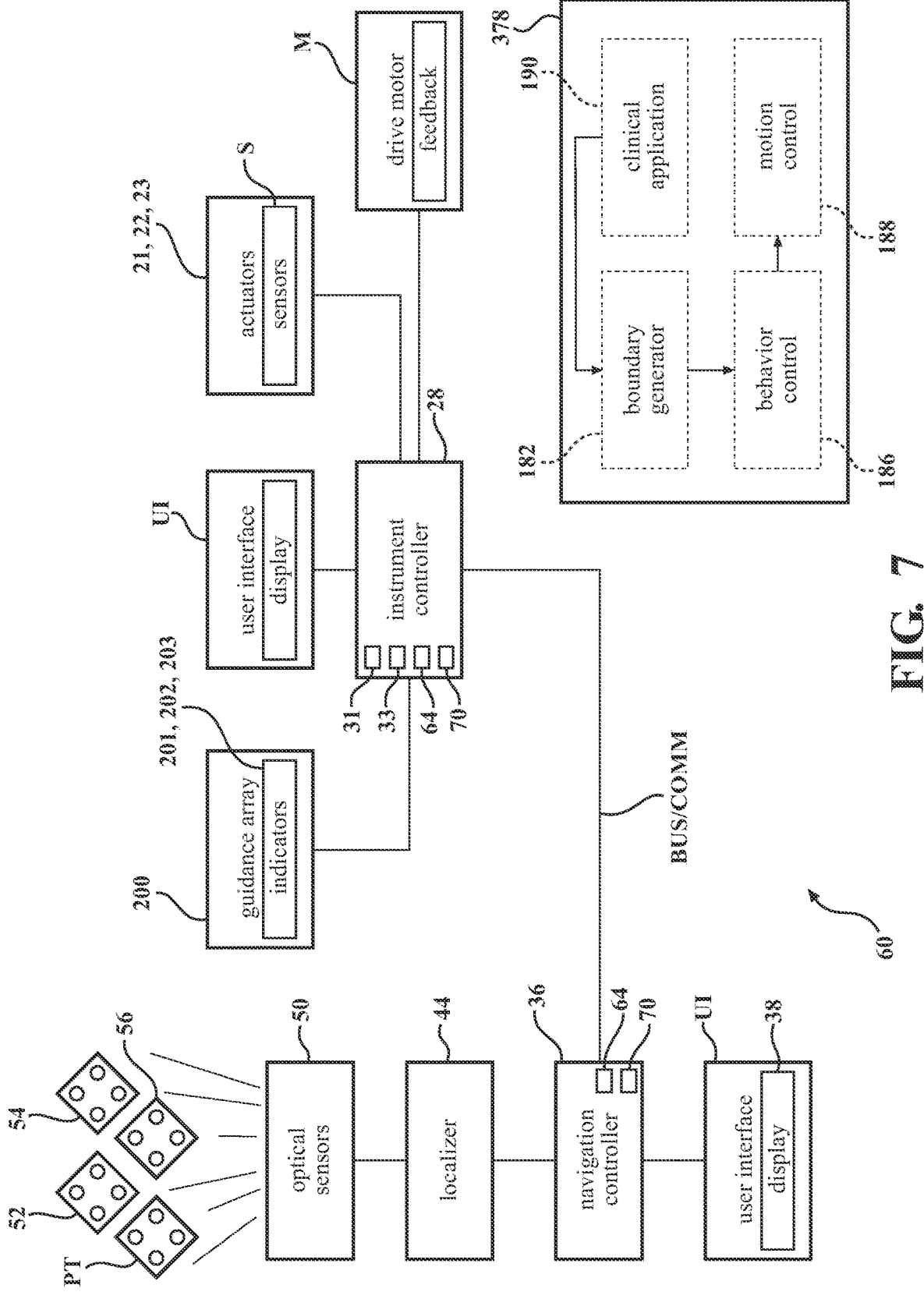
FIG. 7 is a block diagram of a control system, and also illustrates various software modules.

Referring to FIG. 7, an instrument controller 28, or other type of control unit, is provided to control the instrument 14. The instrument controller 28 may comprise one or more computers, or any other suitable form of controller that directs operation of the instrument 14 and motion of the tool support 18 (and tool 20) relative to the hand-held portion 16. The instrument controller 28 may have a central processing unit (CPU) and/or other processors, memory, and storage (not shown). The instrument controller 28 is loaded with software as described below. The processors could include one or more processors to control operation of the instrument 14. The processors can be any type of microprocessor, multi-processor, and/or multi-core processing system. The instrument controller 28 may additionally, or alternatively, comprise one or more microcontrollers, field programmable gate arrays, systems on a chip, discrete circuitry, and/or other suitable hardware, software, or firmware that is capable of carrying out the functions described herein. The term processor is not intended to limit any embodiment to a single processor. The instrument 14 may also comprise a user interface UI with one or more displays and/or input devices (e.g., triggers, push buttons, foot switches, keyboard, mouse, microphone (voice-activation), gesture control devices, touchscreens, etc.).

The control system 60 further includes one or more software programs and software modules. The software modules may be part of the program or programs that operate on the navigation controller 36, instrument controller 28, or both, to process data to assist with control of the robotic system 10. The software programs and/or modules include computer readable instructions stored in non-transitory memory 64 on the navigation controller 36, instrument controller 28, or both, to be executed by one or more processors 70 of the controllers 28, 36. The memory 64 may be any suitable configuration of memory, such as RAM, non-volatile memory, etc., and may be implemented locally or from a remote database. Additionally, software modules for prompting and/or communicating with the user may form part of the program or programs and may include instructions stored in memory 64 on the navigation controller 36, instrument controller 28, or both. The user may interact with any of the input devices of the navigation user interface UI or other user interface UI to communicate with the software modules. The user interface software may run on a separate device from the navigation controller 36, and/or instrument controller 28.

The instrument controller 28 controls operation of the tool 20, such as by controlling power to the tool 20 (e.g., to the drive motor M of the tool 20 that controls cutting motion) and controlling movement of the tool support 18 relative to the hand-held portion 16 (e.g., by controlling the actuators 21, 22, 23). The instrument controller 28 controls a state (e.g., position and/or orientation) of the tool support 18 and the tool 20 with respect to the hand-held portion 16. The instrument controller 28 can control velocity (linear or angular), acceleration, or other derivatives of motion of the tool 20 relative to the hand-held portion 16 and/or relative to the anatomy that is caused by the actuators 21, 22, 23.

As shown in FIG. 2, the instrument controller 28 may comprise a control housing 29 mounted to the tool support 18, and/or the hand-held portion 16 or a combination thereof with one or more control boards 31 (e.g., one or more printed circuit boards and associated electronic components) located inside the control housing 29. The control boards 31 may comprise microcontrollers, field programmable gate arrays (FPGA), drivers, memory, sensors, or other electronic components for controlling the actuators 21, 22, 23 and the drive motor M (e.g., via motor controllers). The instrument controller 28 may also comprise an off-board control console 33 in data and power communication with the control boards 31. The sensors S, actuators 21, 22, 23, and/or drive motor M described herein may feed signals to the control boards 31, which transmit data signals out to the console 33 for processing, and the console 33 may feed control commands (e.g. current commands, torque commands, velocity commands, angle commands, position commands, or a combination thereof, as well as various control and configuration parameters) back to the control boards 31 in order to power and control the actuators 21, 22, 23 and/or the drive motor M. It is contemplated that the processing may also be performed on the control board(s) of the control housing. In some examples, the processing of the control algorithms may be distributed between the console and the control housing. In one example, the position control and velocity control calculations may be in the console and current control may be in the field programmable gate arrays located in the control house. Of course, it is contemplated that no separate control housing is necessary, and/or the processing can be performed in any number of different locations.

In some versions, the console 33 may comprise a single console for powering and controlling the actuators 21, 22, 23, and the drive motor M. In some versions, the console 33 may comprise one console for powering and controlling the actuators 21, 22, 23 and a separate console for powering and controlling the drive motor M. One such console for powering and controlling the drive motor M may be like that described in U.S. Pat. No. 7,422,582, filed on Sep. 30, 2004, entitled, "Control Console to which Powered Surgical Handpieces are Connected, the Console Configured to Simultaneously Energize more than one and less than all of the Handpieces," hereby incorporated herein by reference. Flexible circuits FC, also known as flex circuits, may interconnect the actuators 21, 22, 23 and/or other components with the instrument controller 28. For example, flexible circuits FC may be provided between the actuators 21, 22, 23, and the control boards 31. Other forms of connections, wired or wireless, may additionally, or alternatively, be present between components.

Referring briefly back to FIG. 1, the robotic system 10 further includes a navigation system 32. One example of the navigation system 32 is described in U.S. Pat. No. 9,008, 757, filed on Sep. 24, 2013, entitled, "Navigation System Including Optical and Non-Optical Sensors," hereby incorporated herein by reference. The navigation system 32 tracks movement of various objects. Such objects include, for example, the instrument 14, the tool 20 and the anatomy, e.g., the femur F and tibia T or other bone structures, such as one or more vertebra, the pelvis, scapula, or humerus or combinations thereof. The navigation system 32 tracks these objects to gather state information of each object with respect to a (navigation) localizer coordinate system LCLZ. As used herein, the state of an object includes, but is not limited to, data that defines the position and/or orientation of the tracked object (e.g., coordinate systems thereof) or equivalents/derivatives of the position and/or orientation. For example, the state may be a pose of the object, and/or may include linear velocity data, angular velocity data, and the like.

The navigation system 32 may include a cart assembly 34 that houses a navigation controller 36, and/or other types of control units. A navigation user interface UI is in operative communication with the navigation controller 36. The navigation user interface UI includes one or more displays 38. The navigation system 32 is capable of displaying graphical representations of the relative states of the tracked objects to the user using the one or more displays 38. The navigation user interface UI further comprises one or more input devices to input information into the navigation controller 36 or otherwise to select/control certain aspects of the navigation controller 36. Such input devices include interactive touchscreen displays. However, the input devices may include any one or more of push buttons, pointer, foot switches, a keyboard, a mouse, a microphone (voice-activation), gesture control devices, and the like. In some examples, the user may use buttons located on the pointer to navigate through icons and menus of the user interfaces UI to make selections, configuring the robotic surgical system 10 and/or advancing through the workflow.

The navigation system 32 also includes a localizer 44 coupled to the navigation controller 36. In one example, the localizer 44 is an optical localizer and includes a camera unit 46. The camera unit 46 has an outer casing 48 that houses one or more optical sensors 50. The localizer 44 may comprise its own localizer controller 49 and may further comprise a video camera VC. In certain configurations, the localizer may be coupled to the hand-held robotic instrument.

The navigation system 32 includes one or more trackers. In some examples, the trackers include a pointer tracker PT, a tool tracker 52, a first patient tracker 54, and a second patient tracker 56. In the illustrated example of FIG. 1, the tool tracker 52 is firmly attached to the instrument 14, the first patient tracker 54 is firmly affixed to the femur F of the patient 12, and the second patient tracker 56 is firmly affixed to the tibia T of the patient 12. In this example, the patient trackers 54, 56 are firmly affixed to sections of bone. The trackers 52, 54, 56 and pointer tracker are registered to their respective objects (e.g. bone, tool) and the navigation system 32 manually, automatically, or a combination thereof. In some examples, the pointer tracker PT is firmly affixed to a pointer 57 and used for registering the anatomy to one or more coordinate systems, including the localizer coordinate system LCLZ and/or used for other calibration and/or registration functions. In one example, the pointer 57 may be used to register the patient trackers 54, 56 to the bone which the tracker 54, 56 is attached, respectively, and the tool tracker 52 (and optionally 53) to the tool support 18, the tool 20, the hand-held portion 16, or a combination thereof. In some examples, the pointer tracker PT may be used to register the TCP of the instrument 14 to the tracker 52 relative to a tracker coordinate system. This way, if the localizer 44 is moved from position to position, the registration of the instrument 14 is located relative to the tool tracker 52. However, other means of registration of the trackers 52, 54, 56 are contemplated and may be implemented together or separately with the pointer tracker PT. Other tracker locations are also contemplated.

Throughout this description, various transforms are described, such as 'bone to tracker' or 'instrument TCP to tracker', i.e., relative to the 'tracker coordinate system' rather than to the LCTZ coordinate system. The localizer coordinate system may be used as an intermediate coordinate system during registration and bone prep, since all tracked objects are measured with respect to LCTZ. During registration, ultimately the various localizer-referred poses are combined mathematically and registration results are stored 'with respect to a tracker', such that if the camera (i.e., LCTZ) moves, the registration is still valid.

The tool tracker 52 may be affixed to any suitable component of the instrument 14, and in some versions may be attached to the hand-held portion 16, the tool support 18, directly to the tool 20, or a combination thereof. The trackers 52, 54, 56, PT may be fixed to their respective components in any suitable manner, such as by fasteners, clamps, or the like. For example, the trackers 52, 54, 56, PT may be rigidly fixed, flexibly connected (optical fiber), or not physically connected at all (ultrasound), as long as there is a suitable (supplemental) way to determine the relationship (measurement) of that respective tracker to the associated object. Any one or more of the trackers 52, 54, 56, PT may include active markers 58. The active markers 58 may include light emitting diodes (LEDs). Alternatively, the trackers 52, 54, 56, PT may have passive markers, such as reflectors, which reflect light emitted from the camera unit 46. Printed markers, or other suitable markers not specifically described herein, may also be utilized.

Various coordinate systems may be employed for purposes of tracking the objects. For instance, the coordinate systems may comprise the localizer coordinate system LCLZ, the tool support coordinate system TCS, the base coordinate system BCS, coordinate systems associated with each of the trackers 52, 54, 56, PT, one or more coordinate systems associated with the anatomy, one or more coordinate systems associated with pre-operative and/or intra-operative images (e.g., CT images, Mill images, etc.) and/or models (e.g., 2D or 3D models) of the anatomy—such as the implant coordinate system, and a TCP (tool center point) coordinate system. In some examples, the robotic system 10 does not rely on pre-operative and/or intraoperative imaging to create the 2D or 3D models of the target bone. Rather, the robotic system may be used in an imageless system using the pointer tracker PT to register the target anatomy, capturing various anatomical landmarks, which is then processed by the control system 60 to morph a nominal bone model to match the captured data. In other examples, pre-operative and intraoperative imaging is used to image the target area of the patient and then transform the 2D and/or 3D images into a 3D model of the target bone. It is also contemplated that the robotic surgical system 10 may use a combination of imaged and imageless procedures in creating a 3D model of the target surgical area. One exemplary system is described in U.S. Pat. No. 8,617,174, which is hereby incorporated by reference. Coordinates in the various coordinate systems may be transformed to other coordinate systems using transformations upon establishing relationships between the coordinate systems, e.g., via registration, calibration, geometric relationships, measuring, etc.

As shown in FIG. 2, in some examples, the TCP is a predetermined reference point or origin of the TCP coordinate system defined at the distal end of the tool 20. The geometry of the tool 20 may be defined relative to the TCP coordinate system and/or relative to the tool support coordinate system TCS. The tool 20 may comprise one or more geometric features, e.g., perimeter, circumference, radius, diameter, width, length, height, volume, area, surface/plane, range of motion envelope (along any one or more axes), etc. defined relative to the TCP coordinate system and/or relative to the tool support coordinate system TCS and stored in the non-volatile memory of the control boards 31 in the control housing 29 of the instrument 14, the navigation system 32, the instrument controller 28, or a combination thereof. The tool center point (TCP), in one example, is a predetermined reference point and corresponding coordinate system defined at the tool 20. The TCP has a known, or able to be calculated (i.e., not necessarily static), pose relative to other coordinate systems. The TCP coordinate system includes an origin point and a set of axes (e.g. x axis, y axis, z axis) which define the pose of the TCP. By tracking the TCP (or knowing the pose of the TCP), the system 10 may calculate the position and orientation of the instrument 14 based on the pose of the TCP and the known positional relationship between the TCP and the features of the instrument 14. In some examples, the tool 20 has a blade plane (e.g., for saw blades) that will be described for convenience and ease of illustration, but is not intended to limit the tool 20 to any particular form. In other examples, the tool 20 has an axis. Points, other primitives, meshes, other 3D models, etc., can be used to virtually represent the tool 20. The origin point of the TCP coordinate system may be located at the spherical center of the bur 25 of the tool 20, the tip of a drill bit, or at the distal end of the saw blade 27 such that the TCP coordinate system is tracked relative to the origin point on the distal tip of the tool 200. Alternatively, the TCP may be tracked using a plurality of tracked points. The TCP may be defined in various ways depending on the configuration of the tool 20. The instrument may employ the joint/motor encoders, or any other non-encoder position sensing method, so the control system 60 may determine a pose and/or position of the TCP relative to the hand-held portion 16 and BCS. The tool support 18 may use joint measurements to determine TCP pose and/or could employ techniques to measure TCP pose directly. The control of the tool 20 is not limited to a center point. For example, any suitable primitives, meshes, etc., can be used to represent the tool 20. It should be appreciated that the TCP may alternatively be defined as a point, as opposed to a coordinate system. The TCP coordinate system allows calculate any required reference points or geometry aspects of the tool once you have determined the pose of the saw blade or other tool.

The TCP coordinate system, the tool support coordinate system TCS, and the coordinate system of the tool tracker 52 may be defined in various ways depending on the configuration of the tool 20. For example, the pointer 57 may be used with calibration divots CD in the tool support 18 and/or in the tool 20 for: registering (calibrating) a pose of the tool support coordinate system TCS relative to the coordinate system of the tool tracker 52; determining a pose of the TCP coordinate system relative to the coordinate system of the tool tracker 52; and/or determining a pose of the TCP coordinate system relative to the tool support coordinate system TCS. Other techniques could be used to measure the pose of the TCP coordinate system directly, such as by attaching and fixing one or more additional trackers/markers directly to the tool 20. In some versions, trackers/markers may also be attached and fixed to the hand-held portion 16, the tool support 18, or both. In instances where the hand-held portion includes a tracker, the pose of the hand-held portion relative to the localizer coordinate system LCTZ may be measured directly. In still other alternatives, the TCP may be defined relative to the tool tracker, using the intermediate tool support coordinate system TCS.

Since the tool support 18 is movable in multiple degrees of freedom relative to the hand-held portion 16 via the actuators 21, 22, 23, the instrument 14 may employ encoders, hall-effect sensors (with analog or digital output), and/or any other position sensing method, to measure a pose of the TCP coordinate system and/or tool support coordinate system TCS relative to the base coordinate system BCS. In one exemplary configuration, the instrument 14 may use measurements from sensors that measure actuation of the actuators 21, 22, 23 to determine a pose of the TCP coordinate system and/or tool support coordinate system TCS relative to the base coordinate system BCS, as described further below.

The localizer 44 monitors the trackers 52, 54, 56, PT (e.g., coordinate systems thereof) to determine a state of each of the trackers 52, 54, 56, PT, which correspond respectively to the state of the object respectively attached thereto. The localizer 44 may perform known techniques to determine the states of the trackers 52, 54, 56, PT, and associated objects (such as the tool, the patient, the tool support, and the hand-held portion). The localizer 44 provides the states of the trackers 52, 54, 56, PT to the navigation controller 36. In some examples, the navigation controller 36 determines and communicates the states of the trackers 52, 54, 56, PT to the instrument controller 28.

The navigation controller 36 may comprise one or more computers, or any other suitable form of controller. Navigation controller 36 has a central processing unit (CPU) and/or other processors, memory, and storage (not shown). The processors can be any type of processor, microprocessor or multi-processor system. The navigation controller 36 is loaded with software. The software, for example, converts the signals received from the localizer 44 into data representative of the position and/or orientation of the objects being tracked. The navigation controller 36 may additionally, or alternatively, comprise one or more microcontrollers, field programmable gate arrays, systems on a chip, discrete circuitry, and/or other suitable hardware, software, or firmware that is capable of carrying out the functions described herein. The term processor is not intended to limit any embodiment to a single processor.

Although one example of the navigation system 32 is shown to determine object states, the navigation system 32 may have any other suitable configuration for tracking the instrument 14, tool 20, and/or the patient 12. In another example, the navigation system 32 and/or localizer 44 are ultrasound-based. For example, the navigation system 32 may comprise an ultrasound imaging device coupled to the navigation controller 36. The ultrasound imaging device images any of the aforementioned objects, e.g., the instrument 14, the tool 20, and/or the patient 12, and generates state signals to the navigation controller 36 based on the ultrasound images. The ultrasound images may be 2D, 3D, or a combination of both. The navigation controller 36 may process the images in near real-time to determine states of the objects. The ultrasound imaging device may have any suitable configuration and may be different than the camera unit 46 as shown in FIG. 1.

In another example, the navigation system 32 and/or localizer 44 are radio frequency (RF)-based. For example, the navigation system 32 may comprise an RF transceiver coupled to the navigation controller 36. The instrument 14, the tool 20, and/or the patient 12 may comprise RF emitters or transponders attached thereto. The RF emitters or transponders may be passive or actively energized. The RF transceiver transmits an RF tracking signal and generates state signals to the navigation controller 36 based on RF signals received from the RF emitters. The navigation controller 36 may analyze the received RF signals to associate relative states thereto. The RF signals may be of any suitable frequency. The RF transceiver may be positioned at any suitable location to track the objects using RF signals effectively. Furthermore, the RF emitters or transponders may have any suitable structural configuration that may be much different than the trackers 52, 54, 56, PT shown in FIG. 1.

In yet another example, the navigation system 32 and/or localizer 44 are electromagnetically based. For example, the navigation system 32 may comprise an EM transceiver coupled to the navigation controller 36. The instrument 14, the tool 20, and/or the patient 12 may comprise EM components attached thereto, such as any suitable magnetic tracker, electro-magnetic tracker, inductive tracker, or the like. The trackers may be passive or actively energized. The EM transceiver generates an EM field and generates state signals to the navigation controller 36 based upon EM signals received from the trackers. The navigation controller 36 may analyze the received EM signals to associate relative states thereto. Again, such navigation system 32 examples may have structural configurations that are different than the navigation system 32 configuration shown in FIG. 1.

The navigation system 32 may have any other suitable components or structure not specifically recited herein. Furthermore, any of the techniques, methods, and/or components described above with respect to the navigation system 32 shown may be implemented or provided for any of the other examples of the navigation system 32 described herein. For example, the navigation system 32 may utilize solely inertial tracking or any combination of tracking techniques, and may additionally or alternatively comprise, fiber optic-based tracking, machine-vision tracking, and the like.

Referring to FIG. 7, the robotic system 10 includes a control system 60 that comprises, among other components, the instrument controller 28 and the navigation controller 36. The control system 60 further includes one or more software programs and software modules. The software modules may be part of the program or programs that operate on the instrument controller 28, navigation controller 36, or a combination thereof, to process data to assist with control of the robotic system 10. The software programs and/or modules include computer readable instructions stored in memory 64 on the instrument controller 28, navigation controller 36, or a combination thereof, to be executed by one or more processors 70 of the controllers 28. The memory 64 may be any suitable configuration of memory, such as non-transitory memory, RAM, non-volatile memory, etc., and may be implemented locally or from a remote database. Additionally, software modules for prompting and/or communicating with the user may form part of the program or programs and may include instructions stored in memory 64 on the instrument controller 28, navigation controller 36, or a combination thereof. The user may interact with any of the input devices of the navigation user interface UI or other user interface UI to communicate with the software modules. The user interface software may run on a separate device from the instrument controller 28 and/or navigation controller 36. The instrument 14 may communicate with the instrument controller 28 via a power/data connection. The power/data connection may provide a path for the input and output used to control the instrument 14 based on the position and orientation data generated by the navigation system 32 and transmitted to the instrument controller 28, as shown as the BUS/COMM connection 37 in FIG. 7.

The control system 60 may comprise any suitable configuration of input, output, and processing devices suitable for carrying out the functions and methods described herein. The control system 60 may comprise the instrument controller 28, the navigation controller 36, or a combination thereof, and/or may comprise only one of these controllers, or additional controllers. The controllers may communicate via a wired bus or communication network as shown in one example as the BUS/COMM connection 37 in FIG. 7, via wireless communication, or otherwise. The control system 60 may also be referred to as a controller. The control system 60 may comprise one or more microcontrollers, field programmable gate arrays, systems on a chip, discrete circuitry, sensors, displays, user interfaces, indicators, and/or other suitable hardware, software, or firmware that is capable of carrying out the functions described herein.

Instrument

Figure 8:
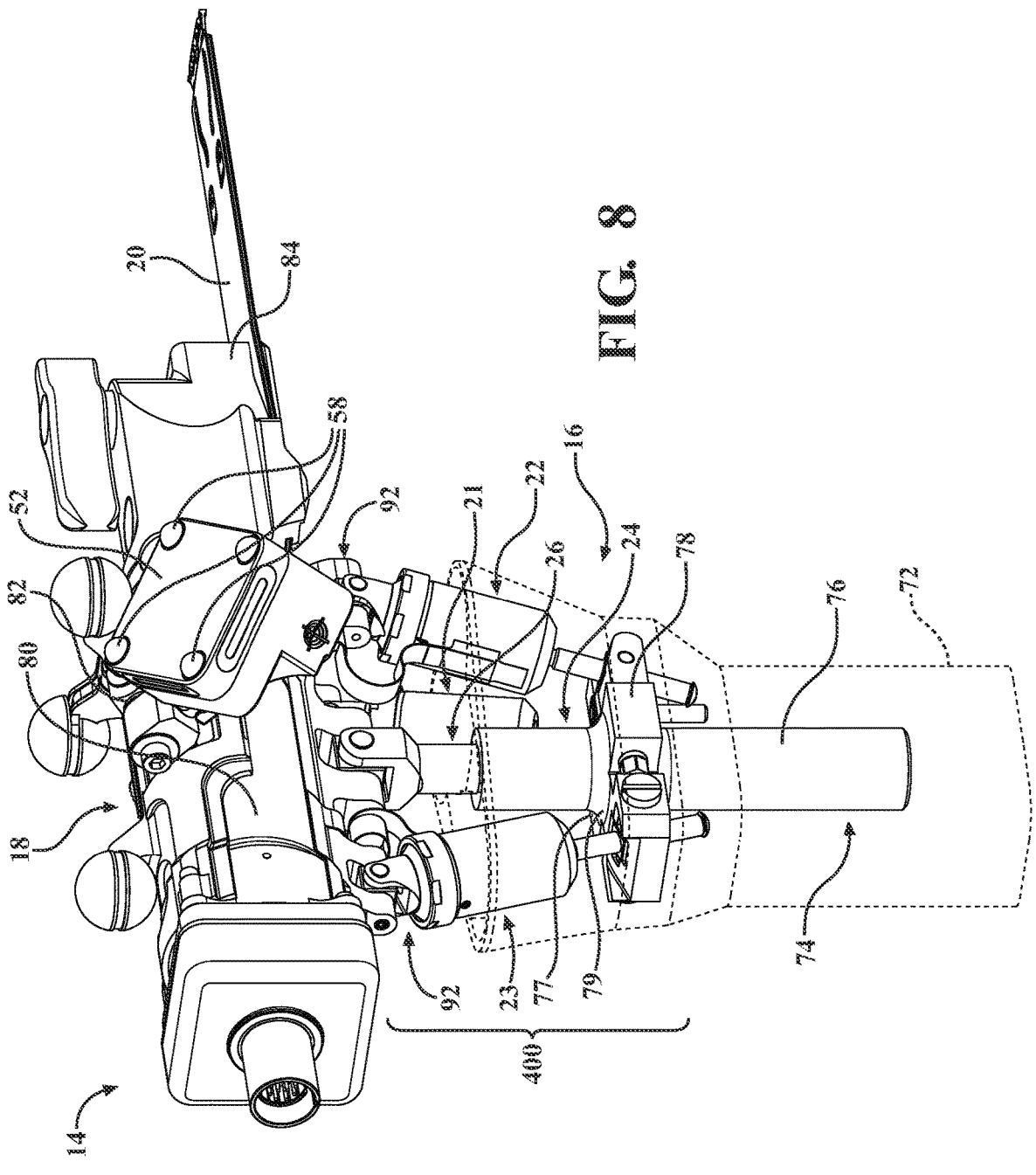
FIG. 8 is a rear perspective view of the robotic instrument.
Figure 9:
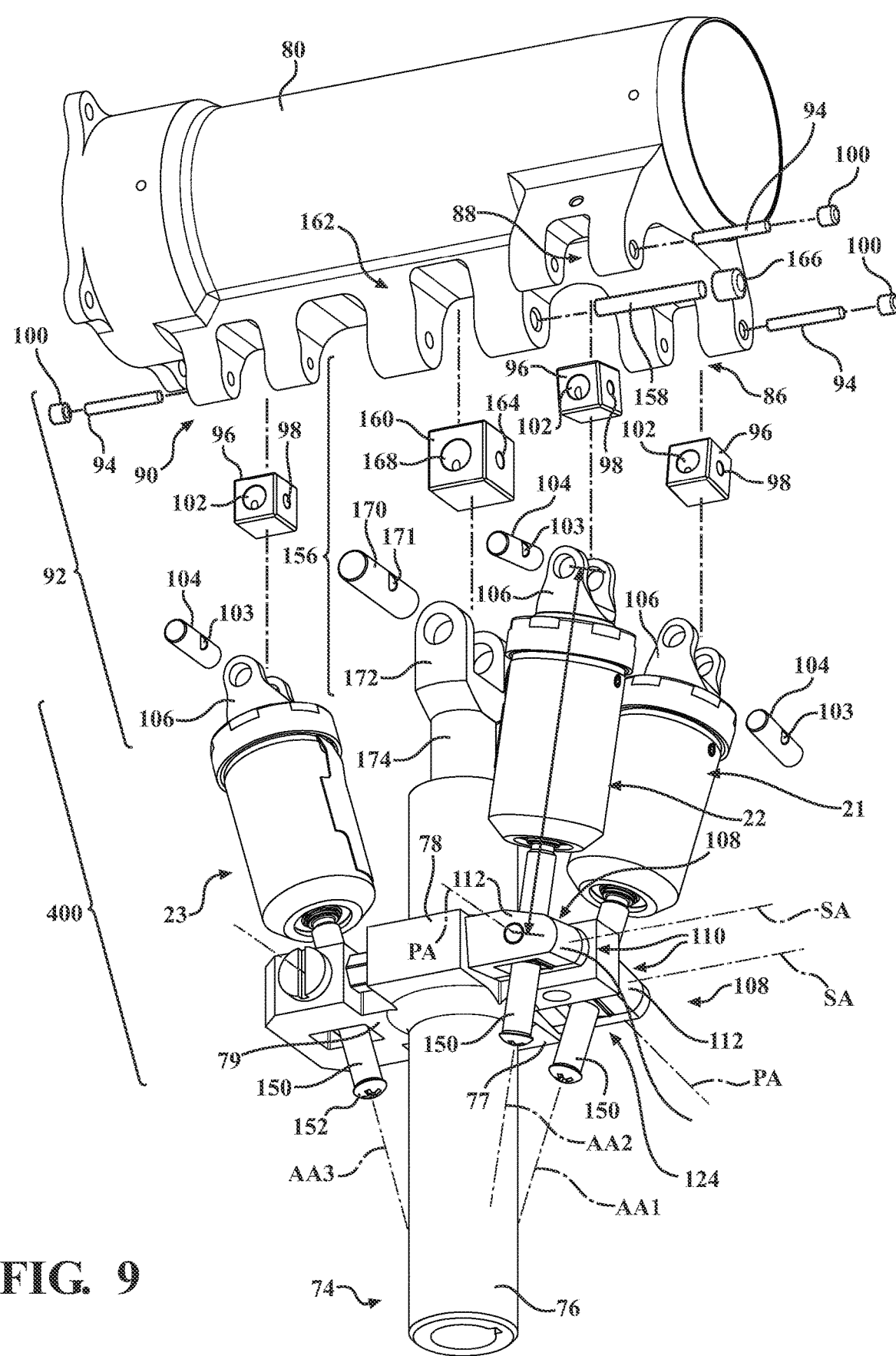
FIG. 9 is an exploded view showing a body of the tool support and associated joint connections to a plurality of actuators.

In one exemplary configuration, the instrument 14 is best shown in FIGS. 8 and 9. The instrument 14 includes the hand-held portion 16 to be held by the user, the tool support 18 movably coupled to the hand-held portion 16 to support the tool 20, the actuator assembly 400 with the plurality of actuators 21, 22, 23 operatively interconnecting the tool support 18 and the hand-held portion 16 to move the tool support 18 in at least three degrees of freedom relative to the hand-held portion 16, and the constraint assembly 24 having the passive linkage 26 operatively interconnecting the tool support 18 and the hand-held portion 16.

The hand-held portion 16 comprises a grip 72 for being grasped by the user so that the user is able to manipulate, guide, and/or grasp the instrument 14. The hand-held portion 16 may be configured with ergonomic features such as a grip for a hand of a user to hold, a textured or mixed material coating for preventing a user's hand from slipping when wet and/or bloody. The hand-held portion 16 may include a taper to accommodate users with different hand sizes and contoured to mate with the contours of a user's hand and/or fingers. The hand-held portion 16 also comprises a base 74 to which the grip 72 is attached by one or more fasteners, adhesive, welding, or the like. In the version shown, the base 74 comprises a sleeve 76 having a generally hollow cylindrical shape. Joint supports 77, 78, 79 extend from the sleeve 76. The actuators 21, 22, 23 may be movably coupled to the base 74 at the joint supports 77, 78, 79 via joints described further below.

The tool support 18 comprises a tool support body 80 to which the tool tracker 52 can be fixed to or removably mounted via one or more tracker mounts fixed to the tool support 18 at one or more mounting locations 82. In one example, the tool tracker 52 is integrated with the tool support 18. In another example, the tool tracker 52 is removably mounted at the one or more mounting locations 82. The tool 20 is removably coupled to the tool support 18 in the version shown. In particular, the tool support 18 comprises a tool coupler, such as head 84 to which the tool 20 is mounted, as described in U.S. Pat. No. 9,820,753 to Walen et al., incorporated herein by reference. The head 84 may be configured to utilize an oscillating-style of saw blade, as well as a sagittal-style saw blade. The drive motor M that drives operation of the tool 20 is disposed in the tool support body 80 (e.g., to drive oscillation of the saw blade in some versions). The tool 20 may be attached to and released from the head 84 in the manner disclosed in U.S. Pat. No. 9,820,753 to Walen et al., incorporated herein by reference. As best shown in FIG. 9, the tool support 18 also comprises a plurality of actuator mounts 86, 88, 90 at which the actuators 21, 22, 23 are to be movably coupled to the tool support 18 via joints, as described further below. The actuator mounts 86, 88, 90 may comprise brackets, or the like, suitable to mount the actuators 21, 22, 23 such that the tool support 18 is able to move in at least three degrees of freedom relative to the hand-held portion 16.

The actuators 21, 22, 23, in the version shown, comprise electric, linear actuators that extend between the base 74 and the tool support body 80. When actuated, an effective length of the actuator 21, 22, 23 changes to vary a distance between the tool support body 80 and the base 74 along a corresponding axis of the actuator 21, 22, 23. Accordingly, the control system 60 commands the actuators 21, 22, 23 to work in a coordinated fashion, responding to individual inputs given to each actuator 21, 22, 23, respectively, by the control system 60 to change their effective lengths and move the tool support 18 in at least three degrees of freedom relative to the hand-held portion 16 into the target pose. In the version shown, three actuators 21, 22, 23 are provided, and may be referred to as first, second, and third actuators 21, 22, 23 or front actuators 21, 22, and rear actuator 23. The first, second, and third actuators 21, 22, 23 are adjustable in effective length along a first active axis AA1, a second active axis AA2, and a third active axis AA3 (see FIG. 9). The first, second, and third actuators 21, 22, 23 are independently adjustable in effective length to adjust one or more of a pitch orientation, a roll orientation, and a z-axis translation position of the tool support 18 relative to the hand-held portion 16, as previously described. More actuators may be provided in some examples. The actuators may comprise rotary actuators in some examples. The actuators 21, 22, 23 may comprise linkages having one or more links of any suitable size or shape. The actuators 21, 22, 23 may have any configuration suitable to enable movement of the tool support 18 relative to the hand-held portion 16 in at least three degrees of freedom. For example, in some versions, there may be one front actuator and two rear actuators, or some other arrangement of actuators.

In this version, the actuators 21, 22, 23 are coupled to the base 74 and the tool support body 80 via a plurality of active joints. The active joints include a set of first active joints 92 that couple the actuators 21, 22, 23 to the tool support body 80 at the actuator mounts 86, 88, 90. In one version, as shown in FIG. 9, the first active joints 92 comprises active U-joints. The U-joints comprise first pivot pins 94 and joint blocks 96. The first pivot pins 94 pivotally connect the joint blocks 96 to the actuator mounts 86, 88, 90 via throughbores 98 in the joint blocks 96. Set screws 100 may secure the first pivot pins 94 to the actuator mounts 86, 88, 90. The U-joints may also comprise second pivot pins 104. The joint blocks 96 have crossbores 102 to receive the second pivot pins 104. The second pivot pins 104 have throughbores 103 to receive the first pivot pins 94, such that the first pivot pins 94, the joint blocks 96, and the second pivot pins 104 form a cross of the U-joint. The first pivot pin 94 and the second pivot pin 104 of each U-joint define pivot axes PA that intersect. The second pivot pins 104 pivotally connect a pivot yoke 106 of the actuators 21, 22, 23 to the joint blocks 96. As a result, the actuators 21, 22, 23 are able to move in two degrees of freedom relative to the tool support body 80. Other types of active joints are also contemplated, such as active spherical joints comprising balls with slots that receive pins.

Referring to FIG. 9, the active joints also comprise a set of second active joints 108 coupling the front two actuators 21, 22 to the base 74 of the hand-held portion 16. In the version shown, the second active joints 108 are supported at the joint supports 77, 78. Each of the second active joints 108 comprises a swivel yoke 110 arranged to swivel relative to the base 74 of the hand-held portion 16 about a swivel axis SA. Each swivel yoke 110 has a swivel head 112 and a post 114 extending from the swivel head 112 to pivotally engage the base 74 at one of the joint supports 77, 78. Nuts 115 threadably connect to one end of the posts 114 to trap the posts 114 in the base 74 while allowing the respective swivel yoke 110 to freely rotate within its respective joint support 77, 78.

Each of the second active joints 108 comprises a carrier 116 pivotally coupled to one of the swivel yokes 110. The carriers 116 have internally threaded throughbores 117 to receive lead screws 150 of the front two actuators 21, 22, as described further below. Each of the carriers 116 also comprises opposed trunnions 118 that allow the carriers 116 to pivot relative to the swivel yokes 110 about pivot axes PA (see FIG. 9) by being seated in pockets in the swivel yokes 110. In some versions, for each of the second active joints 108, the swivel axis SA intersects the pivot axis PA to define a single vertex about which the actuators 21, 22 move in two degrees of freedom.

Covers are fastened to the swivel heads 112 and define one of the pockets, while the swivel head 112 defines the other pocket. During assembly, the carriers are first positioned with one of the trunnions placed in the pocket in the swivel head 112, and the cover is then fastened over the other trunnion such that the carrier is captured between the cover and the swivel head 112 and is able to pivot relative to the swivel yoke 110 via the trunnions and pockets. Owing to the configuration of the swivel yokes 110 and the associated carriers, i.e., the carriers ability to swivel about the swivel axes SA and pivot about the pivot axes PA, the second active joints 108 allow two degrees of freedom of movement of the front two actuators 21, 22 relative to the base 74. Other joint arrangements between the front two actuators 21, 22 and the base 74 are also possible.

The active joints also comprise a third active joint 124 coupling the rear (third) actuator 23 to the base 74 of the hand-held portion 16. In the version shown, the third active joint 124 is supported at the joint support 79. The third active joint 124 comprises a pivot housing 126 fixed to the joint support 79 of the base 74.

The third active joint 124 comprises a carrier pivotally coupled to the pivot housing 126 via trunnions. Fasteners having pockets attach to either side of the pivot housing 126 via throughbores to engage the trunnions. The fasteners are arranged such that the carrier is able to pivot via the trunnions being located in the pockets after assembly. The carrier has an internally threaded throughbore to receive a lead screw 150 of the rear actuator 23, as described further below. Owing to the configuration of the pivot housing 126 and associated carrier, i.e., the ability of the associated carrier to only pivot about the pivot axis PA (e.g., and not swivel), the third active joint 124 allows only one degree of freedom of movement of the rear actuator 23 relative to the base 74. Other joint arrangements between the rear actuator 23 and the base 74 are also possible.

Each of the actuators 21, 22, 23 comprises a housing. The housing comprises a canister and a cap threadably connected to the canister. The pivot yokes 106 that form part of the first active joints 92 are fixed to the housings such that the housings and pivot yokes 106 are able to move together relative to the tool support 18 via the first active joints 92. The caps capture annular shoulders of the pivot yokes 106 to secure the pivot yokes 106 to the canisters.

In some versions, the pivot yokes 106 and canisters comprise one or more alignment features to align each pivot yoke 106 to its respective canister in a predefined, relative orientation. Such alignment features may comprise mating portions, keys/keyways, or the like. During assembly, the pivot yoke 106 may first be secured to the canister in its predefined, relative orientation, and the cap may then be threaded onto the canister (e.g., via mating outer and inner threads) to trap the pivot yoke 106 to the canister at the predefined, relative orientation. This predefined relationship may be helpful in routing and/or aligning the flex circuits FC, preventing rolling of the pivot yoke 106 relative to the canister, and/or for other purposes.

Each of the actuators 21, 22, 23 also comprises a motor disposed in each housing. The motor has a casing disposed in the housing and a motor winding assembly disposed within the casing. The motor winding assembly may also be aligned in a predefined, relative orientation to the canister, such as via a set screw or other alignment feature, such as those described above. Each motor also has a rotor fixed to the lead screw 150. The lead screw 150 is supported for rotation in the housing by one or more bushings and/or bearings. The rotor and associated lead screw 150 are configured to rotate relative to the housing upon selective energization of the motor. The lead screws 150 have fine pitch and lead angles to prevent backdriving (i.e., they are self-locking). As a result, a load placed on the tool 20 does not easily back drive the motor. In some examples, the lead screws 150 have an 8-36 class 3 thread that results in a lead of from 0.02 to 0.03 inches/revolution. Other thread types/sizes may also be employed.

Each of the actuators 21, 22, 23 may be controlled by a separate motor controller. Motor controllers may be wired separately to the actuators 21, 22, 23, respectively, to individually direct each actuator 21, 22, 23 to a given target position. In some examples, the motor controllers are proportional integral derivative (PID) controllers. In some examples, the motor controllers may include cascaded control loops relating to position, velocity, and torque (current). Additionally, and/or alternatively, the motor controller may only include of a torque (current) control loop. In another example, the position control loop may directly feed the torque (current) control loop. Each of these control stages may be implemented as a PID controller, state space controller, and/or utilize alternate or additional control techniques (e.g., velocity feedforward, torque feedforward, etc.). In some cases, the torque (current) control loop is implemented using field-oriented control and space vector modulation. The stages of the control loop could be distributed between various components of the system. In some examples, the position loop and velocity loop are implemented in the instrument controller and the torque control loop is implemented directly in the control boards 31 as part of the control housing 29 on the instrument 14, mitigating the impact of data communication latency from the instrument 14 through the connection to the console 33, since the current control loop does not require any data feedback via the console 33. The position control loop and velocity control loop are not as sensitive to the communication latency and can be implemented in the console 33. In some examples, the motor controllers can be integrated with or form part of the instrument controller 28. For ease of illustration, the motor controllers shall be described herein as being part of the instrument controller 28.

A power source provides, for example, 32 VDC power signals to the motors via the console 33. The 32 VDC signal is applied to the motors through the instrument controller 28. The instrument controller 28 selectively provides the power signal to each motor to selectively activate the motors. This selective activation of the motors is what positions the tool 20. The motors may be any suitable type of motor, including brushless DC servomotors, permanent magnet synchronous motors, other forms of DC motors, or the like. The power source also supplies power to the instrument controller 28 to energize the components internal to the instrument controller 28. In some examples, the actuator motor may be a 3-phase, brushless motor. The actuator motor may be a DC motor. The actuator motor may be a permanent magnet synchronous motor. Each of the actuator motors may be configured with a sinusoidal back-EMF, configured to achieve limited mechanical cogging, allowing smooth and particular motion, limiting torque ripple. However, other motor types are contemplated. It should be appreciated that the power source can provide other types of power signals such as, for example, 12 VDC, 24 VDC, 40 VDC, etc. The instrument may use electronic switches, e.g., MOSFETs or GaN FETs to PWM the voltage signals to the 3-phase motor on/off at a high frequency, e.g., typically at a rate of at least 16 kHz, up to 256 kHz or higher.

In one possible implementation, one or more sensors S (see also FIG. 7) transmit signals back to the instrument controller 28 so that the instrument controller 28 can determine a current position and/or angle of the associated actuator 21, 22, 23 (i.e., a measured position). The levels of these signals may vary as a function of the rotational position of the associated rotor. In one implementation, the sensor(s) S may resolve the rotational position of the rotor within a given turn at a high resolution. These sensors S may be Hall-effect sensors that output analog and/or digital signals based on the sensed magnetic fields from the rotor, or from other magnets placed on the lead screw 150 (e.g., the 2-pole magnet A low voltage signal, e.g., 5 VDC, for energizing the Hall-effect sensors may be supplied from the motor controller associated with the motor with which the Hall-effect sensors are associated. In some examples, two Hall-effect sensors are disposed in the housing and spaced 90 degrees apart from each other around the rotor to sense joint position so that the instrument controller 28 is able to determine the position and count incremental turns of the rotor). In some versions, the Hall-effect sensors output digital signals representing incremental counts.). Various types of motors and sensor arrangements are possible. In some examples, the motors are brushless DC servomotors and two or more internal Hall-effect sensors may be spaced 90 degrees, 120 degrees, or any other suitable spacing from each other around the rotor. The sensors S may also comprise absolute or incremental encoders, which may be used to detect a rotational position of the rotor and to count turns of the rotor. Other type of encoders may be also used as the one or more sensors. The sensors may be placed at any suitable location on the actuator and its surrounding components suitable to determine the position of each actuator as it is adjusted, such as on the housing, nut, screw, etc. In yet another configuration, sensorless motor control may be utilized. In such an implementation, the position of each rotor may be determined by measuring the motor's back-emf and/or inductance. One suitable example may be found in U.S. Pat. No. 7,422,582, which is hereby incorporated by reference in its entirety.

In some examples, the sensors and/or encoders may measure position feedback for joint position control and/or to determine the position of the tool support 18 relative to the hand-held portion 16 when used in conjunction with a kinematic model of the instrument 14. In some examples, the sensors and/or encoders rely on a multi-turn measurement, which accumulates from revolution to the next, used to determine an absolute position of the actuator 21, 22, 23 along its axis and is used in conjunction with the known pitch (i.e. revolutions per inch of the leadscrew). Additionally, or alternatively, the sensors and/or encoders may be used to determine the "electrical angle of the rotor" for use in electronic commutation of the motor. For example, the sensors and/or encoders may be used to determine a rotor position and apply appropriate energization signals to achieve optimal (efficient) torque generation. In this example, the sensors and/or encoders may utilize a single turn or sub-turn (within one electrical revolution) measurement that rolls over each electrical revolution. The number of electrical revolutions is equal to the number of mechanical revolutions divided by the number of magnetic poles of the motor (e.g. number of pole pairs). However, it is contemplated that a sensor-less method be implemented.

In some examples, output signals from the Hall-effect sensors are sent to the instrument controller 28. The instrument controller 28 monitors the received signals for changes in their levels. Based on these signals the instrument controller 28 determines joint position. Joint position may be considered the degrees of rotation of the rotor from an initial or home position. The rotor can undergo plural 360° rotations. The joint position can therefore exceed 360°. A scalar value referred to as a count is representative of joint position from the home position. The rotors rotate in both clockwise and counterclockwise directions. Each time the signal levels of the plural signals (analog or digital) undergo a defined state change, the instrument controller 28 increments or decrements the count to indicate a change in joint position. For every complete 360° rotation of the rotor, the instrument controller 28 increments or decrements the value of the count by a fixed number of counts. In some examples, the count is incremented or decremented between 100 and 3,000 per 360-degree revolution of the rotor. In some examples, there are 1,024 positions (counts) per 360-degree revolution of the rotor, such as when an incremental encoder is used to monitor joint position. Internal to the instrument controller 28 is a counter associated with each actuator 21, 22, 23. The counter stores a value equal to the cumulative number of counts incremented or decremented. The count value can be positive, zero or negative. In some versions, the count value defines incremental movement of the rotor. Accordingly, the rotors of the actuators 21, 22, 23 may first be moved to known positions, referred to as their home positions (described further below), with the count values being used thereafter to define the current positions of the rotors.

As previously described, the carriers have the internally threaded throughbores to threadably receive the lead screws

150 so that each of the lead screws 150 can rotate relative to a corresponding one of the carriers to adjust the effective length of a corresponding one of the plurality of actuators 21, 22, 23 and thereby vary the counts measured by the instrument controller 28. Each of the housings and corresponding carriers are constrained from relative movement in at least one degree of freedom to allow the lead screws 150 to rotate relative to the carriers. More specifically, the lead screws 150 are able to rotate relative to the carriers owing to: the pivot yokes 106 being unable to rotate about the associated active axes AA1, AA2, AA3 (i.e., the pivot yokes 106 are limited from such rotational movement by virtue of the configuration of the first active joints 92); and the carriers being unable to rotate about the associated active axes AA1, AA2, AA3 (i.e., the carriers are limited from such rotational movement by virtue of the configuration of the second active joints 108 and the third active joint 124).

Stops 152, such as threaded fasteners and shoulders formed on the lead screws 150, are fixed to the lead screws 150. The stops 152 are sized to abut the carriers 116 at ends of travel of each lead screw 150.

As previously described, the actuators 21, 22, 23 are actively adjustable in effective length to enable movement of the tool support 18 relative to the hand-held portion 16. One example of this effective length is labeled "EL" on the third actuator 23. Here, the effective length EL is measured from the pivot axis PA to a center of the associated first active joint 92. As each actuator 21, 22, 23 is adjusted, the effective length EL changes, by varying how far the lead screw 150 has been threaded into or out of its associated carrier and thereby changing the distance from the center of the associated carrier to the center of the associated first active joint 92. The actuators 21, 22, 23 are adjustable between minimum and maximum values of the effective length EL. The effective length EL of each actuator 21, 22, 23 can be represented/measured in any suitable manner to denote the distance between the tool support 18 and the hand-held portion 16 along the active axes AA1, AA2, AA3 that changes to cause various movements of the tool support 18 relative to the hand-held portion 16.

The constraint assembly 24 works in concert with the actuators 21, 22, 23 to constrain the movement provided by the actuators 21, 22, 23. The actuators 21, 22, 23 provide movement in three degrees of freedom, while the constraint assembly 24 constrains movement in three degrees of freedom. In the version shown, the constraint assembly 24 comprises the passive linkage 26, as well as a passive linkage joint 156 that couples the passive linkage 26 to the tool support 18.

In one version, as shown in FIG. 9, the passive linkage joint 156 comprises a passive linkage U-joint. The U-joint comprises a first pivot pin 158 and a joint block 160. The first pivot pin 158 pivotally connects the joint block 160 to a passive linkage mount 162 of the tool support body 80 via a throughbore 164 in the joint block 160. A set screw 166 may secure the first pivot pin 158 to the passive linkage mount 162. The U-joint also comprises a second pivot pin 170. The joint block 160 has a crossbore 168 to receive the second pivot pin 170. The second pivot pin 170 pivotally connects a passive linkage pivot yoke 172 of the passive linkage 26 to the joint block 160. The second pivot pin 170 has a throughbore 171 to receive the first pivot pin 158, such that the first pivot pin 158, the joint block 160, and the second pivot pin 170 form a cross of the U-joint. The first pivot pin 158 and the second pivot pin 170 define pivot axes PA that intersect. As a result, the passive linkage 26 is able to move in two degrees of freedom relative to the tool support body 80. Other types of passive linkage joints are also contemplated, such as a passive linkage spherical joint comprising a ball with slot that receives a pin.

The passive linkage 26 comprises a shaft 174 fixed to the passive linkage pivot yoke 172. The passive linkage 26 also comprises the sleeve 76 of the base 74, which is configured to receive the shaft 174 along a constraint axis CA. The passive linkage 26 is configured to allow the shaft 174 to slide axially along the constraint axis CA relative to the sleeve 76 and to constrain movement of the shaft 174 radially relative to the constraint axis CA during actuation of one or more of the actuators 21, 22, 23.

The passive linkage 26 further comprises a key to constrain rotation of the shaft 174 relative to the sleeve 76 about the constraint axis CA. The key fits in an opposing keyway in the shaft 174 and sleeve 76 to rotationally lock the shaft 174 to the sleeve 76. Other arrangements for preventing relative rotation of the shaft 174 and sleeve 76 are also contemplated, such as an integral key/slot arrangement, or the like. The passive linkage 26 operatively interconnects the tool support 18 and the hand-held portion 16 independently of the actuators 21, 22, 23. The passive linkage is passively adjustable in effective length EL along the constraint axis CA during actuation of one or more of the actuators 21, 22, 23. The sleeve 76, shaft 174, and key 176 represent one combination of links for the passive linkage 26. Other sizes, shapes, and numbers of links, connected in any suitable manner, may be employed for the passive linkage 26.

In the version shown, the passive linkage joint 156 is able to pivot about two pivot axes PA relative to the tool support 18. Other configurations are possible, including robotic hand-held instruments that do not include a passive linkage.

Also, in the version shown, the first active joints 92 and the passive linkage joint 156 define pivot axes PA disposed on a common plane. Non-parallel pivot axes PA, parallel pivot axes PA disposed on different planes, combinations thereof, and/or other configurations, are also contemplated.

In some versions, the head 84 of the tool support 18 is arranged so that the tool 20 is located on a tool plane TP (e.g., blade plane) parallel to the common plane when the tool 20 is coupled to the tool support 18. In some examples, the tool plane TP is spaced from the common plane CP by 2.0 inches or less, 1.0 inches or less, 0.8 inches or less, or 0.5 inches or less.

In the version shown, the actuators 21, 22, 23 are arranged such that the active axes AA1, AA2, AA3 are in a canted configuration relative to the constraint axis CA in all positions of the actuators 21, 22, 23, including when in their home positions. Canting the axes AA1, AA2, AA3 generally tapers the actuator arrangement in a manner that allows for a slimmer and more compact base 74 and associated grip 72. Other configurations are contemplated, including those in which the active axes AA1, AA2, AA3 are not in the canted configuration relative to the constraint axis CA. Such configurations may include those in which the actuator axes AA1, AA2, AA3 are parallel to each other in their home positions.

Further configurations of the actuators, active joints, and constraint assembly are possible. It is contemplated that the control techniques described may be applied to other mechanical configurations not mentioned, in particular those for controlling a tool or saw blade relative to a hand-held portion in one or more degrees of freedom. In some versions, the constraint assembly may be absent and the tool support 18 of the instrument 14 may be able to move in additional degrees of freedom relative to the hand-held portion 16. For example, the instrument may include linear actuators, rotary actuators, or combinations thereof. The instrument may include 2, 3, 4, 5, 6 or more different actuators arranged parallel, in series, or in combinations thereof.

Visual Guidance

Figure 10:
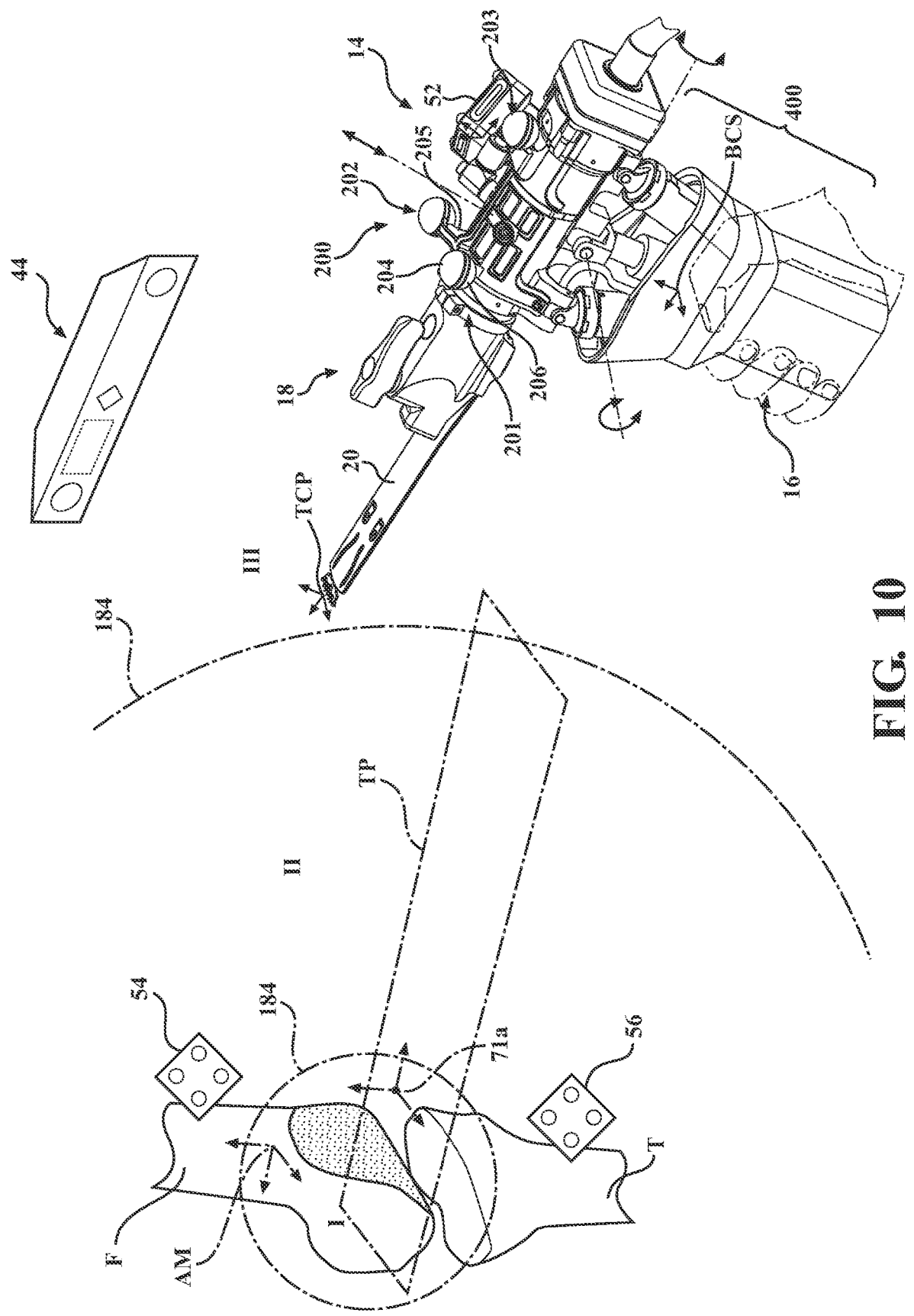
FIG. 10 illustrates various regions in which the robotic instrument is used.

As shown in FIG. 10, a guidance array 200 may be optionally coupled to the tool support 18. Additionally, or alternatively, the guidance array 200 could be optionally attached to the hand-held portion 16, or other portion of the instrument 14. In the version shown, the guidance array 200 comprises at least a first visual indicator 201, a second visual indicator 202, and a third visual indicator 203. Each of the visual indicators 201, 202, 203 comprises one or more illumination sources coupled to the instrument controller 28. In some versions, the illumination sources comprise one or more light emitting diodes (e.g., RGB LEDs), which can be operated in different states, e.g., on, off, flashing/blinking at different frequencies, illuminated with different intensities, different colors, combinations thereof, and the like. In the version shown in FIG. 10, each of the visual indicators 201, 202, 203 comprises upper portion and lower portion 204, 206 (upper segment 204; lower segment 206). It is further contemplated that the each of the visual indicators 201, 202, 203 may be divided into more than two portions 204, 206, such as three or more, four or more, or even ten or more portions. For example, each of the visual indicators 201, 202, 203 may be divided into three portions, with each portion including one or more LEDs. The visual indicators 201, 202, 203 may have generally spherical shapes with the upper and lower portions 204, 206 comprising hemispherical, transparent or translucent domes that can be separately controlled/illuminated as desired. It is contemplated that the visual indicators 201, 202, 203 may have a shape other than a sphere such as a cylinder, a ring, a square, a polygon, or any other shape capable of conveying visual cues to a user. One or more light emitting diodes may be associated with each dome. The visual indicators 201, 202, 203 may be fixed via one or more mounting brackets 205 to the tool support 18 or to the hand-held portion 16.

In some examples, where no guidance array is used, the visual indicators 201, 202, 203 may comprise separate portions of a display screen, such as separate regions on a LCD, or LED display mounted to the tool support 18 or the hand-held portion 16. The display screen may also be included as part of the navigation system, in addition or as an alternative to having a display screen mounted to the instrument.

Alternatively still, visual guidance in the second mode may be provided with a mechanical guide coupled to the hand-held portion, the blade support, or both.

In some configurations, there may be one, two, three, or four portions of the display screen, each corresponding to a different visual indicator. Each portion of the display screen may correspond to a different visual graphic. As described below, each of the visual indicators (or portions of the display screen) may be based on actuator information. In some cases, a single visual indicator may be based on actuator information from two or more actuators. Furthermore, as described throughout, the visual indicator may be used in a first mode indicating where the user should position the tool and a second mode where the visual indicator indicates where the user should position the hand-held portion.

For example, the visual indicator 201, 202, 203 may be configured to output a first indication (a first visual graphic) based on a first commanded position of the first actuator 21, 22, 23 and a second indication (second visual graphic) based on a second commanded position of the first actuator 21, 22, 23, wherein the first indication is different than the second indication, and the first commanded position is different from the second commanded position. As described above, the visual indicator 201, 202, 203 may be controlled based on any suitable type of actuator information. In other words, the visual graphics displayed on the display screen may be based on the commanded position, the previous commanded position, a simulated commanded position, a current measured position, a previous measured position, available travel, an actuator limit (such as a hard or soft stop), a distance needed from current position to commanded position, or a combination thereof.

In some configurations, the instrument controller 28 is configured to control illumination of the upper and lower portions 204, 206 such that the upper and lower portions 204, 206 are operated in different states to indicate the direction of desired movement of the tool 20. It is further contemplated that the instrument controller 28 may be configured to control illumination of multiple portions in different states or with different indications. For example, the different states may indicate to the user: (1) how the user should move the hand-held portion 16 to place the tool 20 (e.g., saw blade) at a desired pose (e.g., on a desired cutting plane/desired cutting trajectory); or (2) how the user should move the hand-held portion 16 such that the actuators 21, 22, 23 move in a preferred direction, such as closer to their home positions while the control system 60 simultaneously works to keep the tool 20 at the desired pose, as will be described further below.

In the first mode, the guidance array or display screen (on the instrument or in part of the navigation system) may be used when the instrument is far enough from the bone that the guide constraints are inactive and joint centering constraints are active. In this configuration, the user desires to use the visual indicators to achieve a good initial alignment of the blade/tool/hand-held portion to be near the center of the joint travel when entering the resection zone/region and enabling the guide constraints so that there is limited abrupt movement on the blade support/tool support and actuators when the guide constraint(s) are first enabled, and to ensure that, when enabled, the actuators will be able to 'reach' the target plane or target trajectory or other target virtual object.

In the second mode, because each of the actuators has only a limited range of motion/travel, it is often important for the user to position the hand-held portion such that the actuators can reach the target plane, target trajectory, or other target object. If one of the actuators reaches its joint limit, the control system must not let it move any more in that direction and in this case the system will not be able to align the blade to the cut plane (and the control system would typically deactivate the saw drive motor to prevent improper resection) or the system will not align the tool to the planned trajectory Accordingly, it may be important to give the user continual feedback so that they can position the hand-held portion appropriately, such that the actuator assembly can reach the target plane or target trajectory. Without continual feedback, the user will not realize how close they are operating to the limits of range of motion until the blade ultimately lifts off the plane since one of the motors has reached the joint limits and the saw blade drive motor is deactivated which may annoy to the user, lengthens the surgical procedure, etc. The goal is to give intuitive, live handle alignment feedback to minimize/reduce the occurrence of any actuator reaching its joint limits. The guidance array, display screen, or mechanical guide may be suitable for this purpose.

During some modes of operation, the instrument controller 28 is configured to automatically control/adjust the guidance array 200 (e.g., change states thereof) to visually indicate to the user desired changes in pitch orientation, roll orientation, and z-axis translation of the tool 20 to achieve the desired pose of the tool 20 while the user moves the tool 20 via the hand-held portion 16. In some versions, the guidance array 200 is coupled to the tool support 18 or to the hand-held portion 16 in a way that intuitively represents the plane of the tool 20. For example, since three points define a plane, the three visual indicators 201, 202, 203 may generally represent the plane of the tool 20. In some cases, each of the indicators 201, 202, 203 corresponds to one of the points P1, P2, P3 having a known position relative to the plane of the tool 20 (e.g., located in the tool plane and defined in the TCP coordinate system, the tool support coordinate system TCS, or defined in any other suitable coordinate system). Points associated with the visual indicators 201, 202, 203 could be defined at other suitable locations in the plane of the tool 20 or at locations having a known relationship to the plane of the tool 20.

Collectively, the guidance array 200, using the one or more visual indicators 201, 202, 203 may be located and their states controlled to visually indicate to the user desired changes in movement (e.g. amount of travel) to change pitch, roll, and translation of the tool 20, and by extension, desired changes in pitch, roll, and translation of the tool support coordinate system TCS to achieve a desired pose. More specifically, the instrument controller 28 is configured to illuminate the guidance array 200 in a manner that enables the user to distinguish between a desired change in pitch orientation, a desired change in roll orientation, and a desired change in translation. The instrument controller 28 may be configured to illuminate the guidance array 200 or control the display screen in a manner that enables the user to indicate an amount of travel required to move the tool 20 to a desired plane. A desired plane may be a plane or a plane segment. The changes in pitch, roll, and translation are, for example, relative to the target plane TP.

In another configuration, the guidance array 200, using the one or more visual indicators 201, 202, 203 may be located and their states controlled to visually indicate to the user desired changes in movement (e.g. amount of travel) to change pitch, roll, and translation of the hand-held portion 16 and by extension, desired changes in pitch, roll, and translation of the base coordinate system BCS to achieve a desired pose. More specifically, the instrument controller 28 is configured to illuminate the guidance array 200 or display screen in a manner that enables the user to distinguish between a desired change in pitch orientation, a desired change in roll orientation, and a desired change in translation. The instrument controller 28 is configured to illuminate the guidance array 200 in a manner that enables the user to indicate an amount of travel required to move the hand-held portion 16 so that the tool 20 is on a desired plane or target trajectory. The changes in pitch, roll, and translation are, for example, relative to target plane TP.

The instrument controller 28 may switch operation of the guidance array 200 and/or visual indicators 201, 202, 203 (or display screen) from a mode where the guidance array/ visual indicators indicate desired changes in movement of the tool 20 to indicate desired changes in movement of the hand-held portion 16 based on an input signal, such as activation of an input device (e.g. footswitch, trigger, mouse click or touch screen press on navigation UI 38, etc.). Alternatively, the instrument controller 28 may be configured to switch between these modes based on the position of the tool 20 and the position of a reference location of bone in a known coordinate system, such as trackers 54, 56. A reference location may be a point, surface, or volume in the coordinate system used to locate the instrument 14 relative a target state, such as a target object. In one particular implementation, the reference location is a planned entry 71*a* of the bone. For example, the reference location may be a surface of a bone, a point within a bone, an imaginary or virtual point within the known coordinate system, a volume in the coordinate system, or a combination thereof. The position and/or orientation of the reference location is known with respect to the patient tracker through registration and suitable planning steps. The instrument controller 28 may switch modes/operate differently based on a distance parameter computed between two objects, such as a distance between the tool and a reference location. A distance parameter may be a distance (e.g., how far apart two objects are), magnitude (the direction of the distance relative to one object), or both. In some examples, the instrument controller 28 may switch modes when the distance parameter has a direction away from bone and a magnitude greater than a first threshold value.

Controls Overview

Figure 11:
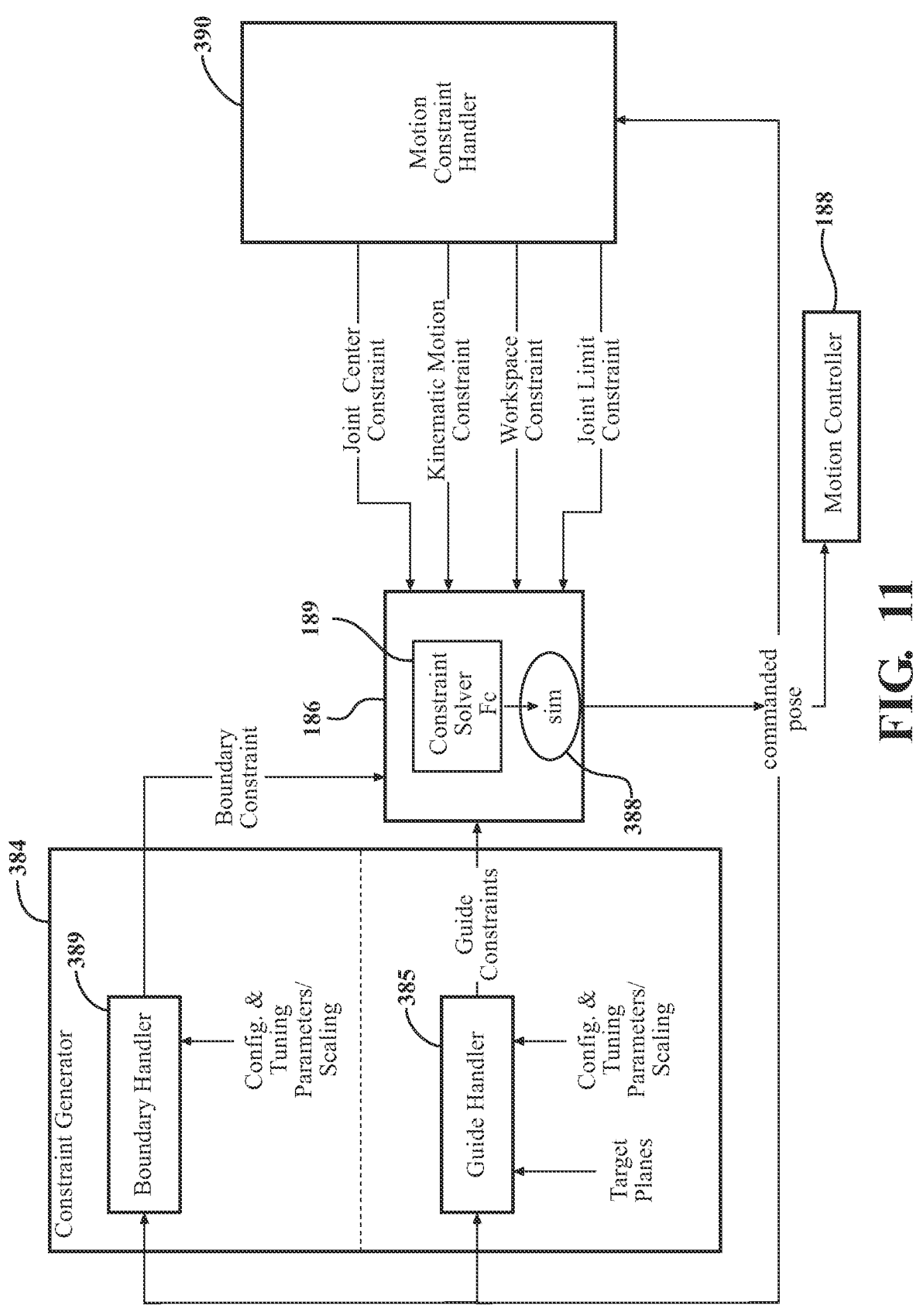
FIG. 11 is a block diagram of particular modules operable by the control system.
Figure 12:
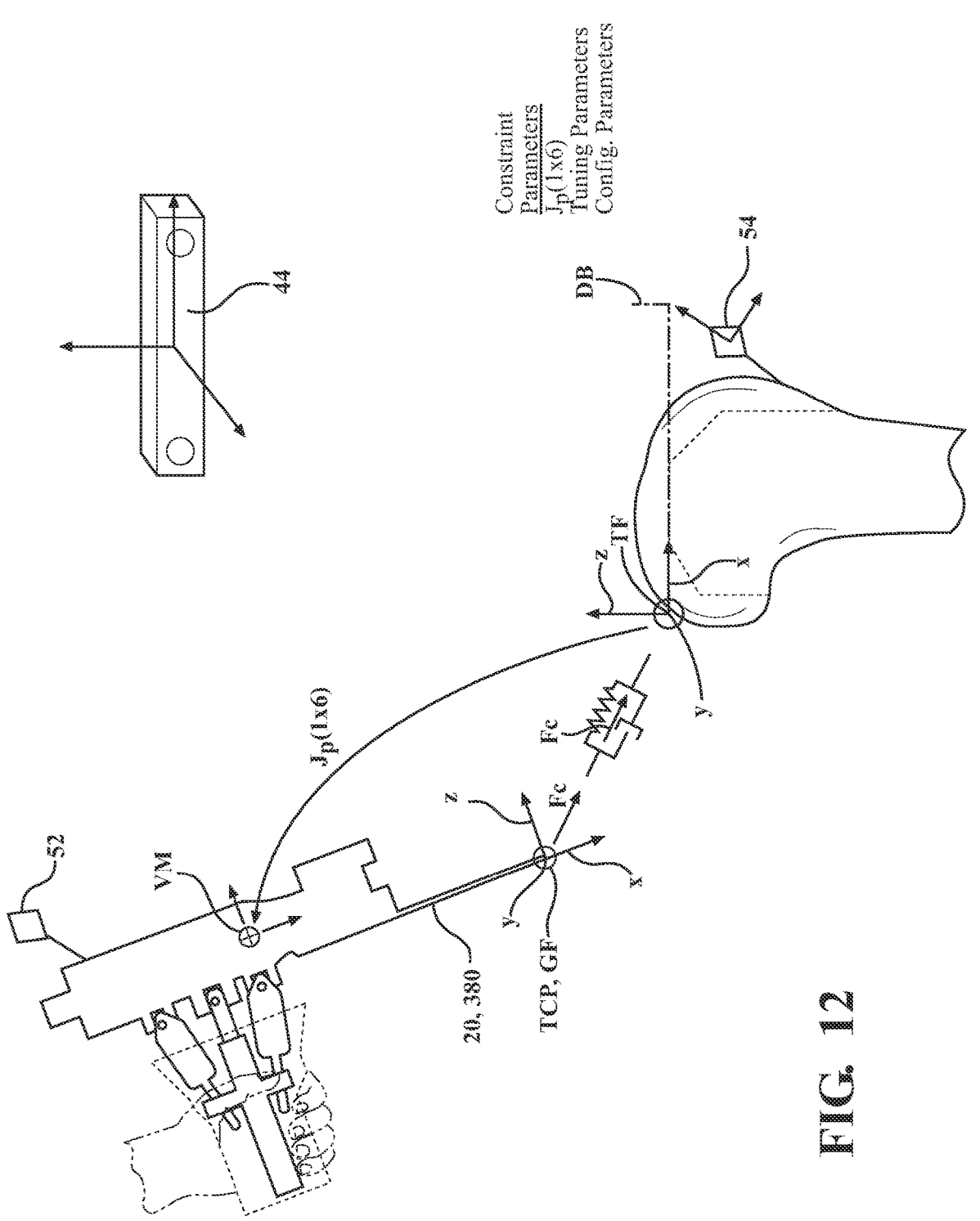
FIG. 12 is an illustration of guide constraints and virtual forces.

Referring to FIGS. 7 and 11, a behavior controller 186 and a motion controller 188 may be run on the instrument controller 28 and/or the navigation controller 36. The control system 60 computes data that indicates the appropriate instruction for the plurality of actuators. In one implementation, the behavior controller 186 functions to output the next commanded position and/or orientation (e.g., pose) for the tool relative to the hand-held portion. During operation, the tool 20 is effectively moved toward the target state using the plurality of actuators. These effects may be generated in one or more degrees of freedom to move the tool 20 toward the target state. Thus, the target state may be defined such that the tool 20 is being moved in only one degree of freedom, or may be defined such that the tool 20 is being moved in more than one degree of freedom. Accordingly, the target state may comprise a target position, target orientation, or both, defined as a target coordinate system TF (also referred to as a target frame TF). The target coordinate system TF may be defined with respect to the coordinate system of an anatomy tracker or target bone(s), however, other coordinate systems may be used. As shown in FIG. 12, the target position may comprise one or more position components with respect to x, y, and/or z axes of the target coordinate system TF with respect to a reference coordinate system, such as the anatomy tracker or bone, e.g., a target x position, a target y position, and/or a target z position. In some cases, the target position is represented as the origin of the target coordinate system TF with respect to a reference coordinate system, such as the anatomy tracker or bone. The target orientation may comprise one or more orientation components with respect to the x, y, and/or z axes of the target coordinate system TF with respect to a reference coordinate system, such as the anatomy tracker or bone, e.g., a target x orientation, a target y orientation, and/or a target z orientation. In some cases, the target orientation is represented as the orientation of the x, y, and z axes of the target coordinate system TF with respect to a reference coordinate system, such as the anatomy tracker or bone. Target pose means a combination of the one or more position components and the one or more orientation components. In some cases, the target pose may comprise a target position and target orientation in less than all six degrees of freedom of the target coordinate system TF. For example, in one specific configuration, the target pose may be defined by a single position component and two orientation components. In some cases, the target position and/or target orientation may also be referred to as starting position and/or starting orientation. In another configuration, the target pose may be defined as an axis anchored relative to the known coordinate system Referring to FIG. 11, the target state is an input to the behavior controller 186. The target state may be a target position, target orientation, or both where the tool 20 is adjusted to a target plane or target trajectory. In some cases, only the position of the TCP is output from the behavior controller 186, while in other cases, the position and orientation of the tool 20 is output. In some examples, the commanded pose output of the behavior controller 186 may include position, orientation, or both. In some examples, output from a boundary generator 182 and one or more sensors, such as an optional force/torque sensor S, may feed as inputs into the behavior control 186 to determine the next commanded position and/or orientation for the tool relative to the hand-held portion. The behavior controller 186 may process these inputs, along with one or more virtual constraints described further below, to determine the commanded pose.

The motion controller 188 performs motion control of the plurality of actuators. One aspect of motion control is the control of the tool support 18 relative to the hand-held portion 16. The motion controller 188 receives data from the behavior controller 186, such as data that defines the next commanded pose. Based on these data, the motion controller 188 determines a commanded joint position of each of the plurality of actuators coupled to the tool support 18 (e.g., via inverse kinematics) so that the tool 20 is positioned at the commanded pose output by the behavior controller. In other words, the motion controller 188 processes the commanded pose, which may be defined in Cartesian space, into commanded joint positions of the plurality of actuators coupled to the tool support 18, so that the instrument controller 28 can command the actuators 21, 22, 23 accordingly, to move the tool support 18 to commanded joint positions corresponding to the commanded pose of the tool relative to the hand-held portion. In one version, the motion controller 188 regulates the joint positions of the plurality of actuators and continually adjusts the torque that each actuator 21, 22, 23 outputs to, as closely as possible, ensure that the actuators 21, 22, 23 lead the instrument to assume the commanded pose. Alternately, and/or additionally, the motion controller 188 can output the commanded joint positions to a separate set of motor controllers (e.g., one for each actuator 21, 22, 23), which handle the joint-level position control. In some examples, the motion controller 188 (or motor controllers) may use feed-forward control to improve the dynamic tracking and transient response. In such a case, in addition to commanded joint positions, the motion controller 188 may also compute feed-forward joint velocities (or rather commanded joint velocities) and potentially feed-forward joint torques (and/or motor currents). This data is then used within the control loop of the motor controllers to more optimally drive the actuators 21, 22, 23.

It should be appreciated that while position control is described in detail, similar control implementations may be used with joint angle control. Furthermore, the motion controller may use joint angle control and joint position control. In some examples, joint angle may interchanged with joint position. Depending on the joint type, actuator type, or both on the instrument, joint angle, joint position, or both may be used. For example, the motion controller may determine a commanded joint angle based on the commanded pose for one or more actuators.

Referring to FIG. 7, the software employed by the control system 60, and run on the instrument controller 28 and/or the navigation controller 36 may include a boundary generator 182. The boundary generator 182 is a software program or module that generates a virtual boundary 184 for constraining movement and/or operation of the tool 20. The virtual boundary 184 may be one-dimensional, two-dimensional, three-dimensional, and may comprise a point, line, axis, trajectory, plane, or other shapes, including complex geometric shapes. The virtual boundary could also be a plane or line defined perpendicular to a planned trajectory. In some embodiments, the virtual boundary 184 is a surface defined by a triangle mesh. The virtual boundaries 184 may also be referred to as virtual objects. The virtual boundaries 184 may be defined with respect to an anatomical model AM, such as a 3-D bone model, in an implant coordinate system. The anatomical model AM is associated with the real patient anatomy by virtue of the anatomical model AM being mapped to the patient's anatomy via registration or other process.

The virtual boundaries 184 may be represented by pixels, point clouds, voxels, triangulated meshes, other 2D or 3D models, combinations thereof, and the like. U.S. Patent Publication No. 2018/0333207 and U.S. Pat. No. 8,898,043 are incorporated by reference, and any of their features may be used to facilitate planning or execution of the surgical procedure. One example of a system and method for generating the virtual boundaries 184 is described in U.S. Pat. No. 9,119,655, entitled, "Surgical Manipulator Capable of Controlling a Surgical Instrument in Multiple Modes," the disclosure of which is hereby incorporated by reference. In some examples, the virtual boundaries 184 may be generated offline rather than on the instrument controller 28 or navigation controller 36. Thereafter, the virtual boundaries 184 may be utilized at runtime by the instrument controller 28.

The anatomical model AM and associated virtual boundaries 184 are registered to the one or more patient trackers 54, 56. Thus, the anatomical model AM (and associated real patient anatomy) and the virtual boundaries 184 fixed to the anatomical model AM can be tracked by the patient trackers 54, 56. The virtual boundaries 184 may be implant-specific, e.g., defined based on a size, shape, volume, etc. of an implant and/or patient-specific, e.g., defined based on the patient's anatomy. The implant-specific virtual boundaries may have a particular size boundary, e.g., a 1:1 implant specific boundary to the specific implant used. In other cases the boundary may be larger or smaller than the actual dimension of the implant (e.g. 2:1, 1:2, etc.). The implant-specific boundary for the particular implant may be arbitrarily shaped. In some examples, the implant-specific boundary may be offset past the implant size by a fixed or configured amount. The virtual boundaries 184 may be boundaries that are created pre-operatively, intra-operatively, or combinations thereof. In other words, the virtual boundaries 184 may be defined before the surgical procedure begins, during the surgical procedure (including during tissue removal), or combinations thereof. In any case, the control system 60 obtains the virtual boundaries 184 by storing/retrieving the virtual boundaries 184 in/from memory, obtaining the virtual boundaries 184 from memory, creating the virtual boundaries 184 pre-operatively, creating the virtual boundaries 184 intra-operatively, or the like. In other words, one or more virtual boundaries may be obtained from the planned pose of the implant, and planned size, shape, volume, etc. of the implant. The implant coordinate system and the anatomical model coordinate system may be considered interchangeable throughout this description.

Figure 13:
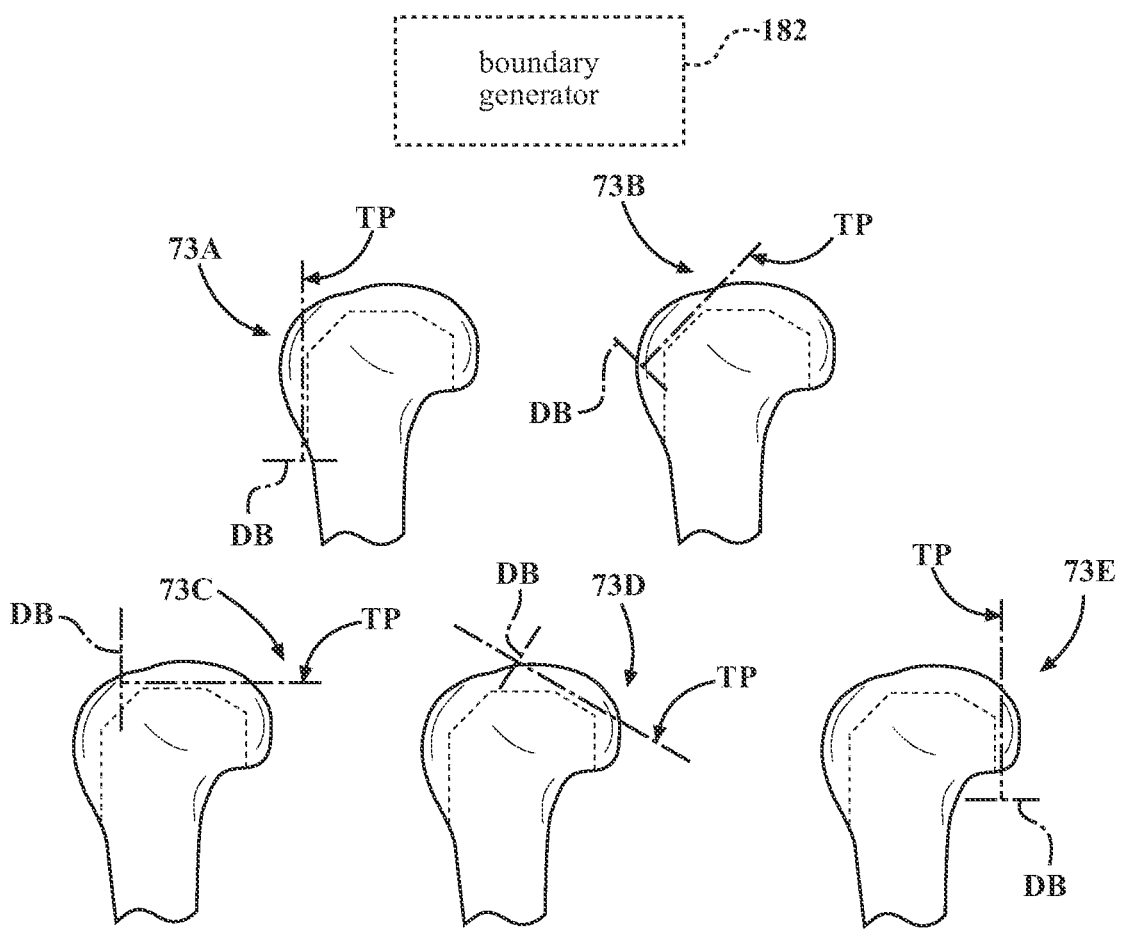
FIG. 13 illustrates output of a boundary generator for a surgical procedure on a femur.

The virtual boundaries 184 may be used in various ways. For example, the control system 60 may: control certain movements of the tool 20 to stay inside the boundary; control certain movements of the tool 20 to stay outside the boundary; control certain movements of the tool 20 to stay on the boundary (e.g., stay on a point, trajectory, and/or plane); control certain operations/functions of the instrument 14 based on a relationship of the instrument 14 to the boundary (e.g., spatial, velocity, etc.), and/or control energization to the drive motor M of the instrument 14. Other uses of the boundaries 184 are also contemplated. With reference to FIG. 13, in one potential implementation, the virtual boundary 184 may comprise a generally planar mesh located distally of the cut, a distal boundary DB. This virtual boundary 184 may be associated with the 3-D bone model. This virtual boundary may be used to control the saw drive motor M. In other examples, the boundary generator 182 provides virtual boundaries 184 for purposes of controlling the plurality of actuators. In this example, the virtual boundaries may be used for generating constraints that affect the movement of the virtual mass and virtual saw blade/tool in the virtual simulation. In such an implementation, the virtual boundaries may establish a virtual cutting guide (e.g., a virtual saw cutting guide). Virtual boundaries 184 may also be provided to delineate various operational/control regions as described below for either control of the saw driver motor or for control of the plurality of actuators. The virtual boundaries 184 may be one-dimensional (1D), two-dimensional (2D), three-dimensional (3D), and may comprise a point, line, axis, trajectory, plane (an infinite plane or plane segment bounded by the anatomy or other boundary), volume or other shapes, including complex geometric shapes.

Figure 14:
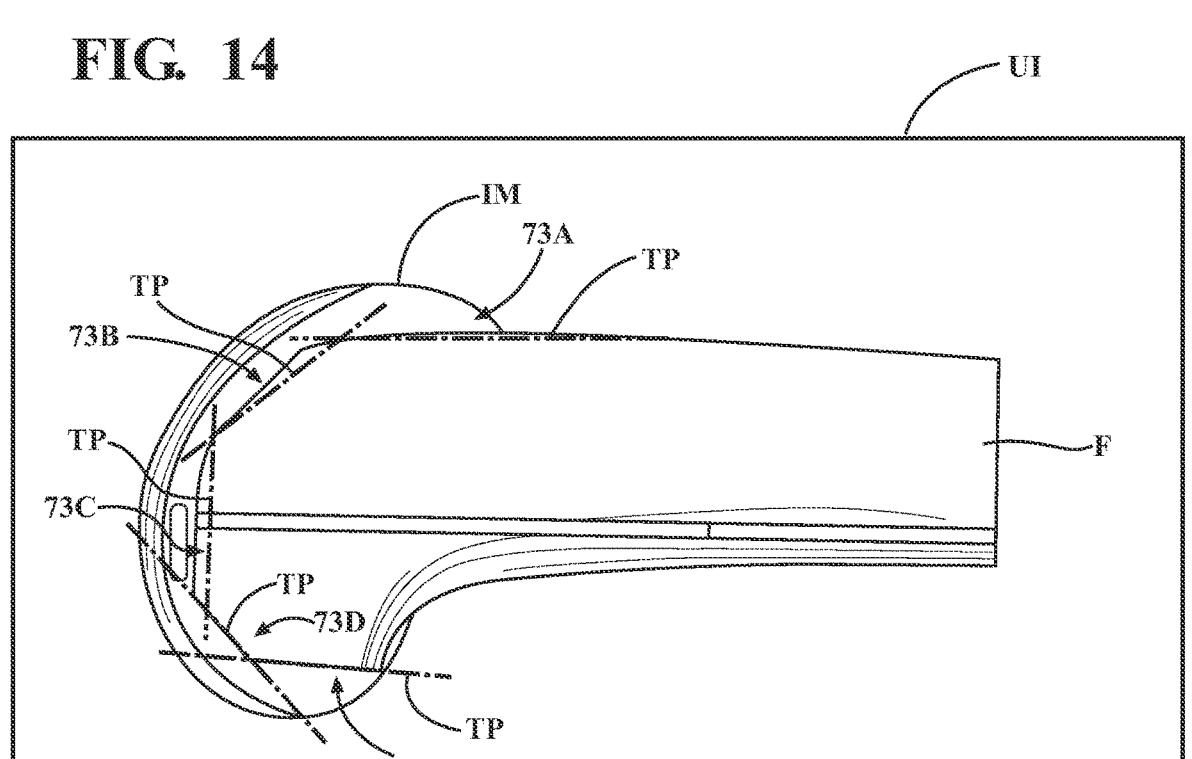
FIG. 14 illustrates the virtual boundaries based on the planned surgical implant.

Referring to FIGS. 10 and 14, the pose of the implant (WI) may be planned relative to the femur F in the implant coordinate system. This planned pose of the implant may be then defined relative to the one of the patient trackers 54, 56 through various navigation transforms, and the pose of the implant may be the basis of planned virtual objects, such as the target plane (TP), or the virtual boundaries. The target plane may be a representation of what cut(s) need to be made relative to bone to achieve the planned implant pose. In other words, the target plane (TP) may be aligned with the plane where the planned implant intends to contact bone. In some examples, the location of the target planes (TP) may need to be adjusted to account for the thickness of the saw blade. In one example, at the distal tip of the saw blade, the TCP coordinate system may be placed at a point half the thickness of the saw blade at the saw blade's center. The location of the cutting plane may be adjusted by the saw blade's half-thickness in a direction based on which side of the saw blade is against the bone during a particular cut. By cutting along the target plane, the resulting bone that will be removed from the femur will allow for the planned implant to seat on the bone properly. The target plane TP may take the form of a target state as will be described below. Alternatively, the target plane TP may be generated as a form of the virtual boundary that may be used to control the plurality of actuators.

The control system 60 will ultimately function to keep the tool 20 on the desired cutting plane in some versions. The virtual boundary 184 that may be used control the plurality of actuators may also be a volumetric boundary, such as one having a thickness equal to and/or slightly larger than a blade thickness to constrain a saw blade to stay within the boundary and on the desired cutting plane. Therefore, the desired cutting plane can be defined by a virtual planar boundary, a virtual volumetric boundary, or other forms of virtual boundary. In some examples, the cutting slot in the virtual boundary 184 needs to be offset to account for the saw blade thickness, so that a slot boundary (corresponding to the side of the saw blade which contacts bone for that cut) is aligned with the final desired implant-bone surface, and the other boundary is offset by the full blade thickness. In another example, a slightly larger thickness is used for the slot boundary, causing the vertical centerline of the cutting slot to be offset by the saw blade half thickness. Virtual boundaries 184 may also be referred to as virtual objects. The virtual boundaries 184 may be defined with respect to an anatomical model AM in an implant coordinate system, such as a 3D bone model (see FIG. 10, which illustrates the anatomical model AM being virtually overlaid on the actual femur F due to their registration). In other words, the points, lines, axes, trajectories, planes, volumes, and the like, that are associated with the virtual boundaries 184 may be defined in a coordinate system that is fixed relative to a coordinate system of the anatomical model AM such that tracking of the anatomical model AM (e.g., via tracking the associated anatomy to which it is registered) also enables tracking of the virtual boundary 184.

The anatomical model AM is registered to the first patient tracker 54 such that the virtual boundaries 184 become associated with the anatomical model AM and associated coordinate system. The virtual boundaries 184 may be implant-specific, e.g., defined based on a size, shape, volume, etc. of an implant and/or patient-specific, e.g., defined based on the patient's anatomy. The implant-specific boundaries may be larger or smaller than the physical dimensions of the implant. The virtual boundaries 184 may be boundaries that are created pre-operatively, intra-operatively, or combinations thereof. In other words, the virtual boundaries 184 may be defined before the surgical procedure begins, during the surgical procedure (including during tissue removal), or combinations thereof. The virtual boundaries 184 may be provided in numerous ways, such as by the control system 60 creating them, receiving them from other sources/systems, or the like. The virtual boundaries 184 may be stored in memory for retrieval and/or updating.

In some cases, such as when preparing the femur F for receiving the total knee implant IM (see FIG. 1), the virtual boundaries 184 comprise multiple planar boundaries that can be used to delineate multiple cutting planes (e.g., five cutting planes) for the total knee implant IM, and are associated with a 3D model of the distal end of the femur F and/or a cutting plane based on the 3D model of the tibia. These multiple virtual boundaries 184 and/or target planes can be activated, one at a time, by the control system 60 to control the plurality of actuators to cut one plane at a time. Each of these cutting planes may be a target plane for the control system. Example virtual boundaries 184 is shown in FIG. 13, for illustrative purposes. While FIG. 13 shows that the target planes are aligned with the implant boundaries, it should be appreciated that this is a schematic representation, and the target planes may be slightly offset from the planned implant boundaries. Other shapes and arrangements are possible. FIG. 13 illustrates a series of cuts with the desired target plane of each. Each of the distal ends of the femurs show an entry portion that provides access to the femur. The entry portion continues into a cutting slot defined along one of the five target cutting planes TP, 73*a*-73*e*. In other cases, the virtual boundaries may be a planned trajectory for insertion of a rotary tool into bone, such as for insertion of a drill bit or tap, into bone, such as into a femur or vertebra. Again, the multiple virtual trajectories may be active one at a time to control the plurality of actuators to drill one trajectory at a time.

Figure 15:
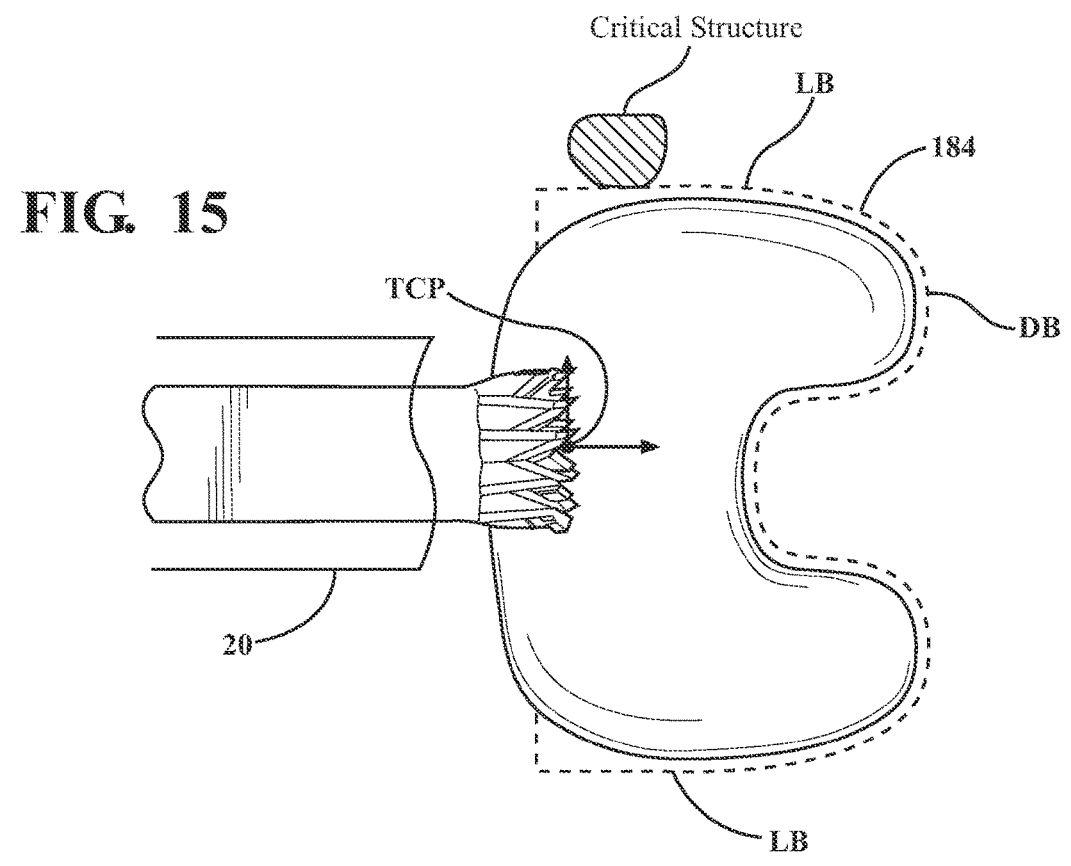
FIG. 15 is a top down view of a saw blade and a portion of patient anatomy relative to certain virtual boundaries.

In cases wherein the virtual boundaries are used to control the saw drive motor (or other drive motor) and referring to FIGS. 13 and 15, the virtual boundaries 184 may represent boundaries that can be used delineate in-plane cutting depths or widths for the saw (DB, LB) or tool when preparing a knee for receiving a total knee implant or other surgical procedure. The in-plane cutting depths or widths for the saw (DB, LV) may be features of a 3D boundary model rather than distinct boundaries. Those distal boundaries DB may be generally perpendicular to the target cutting plane or target trajectory, and may be optionally contoured to the patient's anatomical features (distal face of the femur, ligaments, arteries, soft tissue, etc.). This may avoid inadvertent cutting of a critical structure. The virtual boundaries 184 used to control the drive motor may include one or more lateral boundaries (LB). These lateral boundaries (LB) may serve to prevent cutting beyond a target depth in a lateral direction. In some examples, the cutting slot defined by the depth boundaries and lateral boundaries in the 3D boundary may be used for a secondary error mitigation feature, such as to turn off the drive motor M if the saw blade does not sufficiently stay on plane (in the case of sudden fast motion of the instrument and/or bone or as a mitigation against another system malfunction) or tool does not stay on the trajectory. The boundaries for controlling the saw drive motor may be selectively activated based on the selected target plane. Similarly, the boundaries for control the tool drive motor may be activated based on the selected target axes.

In some cases, the virtual boundaries that delineate cutting depths may be based on a pose of a planned virtual object, such as a fixed boundary offset, such as 5 mm plane offset and perpendicular to each planned cut plane (TP) or target trajectory. Referring again to FIG. 13, where the 5 TPs are aligned with each plane where the planned implant is intended to contact bone, the distal boundaries DB are implemented as perpendicular to the TP for each cut, and offset a predetermined distance from the distal end of plane where the planned implant will contact bone. In some versions, the control system 60 evaluates whether the saw blade will violate the depth boundary DB by more than a threshold amount, and may command the instrument controller 28 to cease operation of the drive motor M. In some examples, the instrument controller 28 may not cease operation of the drive motor M, but rely on user-controlled starting, stopping, and/or speed control of the drive motor M.

In some cases, the instrument controller 28 controls a motor parameter of the drive motor M at a first value and a second value, such that the first value is different than the second value and the instrument controller 28 may change operation from the first value to the second value based on the position of the tool 20 and the position of a reference location associated with bone, such as the virtual boundary, or based on a computed distance parameter.

As the tool 20 proceeds into a cut or hole of the bone, the instrument controller 28, using navigation data of the tool 20 relative to the reference location or based on the pose of the tool associated with the bone, may allow activation of the drive motor M. Further, the instrument controller 28 may turn off the drive motor M based on whether the tool 20 has reached a certain pose, distance parameter value or position relating to the reference point or boundary associated with the bone. In some cases, the user may find difficulty in perceiving the depth of the tool 20 within the bone while performing the surgical procedure because of limited line of sight due to soft tissue, unremoved bone, and other surgical apparatuses used in the procedure. The user may also have difficultly perceiving the depth of the tool 20 because of adjacent anatomy applying pressure onto the saw blade 20 or tool. By controlling the drive motor M based on the pose or position of the tool 20, the user may be able to control with more accuracy the depth of the cut.

In some examples, when the instrument controller 28 changes the operating mode by changing a parameter of the drive motor M, the instrument 14, the input device, the navigation system 32, the instrument controller 28, or a combination thereof may provide an audible indication, a tactile indication, or both that the mode has been changed. In one instance, the input device may be a footswitch, and when the mode of the instrument is changed, controlling the speed of the drive motor M, the footswitch may vibrate. In another example, when the mode and/or control behavior is changed speeding up or slowing down the drive motor M, a user may perceive an audible indication such as the motor speed of the drive motor M changing volume, pitch, vibration, or a combination thereof, indicating that the mode and/or control behavior of the instrument has changed.

As described above, the instrument controller 28 and/or the navigation controller 36 track the state of the tool 20, such as the position and/or orientation of the saw blade relative to the virtual boundaries 184. In one example, it can be described as monitoring the state of the TCP is measured relative to the virtual boundaries 184 for purposes of controlling the tool drive motor M. In other words, the control system may control the saw drive motor M based on the state of the TCP measured relative to the virtual boundaries 184, such as slowing down or stopping the saw drive motor M when any aspect of the instrument virtual model VM violates the virtual boundary 184 by more than a threshold amount. In some examples, the pose of the tool (TCP coordinate system) may be utilized to evaluate whether any aspects of the tool 20 would violate the virtual boundary 184 by more than a threshold amount. The instrument controller 28 may have a model of the blade (e.g., a CAD model or a simplified model using geometric primitives) that may be evaluated for violations of the virtual boundary 184. In some examples, the extents of the tool 20 may be modeled with an array of discrete spheres, placed around the periphery of a swept volute of the tip of the tool 20, with the diameters of the spheres matching the thickness of the tool 20, the locations defined with respect to the TCP coordinate system. Further, the virtual boundary 184 may be an open-ended surface or a closed surface. When the virtual boundary 184 is configured as a closed surface, the virtual boundary 184 may function as a "keep out" boundary where the instrument 14 may be actuated "outside" of the virtual boundary but shut off after crossing the virtual boundary by a threshold amount. Similarly, the closed surface virtual boundary may function as a "keep in" boundary, where the instrument 14 may only operate within the virtual boundary 184, shutting off the instrument 14 when the instrument "leaves" the virtual boundary 184 by more than a threshold amount.

In another example, the state of the TCP is measured relative to the virtual boundaries 184 for purposes of determining forces to be applied to a virtual rigid body model via a virtual simulation so that the tool 20 remains in a desired positional relationship to the virtual boundaries 184 (e.g., not moved beyond them). The results of the virtual simulation are processed when controlling the plurality of actuators coupled to the tool support 18. The boundary generator 182 may be implemented on the instrument controller 28. Alternatively, the boundary generator 182 may be implemented on other components, such as the navigation controller 36.

The boundary generator 182, the behavior controller 186 and motion controller 188 may be sub-sets of a software program 378. Alternatively, each may be software programs that operate separately and/or independently in any combination thereof. The term "software program" is used herein to describe the computer-executable instructions that are configured to carry out the various capabilities of the technical solutions described. For simplicity, the term "software program" is intended to encompass, at least, any one or more of the boundary generator 182, behavior controller 186, and/or motion controller 188. The software program 378 can be implemented on the instrument controller 28, navigation controller 36, or both, or may be implemented in any suitable manner by the control system 60.

A clinical application 190 may be provided to handle user interaction. The clinical application 190 handles many aspects of user interaction and coordinates the surgical workflow, including pre-operative planning, implant placement, registration, bone preparation visualization, and post-operative evaluation of implant fit, etc. The clinical application 190 is configured to output to the displays 38. The clinical application 190 may run on its own separate processor or may run alongside the navigation controller 36. In one example, the clinical application 190 interfaces with the boundary generator 182 after implant placement is set by the user, and then sends the virtual boundary 184 and/or tool plane TP returned by the boundary generator 182 to the instrument controller 28 for execution. The instrument controller 28 executes the target plane TP or target trajectory as described herein. The instrument controller 28 may also process the virtual boundaries 184 to generate corresponding virtual constraints as described further below.

Figure 16:
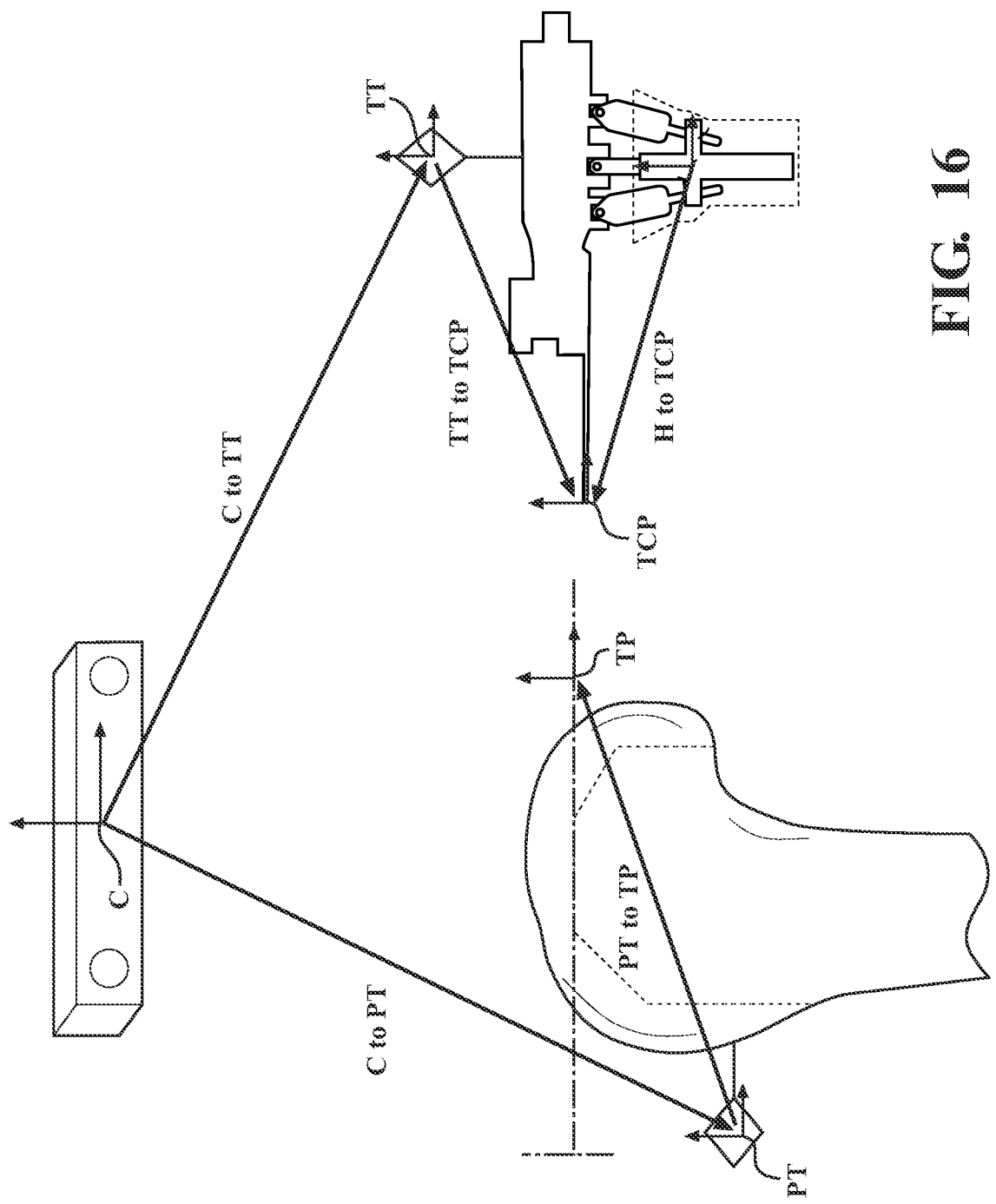
FIG. 16 illustrates a portion of the navigation system relative to the patient anatomy and a surgical robotic instrument, and the potential transform calculations.

Turning to FIG. 16, the exemplary control is described with respect to the various transforms. The TCP is located by tracking the tool 20 with the tool tracker 52 (TT) with respect to the localizer coordinate system LCLZ (LCLZ-TT transform), and determining a transform between tool tracker 52 and the TCP of the tool 20 (TT-TCP transform), such as the saw blade, using registration data or calibration data. Similarly, the patient is tracked using the patient tracker (shown as 54), resulting in the transform from the localizer coordinate system LCLZ to the patient tracker coordinate system (LCLZ-PT transform).

As described with respect to FIG. 11, through a bone registration process, a transform from bone to the patient tracker 54, 56 is established (bone to patient tracker). Through the implant planning process, a bone to implant/ anatomical model transform is determined (bone to IM transform). Then, a patient tracker 54 to planned implant (patient tracker to IM) transform is computed. The planned implant (IM) may be related to the target plane (IM to TP transform), given the locations of the planar sections of the chosen implant component and size, or may be related to a target trajectory (see FIG. 32, described further below). Referring again to FIG. 16, a transform is then computed between the patient tracker 54, 56 and each planned virtual object, such as each target plane (PT-TP transform), or such as each target trajectory (PT—trajectory transform) using the combination of registration data and planning information.

The position and/or orientation of the tool support 18, and therefore TCP, may be related to the tool tracker 52 (tool support to tool tracker transform, computed via registration or calibration process). As described above, in some implementations, a transform between the hand-held portion 16 and the TCP (BCS-TCP) is computed based on the positions of each actuator. The transform between BCS and TCP is utilized to relate the various coordinate systems back to the hand-held portion 16, since the commanded pose may be determined relative to the BCS for certain control implementations. Conceptually, the commanded pose, is an update to the BCS to TCP transform which results in the TCP being aligned with the planned virtual object (the target plane TP) in this example. As an alternative, the pose of the hand-held portion 16 may be determined directly in some instances by using a hand-held portion tracker 53 coupled directly to the hand-held portion 16. This may eliminate the need to utilize the TCP coordinate system and perform a transform between BCS and TCP based on the positions of each actuators.

An initial pose of the TCP with respect to the base coordinate system BCS can be determined based on a known geometric relationship between the tool support and the hand-held portion 16 when the actuators 21, 22, 23 are at their home position/center point or other predetermined position. Additionally, and/or alternately, the initial pose may be "seeded" into the virtual simulation by measuring the initial pose using the encoders and computing forward kinematics to get a measured pose of the TCP with respect to BCS, using that pose to initialize the virtual simulation. This relationship changes when the actuators 21, 22, 23 are adjusted and the associated changes can be determined based on the kinematics of the robotic system 10 (e.g., which establishes a dynamic transformation between these coordinate systems). Thus, the robotic system 10 knows the pose of the tool 20, such as in the home position and its relation to the pose of the hand-held portion 16. Accordingly, when the tool 20 is moved by the user and its pose is tracked using the tool tracker 52, the robotic system 10 also tracks the pose of the hand-held portion 16 and its base coordinate system BCS. In some examples, as a result of prior calibration processes, the position of the tool 20 relative to the tool support 18 is assumed to be known. After the home position/center point and maximum travel of each of the actuators 21, 22, 23 is established, control is based on the position and/or orientation data from the navigation controller 36 and the measured position data of the actuator(s). The home position could also be computed in other manners.

Since both the patient tracker 54, 56 and the tool tracker 52 are each reported by the localizer 44 with respect to the localizer coordinate system LCLZ, providing LCLZ-to-PT and LCLZ-to-TT, these transforms may be processed together to determine a transformation between the tool tracker 52 and the patient tracker 54, 56 (TT-to-PT). From there, a base coordinate system to patient tracker (BCS-to-PT) transformation can be calculated by the control system 60, computing the location of the patient tracker 54, 56 with respect to the hand-held portion 16. Since the target plane TP with respect to the patient tracker 54, 56 is known, the control system 60 may calculate a base coordinate system BCS to target plane TP (BCS-to-TP) transformation, resulting in the pose of the target plane in the coordinate system of the hand-held portion 16 (BCS). In one example, the BCS-to-TP may be used directly to compute the commanded pose BCS-to-TCP which puts the TCP on the target cutting plane TP, which may then be commanded to the actuators 21, 22, 23 to move the tool 20 to the desired pose. In some examples, the BCS-to-TCP calculation may be used to generate constraints to attract the TCP to TP within a virtual simulation VM. While the target plane transforms are described throughout, it should be appreciated that transforms related to the target trajectory in lieu of the target plane are contemplated herein as well.

In some examples, digital filters may be applied to the input data received from the localizer directly to the input data received from the forward kinematics (e.g., motion controller 188 directly), or to any intermediate combination of the previously described transforms. In some examples, a moving average filter may be used, although other digital filtering techniques may be applicable.

The instrument controller 28 may control the one or more actuators 21, 22, 23 by sending command signals to each actuator 21, 22, 23 to adjust the tool 20 towards a target state in at least one degree of freedom. The instrument controller 28 may send command signals to each actuator 21, 22, 23 to move the actuators 21, 22, 23 from a first set of positions to a set of commanded positions which will place the tool 20 into the target state. In some examples, the commanded position may be determined by the instrument controller 28 in conjunction with the navigation system 32 based on the pose of hand-held portion 16 and a target state in a known coordinate system (i.e. defined relative to the patient tracker 54, 56), such as the pose of the virtual object (target cut plane or target trajectory), and send a signal to the actuators 21, 22, 23 to adjust to the commanded position.

The second software module is a motion controller 188. One function of the motion controller 188 is the control of the instrument 14. The motion controller 188 may receive data defining the target state of the saw blade 20, 380, such as the next commanded pose from the behavior controller 186. Based on these data, the motion controller 188 determines the next commanded joint position of the rotors 148 of each actuator 21, 22, 23 (e.g., via inverse kinematics) so that the instrument 14 is able to position the tool 20 as commanded by the behavior control 186, e.g., controlling instrument to the commanded pose. In other words, the motion controller 188 processes the commanded pose, which may be defined in Cartesian space, into actuator positions (such as commanded joint positions) of the instrument 14, so that the instrument controller 28 can command the motors 142 accordingly, to move the actuators 21, 22, 23 of the instrument 14 to commanded positions, such as commanded joint positions corresponding to the commanded pose. In one version, the motion controller 188 regulates the joint position of each motor 142 and continually adjusts the torque that each motor 142 outputs to, as closely as possible, ensure that the motor 142 drives the associated actuator 21, 22, 23 to the commanded joint position. In another version, the instrument controller regulates the joint position of each motor 142 and continually adjusts the torque that each motor 142 outputs to, as closely as possible, ensure that the motor 142 drives the associated actuator 21, 22, 23 to the commanded joint position The instrument controller 28 may know the entire length that an actuator 21, 22, 23 may adjust the tool support 18 relative to the hand-held portion 16. In some examples, the instrument controller 28 knows the entire length which an actuator 21, 22, 23 is capable of adjusting and may send command signals to the actuators 21, 22, 23 to move a measured distance from position to position (e.g., by commanding a desired amount of linear travel via commanded rotation). A measured position may be a known position, or a distance between the present location of an actuator 21, 22, 23 and the actuator limits. Each position that the actuator 21, 22, 23 moves to may be a measured distance from a positive limit and a negative limit of actuator travel (i.e., a position between two ends of a lead screw). The instrument controller 28 may command the actuators 21, 22, 23 to and from positions as described below. The instrument controller may command the actuator 21, 22, 23 to a position in order to reach the desired adjustment of the tool 20. The instrument controller 28 may control the actuators 21, 22, 23 to linearly move a calculated distance to adjust the tool 20 towards a desired pose. In other examples, such as when absolute encoders are used, the instrument controller may send signals to the actuators 21, 22, 23 to place each actuator 21, 22, 23 into a commanded position based on the known location of the actuator 21, 22, 23 between the respective actuator travel limits determined by the absolute encoder. Alternately, in one example, an incremental encoder may be used in conjunction with a homing procedure performed during system setup as described in U.S. Patent Publication No. 2017/0156799, which is hereby incorporated by reference. A homing procedure may be used, placing the actuators 21, 22, 23 and the joints at their centered position, and subsequently determines the absolute offsets of the incremental encoders. By determining the offsets of the incremental encoders, the incremental encoders may perform as absolute encoders going forward.

In some versions, the instrument controller 28, for each actuator 21, 22, 23, determines the difference between a commanded position and a measured position of the actuator. The instrument controller 28 outputs a target current (proportional to a torque of the actuator), changing the voltage to adjust the current at the actuator from an initial current to the target current. The target current effectuates a movement of the actuators 21, 22, 23, moving each actuator 21, 22, 23 towards the commanded joint position, and, as a result, moving the instrument towards the commanded pose. This may occur after the commanded pose is converted to joint positions. In one example, the measured position of each joint may be derived from the sensors S described above, such as an encoder.

Throughout this description, unless otherwise noted, any instance of pose may be a current commanded pose, a current measured pose, a past measured pose, or a past commanded pose. While each of these poses may be different from one another, due to the frequency of control cycles, the difference in position and/or orientation between these poses may be minimal in each control iteration. Furthermore, any instance of position may be a current commanded position, a current measured position, a past measured position, or a past commanded position.

Different control methodologies may be used to control the plurality of actuators to place the tool at a desired location, such as target plane or target trajectory, including but not limited to impedance control, admittance control, position control, or a hybrid control using multiple different control implementations. While an admittance control implementation is described in detail, it should be appreciated that other methodologies may be used. In an admittance control mode, the control system accepts force input (virtual or measured) and commands position (or motion) output. For example, for admittance control, the system models a force and/or torque at a particular location on a virtual mass and acts to modify the pose of the virtual mass to achieve the desired target state of the tool. In an impedance control mode, the control system accepts position (or motion) input and commands a force or torque output. For example, the impedance control system measures, senses, and/or calculates a position (i.e., position, orientation, velocity, and/or acceleration) of the instrument and may apply an appropriate corresponding torque to each of the actuators to achieve the desired target state of the tool. Position control may also be used to control the plurality of actuators towards implementing certain behaviors. It should be appreciated that changes to both the behavior controller and the motion controller would be needed implement these control schemes.

In some versions, once treatment begins, the instrument controller 28 may mitigate the effects of the user's ability to place the tool 20 away from the desired pose (e.g., outside or off of the virtual boundary 184 or planned virtual object (TP)). For example, in some implementations, as soon as the navigation system 32 provides an indication that the tool 20 is moving off the desired cutting plane or away from the bone by a predetermined distance/orientation, the instrument controller 28 immediately terminates the application of energization signals to the drive motor M, preventing the tool 20 from gouging the bone, and minimizing soft tissue damage. In other examples, the drive motor M may be slowed down or stopped using motor braking, for example, as described in U.S. Pat. No. 7,998,157 entitled "Surgical tool system with a powered handpiece and a console, the console able to provide energization signals to the handpiece in either a motor drive mode or a direct drive mode" which is hereby incorporated by reference. In some implementations of this feature, the acceptable misalignment of the tool 20 with the desired pose may vary as the depth of the resection increases.

The boundary generator 182, behavior controller 186, and motion controller 188 may be sub-sets of a software program. Alternatively, each may be software programs that operate separately and/or independently in any combination thereof. The term "software program" is used herein to describe the computer-executable instructions that are configured to carry out the various capabilities of the technical solutions described.

Referring now to FIG. 12, the target coordinate system TF can be any coordinate system whose origin and axes define the target state, and the target state can be specified with respect to any other coordinate system desired for monitoring the state of the tool 20 relative to the target state of the tool 20. The target state can be tracked in a patient tracker coordinate system (e.g., the coordinate system of the patient tracker 54, 56), the localizer coordinate system LCLZ, the base coordinate system BCS, a virtual mass coordinate system VM, the TCP coordinate system, or the like. The target state may be initially defined with respect to the implant coordinate system (IM) for the patient and may be fixed with respect to the patient's anatomy and fixed relative to the one or more patient trackers. For purposes of this disclosure, the target state may include the desired pose of the saw blade.

The current state of the tool 20 may be defined by a guided coordinate system GF (also referred to as a guided frame GF). The guided coordinate system GF may be tied to another coordinate system, or the current state may be transformed to any other coordinate system to enable tracking of the current state relative to the target state. The current state can be tracked in a tracker coordinate system (e.g., the tool tracker coordinate system (TT), the localizer coordinate system LCLZ, the base coordinate system BCS, the virtual mass coordinate system VM, the TCP coordinate system, or the like. In some of the versions described herein, the current state of the tool 20 is initially defined by the TCP coordinate system (e.g., the TCP coordinate system and the guided coordinate system GF are shown as being the same for ease of illustration). Both the guided coordinate system GF and the target coordinate system TF can be transformed to a common coordinate system for tracking purposes. The target state may be defined pre-operatively, intraoperatively, or both.

As described above, to control the plurality of actuators, a commanded pose is often set. This commanded pose may be a desired relationship between the BCS and the TCP, i.e., a desired relationship between the tool support and the hand-held portion. The commanded pose is determined based on the pose of the hand-held portion 16 in a known coordinate system and a target state in the same coordinated system (e.g. the coordinate system associated with the patient tracker 54, 56), such as a pose of a planned virtual object, e.g., a target pose of the saw blade deduced from the pose of the planned implant. The commanded pose may result in the tool 20 being on the desired plane or aligned with the planned virtual object, such as a planned trajectory. As mentioned above, the instrument controller 28 may convert the commanded pose to a commanded position for each of the plurality of actuators using inverse kinematics, then send command instructions to the actuators 21, 22, 23 to move to a commanded position, thereby changing the relative poses of the tool support 18 and tool 20.

Figure 32:
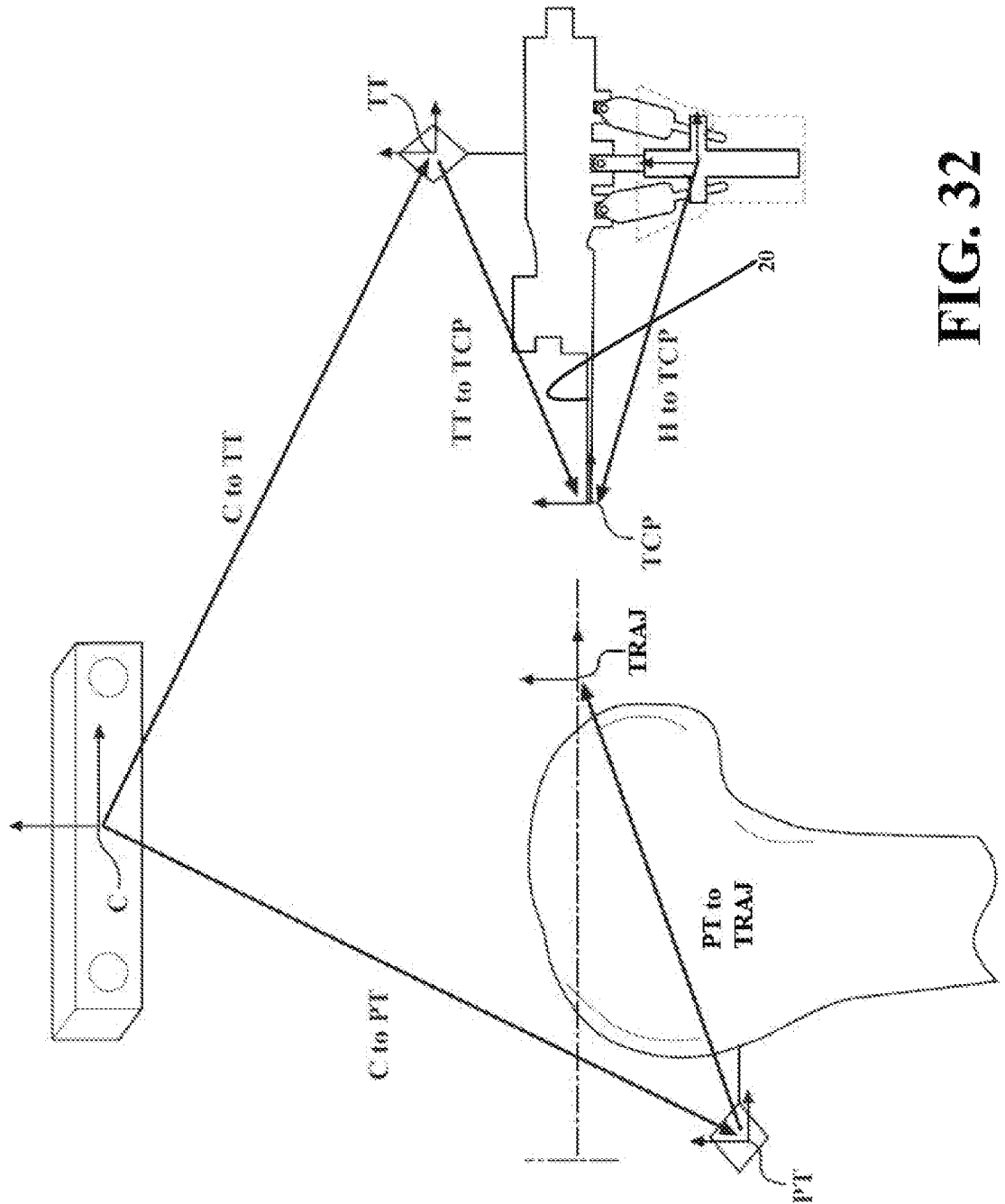
FIG. 32 is another example of a portion of the navigation system relative to the patient anatomy and a surgical robotic instrument, and the potential transform calculations related to a target trajectory.

It is contemplated that the control system 60 may be configured to control other types of instruments and actuator assembly arrangements, such as drills, burs, probes, guides, the like, or a combination thereof. For example, the present teachings may be implemented to control the instrument described in U.S. Pat. No. 9,707,043, entitled "Surgical instrument including housing, a cutting accessory that extends from the housing and actuators that establish the position of the cutting accessory relative to the housing" which is incorporated by reference. For example, as shown in FIG. 32, an alternative example of the instrument is shown with tool 20 as a drill or a bur. The exemplary control is described with respect to the various transforms. The TCP is located by tracking the tool 20 with the tool tracker 52 (TT) with respect to the localizer coordinate system LCLZ (LCLZ-TT transform), and determining a transform between tool tracker 52 and the TCP of the tool 20 (TT-TCP transform), such as the drill/bur, using registration data or calibration data. Similarly, the patient is tracked using the patient tracker (shown as 54), resulting in the transform from the localizer coordinate system LCLZ to the patient tracker coordinate system (LCLZ-PT transform).

As described with respect to FIG. 11, through a bone registration process, a transform from bone to the patient tracker 54, 56 is established (bone to patient tracker). Through the implant planning process, a bone to implant/anatomical model transform is determined (bone to IM transform). Then, a patient tracker 54 to planned implant (patient tracker to IM) transform is computed. The planned implant (IM) may be related to the target trajectory (IM to Trajectory transform), given the locations of the chosen implant component. Referring again to FIG. 32, a transform is then computed between the patient tracker 54, 56 and each planned virtual object, such as each target trajectory (PT-TTRAJ transform), using the combination of registration data and planning information.

The position and/or orientation of the tool support 18, and therefore TCP, may be related to the tool tracker 52 (tool support to tool tracker transform, computed via registration or calibration process). As described above, in some implementations, a transform between the hand-held portion 16 and the TCP (BCS-TCP) is computed based on the positions of each actuator. The transform between BCS and TCP is utilized to relate the various coordinate systems back to the hand-held portion 16, since the commanded pose may be determined relative to the BCS for certain control implementations. Conceptually, the commanded pose, is an update to the BCS to TCP transform which results in the TCP being aligned with the planned virtual object (the target trajectory TTRAJ) in this example. As an alternative, the pose of the hand-held portion 16 may be determined directly in some instances by using a hand-held portion tracker 53 coupled directly to the hand-held portion 16. This may eliminate the need to utilize the TCP coordinate system and perform a transform between BCS and TCP based on the positions of each actuators.

An initial pose of the TCP with respect to the base coordinate system BCS can be determined based on a known geometric relationship between the tool support and the hand-held portion 16 when the actuators 21, 22, 23 are at their home position/center point or other predetermined position. Additionally, and/or alternately, the initial pose may be "seeded" into the virtual simulation by measuring the initial pose using the encoders and computing forward kinematics to get a measured pose of the TCP with respect to BCS, using that pose to initialize the virtual simulation. This relationship changes when the actuators 21, 22, 23 are adjusted and the associated changes can be determined based on the kinematics of the robotic system 10 (e.g., which establishes a dynamic transformation between these coordinate systems). Thus, the robotic system 10 knows the pose of the tool 20, such as in the home position and its relation to the pose of the hand-held portion 16. Accordingly, when the tool 20 is moved by the user and its pose is tracked using the tool tracker 52, the robotic system 10 also determines the pose of the hand-held portion 16 and its base coordinate system BCS. In some examples, as a result of prior calibration processes, the position of the tool 20 relative to the tool support 18 is assumed to be known. After the home position/center point and maximum travel of each of the actuators 21, 22, 23 is established, control is based on the position and/or orientation data from the navigation controller 36 and the measured position data of the actuator(s).

Since both the patient tracker 54, 56 and the tool tracker 52 are each reported by the localizer 44 with respect to the localizer coordinate system LCLZ, providing LCLZ-to-PT and LCLZ-to-TT, these transforms may be processed together to determine a transformation between the tool tracker 52 and the patient tracker 54, 56 (TT-to-PT). From there, a base coordinate system to patient tracker (BCS-to-PT) transformation can be calculated by the control system 60, computing the location of the patient tracker 54, 56 with respect to the hand-held portion 16. Since the target trajectory TTRAJ with respect to the patient tracker 54, 56 is known, the control system 60 may calculate a base coordinate system BCS to target trajectory TTRAJ (BCS-to-TTRAJ) transformation, resulting in the pose of the target trajectory in the coordinate system of the hand-held portion 16 (BCS). In one example, the BCS-to-TTRAJ may be used directly to compute the commanded pose BCS-to-TCP which puts the TCP on the target trajectory TTRAJ, which may then be commanded to the actuators 21, 22, 23 to move the tool 20 to the desired pose. In some examples, the BCS-to-TCP calculation may be used to generate constraints to attract the TCP to TTRAJ within a virtual simulation VM.

The instrument controller 28 may control the one or more actuators 21, 22, 23 by sending command signals to each actuator 21, 22, 23 to adjust the tool 20 towards a target state in at least one degree of freedom. The instrument controller 28 may send command signals to each actuator 21, 22, 23 to move the actuators 21, 22, 23 from a first set of positions to a set of commanded positions which will place the tool 20 into the target state, aligning the tool 20 with the target trajectory. In some examples, the commanded position may be determined by the instrument controller 28 in conjunction with the navigation system 32 based on the pose of hand-held portion 16 and a target state in a known coordinate system (i.e. defined relative to the patient tracker 54, 56), such as the pose of the virtual object (target trajectory), and send a signal to the actuators 21, 22, 23 to adjust to the commanded position.

Virtual Constraints

In some implementations, the control system uses one or more virtual constraints to compute the commanded pose. Generally, virtual constraints are restrictions and/or enhancements on the motion of rigid bodies in certain directions that are considered by the control system 60, along with other motion-related information, as part of a virtual simulation. Each virtual constraint may be considered to act along a particular direction, called the direction of the constraint. These one-direction constraints can be combined to produce multi-degree-of-freedom constraints that may, for example, work to align or repel two coordinate systems from each other in the virtual simulation. A virtual constraint can both restrict motion or enhance motion in a certain direction. A constraint 'restricts' the motion not in a directional sense (attract/repel) but rather than it doesn't allow free (unconstrained) motion but influences it in a certain way based on the relative motion or pose of two tracked objects/coordinate systems in the virtual simulation. The active virtual constraints are all added into a constraint solver where the constraint solver determines a set of parameters which account for each virtual constraint and compute a force. This resulting force may be represented as a 6-DOF force/torque vector which represents a balance or equilibrium of the various virtual constraints, each acting along potentially separate constraint directions. It should be noted in the present teachings that the term "force" is used, it may refer to a generalized force/torque vector, in which components of linear force and/or rotational torques are specified in one or more degrees of freedom. For example, "force" may refer to a single force in a single direction, a single torque about a single axis, or any combination thereof, e.g., a 6-DOF force/torque vector in a given coordinate system defining a force consisting of x, y, and z components and a moment consisting of torque components about an x, y, and z axis.

In some examples, each virtual constraint does not have an equal force, and, depending on the location of the rigid bodies being acted upon by the virtual constraint, may be adjusted so that the virtual constraint is flexible. For example, depending on the location of the instrument 14 relative to the patient anatomy and the target cutting plane or target trajectory, the virtual constraint may be adjusted so that the virtual constraint is flexible. The virtual constraints are not infinitely rigid, but instead each of the virtual constraints has tuning parameters to adjust the stiffness of the virtual constraints, e.g., by incorporating spring and damping parameters into the virtual constraints. Such parameters may include a constraint force mixing parameter (C) and an error reduction parameter (E). The virtual force may then be applied to a virtual rigid body (representing the tool 20 or blade support 18) in the virtual simulation. The 6-DOF forward dynamics computation is performed to determine the resulting motion of the virtual rigid body. The simulation is conducted over a time-step and the result is utilized as the commanded pose.

The values of the tuning parameters may be greater (e.g., stiffer) for position constraints than for orientation constraints, or vice versa. Thus, the computation of the virtual constraints leads to direct control of the motion parameter of the tool support moving relative to the hand-held portion. The tuning parameters can be determined as described, for example, in PCT Application No. PCT/US2020/053548, entitled "Systems and Methods For Guiding Movement Of A Tool," filed on Sep. 30, 2020, which is hereby incorporated herein by reference.

The states of the virtual constraints may be controlled during operation of the instrument. For example, the states of the virtual constraints may change based on a relationship between a first state and a second state (e.g. the current state and the target state of the tool). For example, the state may be configured as a function of a distance parameter between a position of the tool and a position of the reference location such that the state varies during use. In another example, the state may be configured as a function of an angle parameter between a position of the tool and a position of the reference location such that the state caries during use. The state of each virtual constraint may be an active state, an inactive state, including a first value for a tuning parameter, and/or including a second value for a tuning parameter. In some examples, the value of the state may be defined by a look-up table. Thus, certain constraints may be activated and/deactivated based on the state of the tool.

In instances where the tool is a saw blade, the state of the saw blade relative to the target states of the saw blade for the plurality of cutting planes may include determining angles between a current orientation of the saw blade and a plurality of target orientations of the saw blade, determining distances between a current position of the saw blade and a plurality of target positions of the saw blade, or determining both the angles and the distances. Determining the current state of the saw blade relative to the target state of the saw blade may also include determining a location of a plane defined by the saw blade relative to a plurality of cutting planes in the known coordinate system. Thus, if the saw blade is positioned adjacent to a particular target cutting plane, the state of one or more virtual constraints may be altered and the control system may further be updated to update the target pose to reflect the chosen cutting plane. Similar techniques may be implemented for controlling the instrument when a rotary cutting tool is used to align with one or more target trajectories.

A virtual constraint may be activated when with a user input device, or when the robotic system 10 automatically activates the virtual constraints. Additionally, or alternatively, the user may be able to manually set the virtual constraints (e.g., change one or more parameters of the virtual constraints, activate/deactivate the virtual constraints, etc., via one or more of the user interfaces UI). The user may employ the clinical application 190 for this purpose. The virtual constraints may also be triggered when certain surgical steps are being performed, e.g., cutting a desired section of tissue, etc.), or when the robotic system 10 detects or otherwise recognizes certain conditions.

In one example, referring to FIG. 10, the states of the virtual constraints may be changed depending on which region the tool is located in relative to the planned cut or surgical site. These regions may be defined by a virtual object 184 (see spherical object depicted) in one or more known coordinate systems.

In one example of changing the states of the virtual constraints, the spring and damping parameters may be adjusted during operation. In some versions, values for the tuning parameters may change based on a relationship between the current state and the target state of the tool. For example, the tuning parameters may be configured to increase in stiffness the closer the tool 20 gets to the target state, or the tuning parameters may decrease in stiffness as the tool 20 approaches the target state. The tuning parameters may be different for different constraints. For example, the virtual constraints may comprise a first virtual constraint that has a first value for a tuning parameter and a second virtual constraint that has a second value for the tuning parameter, the first value being greater than the second value so that the resulting virtual forces and/or torques embodied in the constraint force Fc are adapted to move the tool more strongly as a result of the first virtual constraint as compared the second virtual constraint. The values of the tuning parameters may be greater (e.g., stiffer) for position constraints than for orientation constraints, or vice versa.

Figures 18, 19, 20:
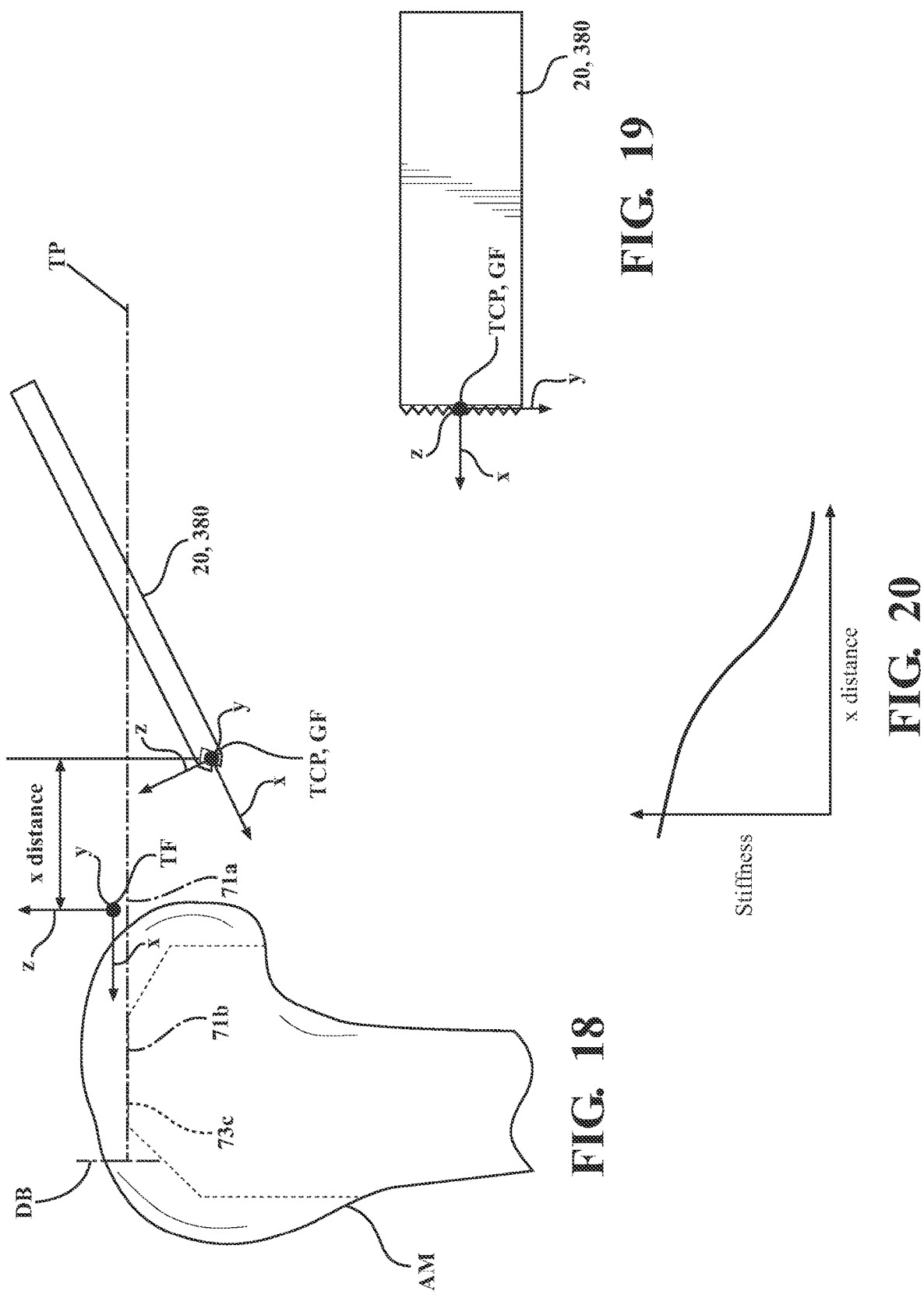
FIGS. 18 and 19 illustrate another application of guide constraints to attract the tool to a target plane.
FIG. 20 illustrates how stiffness of the guide constraint may vary with the distance.

The tuning parameters may also be set to: remain constant regardless of the distance/angle from the current state of the tool to the target state of the tool; rise/fall exponentially with distance; vary linearly with distance between the current state and the target state; vary with constraint direction; vary as a function of time; take gravitational effects into account; or combinations thereof. Referring to FIGS. 18-20, a tuning parameter for one constraint associated with one degree of freedom may be set based on a relationship associated with another degree of freedom, e.g., the stiffness of an y-axis constraint may change based on the distance along the x-axis between the current state and the target state. The tuning parameters may also vary depending on the direction in which the tool 20 needs to move to reach the target state, e.g., more stiff when moving in one direction along the x-axis versus the opposite direction along the x-axis. The tuning parameters can also be scaled depending on the constraint force Fc that is ultimately computed based on the virtual constraints, such as by increasing/decreasing the stiffness depending on the magnitude of the constraint force Fc, or any components thereof. Fixed values for one or more virtual forces could also be added into the virtual simulation in some cases. The tuning parameters for the virtual constraints may be: set preoperatively; set intraoperatively; updated intraoperatively; and combinations thereof. The tuning parameters and their values, their correlation to a particular relationship, and the manner in which they may be scaled, may be stored in one or more look-up tables in any suitable memory in the control system 60 for later retrieval.

Changing the stiffness of one or more tuning parameters of one or more constraints as a function of time and distance may provide advantageous actuator behavior in response to one or more events. For example, in the event of a line of sight of to a tracker being temporarily interrupted, by slowly increasing the stiffness once the tracker comes back into line of sight of the camera, this can minimize abrupt and intense actuator movements in the user's hand, which can be distracting for the user. Instead, once the tracker of the instrument comes back into line of sight, the stiffness can be slowly increased. This control of the tuning parameters based on a function of time and distance may also be useful when the hand-held instrument transitions between different control regions, as described below. As described above, the one or more virtual constraints may be activated automatically. Additionally, or alternatively, the user may be able to manually set the virtual constraints (e.g., change one or more parameters of the virtual constraints, activate/deactivate the virtual constraints, etc., via one or more of the user interfaces UI). The user may employ the clinical application 190 for this purpose. The virtual constraints may also be triggered when certain surgical steps are being performed, e.g., cutting a desired section of tissue, etc.), or when the robotic system 10 detects or otherwise recognizes certain conditions.

Each virtual constraint also has configuration settings. The configuration settings may comprise: information regarding the tuning parameters, such as the constraint force mixing parameter (C) and the error reduction parameter (E); upper and/or lower force limits; and/or upper and lower constraint distance offsets. The upper and lower force limits refer to limits on the forces computed for each virtual constraint that are ultimately solved by the constraint solver 189 to produce the constraint force Fc, as described further below. The virtual constraints may be two-sided constraints (e.g., the forces computed to satisfy the constraints can be positive or negative), and may apply attractive forces in either direction regardless of which side of the target coordinate system TF the guided coordinate system GF is located (in each degree of freedom). The force limits can be set high in positive and negative directions (e.g., −100,000/+100,000 Newtons) or at any desired limit. Alternately, a virtual constraint may be a one-sided constraint (e.g., the forces computed to satisfy the constraint can only act in one direction, i.e., can only either be positive or negative, depending on the direction configured by the force limits). Further, constraints may be configured to be "attractive," applying forces towards meeting the constraint criteria, or "repellant," applying forces away from meeting the constraint criteria. The upper and lower constraint distance offsets dictate when the constraint is active. With respect to the virtual constraints, the upper and lower constraint distance offsets can be set so that the constraint is active any time the current state is different than the target state.

If the control system receives a higher force associated with one or more of the virtual constraints, the higher force can lead to higher rates of acceleration for the rigid bodies being affected by the virtual constraints in the simulation. The output of the virtual simulation as the commanded pose of the tool, commanding the actuators 21, 22, 23 accordingly, causing the higher forces and higher acceleration seen in the virtual simulation to result in a higher acceleration of the tool support 18 relative to the hand-held portion 16. The higher force may be based on the value computed for that particular constraint, the values of the tuning parameters, or combinations thereof. For example, the virtual constraints may comprise a first virtual constraint that has a first value for a tuning parameter and a second virtual constraint that has a second value for the tuning parameter, the first value being greater than the second value so that the resulting virtual forces and/or torques embodied in the constraint force Fc are adapted to move the tool more strongly as a result of the first virtual constraint as compared the second virtual constraint.

FIGS. 11 and 17A-17E are control diagrams of processes carried out to execute computation of the commanded pose using the one or more virtual constraints. FIG. 11 is a simplified control diagram and FIGS. 17A-17E are more in-depth. In these versions, the behavior controller 186 may be connected with a constraint generator 384. The constraint generator 384 may include a boundary handler 389, which sends boundary constraints to the behavior controller 186, and a guide handler 385, which sends guide constraints to the behavior controller 186. The behavior controller 186 may include a constraint solver 189, and a virtual simulator 388. A motion constraint handler 390 sends joint center constraints, kinematic motion constraints, workspace constraints, and joint limit constraints to the behavior controller

186 to be added into the constraint solver 386 and virtual simulator 388. In some examples, the motion constraint handler 390 is part of the motion controller 188. The virtual simulator (indicated as sim in FIG. 11 and virtual forward dynamics in FIGS. 17A-E) may simulate the virtual dynamics on the tool 20 based on the constraint forces and potentially additional forces, including damping, inertial, and external sensed forces. The constraint generator 384, constraint solver 189, and virtual simulator 388, each comprise executable software stored in a non-transitory memory of any one or more of the aforementioned controllers and implemented by the control system 60. The constraint forces may be applied to a virtual mass coordinate system VM in which a virtual simulation is carried out on the virtual rigid body model of the tool 20 so that the forces and torques can be virtually applied to the virtual rigid body in the virtual simulation to ultimately determine how those forces and torques (among other inputs) would affect movement of the virtual rigid body, as described below. The virtual forces and torques that can be applied to the virtual rigid body in the virtual simulation are adapted to move the tool 20 toward the target state. The virtual forces and torques influence overall movement of the tool 20 towards the virtual object, i.e., a target state.

In one example, as shown in FIG. 11, the behavior controller 186 does not utilize an external force sensor input to the virtual simulation. The use of virtual-constraints based control provides for some advantageous outcomes, even in the absence of an external force sensor. The constraint system and modeling of virtual forces in a virtual simulation allows you to easily blend together constraints tied to different outcomes with ease. The constraint system also allows you to tune parameters for each constraint in an intuitive way. Furthermore, the use of velocity constraints provides for a higher responsiveness (e.g., higher stiffness) for a given sample rate given its improved numerical stability over other numerical integration or simulation methods. As described, however, the use of an external force sensor or other approximation for external force, such as current-based estimation of external force, may be used with the systems and methods described herein.

Guide Constraints

One type of virtual constraints are referred to herein as guide constraints. The guide constraints are defined to ultimately influence movement of the tool 20 toward the target state. The guide constraints, as described further below, have configurable spring and damping properties so that the guide constraints are not infinitely stiff. More specifically, in some versions, the guide constraints are defined as "soft constraints" such that they do not completely prevent motion that violates them, such as motion resulting from forces and torques applied by other constraints in opposite directions to the target state.

One or more guide constraints may be used by the control system 60 to guide the tool support 18, including up to three guide constraints associated with the target position and up to three guide constraints associated with the target orientation. As described in more detail below, the control system 60 operates to calculate the constraint force Fc that satisfies, or attempts to satisfy, the guide constraints (and other virtual constraints, if used). The constraint force Fc incorporates the virtual forces and torques therein to move the tool 20 to the target state. Each of the guide constraints are considered one-dimensional, virtual constraints. The control system may utilize a plurality of one-degree of freedom constraints to align a guided frame to a target frame. As noted previously, the guide constraints are "two-sided" constraints in that guide constraints may apply attractive forces in either direction regardless of which side of the target coordinate system TF the guided coordinate system GF is located (in each degree of freedom). In some versions, the guide constraints are velocity impulse constraints in which forces and/or torques are calculated to apply a virtual impulse to an object in the virtual simulation to cause a change in the object's velocity in accordance with desired constraint parameters. In some versions, the constraints are similar to those used in the impulse modeling described in U.S. Pat. No. 9,119,655, incorporated herein by reference.

In FIG. 12, guide constraints GC associated with a target pose in at least one degree of freedom is illustratively represented as being defined in the target coordinate system TF. The constraint force Fc that is ultimately calculated as a result of these guide constraints GC (and other active virtual constraints) is illustrated as comprising a force that incorporates virtual spring and damping properties that guides the TCP of the tool 20 to the target pose. The guide constraint may be based on the pose of the guided coordinate system GF (e.g., defined with respect to the virtual mass coordinate system VM) and the pose of the target coordinate system TF (e.g., defined with respect to the patient tracker(s)). The poses (in at least one degree of freedom) of the guided coordinate system GF and the target coordinate system TF are used to compute the current state of the saw blade and the target state of the saw blade, respectively, or the current state of the tool and the target state of the tool respectively.

Each guide constraint has a constraint direction defined along or about the x, y, or z axis of the target coordinate system. The constraint direction is the direction along which the constraint can effectively apply force. For the case of rotational constraints, the constraint direction is the axis about which the constraint can effectively apply torque. The constraint directions could also be defined in the guided coordinate system (GF), or the constraint directions could be defined using any known relationships to either the target coordinate system (TF) or the guided coordinate system (GF). In one example, 3 translational guide constraints and 3 rotational constraints may be used to fully align the position and orientation of the guided frame with the target frame. However, fewer than 3 translational constraints may be used, and fewer than three rotational constraints may be used.

In one example, the guide constraints are computed in three degrees of freedom—1 position and 2 orientations. The position guide constraint is defined in elevation, and the orientation constraints are defined in pitch and roll, which are used to align the saw blade to the target plane TP. The orientations are computed by comparing the orientation of the target pose (TF) and the guided frame on the saw blade. The roll (rotation about X-axis) and pitch (rotation about Y-axis) are used to define how much the saw blade needs to be rotated until the X-Y plane of the saw blade (the guided coordinate system) is parallel to the X-Y plane of the target pose (the target coordinate system). For this example, the three constraint directions would be along the z axis of TF (elevation), about the x axis of TF (roll), and about the y axis of TF (pitch). In another example for other virtual objects, 2 position guide constraints and 2 orientation guide constraints may be used.

Alternatively, any number of degrees of freedom could be used in the guided coordinate system to align the saw blade or other tool to the target pose. For example, a 1-DOF position—point on a plane, the 3-DOF position and orientation described above, the 4-DOF position and orientation, or a full 6-DOF pose, which would include guide constraints to align three positions and three orientations.

The guide constraints (and other virtual constraints, if used) are defined primarily by three runtime parameters: a constraint Jacobian Jp, which maps each one-dimensional, guide constraint to a coordinate system employed for the virtual simulation (e.g., between the target coordinate system TF and the virtual mass coordinate system VM); a desired velocity Vdes (or Vp2) which is a scalar velocity (linear or angular) of the guide constraint along or about the applicable constraint direction defined by the target coordinate system TF (e.g., the desired velocity may be zero when the patient is immobile and the associated target state defined relative to the patient is not moving, but may be other than zero when the patient moves since the target state may be tied to the patient); and a constraint distance Δd, which is how close the guided frame GF is to the target frame TF along or about the applicable constraint direction defined by TF and which dictates whether the constraint is being violated. In some cases, Δd refers to a distance/angle of the current state from the target state, and a guide constraint is violated any time the current state does not match the target state for the associated degree of freedom.

It should be appreciated that when other constraints are employed other than the guide constraint, the constraint solver is ultimately tasked with providing a solution for the constraint force Fc that satisfies, or attempts to satisfy, all the virtual constraints, and thus other constraints may influence the magnitude and/or direction of the constraint force.

Joint Centering Constraints

A joint centering constraint is another virtual constraint representing a virtual force and/or torque employed in the virtual simulation to influence the movement of the tool support 18 relative to a centering position for each actuator of the plurality of actuators. The joint centering constraint is used in implementing a particular restriction in the motion of tool support 18 relative to the hand-held portion that is considered by the control system 60 to maximize the amount of travel of the tool support 18 available relative to the hand-held portion 16. In one example, the particular restriction of motion to the tool 20 may be to have the joints return to their centered positions (or another joint position determined by the user, the control system 60, or both) when other constraints are not active. Alternatively, the joint centering constraint may facilitate positioning of the tool support 18 relative to the hand-held portion 16 for optimal balance for particular surgical procedures, such as for particular cuts in a total knee procedure or for particular trajectories in certain bone drilling procedures. The joint centering constraint, as described further below, may have configurable spring and damping properties so that the joint centering constraint is not infinitely stiff. More specifically, in some versions, the joint centering constraint is defined as a "soft constraint" such that the joint centering constraint does not completely prevent motion that violates it, such as motion resulting from forces and torques applied by other constraints in opposite directions.

The joint centering constraint may be used by the control system 60 to move the tool support 18. As described in more detail below, the control system 60 may operate to calculate the constraint force Fc that satisfies, or attempts to satisfy, the joint centering constraint. The constraint force Fc incorporates the virtual forces and torques therein to move the tool support 18 towards the centering position. The joint centering constraint is considered as a one-dimensional, virtual constraint. In some versions, the joint centering constraint is a velocity impulse constraint in which forces and/or torques are calculated to apply a virtual impulse to an object in the virtual simulation to cause a change in the object's velocity in accordance with desired constraint parameters. It should be appreciated that when other constraints are employed other than the joint centering constraint, the constraint solver is ultimately tasked with providing a solution for the constraint force Fc that satisfies, or attempts to satisfy, all the virtual constraints, and thus other constraints may influence the magnitude and/or direction of the constraint force.

Figure 21:
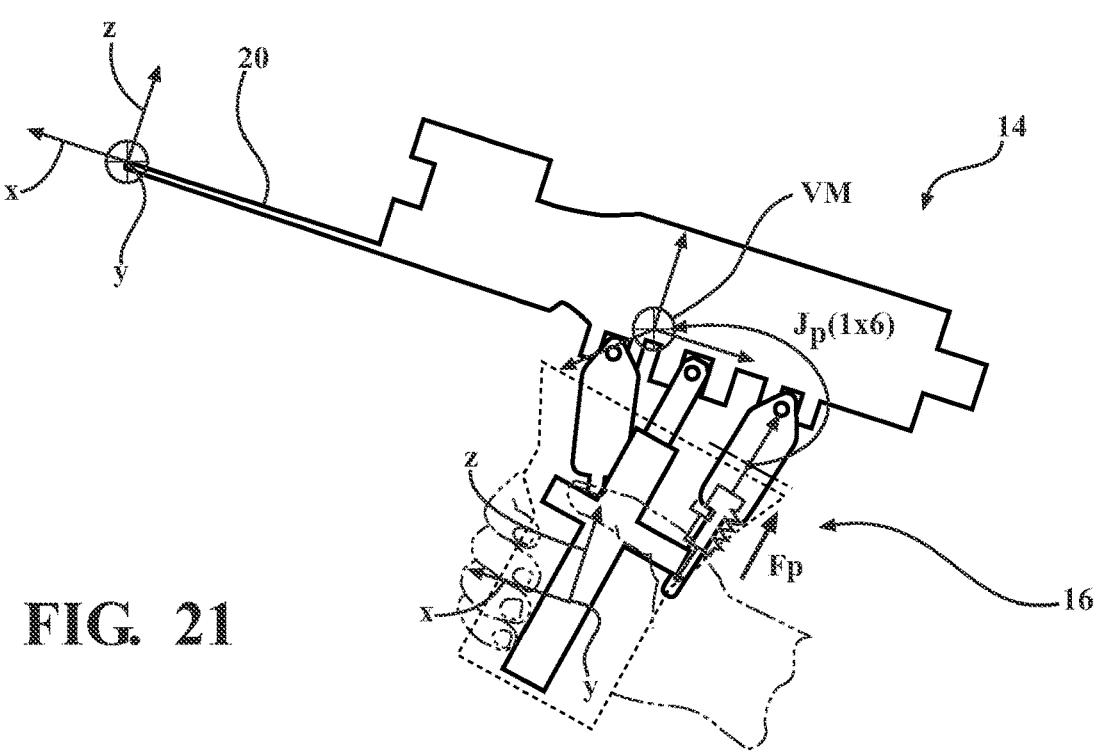
FIG. 21 shows an illustration of a joint centering constraint and associated virtual forces.

In FIG. 21, the joint centering constraint is illustratively represented in the joint space of the respective actuators, (along the translation axis of the actuator 21, 22, 23). The constraint direction for a joint centering constraint is along the translation axis of that actuator 21, 22, 23, and therefore may only apply linear force along that direction. The constraint force that is calculated as a result of each jointing centering constraint is illustrated as comprising a linear force that incorporates spring and damping properties which acts along the translation axis of corresponding actuator that guides the actuator position to the centering position. It should be appreciated that the joint centering constraint may defined in other coordinate systems as well. It should be appreciated also that all or fewer than all of the actuators in the instrument may utilize joint centering constraints.

The joint centering constraint is defined primarily by three runtime parameters: a constraint Jacobian Jp, which maps the one-dimensional joint centering constraint to a coordinate system employed for the virtual simulation (e.g., between the motion of the joint and the virtual mass coordinate system VM); a previous commanded joint position, which is a position commanded used to control each actuator in a previous control iteration; and a joint centering position, which is a configured joint position to which it is desired for the actuator to return to when no other constraints are active. It should be appreciated that the current measured position of the actuators may also be used for the joint centering constraint. The previous commanded position may provide for less lag in control and improved stability. The joint centering constraint may be two-sided and always pulling the joint to the centering position when active.

The joint centering position may be the location at which each of the rotors 148 have a relatively high amount of travel along their respective leadscrews. In other words, the joint centering position may be considered the 'home' or 'idle' position of each of the actuators as described above. By setting the joint centering position to the home position, a median position for the rotor along the leadscrew, for each actuator, the tool support may achieve maximum range of motion. Alternatively, the joint centering position may be set to a position other than the home position for one or more of the plurality of actuators. This may be considered a secondary joint centering position. The secondary joint centering position may be different for each of the actuators 21, 22, 23. It should be understood that the when the actuator is located at the secondary joint centering position, the one or more actuators 21, 22, 23 may only capable of a fraction of the travel in one direction that the same actuator may have had when the joint centering position was the home position. In one example, a first joint centering position is the 'home position' and a second joint centering position is a position other than the home position. Without being particularly limited, when the actuator is in the secondary joint centering position, the actuator may have less than 50 percent, less than 40 percent, or less than 30 percent of the range of motion in a particular direction than that same actuator would have had when set in the joint centering position equivalent to home. However, for certain surgical procedures or for certain users, it may be helpful to bias a joint centering position away from the actuator's median position in order to provide more travel in a certain (potentially challenging) direction, to improve ergonomics or to account for how the instrument is held. It should be appreciated that each actuator may have a multitude of different joint centering positions, or presets for preferred balance arrangements. Groups of joint centering positions may be aggregated together (sets of joint centering positions for all of the actuators) which correspond to preferred grips/balance scenarios. These centering positions may be selectable by a user using one or more user input devices.

When each actuator 21, 22, 23 is at the first joint centering position (the home position), the amount of adjustability of the actuators 21, 22, 23 is typically symmetrically maximized to make it easier for the user to keep the tool 20 at a desired pose, i.e., the joint centering position is typically set to the median position or 'home' position of the actuator. Various levels of adjustment are possible depending on the particular geometry and configuration of the instrument 14. In some examples, when all the actuators 21, 22, 23 are in their first joint centering positions, the tool 20 may be adjusted in pitch orientation about +/−18° relative to the joint center position, assuming zero changes in the roll orientation and no z-axis translation. In some examples, when all the actuators 21, 22, 23 are in their centering positions, the tool 20 may be adjusted in roll orientation about +/−33° relative to the centering position, assuming zero changes in the pitch orientation and no z-axis translation. In some examples, when all the actuators 21, 22, 23 are in their first joint centering positions, the tool 20 may be adjusted in z-axis translation about +/−0.37 inches relative to the first joint centering position, assuming zero changes in the pitch orientation and roll orientation. The tool 20, of course, may be adjusted in pitch, roll, and z-axis translation simultaneously, sequentially, or combinations thereof during operation.

The joint centering constraint may be used to 'freeze' the one or more actuators into a free-hand mode at the position of the one or more actuators to prevent unnecessary actuation and movement, preventing the actuators from generating excessive heat from movement, such as when the instrument 14 is a substantial distance away from the target bone. The free-hand mode may be useful to perform some types of treatment, such as cutting the patella or other portions of the anatomy. When the actuators 21, 22, 23 are frozen from further movement in the free-hand mode, then the instrument 14 behaves much like a conventional cutting instrument, without any movement of the tool support 18 relative to the hand-held portion 16. The virtual boundaries 184 may also be deactivated in the free-hand mode. The free-hand mode may be engaged by any suitable input device of any suitable user interface (e.g., push-button, foot switch, etc.). In some versions, the user may select this tool behavior (i.e., activate the joint centering constraint with a particular joint centering position and/or change the joint centering position) by actuating an input device, and selecting the free-hand mode where the instrument controller 28 commands a tool pose to be held or frozen in position. In some examples, to freeze the tool 20 at a particular pose, the instrument controller 28 may enable the joint centering constraints and set centering positions for each actuator 21, 22, 23 to the joint positions which correspond to the desired tool pose (e.g., by performing inverse kinematics on the desired tool pose to get the corresponding joint positions). Alternately, in another example, the joint centering positions may be left at or reset to zero (i.e., a home position). Further, the joint centering positions may be set to the current positions of the actuators, as determined using encoders or other actuator position feedback, at the time the mode is requested by the user. As described above, the joint centering position is adjustable. The secondary joint centering position may be set using a user input device, or may be set automatically.

The instrument controller 28 may automatically control a state of the joint centering constraint or behavior. For example, the state of the joint centering constraint may be controlled based on a state of the tool and the target state. Alternatively, the state of the joint centering constraint may be controlled based on the position of the tool 20 and the position of a reference location associated with bone in a known coordinate system. The state of the joint centering constraint could include a value of the joint centering position for each of the plurality of actuators 21, 22, 23 and/or a tuning parameter of the joint centering constraint. For example, the instrument controller 28 may automatically enable the joint centering constraint with a particular joint centering position for each of the actuators when the tool 20 is removed from a cut based on a state of the tool 20 and the reference location associated with the bone as determined by the navigation system 32 so that the user may resume the procedure with the same grip about the hand-held portion 16 relative to the tool 20 for—maintaining a comfortable grip, control, convenience, familiarity with anatomy, unexpected anatomy, or a combination thereof. In such an example, the joint centering position is set to the positions of each actuator 21, 22, 23 that was measured at the time before removal of the saw blade 380 from the cut.

It should also be appreciated that while the joint centering positions were described in terms of the joint centering constraint, the joint centering position control described above may be utilized without the use of virtual constraints, such as with a position control system of the actuators. In such an implementation, the control system may simply control the position of each actuator to the set joint centering position. In instances where the joint centering behavior is utilized without implementing a constraint solver, the state of the joint centering behavior may be controlled in the same way as the joint centering constraint.

The instrument controller 28 may be configured to control the state of the joint centering constraint based a distance parameter (e.g. distance; magnitude) calculated between the position of the tool 20 and the position of the reference location associated with the bone. The distance parameter may be a direction, a magnitude, or both. In some cases, when the distance parameter has a direction away from bone and a magnitude greater than a first threshold value, such as 15 cm, the controller may switch to a different state.

As described above, the joint centering position is adjustable. The secondary joint centering position may be set using a user input device, or may be set automatically. In certain configurations, the secondary joint centering position and activation of joint centering constraint may be based on the state of a plane defined by the saw blade relative to a plurality of cutting planes in the known coordinate system, or may be based on the state of an axis defined by a tool relative to a plurality of planned trajectories.

More particularly, the secondary joint position of and activation of the joint centering constraint may be based on angles between a current orientation of the saw blade and a plurality of target orientations of the saw blade, a distance between a current position of the saw blade and a plurality of target positions of the saw blade, or both the angles and the distances, and determining the one of the plurality of the plurality of cutting planes selected by the user based on the values of the angles, values of the distances, or both the values of the angles and the values of the distances. Thus, a particular secondary centering position for each of the actuators may be selected to optimize the pose of the tool support relative to the hand-held portion for purposes of improved usability. Similar implementations could be used for trajectories for other types of surgical tools.

Figure 22:
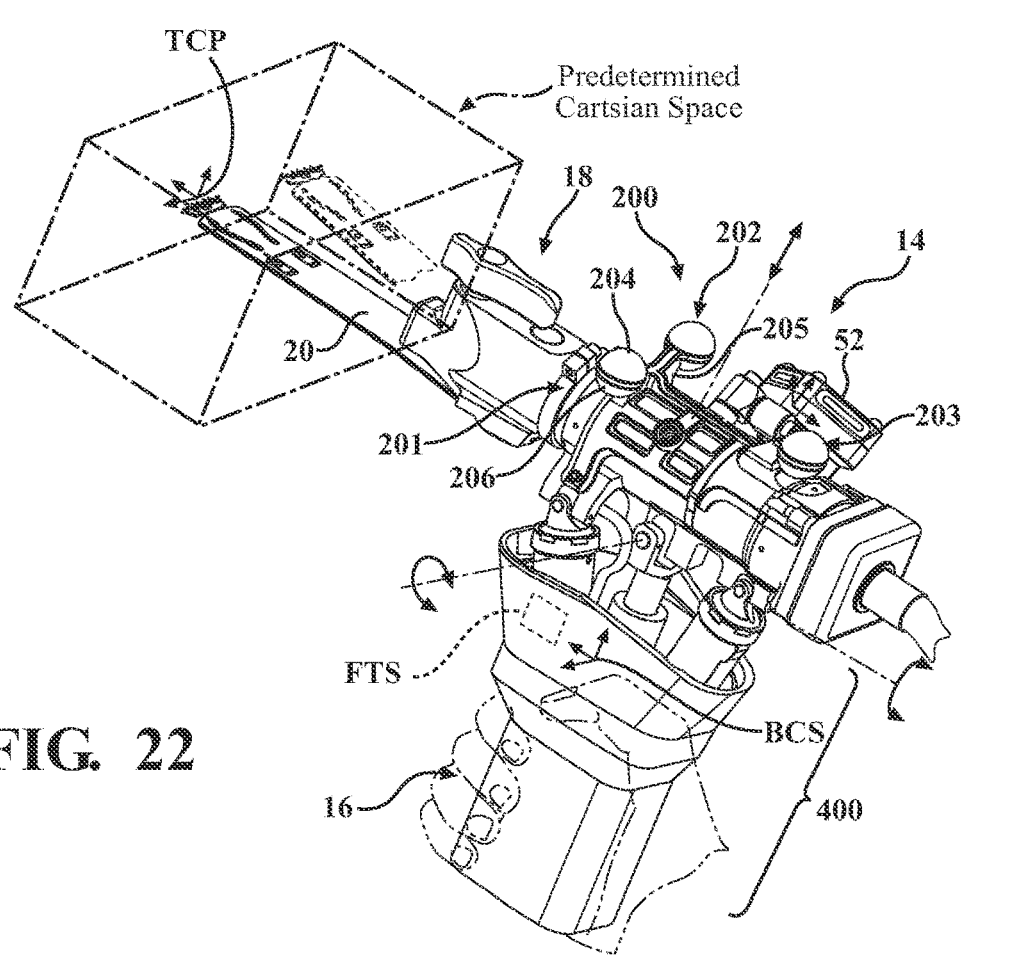
FIG. 22A-22C illustrate one example of actuator control with respect to joint centering behavior.

With reference to FIGS. 22A-22C, one example of controlling the joint centering behavior is described below. In this example, virtual boundaries or distance parameters may be used to distinguish between regions IV and V, and a region immediately adjacent to the bone. In this example, referring first to FIG. 22A and FIG. 22B, the control system is configured to automatically save the current joint positions, which may be used later as joint centering positions when the tool moves from a first region (region IV) to a second region (region V). As can be seen in FIG. 22A, the tool is on the cutting plane with the guide constraints actively aligning the tool 20 to the cutting plane. The control system 60 analyzes the current joint positions as the tool 20 moves from region IV to region V taking a "snapshot" of the joint positions, turning off the guide constraint, allowing the tool 20 to return to the centered position via its previously configured joint centering constraints (FIG. 22B). When transitioning from region V back to region IV, the joint centering constraints are re-set to the value at the "snapshot" (e.g. restore alignment), causing the tool to align to an exit position (FIG. 22C). The guide constraint may not be enabled until the tool 20 is within the zone defined by the region immediately adjacent to the entry of the bone. The restored joint positions may be implemented to re-align the user to an ergonomic start position for the handle, as captured when they previously exited the cut. The guide constraint may be reactivated when the pose of the blade (such as the VM of the blade) is close to the bone (consider a threshold distance from the VM of the blade to a reference coordinate system/reference position).

It should be appreciated that the joint centering constraint may be active at the same time as the guide constraint, the joint limit constraint, or the workspace constraint. In such a scenario, the constraint solver would seek to balance the forces exerted from each of the virtual constraints when computing how the actuators should be controlled, e.g., when computing the commanded pose. Thus, in certain instances, despite activation of the joint centering constraint with a particular joint centering position, the actuator may not actually be controlled to that joint centering position. This is because other constraints may have higher priority. The priority of the various constraints may be adjusted through the use of the various tuning parameters, such as stiffness or damping. Of course, it is also contemplated that the different virtual constraints need not be active at the same time.

In one example, the virtual guide constraint may be activated as the TCP transitions from the region II to region I. A virtual joint centering constraint may be activated as it transitions from region III to region II. Similarly, the joint centering constraint may be deactivated as the TCP transitions from region II to region I. Of course, any number of regions may be defined, with any particular shape. It is contemplated that virtual joint limit constraints may be active in all three regions. As mentioned throughout, these regions may be defined as virtual objects of various shapes or as distance parameters relative to a reference location.

In some examples, the control system 60 modifies each of the virtual forces (the virtual constraints) with tuning parameters based on a pose of the instrument 14, a pose of the blade support or tool support, a pose of the hand-held portion, a commanded joint position of at least one of the actuators, a measured position of at least one actuator 21, 22, 23, a previous commanded position of at least one actuator 21, 22, 23, a previous measured position of at least one actuator 21, 22, 23, or combinations thereof. In some examples, the control system 60 generates a guide constraint based on the target pose of the saw blade 380 or tool and the measured pose of the hand-held portion 16. The control system 60 also generates a centering position for at least one actuator 21, 22, 23 and a joint centering constraint based on the position of at least one of the actuators 21, 22, 23. The control system 60 calculates a constraint force based on the guide constraint and the joint centering constraint by simulating dynamics of the virtual saw blade or tool in a virtual simulation based on the constraint force. In some examples, the control system 60 may also determine an external force applied to the instrument 14, such as the blade support or tool support, the hand-held portion, or between the blade/tool support and the hand-held portion and use the external force in the calculation to determine the constraint force and to apply it to the virtual rigid body in the virtual simulation. The external force could be measured in one or more degrees of freedom, and may be modeled as a force/torque vector. The result of the virtual simulation s a commanded pose which may ultimately used to determine commanded joint positions for each of the plurality of actuators 21, 22, 23. The centering position may be between the median point of the actuator range, and the joint limit of that actuator.

In the virtual simulation, each of the virtual constraints may be modified with a tuning parameter. Each tuning parameter may cause the respective virtual constraints to have an increased effect on the constraint force in the virtual simulation. In one example, the joint centering constraint may have a tuning parameter with a first value, and the guide constraint may have a tuning parameter with a second value, each of the tuning parameters causing the respective virtual constraints to have an increased effect on the ultimately calculated constraint force. In one example, the tuning parameter of the joint centering constraint is less than the tuning parameter of the guide constraint so that the constraint force biases the virtual simulation, and subsequently the commanded pose and commanded joint position, towards moving the tool 20 to the target pose while moving at least one of the actuators away from a joint centering position, e.g., a center point/home position. The control system 60 may further activate a joint limit constraint based on the position of at least one of the plurality of actuators and a position limit. The joint limit constraint may be solved along with other virtual constraints (e.g. guide constraint; joint centering constraint) to determine the constraint force. In one example, a joint centering constraint tuning parameter has a first value, a guide constraint tuning parameter has a second value, and a joint limit constraint tuning parameter has a third value greater than the value of guide constraint tuning parameter and the joint centering constraint parameter. The tuning parameter of the joint limit constraint being greater than the tuning parameter of the guide constraint and the tuning parameter of the joint centering constraint, the virtual simulation ensures that the constraint force applied to the virtual saw blade is more likely to satisfy the joint limit constraint. In this example, since the joint limit constraint has the highest value, the virtual force exerted on the virtual saw blade will be guided to a position within the joint limits, resulting in a commanded position which does not exceed the joint limit positions. One such tuning parameter that could be used in this example would be the stiffness of the constraint.

Joint Limit Constraint

A joint limit constraint is another virtual constraint representing a virtual force and/or torque employed in the virtual simulation to influence the movement of the tool support 18 when controlling a plurality of actuators. The joint limit constraint is used by the control system 60 to implement a particular restriction in the motion of tool support 18 that is intended to prevent the actuators 21, 22, 23 from traveling outside their range of motion. The joint limit constraint may also enforce a threshold of travel which is considered too close to the actuator travel limit. The joint limit constraint, as described further below, has configurable spring and damping properties. However, joint limits, such as soft stops and hard stops are still operable to prevent the tool from overextending or retracting.

The joint limit constraint may be used by the control system 60 to guide the tool support 18. As described in more detail below, the control system 60 operates to calculate the constraint force Fc that satisfies, or attempts to satisfy, the virtual constraints (including the joint limit constraint). The constraint force Fc incorporates the virtual forces and torques therein to move the tool support 18 and tool 20 in a manner intended not to violate the actuator joint limits. The joint limit constraint is considered as a one-dimensional, virtual constraint. For example, a joint limit constraint may be one-sided, and thus may 'push away' from the joint limit but does not attract towards the joint limit. In some versions, the joint limit constraint is a velocity impulse constraint in which forces and/or torques are calculated to apply a virtual impulse to an object in the virtual simulation to cause a change in the object's velocity in accordance with desired constraint parameters. It should be appreciated that when other constraints are employed in addition to the joint limit constraint, the constraint solver is ultimately tasked with providing a solution for the constraint force Fc that satisfies, or attempts to satisfy, all the virtual constraints, and thus other constraints may influence the magnitude and/or direction of the constraint force.

The joint limit constraint is defined primarily by three parameters: the previous commanded joint positions, the positions of the joint limits, and the same constraint Jacobian Jp, as used for the Joint Centering Constraint, relating the motion of the joint to the motion of the virtual mass. The joint limit constraint utilizes a computation of the difference in position between a joint limit position and the previous commanded position. In some implementations, the joint limit constraint may be computed based on current measured position instead of the previous commanded position.

The joint limit constraints are determined and calculated as a force to prevent the actuators 21, 22, 23 from extending and/or retracting past the physical and virtual limits of each of the actuators 21, 22, 23. The instrument controller 28 analyzes the previous commanded position along each active axis AA1, AA2, and AA3 to determine joint limit constraint. The joint limit constraint is balanced with the joint centering constraints, the guide constraints, a workspace constraint, and/or other virtual constraints when computing the commanded pose. The joint limit constraint may be based on the joint limits (soft stops) which may be software enabled stops set at count values just shy of the extreme ends of travel measured during the homing procedure. The soft stops may be values preprogrammed into the software. The soft stops may be a combination of count values and preprogrammed values.

Workspace Constraint

A workspace limit constraint is another virtual constraint representing a virtual force and/or torque employed in the virtual simulation to influence the movement of the tool support 18 when controlling a plurality of actuators. The workspace limit constraint is used by the control system 60 to implement a particular restriction in the motion of tool support 18 that is intended to prevent the tool 20 from traveling outside its workspace. The workspace limit constraint exerts force along a direction defined in Cartesian space, rather than in joint space (which is the case for the joint limit constraint). The workspace limit constraint, as described further below, has configurable spring and damping properties so that the workspace constraint is not infinitely stiff. More specifically, in some versions, the workspace limit constraint is defined as a "soft constraint" such that the workspace constraint impedes but does not prevent motion that violates it, such as motion resulting from forces and torques applied by other constraints in opposite directions.

The workspace limit constraint may be used by the control system 60 to prevent the movement of the tool support 18 and the tool 20 into various locations outside a defined workspace. As described in more detail below, the control system 60 operates to calculate the constraint force Fc that satisfies, or attempts to satisfy, the virtual constraints (including the workspace constraint). The constraint force Fc incorporates the virtual forces and torques therein to move the tool support 18 and tool 20 in a manner intended not to violate the workspace limits. The workspace limit constraint is considered as a one-dimensional, virtual constraint, in that the workspace limit constraint may only apply forces in a single direction (i.e., 'push away' from the workspace limit but does not attract towards the workspace limit). In some versions, the workspace limit constraint is a velocity impulse constraint in which forces and/or torques are calculated to apply a virtual impulse to an object in the virtual simulation to cause a change in the object's velocity in accordance with desired constraint parameters. As described above, the workspace limit constraint may include one or more tuning parameters that are adjustable either manually, or automatically (based on various positional/angular relationships described throughout).

The workspace limit constraint may be based on a pose of the tool and a predetermined Cartesian space, typically defined with respect to the BCS coordinate system. The pose of the tool 16 may be calculated as described above. As described in more detail below, the control system 60 operates to calculate the constraint force Fc that satisfies, or attempts to satisfy, the workspace limit constraints (and other virtual constraints, if used). The constraint force Fc incorporates the virtual forces and torques therein to move the tool 20 in such a way that the workspace limit constraint is not violated. Each workspace limit constraint has a constraint direction that is along the normal to the workspace boundary at the point where the tool 20 contacts the workspace boundary, pointing inward towards the allowed workspace region. Typically, the constraint direction is defined in the BCS coordinate system; however other coordinate systems may be used. The constraint direction is the direction along which the workspace constraint can effectively apply force. The constraint Jacobian Jp may then be determined, relating the motion of the tool 20 along the constraint direction to the motion of the virtual mass VM. Additionally, the workspace limit constraint may also utilize the computation of a penetration depth (i.e. how much the workspace limit was violated along the constraint direction) by comparing the tool pose with the applicable workspace limit boundary being contacted by the tool.

It should be appreciated that when other constraints are employed other than the workspace limit constraint, the constraint solver is ultimately tasked with providing a solution for the constraint force Fc that satisfies, or attempts to satisfy, all the virtual constraints, and thus other constraints may influence the magnitude and/or direction of the constraint force.

Figure 3A:
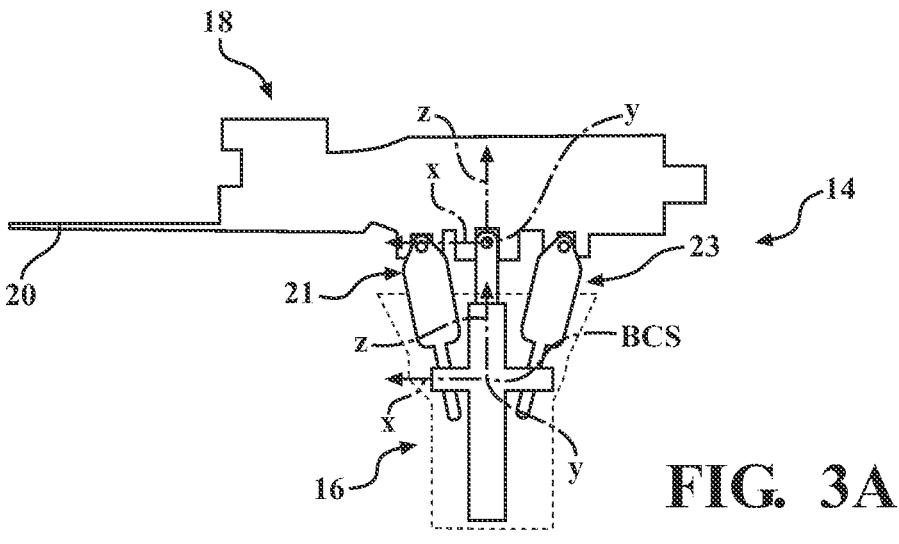
FIGS. 3A-3C are illustrations of various pitch orientations of the robotic instrument.
Figure 3B:
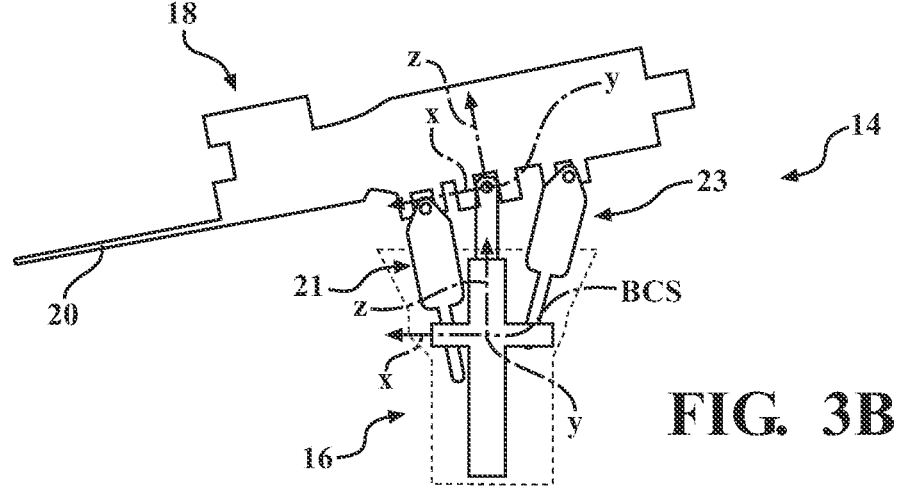
Figure 3C:
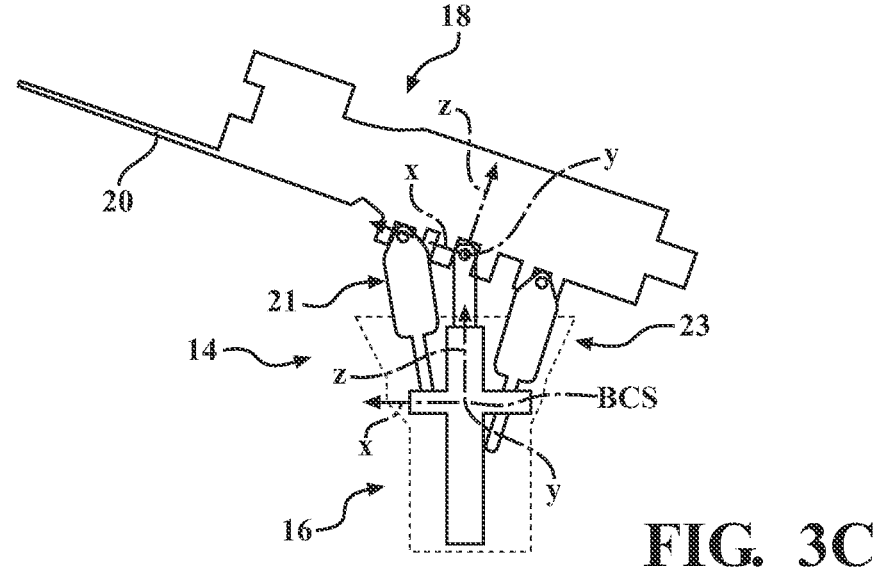
Figures 4A, 4B, 4C:
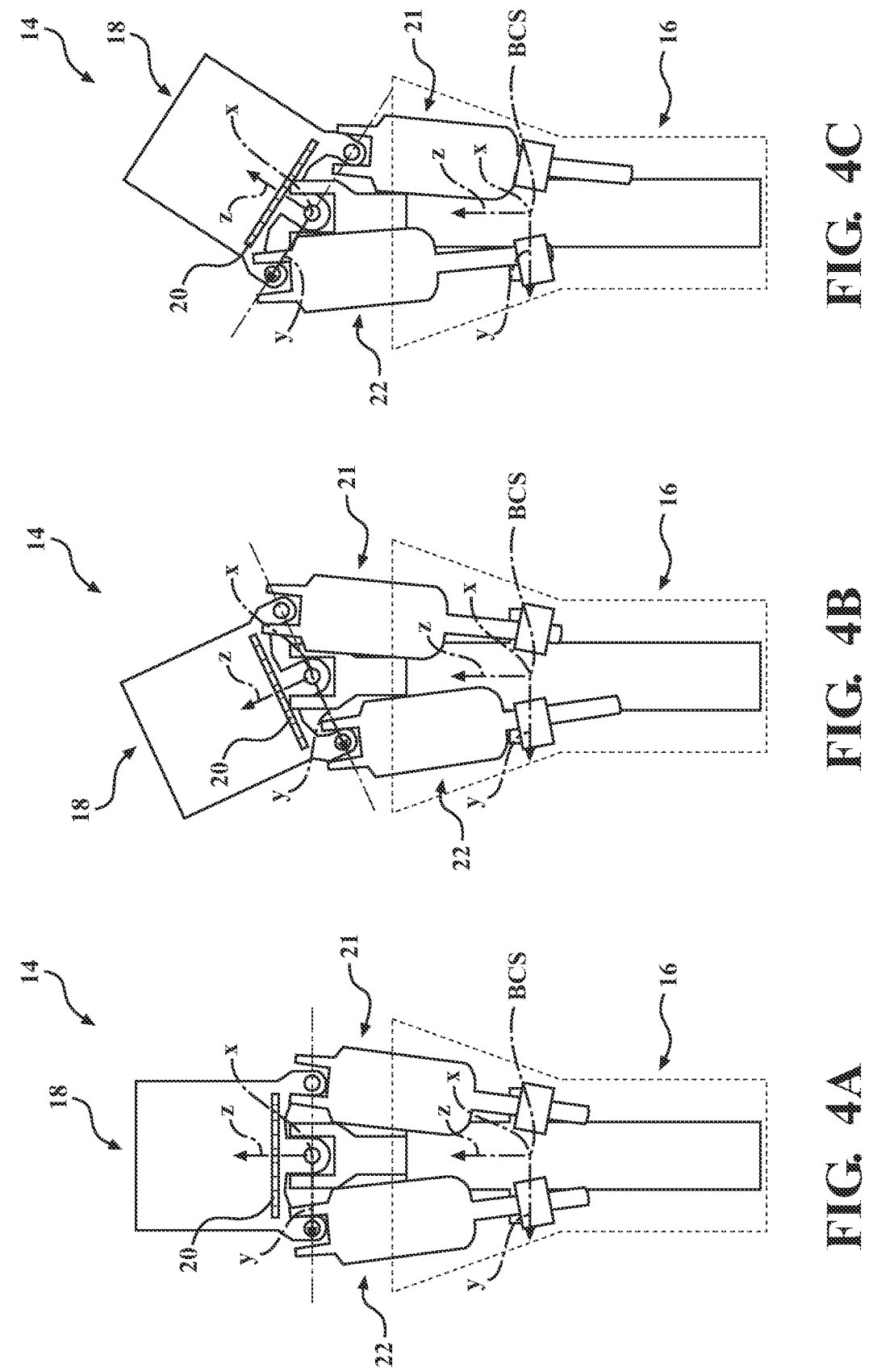
FIGS. 4A-4C are illustrations of various roll orientations of the robotic instrument.
Figures 5A, 5B, 5C:
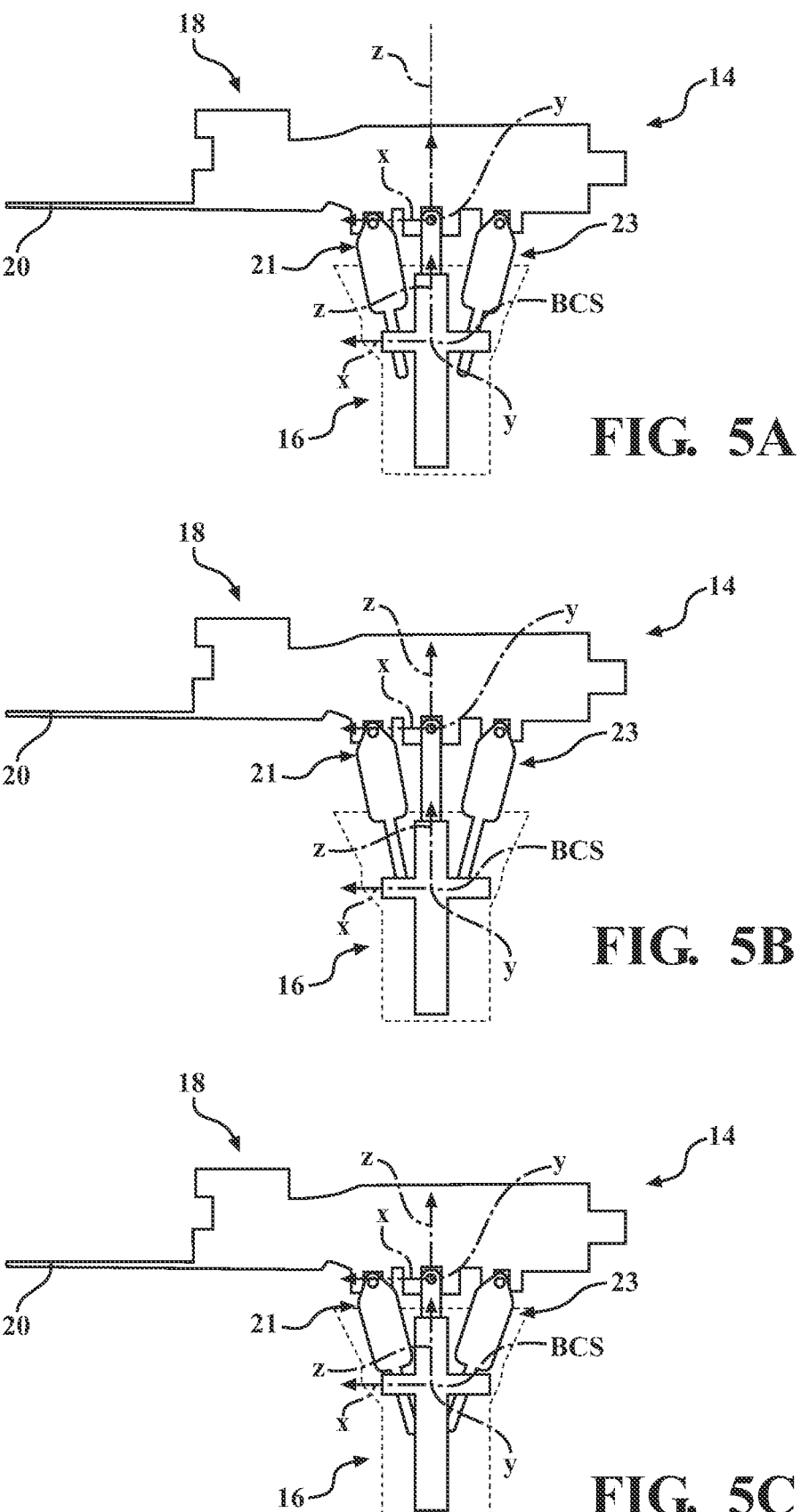
FIGS. 5A-5C are illustrations of various z-axis translation positions of the robotic instrument.
Figures 23A, 23B, 23C:
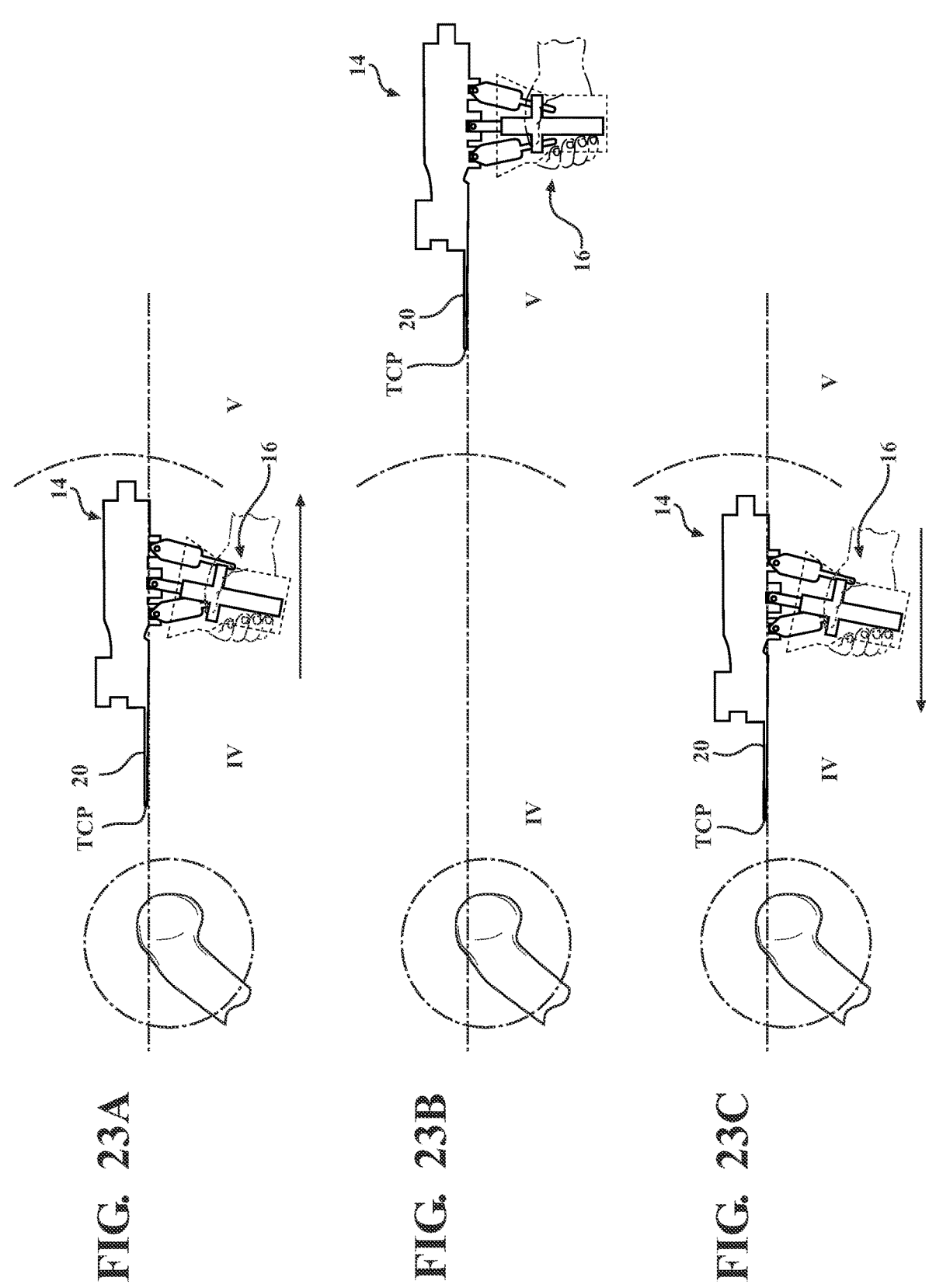
FIG. 23 is a perspective view of the instrument illustrating the range of motion of the tool as controlled in view of a Cartesian space.

As best shown in FIGS. 3A-5C and 23, the plurality of actuators 21, 22, 23 are capable of moving the tool support 18 and tool 20 relative to the hand-held portion 16 in at least three degrees of freedom including pitch, roll, and translation along the axis Z (vertical translation). These individual degrees of freedom are best shown in FIG. 3A-3C (pitch), FIGS. 4A-4C (roll), and FIGS. 5A-5C (z-axis). FIG. 23 shows one exemplary predetermined Cartesian space, illustrated as a volume in the shape of a cube. Other shapes of the predetermined Cartesian space may be implemented as a volume, such as an octahedron, an asymmetrical octahedron, a sphere, a cuboid, a cylinder, etc. Particularly, in some examples, the Cartesian space when defined as a volume, may be asymmetrical in shape, such as asymmetrical about a plane position between the tool support 18 and the hand-held portion when each of the actuators are in the home position, with the Cartesian volume being greater above the plane than below the plane. In this example, the volume may be defined by a plurality of Cartesian points. This volume may be less than the dexterous workspace (less than all reachable configurations). Alternatively, the predetermined Cartesian space may be defined in each degree of freedom separately. For example, the Cartesian space may be defined with a plurality of Cartesian points. The predetermined Cartesian space may also be defined by one or more orientations, based on any one, two or three of the axes along which or about which the saw blade 380 can be displaced (x, y, and z).

The instrument may be controlled in such a way that the range of motion of the blade support relative to the hand-held portion may be greater in pitch than in roll. Alternatively, or in addition, the instrument may be controlled in such a way that the range of motion of the blade support relative to the hand-held portion is greater in elevation than in roll. In one potential implementation, the instrument may be controlled using a combination of the joint limit constraint and a workspace constraint. In addition, one or more other virtual constraints may be used simultaneously with the joint limit constraint and the workspace constraint, such as the guide constraint and/or the joint centering constraint. The constraint solver may be configured to calculate a constraint force adapted to move a virtual saw blade based on the joint limit constraint and the workspace constraint (and any other virtual constraint being utilized). The dynamics of the virtual saw blade are simulated based on the constraint force and output a commanded pose. Based on that commanded pose, the system determines a commanded joint position of each of the plurality of actuators based on the commanded pose. Each of the plurality of actuators is then controlled using the commanded position.

The use of workspace limits (defined in Cartesian coordinates) in combination with joint limits (defined in joint space) may provide advantages with respect to control of the instrument. Implementation of both limits may provide additional options to avoid singularities in control, may provide additional robustness in design by avoiding vulnerable poses that could cause damage to the one more flex circuits, and/or may provide additional options to avoid mechanical interference. For example, the control system 60 may implement workspace limits in order to limit the amount of roll of the blade support 18 relative to the hand-held portion 16 by limiting the workspace constraint and the joint limit constraint more than the workspace constraint and joint limit constraints in pitch, z-axis elevation, or both. By setting the workspace limit on roll higher than in the other controlled degrees of freedom (pitch and elevation), the limited roll may be less roll than the mechanical capabilities. In some cases, the workspace constraint in the roll direction may have the same amount or less mechanical movement as the other controlled degrees of freedom in the pitch and z-axis directions.

Alternatively, the range of motion of the plurality of actuators may be controlled without constraints. In such an implementation, a joint limit behavior is determined based on a position of the actuators and a limit position and determining a workspace limit based on the pose of the tool and a predetermined Cartesian space. Then, the control system 60 is configured to limit each of the plurality of actuators 21, 22, 23 based on the pose of the saw blade 380, the joint limit position, and the predetermined cartesian space.

Kinematic Motion Constraint

A kinematic motion constraint may be used by the control system to control the degrees of freedom that are not controlled by the plurality of actuators, i.e., the uncontrolled degrees of freedom. In one example, where the instrument includes three controlled degrees of freedom and three uncontrolled degrees of freedom, the kinematic motion constraint may be used with the three uncontrolled degrees of freedom (yaw, x-translation and y-translation). Because the virtual simulator models the virtual constraints using a virtual mass subjected to forces in six degrees of freedom, the kinematic motion constraints are utilized to ensure that the virtual mass model in the virtual simulator remains coincident with the physically-relevant kinematic pose of the tool 20, preventing the tool 20 from drifting away in the virtual simulation in the uncontrolled degrees of freedom. The kinematic motion constraints are used to measure the difference in yaw, X-translation and Y translation between the kinematic pose and the virtual mass. The constraint force computed based on these kinematic motion constraints is computed to counteract those differences, whether they are positive or negative; thus, this is a two-sided constraint. The kinematic motion constraints are computed in Cartesian space. While the joint limit constraints ensure that the plurality of actuators do not exceed their joint threshold, the kinematic motion constraints are always active, ensuring that the uncontrolled degrees of freedom are aligned in the coordinate system of the virtual mass.

Boundary Constraint

The control system may also utilize one or more boundary constraints. The boundary constraint may be based on the one or more virtual boundaries described above, along with the pose of the tool. A boundary constraint may function for constraint generation and actuator control (described here), drive motor control, be used together, separately, or a combination thereof. The boundary constraint may result in a force on the virtual mass that prevents the tool from crossing the virtual boundary. It should be understood that the boundary constraint may utilize any of the virtual boundaries described above with respect to control of the drive motor. In the case of the boundary constraint, it should be understood that the virtual boundaries are utilized to control the plurality of actuators rather than controlling the saw drive motor. In some examples, the boundary constraint or other boundary control methods may utilize collision detection.

In one example, the boundary may be defined as a triangle mesh and collision detection algorithms may be used to determine which part of the mesh may be contacted by the tool 20. First, the control system 60 performs a broad phase collision detection to generate a list of candidate triangles located in the region of the tool 20. Next, for each of the candidate triangles, a narrow phase collision detection is performed to confirm whether the tool 20 contacts the triangle and how much penetration depth (along the normal to the triangle) the tool 20 reaches through the boundary. Boundary constraints may only be generated for those triangles in contact with the tool, i.e., the output triangles from the narrow phase collision detection. In some cases, the tool 20 may be modeled using an array of primitive geometric shapes, such as discrete spheres (with diameters equal to the tool thickness) or discrete swept spheres (capsule shapes) located along the periphery of the tool 20. The collision detection process may be repeated for each for the primitive elements (e.g., discrete spheres) to look for collisions with the mesh triangles. Boundary constraints may be generated for each contact between a tool geometric primitive and a mesh triangle.

Typically, the boundary is defined relative to a patient tracker 54, 56, but other reference coordinate frames can be used. After the control system 60 determines the points of the boundary mesh which contact the geometric primitives or VM of the tool 20, the boundary constraints may be computed. A one-DOF, one-sided (force applied away from the boundary) boundary constraint may be computed for each resulting narrow phase triangle. The boundary constraint direction is along the normal to the triangle. The penetration depth of the boundary may also be measured along this boundary constraint direction. A constraint Jacobian Jp is computed mapping movement of the tool 20 along the triangle normal (boundary constraint direction) to resulting motion of the virtual mass. For any boundary constraints attached to an anatomy tracker (i.e., having a relative velocity with respect to the tool 20), $V_{desired}$ may need to be computed. $V_{desired}$ may be a projection of the relative velocity between bone and tool 20 onto the constraint direction. In another example, when the tool is completely beyond the boundary, is handled by drive motor M control rather than via boundary constraint generation (and resulting actuator control).

It should be appreciated that when other constraints are employed other than the boundary constraint, the constraint solver is ultimately tasked with providing a solution for the constraint force Fe that satisfies, or attempts to satisfy, all the virtual constraints, and thus other constraints may influence the magnitude and/or direction of the constraint force.

External Force

In one version, the instrument 14 may be configured to calculate, estimate, or measure forces and torques placed on the instrument 14 by the user or by the bone in order to affect or influence the tool 20. For example, the instrument 14 may detect and measure the forces and torques applied by the user or by the bone onto the tool 20 and generates corresponding input used by the control system 60 (e.g., one or more corresponding input/output signals). The forces and torques applied by the user at least partially define an external force $F_{ext}$ that is used to determine and facilitate control of the plurality of actuators. By including an external force/torque measurement into the virtual simulation, the forces applied by the user or bone may be brought into the virtual simulation. This may allow the virtual constraints to have compliance against physically applied forces. For example, the guide constraint has a particular stiffness and damping. When the external force ($F_{ext}$) is included in the virtual simulation, the tool may be positioned in a way such that the user would "feel" the compliance of the guide constraint. This may allow the control of the tool to be more responsive to the user applied force (i.e., an equilibrium may be found in the virtual simulation between the applied user/bone force and the guide constraint stiffness). If the user applies heavy force, then, if desired, the guide constraint may be partially overridden by the user based on its tuning parameters. This may be used to limit binding or fighting of the tool against the user in the case of small positional misalignments between the saw blade and cutting plane or the tool and the planned trajectory, the virtual compliance allowing that small error to be resolved (balanced out) without exerting high forces or positive feedback felt by the user through the handle when the blade or tool cannot perfectly reach its target pose. Without the $F_{ext}$ measurement, the stiffness of the virtual constraints may find an equilibrium with forces applied by other virtual constraints, without taking into account any physical forces applied by the user or bone against the blade. Without including the external force into the virtual simulation, the force applied by the user is not considered in determining the commanded pose. For example, this external force may be used in computing the commanded pose by including the external force in the constraint solver in combination with the other virtual constraints described above, and then applying the external force to the virtual rigid body in the virtual simulation. The external force $F_{ext}$ may comprise other forces and torques, aside from those applied by the user or by the bone, such as gravity-compensating forces, backdrive forces, other virtual forces, and the like, as described in U.S. Pat. No. 9,119,655, incorporated herein by reference. Thus, the forces and torques applied by the user at least partially define the external force $F_{ext}$, and in some cases may fully define the external force $F_{ext}$ that influences overall movement of the tool 20. In some instances, the instrument may comprise a force/torque sensor S that is implemented as a 6-DOF force/torque transducer positioned on the hand-held portion, the tool platform, or between the two components. In other examples, a linear force sensors in each of the actuators 21, 22, 23, or torque sensors in each of the actuator motor outputs may also be used. Additionally, motor current may be used as a lower-fidelity approximation of motor torque, in place of a force/torque sensor. Each of these joint space force/torque measurements may be converted to an equivalent force/torque acting on the virtual mass VM using the appropriate Jacobian based on the manipulator kinematics. The instrument controller 28 and/or the navigation controller 36 may receive the input (e.g., signals) from the force/torque sensor. In some versions, the external force is transformed from a force/torque coordinate system FT to another coordinate system, such as the VM coordinate system. In such a method, the method may include sensing an amount of current supplied to each of the plurality of actuators, estimating an amount of external force applied between the blade support and the hand-held portion based on the output of the one or more current sensors, and calculating a constraint force adapted to move a virtual saw blade towards the target pose based on the estimated amount of external force.

Operation

Control of the instrument 14 takes into account the latest positions and/or orientations of the anatomy (e.g., the femur F or the tibia T) and the instrument 14, which are transmitted from the navigation controller 36 to the instrument controller 28 over the data connection. Using these data, the instrument controller 28 determines the pose (i.e., position and/or orientation) of the target plane or target trajectory and/or virtual boundaries 184 in a desired coordinate system. The relative pose of the tool 20 (e.g., the TCP) to the target plane and/or virtual boundaries 184 is also computed. The instrument controller 28 updates the navigation system 32 (including the displays 38) with the position and/or orientation of the tool 20 relative to the anatomy to which the tool 20 is to be applied. An indication of the location of the target plane and/or virtual boundaries 184 may also be presented.

The relative location of the tool 20 to the target plane and/or virtual boundaries 184 is evaluated by the instrument controller 28 to determine if action needs to be taken, i.e., moving the tool 20, changing a speed (such as an oscillation speed) of the tool 20, stopping operation of the tool 20, etc. Instructional data packets are sent, for example, to the motor controllers, such as from the instrument controller 28. These instructional data packets include the commanded positions for the rotors 148 of the motors 142 (or target position of the actuator). Here, each commanded position may be a positive or negative number representative of a targeted cumulative encoder count for the associated rotor 148, or other representation of the actuator's position. The instrument controller 28 generates and sends these instructional data packets to each motor controller at the rate of one packet every 0.05 to 4 milliseconds. In some examples, each motor controller receives an instructional data packet at least once every 0.125 milliseconds. Instrument controller 28 may also selectively regulate a cutting speed of the instrument 14 based on the relative location of the tool 20 to one or more of the virtual boundaries 184. For instance, the drive motor M that controls oscillation of the tool 20 and corresponding cutting, may be disabled by the instrument controller 28 any time the tool 20 is in an undesired relationship to the virtual boundaries 184, e.g., the tool 20 is off a target plane by more than a threshold value, the penetration of the tool 20 into the virtual boundary 184 is greater than a threshold, etc. It is contemplated that the control system 60 may also control the drive motor M based on whether the optical tracking system retains line of sight for the tool tracker 52 and/or the patient tracker 54, 56. For example, the control system 60 may deactivate the drive motor M if line of sight has been compromised for a predetermined amount of time.

During use, in one potential implementation, the control system 60 determines a pose (a current pose) of the tool 20 with the navigation system 32 by virtue of the tool tracker 52 being located on the tool support 18. The instrument controller 28 may also determine a current position of each of the actuators 21, 22, 23 based on an output encoder signal from the one or more encoders located on each of the actuators 21, 22, 23. Once the current position of each of the actuators 21, 22, 23 is received, the instrument controller 28 may calculate a current pose of the tool (TCP) with respect to the hand-held portion 16 (BCS) using forward kinematics. The localizer data may be used to determine the relative pose between the patient tracker 54, 56 and the tool tracker 52. The aforementioned poses may be combined, along with additional calibration and registration data, to compute the pose of the hand-held portion 16 (e.g., a current pose of the base coordinate system BCS) with respect to a desired coordinate system, such as the patient tracker coordinate system.

Figure 24:
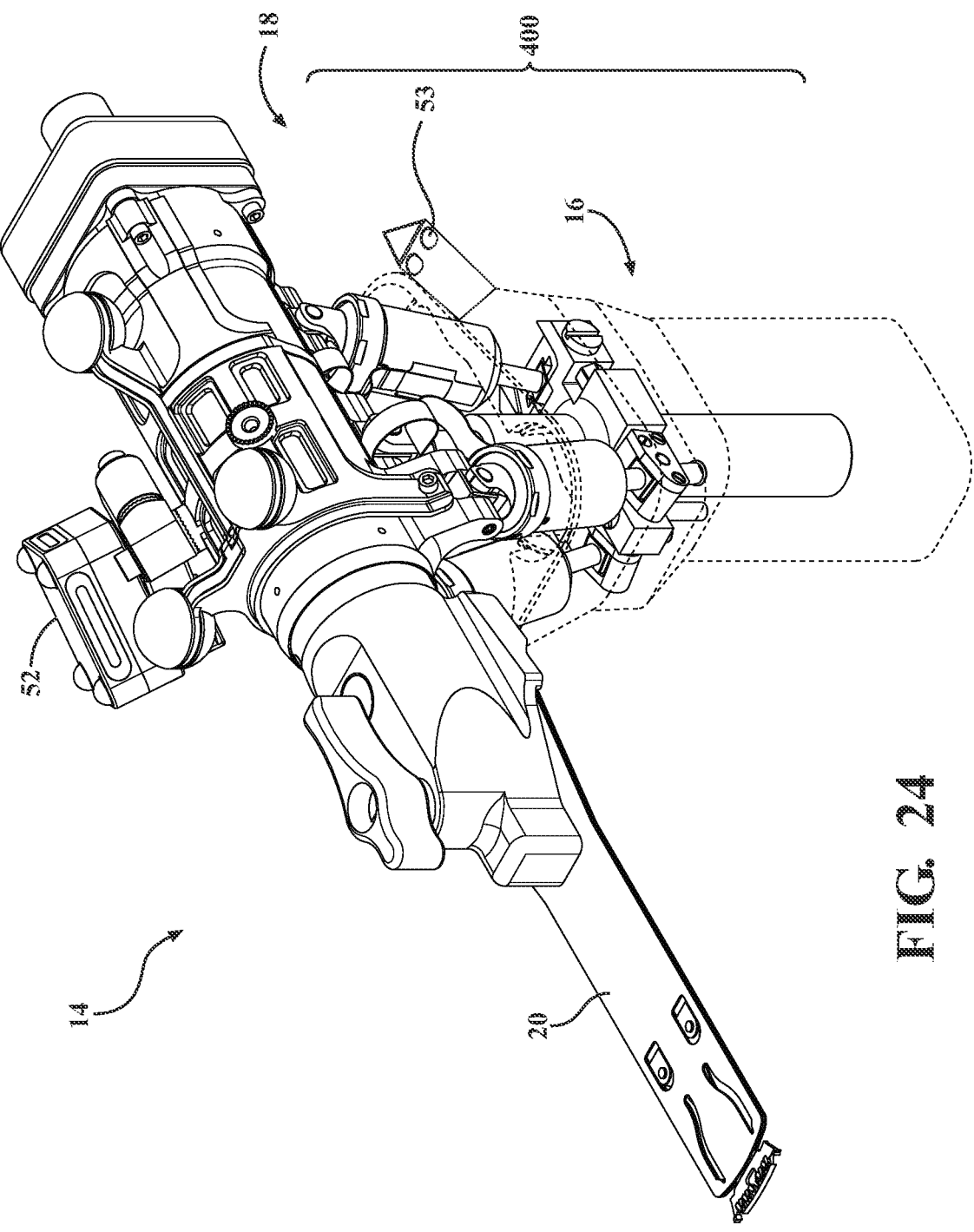
FIG. 24 is a perspective view of one example of the hand-held robotic instrument.

In some examples, the current pose of the hand-held portion is determined with the navigation system 32 by virtue of tracker 53 located on the hand-held portion 16. The pose of BCS with respect to the desired coordinate system (e.g., patient tracker) may be determined directly using localization data in conjunction with additional calibration and registration data. In one instance, the instrument includes two trackers on the instrument 14, a hand-held portion tracker 53 on the hand-held portion 16 and a tool tracker 52 located on the tool support 18 as shown in FIG. 24. The navigation system 32 determines the pose of BCS with respect to the desired coordinate system (e.g., patient tracker) from the location of the tracker 52 on the hand-held portion 16 and a tracker 54, 56 on the desired coordinate system (e.g., patient anatomy).

Once the instrument controller 28 has the pose of the hand-held portion 16 in the desired coordinate system, the instrument controller 28 may then control the plurality of actuators 21, 22, 23. In one implementation, the instrument controller 28 may determine a commanded pose of the tool 20 based on the current pose of the hand-held portion 16 and based on a position and/or orientation of a planned virtual object, subject as a target plane. The instrument computes a pose (a commanded pose) of TCP with respect to BCS that results in the TCP being on the desired plane or aligned with the planned virtual object. This commanded pose may optionally be computed using the virtual constraints (guide constraints, joint centering constraints, joint limit constraints, workspace constraints). The instrument controller 28 may convert the commanded pose to a commanded position for each of the plurality of actuators 21, 22, 23 using inverse kinematics, then send command instructions to the actuators 21, 22, 23 to move to a commanded position, thereby changing the pose of the tool support 18 and tool 20 relative to the hand-held portion.

Figure 17A:
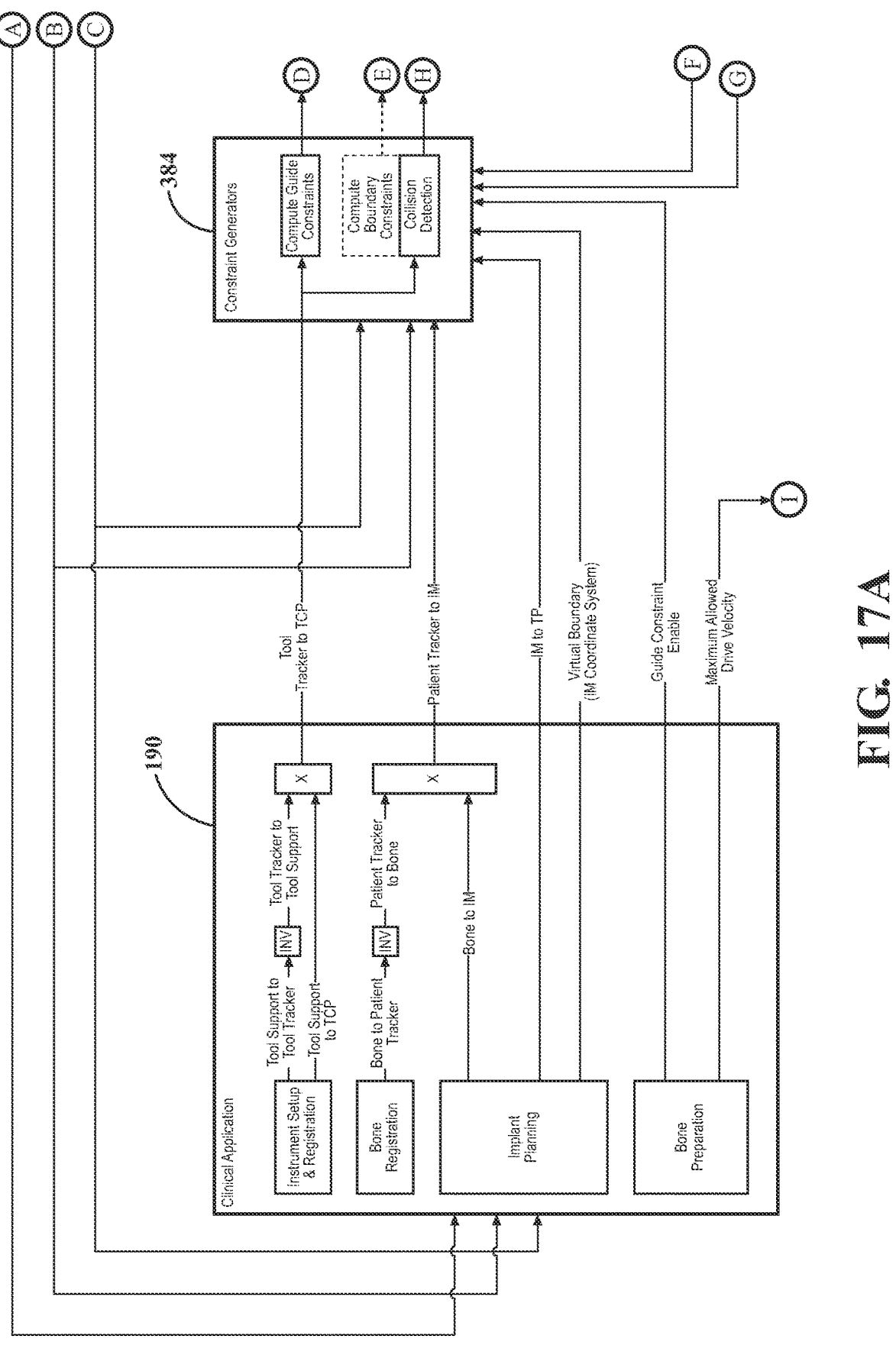
FIG. 17A-17E is a block diagram of various portions of the control system.
Figure 17B:
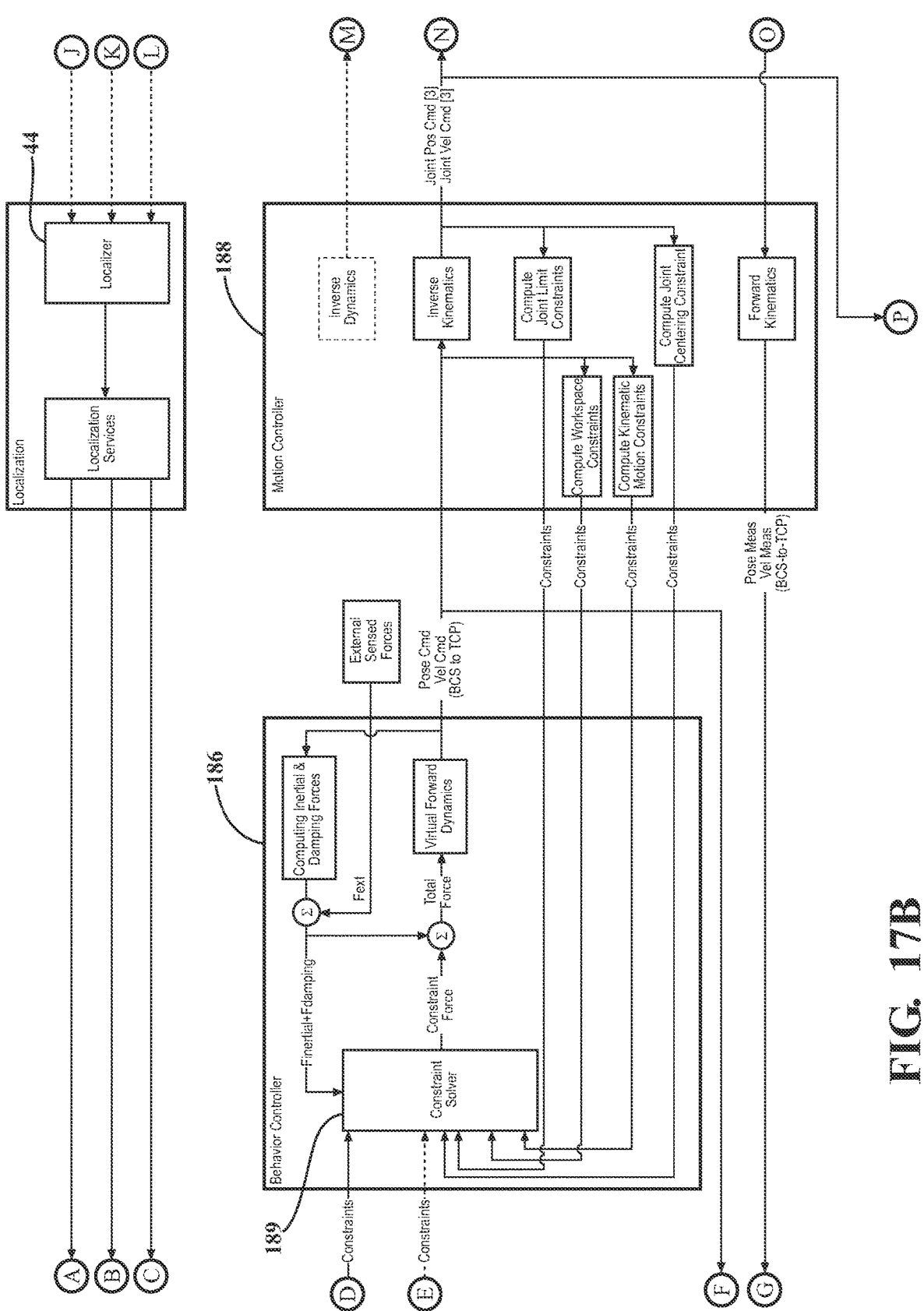

As can be seen in FIGS. 17A-17E, the control system determines the movements of the instrument and the energization of the drive motor M based on particular conditions and parameters. Starting at FIG. 17D, one or more trackers 54, 56 are placed on a patient's anatomy (e.g. femur, tibia) and one or more trackers 52 are placed on the instrument 14. The localizer 44 captures the position of each the trackers 52, 54, 56, and processes the position information into a common coordinate system (FIG. 17B). From the localizer 44, the data is then passed to the clinical application 190 and constraint generator 384.

The clinical application 190 is used to calculate registration and planning transforms used by the control system to command the tool. In FIG. 17A, the clinical application receives the pose information of the device tracker 52 and the patient tracker(s) 54, 56 from the localizer 44. The clinical application 190 may also use the localizer data relating to the pointer tracker PT, device tracker 52 and patient tracker 54, 56 to calculate device command transforms based on the handpiece setup and registration, bone registration, implant planning, and bone preparation.

Within the clinical application 190, the tool tracker 52 and pointer tracker PT information is processed with hand piece setup and registration information to create tool tracker-to-TCP (tool tracker-to-TCP) transform. This may be computed by combining results of two registration steps: 1) registration of the tool support 18 to the tool tracker 52, and 2) registration of the tool support 18 to the tool (TCP). The resulting tool tracker-to-TCP transform (i.e., the instrument registration result) is then forwarded to the constraint generator 384. The position information from the localizer 44 is used with the bone registration data to calculate a bone-to-patient tracker transform and then inverts to yield a patient tracker-to-bone transform, associating the location of the patient tracker with the bone. Utilizing one or more of the user interfaces UI, the user may adjust the size and positioning of the desired implant with respect to an on-screen bone model to allow the Clinical Application to create a bone-to-implant transform based on the location of the bone relative to the planned position and/or orientation of the implant. Based on the known geometry and size of the selected implant, the Clinical Application looks up the transform of the planned pose of the implant to a desired one or more target cutting planes TP, an implant-to-target-plane transform or a desired one or more target trajectories. A virtual boundary may also be calculated based on the selected implant. The patient tracker-to-bone transforms and the bone to implant transform (B-to-IM) are combined to yield a patient tracker 54, 56 to implant pose transformation (patient tracker-to-IM), which is a combined result of bone registration and implant planning, which is forwarded to the constraint generator 384. The IM to TP transform may be used to generate the guide constraint and the boundary may be used to generate a boundary constraint (if used) with the boundary generator. The boundary information may also be sent to the drive command handler 192.

Three transforms are utilized to ultimately determine the hand-held portion to localizer transform: a) a hand-held portion to TCP transform, the forward kinematic result received from the motion controller 188; b) a tool support to TCP transform, the tool registration result received from the clinical application 190; and c) a tool tracker to localizer transform received from the localizer 44. A localizer to patient tracker(s) transform(s) may also be received from the localizer 44. Then, a hand-held portion to patient tracker transform may be computed based on: a) a hand-held portion to localizer transform; and b) a localizer to patient tracker(s) transform. It should be appreciated that the tool tracker coordinate system and the tool support coordinate system may be used interchangeable with one another as the pose of the tool support may be fixed relative to the TCP with a known, calibrated, and/or registered transform.

As noted above, the constraint generator 384 receives the location data of the patient tracker(s) 54, 56, and device trackers from the localizer, the registration and planning transforms from the clinical application 190, and additional data inputs from the behavior controller 186 and the motion controller 188, including the motion constraint handler 390 (described further below) in order to compute the guide constraints and/or the optional boundary constraint(s). The constraint generator 384 processes the received data to create a set of constraints to be solved in order to compute a commanded pose for the tool 20. As noted above, the guide constraints are virtual constraints that are defined to yield the virtual forces and torques employed in the virtual simulation that move the tool 20 to the target state. Once the constraint generator 384 determines the set of active constraints to be solved, that information is transferred to the behavior controller 186.

The behavior controller 186 computes data that indicates the next commanded position and/or orientation (e.g., pose) for the tool 20. In some examples, the behavior controller 186 computes the next commanded pose based on solving the set of constraints and performing a virtual simulation. Output from the motion constrain handler 390 of the motion controller 188 may feed as inputs into the behavior controller 186 to determine the next commanded position and/or orientation for the tool 20. As can be seen in FIG. 17B, the behavior controller 186 processes various virtual constraints to determine the commanded pose. The constraint solver 189 takes in constraints generated by the motion constraint handler 390 of the motion controller 188 such as joint limit constraints and joint centering constraints, as well as workspace constraints and kinematic motion constraints. The constraint solver 189 also takes in constraints from the constraint generator 384 such as guide constraints and boundary constraints from the boundary handler 385. The constraint solver 189 further receives inertial and damping forces which are processed by the behavior controller 186 and added back into the constraint solver 189. Once these constraints are added into the constraint solver 189, the constraint solver 189 generates a constraint force, which is then summed with all virtual forces, such as the inertial and damping forces, and, optionally, an external force. The total virtual force is then processed with virtual forward dynamics. The pose and velocity output from the virtual forward dynamics is then sent to compute the inertial and damping forces within the behavior controller 186, and also forwarded as a commanded pose and a velocity command of the tool support (hand-held portion-to-TCP) into the motion controller 188. The commanded pose (hand-held portion-to-TCP) is also sent back to the constraint generator 384 for use in generating the constraints.

The motion controller 188 controls the motion of the tool support 18, and specifically the TCP coordinate system. The motion controller 188 receives data defining the next commanded pose from the behavior controller 186. Based on the data, the motion controller 188 determines the next position of each of the actuators (e.g., via inverse kinematics and Jacobian calculators) so that the tool support can assume the pose relative to the hand-held portion as commanded by the behavior controller 186, e.g., at the commanded pose. In other words, the motion controller 188 processes the commanded pose of the tool support relative to the hand-held portion, which may be defined in Cartesian coordinates, into commanded joint positions of the plurality of actuators 21, 22, 23 so that the instrument controller 28 can command the actuators accordingly. In one version, the motion controller 188 regulates the position of the tool support with respect to the hand-held portion and continually adjusts the torque that each actuator 21, 22, 23 outputs to, as closely as possible, ensure that the actuators 21, 22, 23 move the tool support 18 relative to the hand-held portion 16 such that the commanded pose can be reached.

Once the hand-held portion-to-TCP relationship enters the motion constraint handler 390 of the motion controller 188, the hand-held portion-to-TCP relationship is used to compute workspace constraints and kinematic motion constraints. These constraints are computed in the Cartesian coordinate system of the commanded pose—using the relationship between the hand-held portion and the TCP. Once the workspace constraints and kinematic motion constraints are calculated, the data from the motion constraint handler 390 is forwarded back to into the behavior controller 186 and into the constraint solver 384.

The hand-held portion-to-TCP data is also transformed with an inverse kinematics calculation. After the inverse kinematic modification is performed resulting in a set of commanded joint positions, the data is further processed to compute joint limit constraints and joint centering constraints. These constraints are computed in joint space. The joint limit constraint may be calculated based on the previous commanded joint position or measured joint position of each actuator, a constraint Jacobian Jp, which maps the one-dimensional joint limit constraint to a coordinate system employed for the virtual simulation (e.g., between the motion of the joint and the virtual mass coordinate system VM); and one or more limit positions. The joint centering constraint is calculated based on a constraint Jacobian Jp, which maps the one-dimensional joint centering constraint to a coordinate system employed for the virtual simulation (e.g., between the motion of the joint and the virtual mass coordinate system VM), a previous commanded joint position or measured joint position, and a joint centering position. Once the joint limit constraints and joint centering constraints are calculated, the data is sent back to the constraint solver 189 in the behavior controller 186.

Further, the inverse kinematic data transformation creates a commanded joint position (Joint Pos Cmd) and a joint velocity command (Joint Vel Cmd) for each of the actuators and sends the processed data to the joint position-velocity controllers (one for each actuator) and to the drive command handler 192 to be processed to determine a joint travel velocity override.

The motion controller 188 sends the commanded position of each actuator to the drive command handler 192, which may compares the one or more commanded or measured positions of each actuator and the respective joint thresholds to determine whether an override to the drive motor M is necessary (see box identified as joint position velocity override) in the drive command handler 192. In other words, as the control system 60 determines the commanded position for each actuator to move the TCP to the target pose, the control system 60 may control activation of the drive motor M based on one or more positions of the plurality of actuators. The one or more actuator positions may be based on the commanded joint position of at least one actuator, a measured position of at least one actuator, a previous commanded position of at least one actuator, a previous measured position of at least one actuator, or combinations thereof. In one example, the drive motor M is controlled based on a commanded position of at least one of the actuators 21, 22, 23. The commanded joint position of the at least one actuator 21, 22, 23 is compared with an actuator motor override limit of the at least one actuator 21, 22, 23. The motor override limit may be a value, or a series of values defining the outer bounds of a range. Although this example demonstrates monitoring one actuator, the control system may monitor the commanded position and the actuator motor override limits of each actuator 21, 22, 23. The upper limit and the lower of the actuator motor override limit may be values corresponding to the position of the actuator relative to the operational range of each actuator. The upper limit may correspond to a maximum allowed traveled in a first direction, and the lower limit may correspond to a maximum allowed travel in a second, opposite direction before the drive motor parameter will be adjusted. More specifically, the control system 60 controls a motor parameter of the drive motor M at a first value and a second value based on whether the commanded joint position would keep the actuator position between the upper limit and lower limit of the motor override limits. The control system 60 may control one or more motor parameters of the drive motor M, the one or more motor parameters may be a speed, a torque, an operation time, a current, or a combination thereof. In one example, the motor parameter controlled by the control system 60 is the motor speed, the first value being zero (drive motor M is off) and the second value being greater than zero (drive motor M is on). The control system 60 switches the motor parameter between the first and second values based on the commanded position of the actuator 21, 22, 23. When the commanded position of the actuator 21, 22, 23 places the actuator within the upper limit and lower limit of the motor override limits, the control system 60 may command the second value of the drive motor parameter, allowing the drive motor M to be actuated and/or continue to be energized. When the commanded actuator position is between the lower and upper motor override limits, a joint velocity command override is not modified In some examples, the drive motor override may be implemented as a lookup table or function that is evaluated based on the actuator position (P) data received. For the example of the joint position velocity override, this would allow the speed of the drive motor to get ramped down proportionally as the joint position approaches its motor override limit. In some examples, there may be no modification when the actuator position is within the lower and upper motor override limits o In other examples, proportional ramp down of drive motor M speed when one or more of the actuators 21, 22, 23 are at a position between 80% travel to 95% travel range, and may be fully disabled above 95% travel, which may provide a continual and gradual feedback to the user that the tool 20 is approaching the operational limits (the lower and upper motor override thresholds). In such an implementation, there may be a plurality of lower motor override thresholds and a plurality of upper motor override threshold, each threshold corresponding to a motor parameter (such as a motor speed) In some cases, the drive motor M speed may not be reduced to zero completely, but rather to a fixed lower speed, allowing the surgeon to be alerted but allowing a determination as to whether to proceed at the surgeon's discretion. When the commanded position of the actuator 21, 22, 23 places the actuator outside of the upper limit and lower limit of the motor override limit, the control system 60 may command the first value of the drive motor parameter, preventing the drive motor M from being actuated and/or continuing to be energized. The motor override limits for each actuator may be different than the joint thresholds for each actuator described above. For example, the motor override limits may define a narrower range than a range defined the joint thresholds, and the range of the motor override limits may be wholly within the joint threshold range.

The joint position velocity controllers 194 are used to process the data from the motion controller 188 and process the commanded joint position command (Joint Pos Cmd) and the joint velocity command (Joint Vel Cmd) to determine a joint torque command (Joint Torque Cmd) for each of the actuators. The calculation of the joint torque command may be done through a closed-loop control algorithm, such as PID control. The joint torque command is sent into the surgical instrument where each of the current controllers corresponding to each actuator interprets the joint torque command into a current. The current controller then selectively applies voltage as needed to drive the commanded current to each actuator motor causing each actuator to move the tool support towards a commanded position. The applied torque (or current) may cause each of the actuators to move and accelerate in the corresponding direction. The amount of travel and the speed the actuators move/accelerate may depend on the mechanical load, friction, other outside factors, or a combination thereof. By monitoring each of the actuators position feedback over time, the commanded torque (current) is adjusted by the position-velocity controller so that the commanded position of each actuator is tracked closely. As the actuator motors are adjusting the tool support, each motor encoder is collecting rotational and/or positional data for each rotor and sending the joint position data back to the current controller. The current controller then processes the joint position data of each actuator into a joint velocity measurement (Joint Vel Meas) and a joint position measurement (Joint Pos Meas) and sends the joint velocity measurement data and the joint position measurement data through the joint position-velocity controller to the motion controller 188. The motion controller 188 then transforms the joint position and velocity measurement data of each actuator with forward kinematics to generate pose and velocity relationships between the TCP and the hand-held portion 16. The hand-held portion-to-TCP relationships are then sent into the constraint generators 384 so that they can utilize this data for generation of the various virtual constraints.

Figure 31:
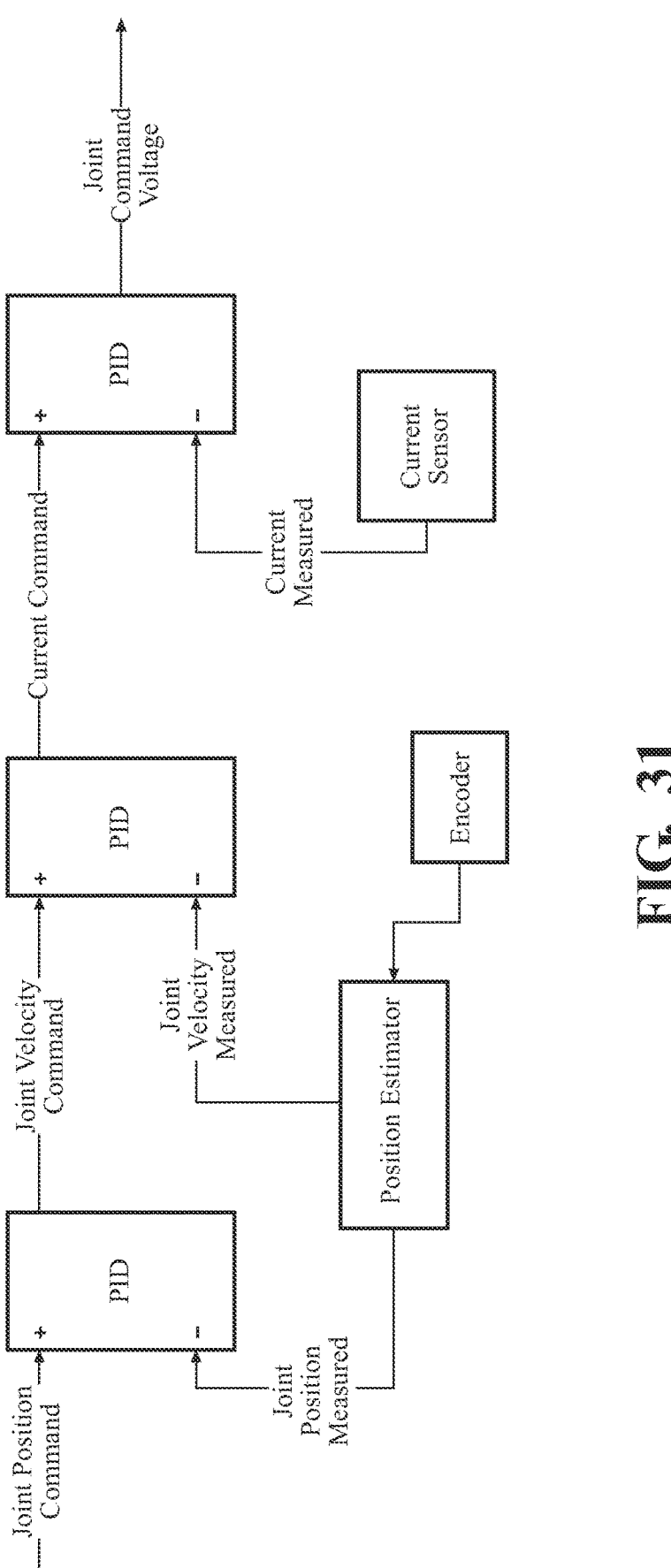
FIG. 31 is a block diagram of a control system.

In addition, with reference to FIG. 31 the joint velocity measurement and the joint position measurement may be used in the PID control loops. For example, PID loop may compute an error between the joint commanded position and the joint measured position, which may be used with a PID loop to control the joint commanded velocity. The commanded velocity of the joint may be compared versus the joint measured velocity to determine an error. That error may be used in a PID loop to control the commanded current. The commanded current may be compared versus the measured current to determine an error. That error may be used in a PID loop to output a commanded joint voltage.

Figure 17C:
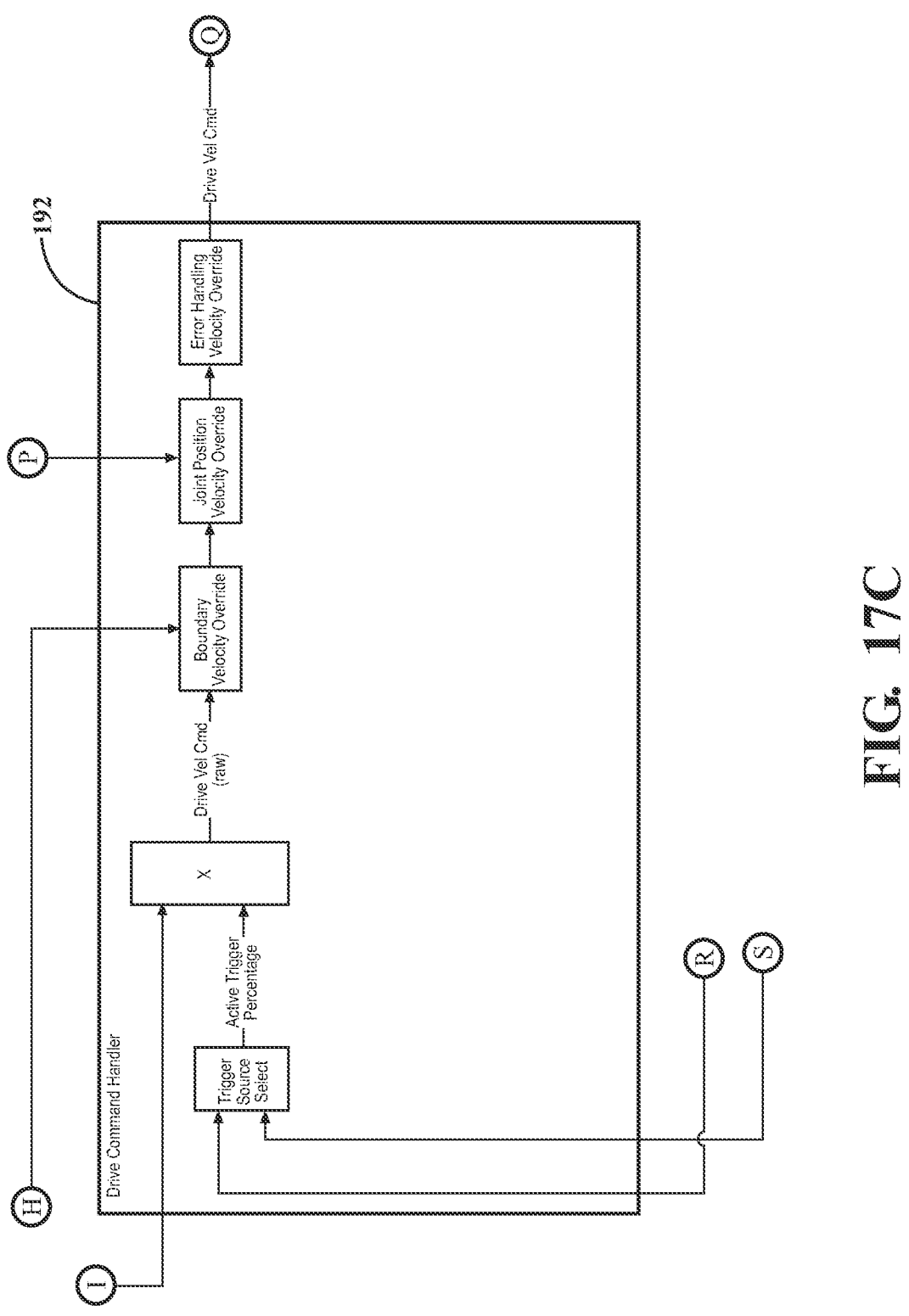
Figure 17D:
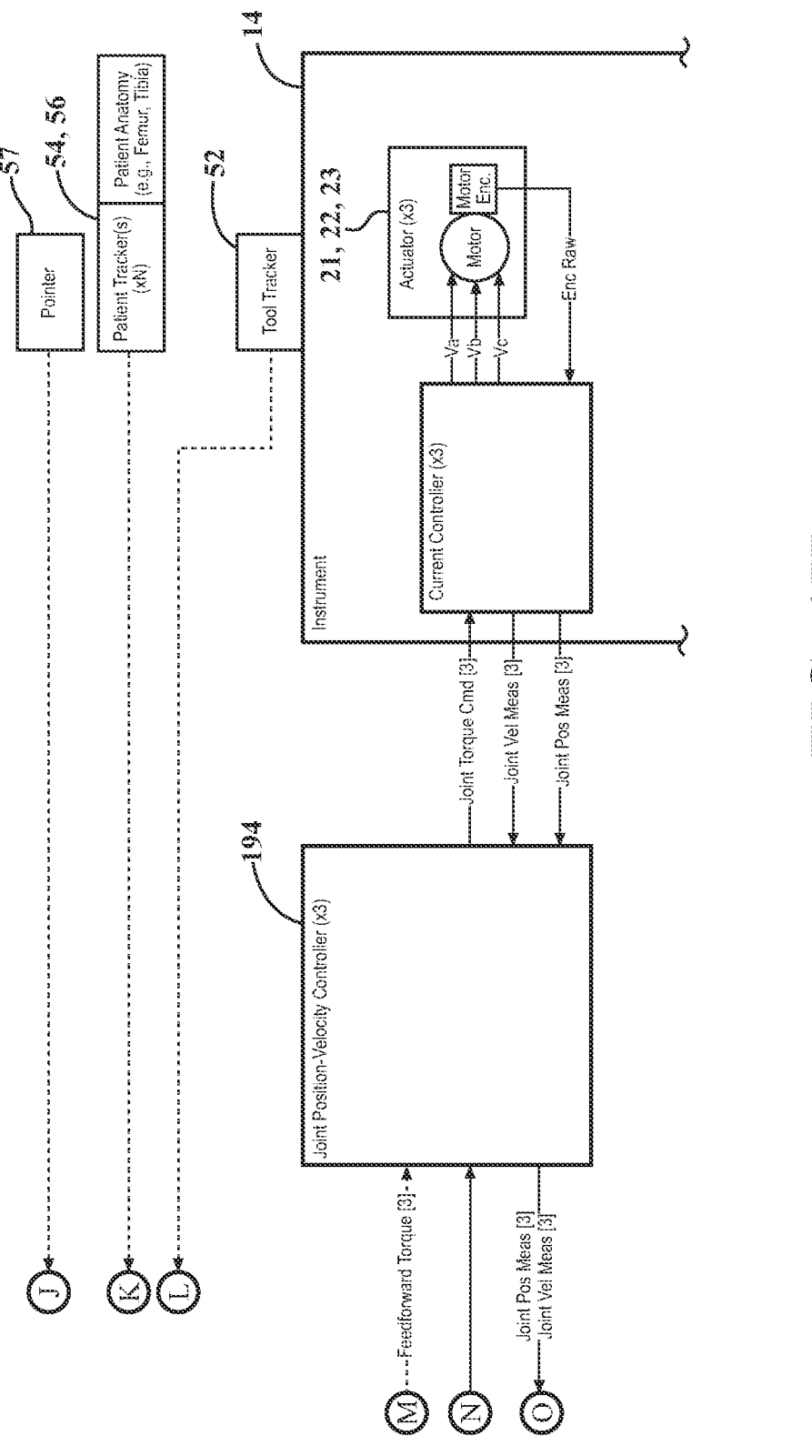
Figure 17E:
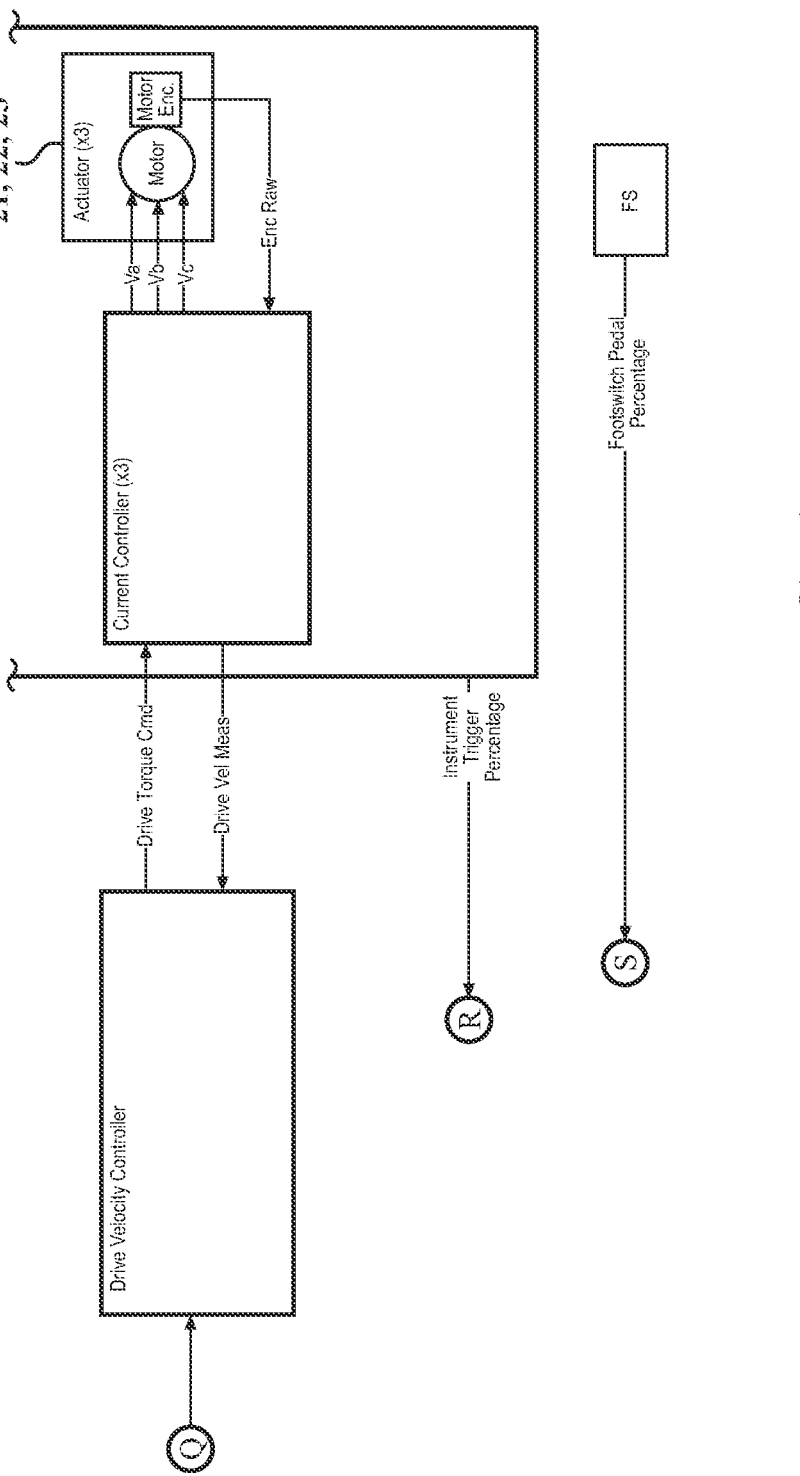

The drive command handler 192 is a part of the control system which calculates and determines particular parameters for controlling the drive motor M (FIG. 17C). The drive command handler 192 receives input command signals from one or more input devices to actuate the drive motor M. As can be seen in FIG. 17E, one example of an input device is a trigger on the hand-held portion of the instrument. Another example, also displayed in FIG. 17E is a foot switch. In another example, the drive command handler has a trigger source select, which may be used to multiplex between multiple user input devices (such as a button, a trigger, and a foot switch). In some examples, the trigger source select only evaluates a change in trigger source when both input devices are inactive, and then evaluates which input device becomes active first. The selected input device may then determines the active trigger percentage. In other examples, potentially one input device may have priority over the other. When one or more of the input devices are actuated, a command signal is sent to the drive command handler 192 which then analyzes the percentage which the input device was actuated (e.g. how far the trigger was squeezed by a user). The drive command handler 192 analyzes the command percentage with the maximum allowed velocity output from the bone preparation portion of the clinical application and modifies the command signal according to the data received.

The drive command handler 192 may also utilize results from the collision detection performed within constraint generator 384 or other component of the control system. In the illustrated configuration, the constraint generator 384 compares the position and/or orientation of the tool to a boundary. Specifically, as described previously, collision detection determines whether the tool is violating the boundary by more than a threshold amount. Further, the collision detection step processes this location information to determine a boundary velocity override signal. As mentioned above, any number of suitable boundaries may be used for this collision detection step, such as the distal or lateral boundaries. The boundary may also be implemented as a distance between the tool and a reference location on bone.

Based on this comparison, the instrument controller 28 may alter a motor parameter, which may be used to slow or stop the drive motor M.

In this example, a separate global inside/outside check, using techniques such as ray casting or a voxel lookup to determine whether the tool 20 is completely beyond the boundary. It should be appreciated that the drive motor control relative to the boundary may use the penetration depth computed above, for the case that the tool is in contact with the boundary, to determine if any part of the blade is penetrating by more than a threshold amount.) In examples in which the tool 20 is modeled with discrete geometric primitives (e.g., spheres), the in/out check will evaluate whether any of these spheres are located beyond the boundary. Once the control system 60 evaluates whether the tool 20 is beyond the boundary, the constraints may be generated and the tool support pose may be updated in a manner to prevent the tool from violating the boundary. However, if the user continues to move the tool beyond the boundary after the joint limits are reached, moves the hand-held portion 16 too quickly, or the bone moves too quickly, or proceeds beyond the boundary in an uncontrolled DOF of the tool 20, then the boundary may be violated. In this instance, the global in/out check may fail, and the drive motor M may be turned off or altered as described previously.

In addition to the boundary velocity override and the joint position velocity override functions, the command signal is then sent through to determine whether the error handling override conditions are met (whether the commands are within expected ranges for normal processing). If the error handling conditions are also met, a drive velocity command is sent from the drive command handler 192 to the drive velocity controller.

It should be appreciated that the boundary velocity override (controlling the speed of the driver motor based on the boundary), the joint position velocity override (controlling the speed of the driver motor based on the actuator position, and the error handling override may all be active simultaneously, and each provide a partial override. For example, the boundary velocity override might reduce the speed by 10%, i.e., multiple the input by 0.9 and then then next block might reduce the speed further by 20%, i.e., multiple its (already reduced) input by 0.8 in that case the resulting output speed is 0.9*0.8=0.72 times the original requested speed command. In other words, the override multiplier (gain from input to output) applied by each block is not dependent on what the other override blocks determined. There may be other ways to combine the multiple override sources in addition to this (cascaded multiplication) approach, such as using only the most restrictive override, etc.

The drive velocity controller processes the drive velocity command signal and determines a drive torque command which is sent to the current controller in the handpiece. The current controller converts this drive torque command to a commanded current and selectively applies voltage as needed to drive the commanded current to the drive motor M, causing the tool to operate (e.g., cut). The drive motor encoder monitors the actuation of the drive motor sending an encoder signal relating to the operation of the drive motor back through the current controller in the instrument. The current controller transforms the encoder data into a drive velocity measurement and sends the transformed feedback data into the drive velocity controller.

As shown in FIGS. 17A-17C, two inputs into the constraint generator 384 comprise the current state (localizer data, kinematic data) and the target state (cutting planes relative to a localized tracker). The constraint generator 384 obtains the target state for the tool 20 and generates one or more guide constraints based on the target state and the current state of the hand-held portion. The current state may be defined based upon the previous commanded pose CP, since the previous commanded pose CP correlates to the current pose of the tool 20. The target state may be defined in the anatomical coordinate system, anatomy tracker coordinate system, or the like, and transformed to a common coordinate system with the current state. Other inputs into the constraint generator 384 comprise the configuration and tuning parameters for the guide constraints. The constraint generator 384 defines the one or more guide constraints based on the relationship between the current state and the target state and the configuration and tuning parameters. The guide constraints are output from the constraint generator 384 into the constraint solver 189.

Various virtual constraints may be fed into the constraint solver 189, including, but not limited to, the guide constraints, joint limit constraints, joint centering constraints, kinematic motion constraints, boundary constraints, and other inputs such as external sensed forces. These constraints may be turned on/off by the control system 60. For example, in some cases, there may be neither joint centering constraints nor boundary constraints being generated. Similarly, there may be no guide constraints being generated in some instances, and in certain modes of operation. All of the virtual constraints employed in the behavior control 186 may affect movement of the tool 20.

The constraint solver 189 calculates the constraint force Fc to be virtually applied to the tool 20 in the virtual simulator 388 based on the virtual constraints fed into the constraint solver 189. When the guide constraint is active, the constraint force Fc comprises components of force and/or torque adapted to move the tool 20 toward the target state from the current state based on the one or more virtual constraints. In cases where only the guide constraints are input into the constraint solver 189, the constraint force Fc can be considered to be the virtual force computed to satisfy the guide constraints. However, when other constraints are employed, such as the boundary constraint, the joint centering constraint, an/or the joint limit constraint, the constraint solver 189 is ultimately tasked with providing, as closely as possible, a solution for the constraint force Fc that satisfies all of the constraints based on their respective tuning parameters, and thus other constraints may also influence the magnitude/direction of the constraint force Fc.

189 In order to solve for Fp, as described below, the equation shown in FIG. 26 is converted into a matrix equation where each row represents a single, one-dimensional constraint. The constraint data is placed in the constraint equation, along with other information known by the constraint solver 189, such as the external force Fcgext, (if applied) a damping force Fdamping, an inertial force Finertial, the virtual mass matrix M, a virtual mass velocity Vcg1, and the time step $\Delta t$ (e.g., 125 microseconds). The resulting Fp is a force vector expressed in a constraint space, in which each component of Fp is a scalar constraint force or torque acting along or about the constraint direction corresponding to that row of the constraint equation.

The virtual mass matrix M combines 3×3 mass and inertia matrices. The damping and inertial forces Fdamping and Finertial are calculated by the virtual simulator 388 based on the virtual mass velocity Vcg1 (e.g., the velocity of the virtual mass coordinate system VM) output by the virtual simulator 388 in a prior time step. The virtual mass velocity Vcg1 is a 6-DOF velocity vector comprising linear and angular velocity components. The damping force Fdamping is a 6-DOF force/torque vector computed as a function of the virtual mass velocity Vcg1 and a damping coefficient matrix (linear and rotational coefficients may not be equal). Damping is applied to the virtual mass to improve its stability. The inertial force Finertial is also a 6-DOF force/torque vector computed as a function of the virtual mass velocity Vcg1 and the virtual mass matrix M. The damping and inertial forces, Fdamping and Finertial, can be determined in the manner described in U.S. Pat. No. 9,566,122 to Bowling et al., hereby incorporated herein by reference.

The constraint solver 189 may be configured with any suitable algorithmic instructions (e.g., an iterative constraint solver, Projected Gauss-Seidel solver, etc.) to solve this system of constraint equations in order to provide a solution satisfying the system of equations (e.g., satisfying the various constraints). In some cases, all constraints may not simultaneously be met. For example, in the case where motion is over-constrained by the various constraints, the constraint solver 189 will essentially find a 'best fit' solution given the relative stiffness/damping of the various constraints. The constraint solver 189 solves the system of equations and ultimately outputs the constraint force Fc.

When a Projected Gauss-Seidel solver is employed, the constraint solver 189 constructs A and b matrices based on the constraints, uses Projected Gauss-Seidel to solve the system of equations to determine the resulting force vector Fp, takes the output of Projected Gauss-Seidel and transforms it from constraint space to the virtual mass coordinate system VM using the aggregate constraint Jacobian Jp for the full set of constraints. For example, using the equation Fc=JpT Fp, wherein Fc is the constraint force, in which the aggregate action of the components of Fp is converted to a force/torque vector Fc applied to the virtual mass coordinate system VM.

Methods of using Project Gauss-Seidel to solve a system of equations for multiple constraints is shown, for example, in "Constraint based physics solver" by Marijn Tamis and Giuseppe Maggiore, dated Jun. 15, 2015 (v1.02), which can be found at http://www.mft-spirit.nl/files/MTamis_ConstraintBasedPhysicsSolver.pdf, or in "Comparison between Projected Gauss-Seidel and Sequential Impulse Solvers for Real-Time Physics Simulations," by Marijn Tamis, dated Jul. 1, 2015 (v1.01), which can be found at http://www.mft-spirit.nl/files/MTamis_PGS_SI_Comparison.pdf, both of which are hereby incorporated herein by reference in their entirety.

The Projected Gauss-Seidel method addresses Linear Complementarity Problems (LCP). Inequality associated with LCP arises since some constraint types (e.g., one-sided constraints, such as the boundary constraints, joint limit constraints, and workspace limit constraints) can only push (apply force) in one direction, e.g., positive constraint force. If the calculated force for such a constraint is negative (or, more broadly, outside its allowed range) for a given iteration of the constraint solver 189, which is invalid, the given constraint must be pruned (or alternately limited/capped at its upper or lower allowed value) and the remaining constraints solved, until a suitable result (i.e., convergence) is found. In this manner, the constraint solver 189 determines the active set of constraints for a given time step, and then solves for their values. Other constraint types can apply forces in both positive and negative directions, e.g., two-sided constraints. Such constraints include the guide constraints, joint centering constraints, and kinematic motion constraints. Such two-sided constraints, when enabled, are usually active and not pruned/limited during the constraint solver 189 iterations.

The constraint force Fc calculated by the constraint solver 189 comprises three components of force along x, y, z axes of the VM coordinate system and three components of torque about the x, y, z axes of the VM coordinate system. The virtual simulator 388 utilizes the constraint force Fc, along with the external force Fcgext (if used), the damping force Fdamping, and the inertial force Finertial (all of which may comprise six components of force/torque), in its virtual simulation. In some cases, these components of force/torque are first transformed into a common coordinate system (e.g., the virtual mass coordinate system VM) and then summed to define a total force FT. The resulting 6-DOF force (i.e., force and torque) is applied to the virtual rigid body and the resulting motion is calculated by the virtual simulator 388. The virtual simulator 388 thus acts to effectively simulate how the various constraints, among other things (e.g. external forces), affects motion of the virtual rigid body. The virtual simulator 388 performs forward dynamics to calculate the resulting 6-DOF pose and velocity of the virtual rigid body based on the given total force FT being applied to the virtual rigid body. In one example, the virtual simulator 388 comprises a physics engine, which is executable software stored in a non-transitory memory of any one or more of the aforementioned controllers 28, 36 and implemented by the control system 60.

For the virtual simulation, the virtual simulator 388 models the tool 20 as the virtual rigid body in the virtual mass coordinate system VM with the origin of the virtual mass coordinate system VM being located at the center of mass of the virtual rigid body, and with the coordinate axes being aligned with the principal axes of the virtual rigid body. The virtual rigid body is a dynamic object and a rigid body representation of the tool 20 for purposes of the virtual simulation. The virtual rigid body is free to move according to six degrees of freedom (6-DOF) in Cartesian space according to the virtual simulation. The virtual simulation may be processed computationally without visual or graphical representations. Thus, it is not required that the virtual simulation display dynamics of the virtual rigid body. In other words, the virtual rigid body need not be modeled within a graphics application executed on a processing unit. The virtual rigid body may exist only for the virtual simulation.

The virtual rigid body and its properties (mass, inertia matrix, center of mass, principal axes, etc.) define how the tool 20 will move in response to applied forces and torques (e.g., from the total force FT, which optionally incorporates forces and torques applied by the user with virtual forces and torques). It governs how the tool 20 will move (e.g., accelerate in translation and rotation) in response to present conditions. By adjusting the properties of the virtual rigid body, the control system 60 can adjust how the tool 20 reacts. It may be desirable to have the properties of the virtual rigid body modeled to be reasonably close to the actual properties of the tool 20, for as realistic motion as possible, but that is not required. For control stability reasons (given the finite acceleration of the actuator assembly, control latencies, etc.), the virtual mass and inertia may be modeled to be somewhat higher than that of the instrument.

The virtual rigid body may correspond to components, which may be on or within the tool 20. Additionally, or alternatively, the virtual rigid body may extend, in part, beyond the physical tool 20. The virtual rigid body may take into account the tool 20 with the tool support 18 or may take into account the tool 20 without the tool support 18. Furthermore, the virtual rigid body may be based on the TCP. In one example, the center of mass of the virtual rigid body is understood to be the point around which the virtual rigid body would rotate if a virtual force is applied to another point of the virtual rigid body and the virtual rigid body were otherwise unconstrained. The center of mass of the virtual rigid body may be close to, but need not be the same as, the actual center of mass of the tool 20. The center of mass of the virtual rigid body can be determined empirically. Once the tool 20 is attached to the tool support 18, the position of the center of mass can be reset to accommodate the preferences of the individual practitioners. In some examples in which no external force is used in the virtual simulation, the precise numerical properties and units of the virtual mass (e.g., center of mass location, mass, inertia matrix) are somewhat arbitrary, because for such a case the virtual simulation does not interact with physical forces measured from the real-world. In such cases, for computational simplicity, it may be desired to simply place the virtual mass at the TCP, setting the mass to 1 and setting the inertia matrix to identity. Other options are possible as well, however, to allow for tuning of the constraints in physically sensible units, more realistic properties for the virtual rigid body may be set if desired. In either case, the constraint tuning parameters should take into account the properties chosen for the virtual mass.

The virtual simulator 388 effectively simulates rigid body dynamics of the tool 20 by virtually applying forces and/or torques on the virtual rigid body in the virtual simulation, i.e., by virtually applying the components of force and torque from the total force $F_T$ on the center of mass of the virtual rigid body in the virtual mass coordinate system VM. Thus, the forces/torques virtually applied to the virtual rigid body may comprise forces/torques associated with the external force $F_{cgext}$ (e.g., which may be based on input from the one or more sensors), the damping force $F_{damping}$, the inertial force $F_{inertial}$, and/or the forces/torques from the constraint force $F_c$ associated with the various constraints (by virtue of being embodied in the constraint force $F_c$).

Rigid body Jacobians can be used to transform velocities and forces from one coordinate system (reference frame) to another on the same virtual rigid body and may be employed here to transform the forces and torques of $F_{ext}$ to the virtual mass coordinate system VM as well (e.g., to yield $F_{cgext}$ used in the constraint equation). The virtual simulator 388 then internally calculates the damping force $F_{damping}$ and the inertial force $F_{inertial}$ and also to output the damping force $F_{damping}$ and the inertial force $F_{inertial}$ for use by the constraint solver 189 in its system of equations in the next time step. If used, the $F_{ext}$ may also be fed to the constraint solver. These forces may be summed together, and then input with the constraint force, to get a total calculation.

A virtual forward dynamics algorithm, as shown in FIGS. 26 and 27, may be employed in the virtual simulation to simulate the motion of the virtual rigid body as it would move upon application of the total force $F_T$. Effectively, the virtual forward dynamics algorithm solves the equation F=ma (or a=F/m) in 6-DOF and integrates the acceleration to yield velocity, which is then integrated again to determine a new pose, with details shown in FIG. 27. The control system 60 inputs the virtual forces and/or torques (e.g., the total force $F_T$) into the virtual simulator 388 and these virtual forces and/or torques are applied to the virtual rigid body at the center of mass (e.g., the CG) in the virtual simulation 388 when the virtual rigid body is in the initial pose with the initial velocity. The virtual rigid body is moved to a final pose having a different state (i.e., position and/or orientation) and with a final velocity within Cartesian space in response to the control system 60 satisfying the inputted virtual forces and/or torques. The next commanded pose CP to be sent to the instrument controller 28 is based on the final pose calculated by the virtual simulator 388. Thus, the virtual simulator 388 operates to determine the next commanded pose CP by simulating the effects of applying the total force $F_T$ on the virtual rigid body using virtual forward dynamics as shown in FIG. 27.

While the virtual simulation is conducted in six degrees of freedom, it should be noted that the actuator assembly may be controllable in fewer than six degrees of freedom, such as three degrees of freedom. In such a situation, the kinematic motion constraint may be used to constrain the uncontrolled degrees of freedom such that the simulation may be meaningfully conducted (i.e., to keep the VM coordinate system aligned to the physical tool).

Velocity limits may be imposed on the virtual rigid body in the simulation. In some cases, the velocity limits may be set high so that they generally don't affect the simulation, or they may be set at any desired value. In some cases, velocity limits may be implemented by computing the damping force to be applied to the virtual rigid body in a non-linear way, in which the amount of damping increases significantly above a threshold velocity. The virtual rigid body is in an initial pose (initial state) and has an initial velocity at commencement of each iteration of the virtual simulation (e.g., at each time step/interval dt). The initial pose and initial velocity may be defined as the final pose and the final velocity output by the virtual simulator 388 in the previous time step.

Thereafter, the virtual simulator 388 calculates and outputs the next commanded pose CP based on its virtual simulation. In this implementation, the control system 60 is configured to command the tool support 18 to move the tool 20 based on the commanded pose CP, which ideally causes movement of the tool 20 in a manner that guides the tool 20 to the target state and in accordance with other virtual constraints.

Figure 28:
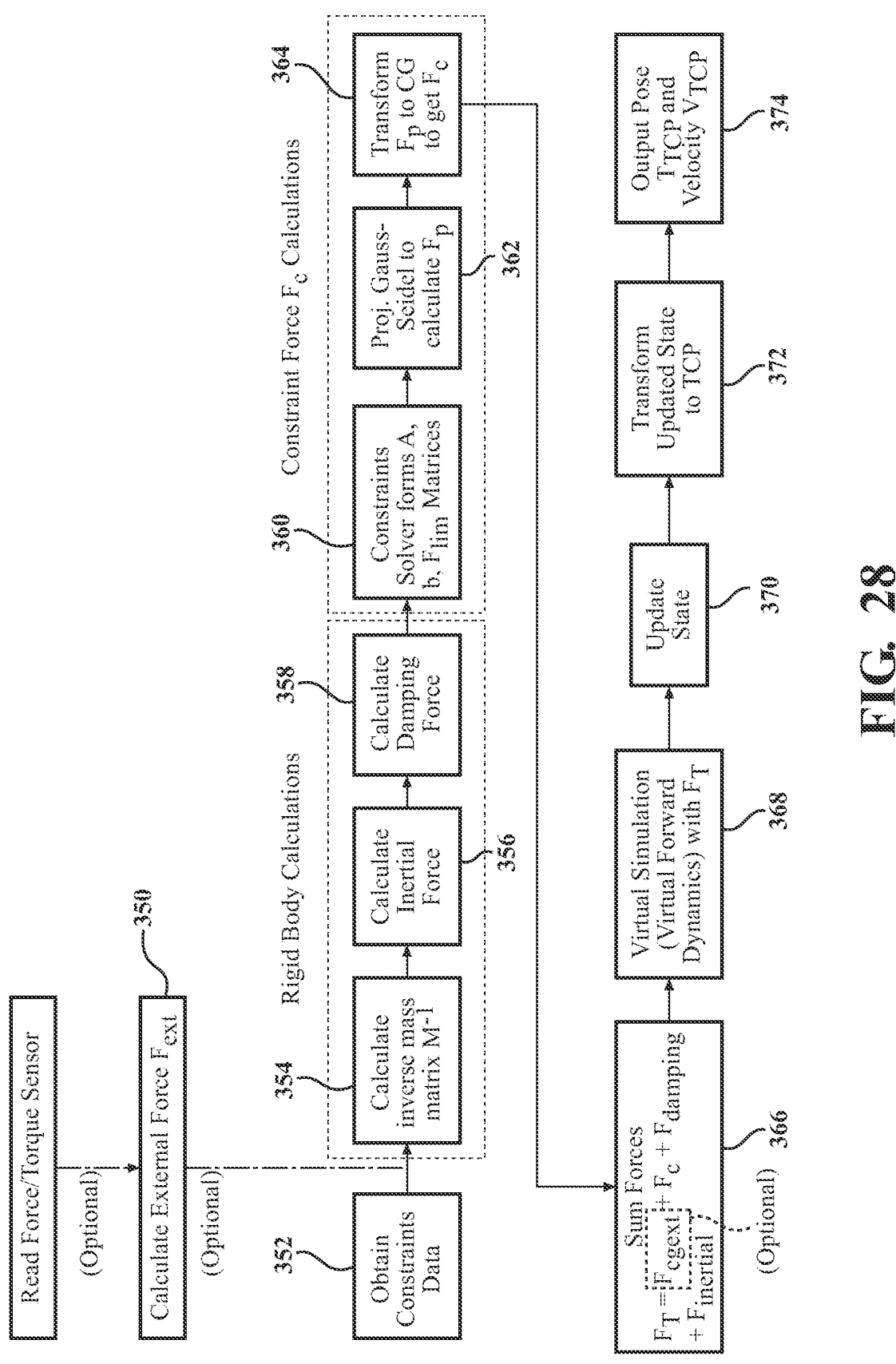
FIG. 28 shows an example set of steps carried out by the control system to solve constraints, perform forward dynamics, and determine a commanded pose
Figure 29A:
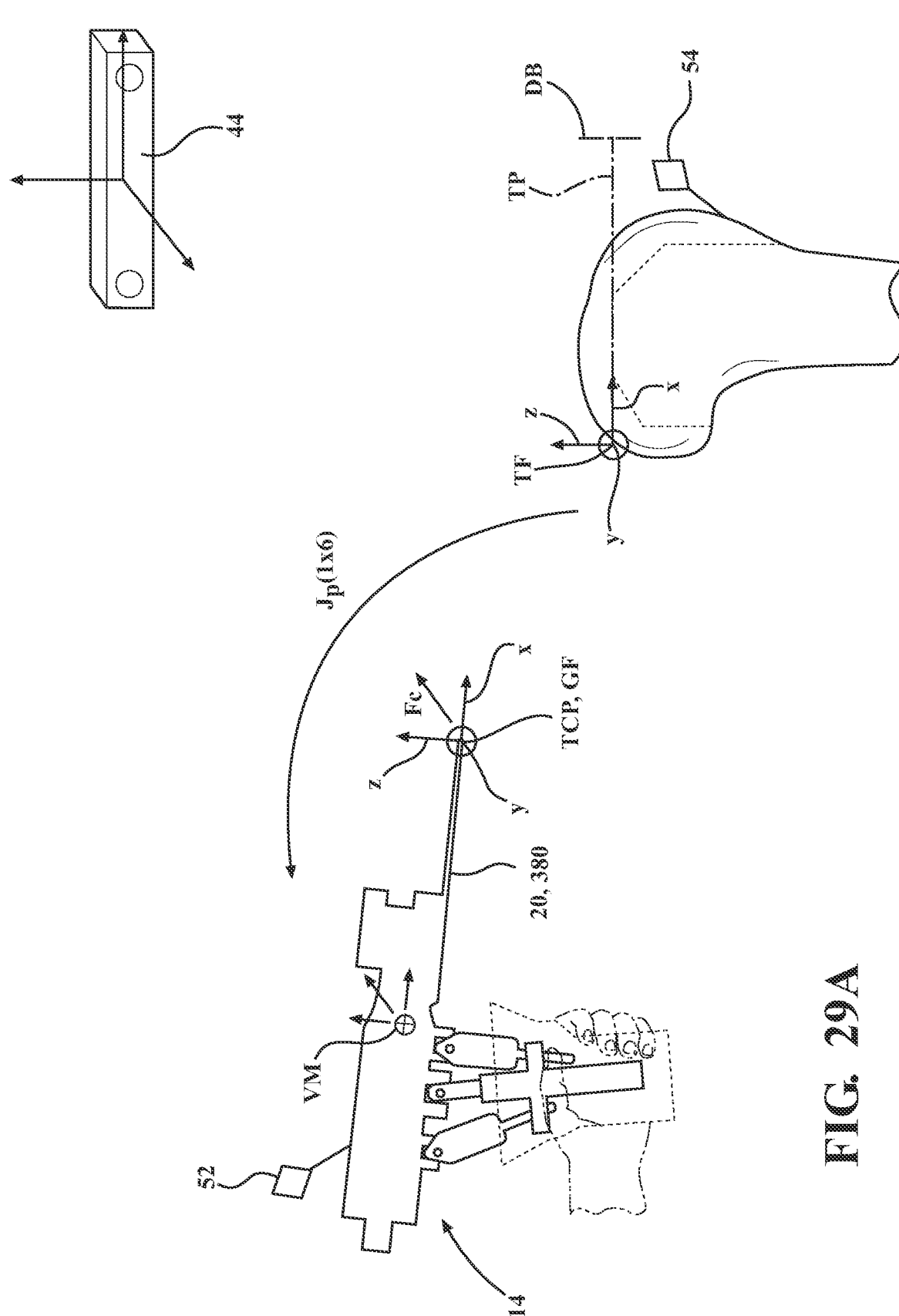
Figure 29B:
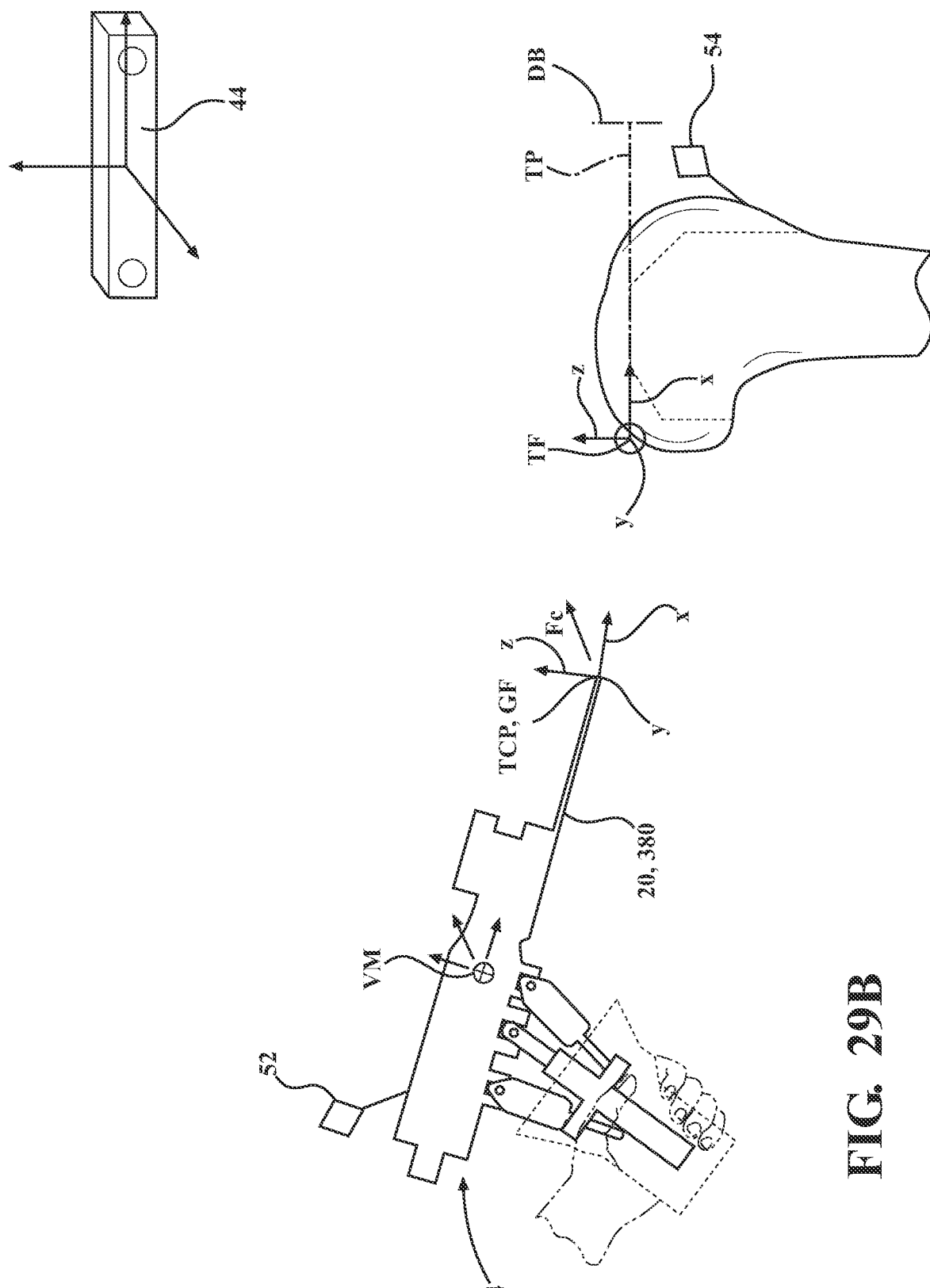
Figure 29C:
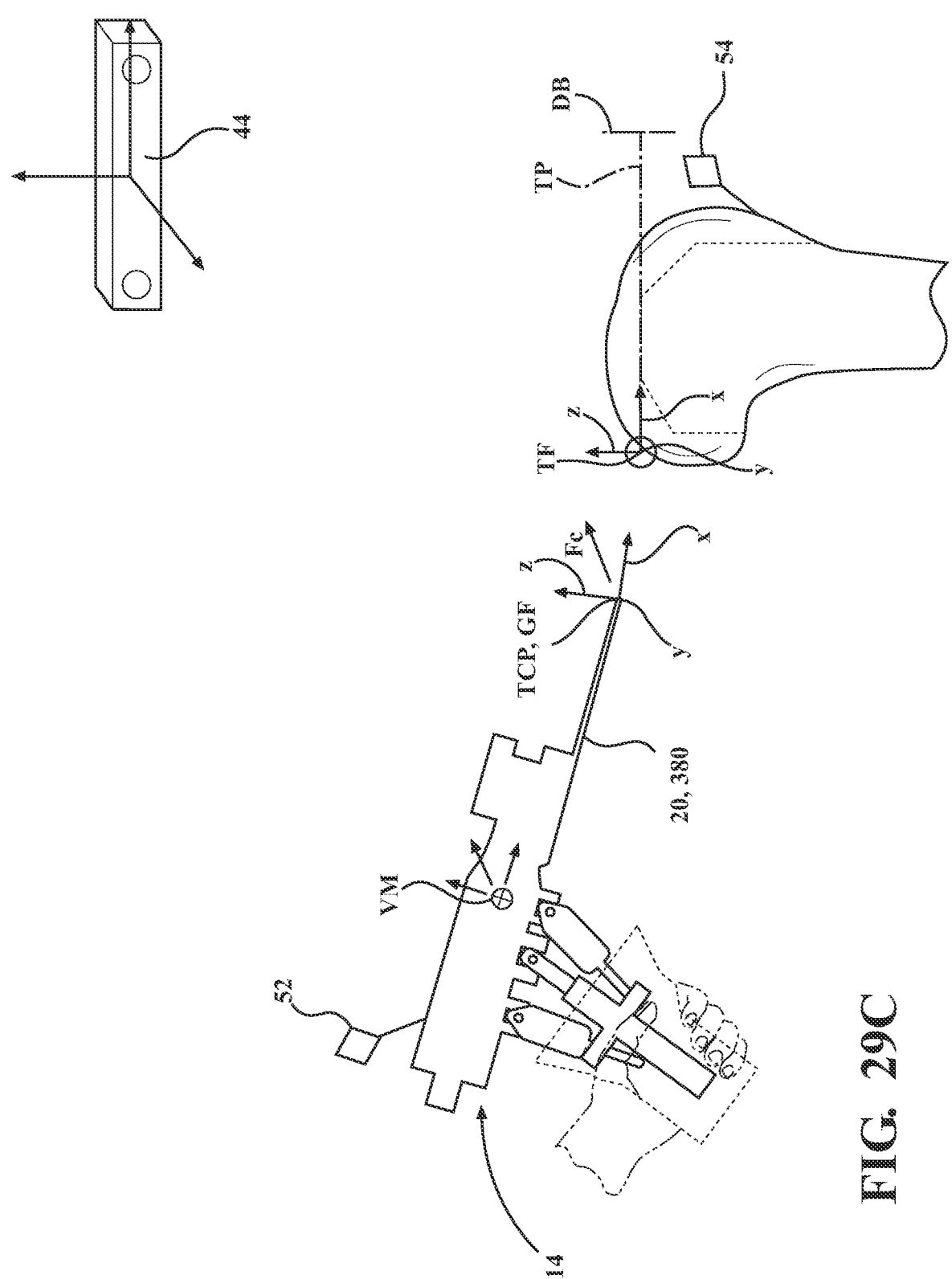

FIG. 28 summarizes various steps carried out by the behavior control 186. These include steps performed by the constraint solver 189 and the virtual simulator 388 as described above. In step 350, the external force $F_{ext}$ is (optionally) calculated based on readings taken from the force/torque sensor S or alternate sensing method. In step 352, the constraints data associated with the various virtual constraints are fed into the constraint solver 189.

In steps 354-358, rigid body calculations are carried out by the virtual simulator 388 to determine the inverse mass matrix $M^{-1}$, the inertial force $F_{inertial}$, and the damping force $F_{damping}$ of the virtual rigid body. In steps 360-364, the constraint solver 189 utilizes the output from the rigid body calculations performed in steps 354-358 and the constraints data provided in step 352 to perform the constraint force calculations previously described to ultimately yield the constraint force $F_c$. In step 366, the constraint force $F_c$ is summed with the external force $F_{ext}$ transformed to the virtual mass coordinate system VM ($F_{cgext}$), the damping force $F_{damping}$, and the inertial force $F_{inertial}$ to yield the total force $F_T$. In step 368, the total force $F_T$ is applied to the virtual rigid body in the virtual simulation conducted by the virtual simulator 388 to determine a new pose and velocity of the virtual rigid body in step 370, and ultimately to transform the new pose and velocity to the TCP in step 372.

The new commanded pose and velocity ($V_{TCP}$) are output by the virtual simulator 388 in step 374.

Knee Application

FIGS. 29A-29D illustrate an application of the guide. In this example, the control system 60 has activated the guide constraint and the virtual constraints to in place the TCP of the tool 20 at a target pose. The localizer LCLZ detects a tool tracker 52 and the patient tracker 54. The localizer LCLZ monitors the position of the instrument 14 relative to the target anatomy. The clinical application uses the implant plan to determine the target cutting plane TP relative to the patient tracker 54 and provides this to the control system. Once the particular cut is selected, receives location information from the localizer LCLZ relating to the position of the instrument 14 and the patient anatomy. The control system 60 further uses the device tracker and patient tracker locations and the encoder data of the joint position of each actuator 21, 22, 23 to determine the pose of the base coordinate system BCS of the hand-held portion 16 with respect to the patient tracker 54. The control system 60 determines a set of virtual constraints which will move the tool support 18 and the saw blade 20, 380 towards the target pose. In this instance, the control system will attempt to place the saw blade 20, 380 onto the target pose TP while balancing a plurality of virtual forces to keep the actuators 21, 22, 23 within their operating limits. The control system 60 generates several guide constraints based on the location data. The guide constraints are employed in three degrees of freedom to guide the tool support 18 toward the target state, i.e. a position constraints along the z axes of the target coordinate system TF to guide the origin of the guided coordinate system GF to the origin of the target coordinate system TF and two orientation constraints about the x, and y axes of the target coordinate system TF to guide the z axis of the guided coordinate system GF to align with the z axis of the target coordinate system TF. Additionally, joint limit constraints are computed, typically having a much larger stiffness than the guide constraints, to ensure that the actuators 21, 22, 23 are not commanded to a position outside the limits of travel.

In some cases, only one, two, three, four, or more guide constraints may be used. More than six guide constraints could also be used, such as when more than one guide constraint is defined for any degree of freedom. The progression from FIG. 29A through 29D shows the guided coordinate system GF aligning with the target coordinate system TF in three degrees of freedom for illustration purposes. In the progression from FIG. 29A through FIG. 29D, the TCP of the tool 20 is shown moving toward the target state (in this case, toward the origin of the target coordinate system TF). At each time step, the constraint force $F_c$ is calculated and takes into account the guide constraints, the joint limit constraints, the workspace constraints, the joint centering constraints the kinematic motion constraints, or a combination thereof to effectively guide the tool support 18 into applying forces and torques that ideally move the saw blade 380 toward the target state. In one example, only the guide constraint and joint limit constraint are active when the TCP is at this position. The virtual constraints may be dynamic by virtue of their tuning parameters being adjusted at each time step. For example, some of the virtual constraints may have stronger spring and/or damping properties and other virtual constraints may have weaker spring and/or damping properties the closer the current state gets to the target state (e.g., the closer the guided coordinate system GF gets to the target coordinate system TF). In one instance, the guide constraint has stronger spring and/or damping properties the closer the current state gets to the target state. Thus, the constraint force $F_c$ (which may comprise components of force and/or torque that correlate to the stronger spring and/or damping properties) may increase in magnitude as the guided coordinate system GF approaches the target coordinate system TF.

In one example, the control system determines a target pose of the saw blade 380 in at least one degree of freedom with respect to a known coordinate system, such as the patient anatomy. The control system 60 also determines the pose of the hand-held portion 16 within the same coordinate system, i.e., relative to the patient anatomy. The control system 60 then processes the location information of the saw blade 380 and the hand-held portion 16 to calculate one or more guide constraints based on the target pose of the saw blade 380 and the pose of the hand-held portion 16. Once the one or more guide constraints are generated, a constraint force is calculated by the control system 60 and adapted to move a virtual saw blade within a virtual simulation. The virtual simulation simulates dynamics of the virtual saw blade based on the constraint force and calculates a commanded pose based on the virtual simulation. The commanded pose is output from the virtual simulation and used to determine a commanded joint position of each of the actuators 21, 22, 23. The control system 60 forwarding the commanded joint position signal to each actuator 21, 22, 23, energizing the actuator 21, 22, 23 to move the tool support 18 and the saw blade 380 to the target pose.

FIGS. 18-20 illustrate another example of the guide being used in placing the tool 20 (e.g., with the saw blade 380) at the target state. In this example, the control system 60 has activated the guide and the associated guide constraints to assist the user in placing the TCP of the tool 20 at a target pose in at least one degree of freedom located relative to a desired cutting plane 73c for a total knee replacement, which includes placing the TCP at a target orientation and elevation that aligns the tool 20 with the desired cutting plane 73c. In this case, the origin of the target coordinate system TF is offset from the desired cutting plane 73c by at least half the blade thickness to account for blade thickness. At least one guide constraint is calculated and employed in at least one degree of freedom to move the tool support 18 towards the target pose. In one example, three guide constraints are employed in three degrees of freedom to move the saw blade to the target state, i.e., one position constraint along the z axis of the target coordinate system TF and two orientation constraints about the x, y axes of the target coordinate system TF.

At each time step, the constraint force $F_c$ is calculated and takes into account the active virtual constraints (e.g. guide constraints, joint limit constraints, joint centering constraints, kinematic motion constraints, and/or workspace constraints), to effectively guide the tool support 18 into applying forces and torques that ideally move the saw blade 380 toward the target state. The virtual constraints may be dynamic by virtue of their tuning parameters being adjusted at each time step. Referring to FIG. 20, for example, the guide constraints may have greater stiffness the closer the current state gets to the target state (e.g., the closer the guided coordinate system GF gets to the target coordinate system TF in the x-axis direction—see the x distance). Thus, referring to FIG. 20, the stiffness associated with the tuning parameters for the guide constraints may increase in magnitude as the x distance decreases.

Alignment of the tool 20 to the desired cutting plane assists the user in making precise cuts along the femur and/or tibia to make room for a total knee implant, for example. Referring back to FIG. 13, guide constraints could be used to align the tool 20 to each of the five target cutting planes TP, 73a-73e that may be required for the femur. The guide constraints can similarly remain active during the cutting process so that the blade is maintained at the target state.

Further, the virtual boundary 184 may be optionally employed to control the operation of the drive motor M. As the drive motor M is actuated, oscillating the saw blade 380 during the cut, the actuation signal to the drive motor M may be stopped and/or changed based on the state of the saw blade 380 relative to the virtual boundary 184. The virtual boundary 184 may prevent the user from cutting the patient anatomy incorrectly, particularly preventing the saw blade 380 from cutting a portion of the patient anatomy that is not intended to be affected (e.g. ligaments). Looking at FIG. 18, as the saw blade 380 is advanced along target cut plane, one or more motor parameters of the drive motor are controlled. In one example, the motor parameter is a speed of the drive motor (and thus the cutting speed of the saw blade 380) based on the location of the saw blade 380 relative to a virtual boundary 184. However, other motor parameters are contemplated, such as torque, operation time, current, acceleration, or a combination thereof. The virtual boundary, such as that shown in FIG. 13, corresponds with an end point of a particular cut, depending on which cut the user is making to fit the implant to the patient anatomy. In other examples, the virtual boundary 184 may be a mesh, a point, a plane, or a combination thereof as described above. The virtual boundary may be based on the anatomy, the planned implant, image data, etc. As the saw blade 380 progresses through the patient anatomy, the location data of the instrument 14 relative to the patient tracker, and subsequently the target plane is updated in real time. When the saw blade 380 reaches the virtual boundary 184, the motor parameter (speed of the motor) may be set to 0 or reduced. When the motor parameter has a value of 0, the drive motor M is shut off so the user does not cut past the virtual boundary 184.

In another example, the drive motor M is controlled based on the pose of the tool relative to the boundary 184 in at least one uncontrolled degree of freedom which the actuators 21, 22, 23 are incapable of adjusting the tool support 18. A controlled degree of freedom is a movement direction which is controlled by the actuator assembly 400 and is based on the arrangement of the actuators 21, 22, 23. In some configurations, the arrangement of the actuator assembly 400 may provide for six controlled degrees of freedom, five controlled degrees of freedom, four controlled degrees of freedom, three controlled degrees of freedom, or at least one controlled degree of freedom. For example, the actuator assembly 400 is arranged to control pitch (FIGS. 3A-3C), roll (FIGS. 4A-4C), and z-axis translation (elevation relative to the hand-held portion 16—FIGS. 5A-5C). The instrument 14 is able to adjust the tool support 18 and the tool 20 relative to the hand-held portion in these movement directions. When a degree of freedom is uncontrolled, the actuators, 21, 22, 23 are incapable of adjusting in that particular direction. For example, in some configurations, the yaw of the tool support 18 cannot be adjusted since the actuators 21, 22, 23 are arranged to control pitch, roll, and z-axis translation (elevation relative to the hand-held portion 16). As another example, when the actuators 21, 22, 23 are arranged to control pitch, roll, and z-axis translation (elevation relative to the hand-held portion 16), the linear translation along a longitudinal axis (x translation) is an uncontrolled degree of freedom since the actuator assembly 400 does not control translational movement along the longitudinal axis. In this way, the virtual boundaries may be established to control the boundary in those degrees of freedom that are uncontrollable by the actuator assembly, such as x-axis translation. This may be configured as the boundary for controlling depth of the tool described above. As mentioned, the boundary for controlling depth may be generally perpendicular to the target plane. As such, while this boundary may not be used for controlling the plurality of actuators, the boundary may be used for controlling the drive motor. In some examples, both the uncontrolled degrees of freedom and the controlled degrees of freedom may be used as an in/out check to control the drive motor M. The control system 60 may use the controlled degrees of freedom as a secondary error mitigation, such as when the saw blade does not stay on plane due to an error or malfunction. In this example, both the controlled degrees of freedom and uncontrolled degrees of freedom, along with the boundary, control the energization of the drive motor M. Thus, while the actuator assembly would not function to prevent the tool from being positioned by a user beyond this boundary, the control system 60 would prevent the user from actuating the drive motor M when the TCP was indicative of the distal end of the tool being beyond the boundary. It should be appreciated that the virtual boundaries may also be used to control the drive motor in the controlled degrees of freedom.

The control system may compute the appropriate motion parameter to move the tool support relative to the hand-held portion. The motion parameter may be computed based on the commanded pose. Based on this determined motion parameter, the control system may compute the appropriate signal to send to each of the plurality of actuators. In one example, the control system may output a joint velocity command based on the determined motion parameter and the commanded position for that actuator. It should be appreciated that in some examples, the tool support moves relative to the hand-held portion at a variable velocity. The motion of each actuator may be based on the force applied to the tool support by each of the plurality of actuators.

Figure 30A:
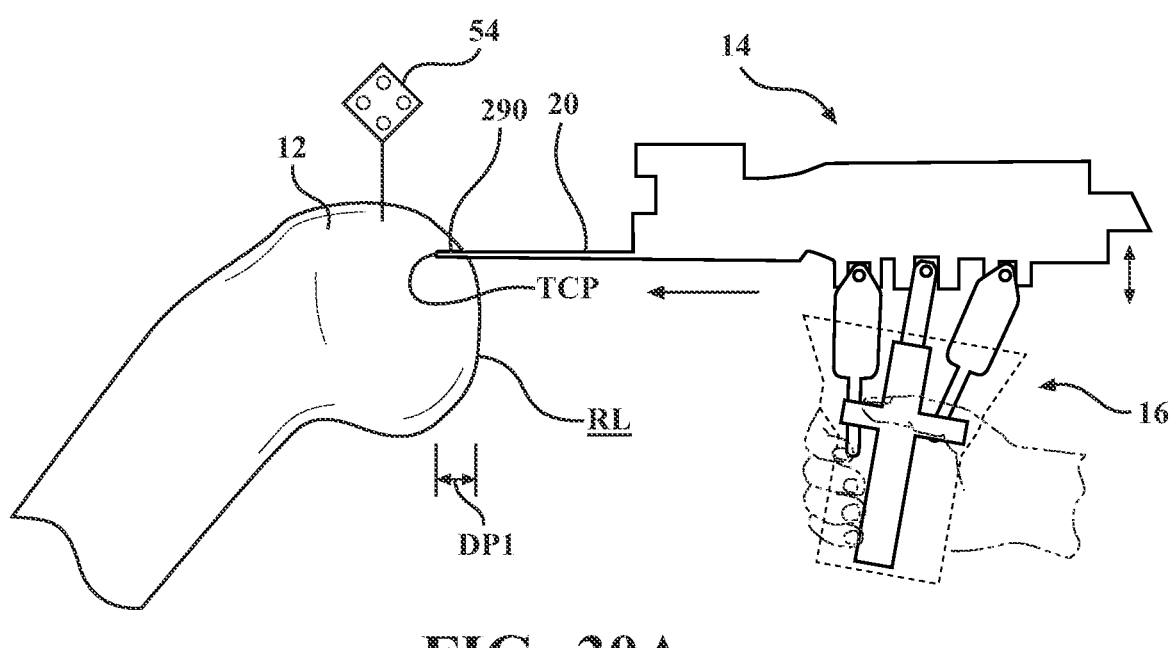
FIGS. 30A and 30B show a schematic view of a robotic instrument performing a cut with respect to the guide behavior.
Figure 30B:
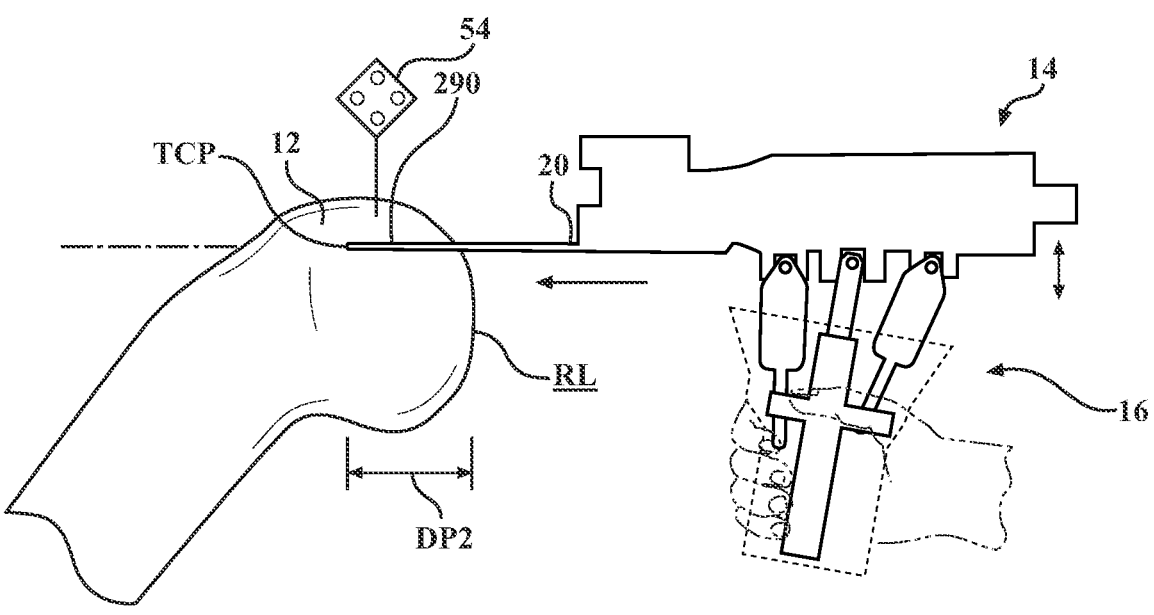

Referring to FIGS. 30A and 30B, once a kerf is established, the control system 60 may automatically adjust values of one or more motion parameters of the tool 20 relative to the hand-held portion 16 with the one or more virtual constraints as the user cuts the target cut plane which is associated with anatomy of a patient (e.g. bone to be cut). In one example, while approaching the cut, the guide constraints enabled and the tool is automatically aligning to the target plane. The control system 60 maintains the active state of the guide constraints as the tool contacts bone and enters beyond a specified depth boundary, distance parameter relative to a reference location/reference coordinate system. At the moment the tool passes the specified depth, the control system 60 senses the current positions of the actuators, and sets the current position of the actuators as the new joint centering positions, enabling the joint centering constraints and disabling the guide constraints. This causes the system to enter a free hand mode with the 'saw blade to handle' alignment frozen as it was when it first entered and proceeded into the bone. The user may continue cutting, but the control system 60 does not automatically correct for alignment while the blade remains within the bone beyond the specified depth because the guide constraints are inactive. Even though the instrument is frozen in a fixed pose, the blade still stays approximately on the cutting plane, since the slots in the bone formed by the initial cut is mechanically constraining the motion of the blade to stay in that cut plane. As the user starts to move the blade towards the bone exit, the system returns to a mode where the guide constraints are active once the depth is less than the earlier configured value (e.g., the pose of the blade relative to a reference location/reference coordinate system is at a threshold value). At this point, joint centering constraints are disabled and the guide constraint is reenabled to resume aligning the blade to the plane. By disabling the guide constraints and enabling joint centering constraints, the tool is prevented or less likely to bind the blade within bone. Once a certain depth of cut is reached in hard bone, the blade is effectively constrained on the top and bottom by bone slot formed during the initial cut entry. If the accuracy of the blade alignment has any small errors (due to calibration inaccuracy, blade skiving or diving due to compliance, etc.), the robotic system may be prevented from restoring the blade to the cutting plane since the top and bottom of the blade do not remove bone, and the already machined surface of the bone may block the blade from returning to the cut plane. As a result, the control system is limited in restoring the alignment of the blade when deep into the bone, and, if binding occurs, cause the user to have to apply increased force to complete the cut. Such an approach may ensure that the guide constraints are enabled upon bone approach (within a threshold value of a reference location/reference coordinate system) and first cut entry, to ensure that the initial cut entry performed in the bone is as accurate as possible, and to continue this alignment until a certain depth is reached sufficient to mechanically constrain further (deeper) motion of the blade.

In this example, the guide constraints may have a virtual force approaching 0, meaning that the guide constraints may be shut off and/or their tuning parameters adjusted since the saw blade is established within the kerf (FIG. 30B). The joint centering constraints, which direct the rotors 148 towards a center point on the leadscrew of each actuator 21, 22, 23, may also be shut off and/or have the centering positions re-set to the current position of the actuators 21, 22, 23 when a specified cutting depth is reached, while the saw blade 380 cuts into the patient anatomy (FIG. 30B). The control system 60 may change the rate of adjustment of the actuators 21, 22, 23 automatically based on a distance parameter (e.g. direction, magnitude) determined from the pose of the tool 20 (e.g., from the TCP) relative to the reference location associated with the bone. The pose of the tool 20 may be maintained while the guidance array 200 directs the user to move the hand-held portion 16 to maintain or correct to the desired plane. It is contemplated that the joint limit constraints and/or the workspace constraints may remain active even after the kerf is established.

With reference to FIG. 30A, one exemplary way of controlling the plurality of actuators is described. When the position of the saw blade (TCP) is spaced from the reference location associated with bone (RL) with a first distance parameter (DP1), the instrument is controlled such that the tool support is moved relative to the handheld portion, e.g., a motion parameter with a magnitude greater than zero is used. This is because the kerf has not yet been sufficiently established. In this instance, the guide constraints have a value greater than zero and have a high stiffness value, actively adjusting and commanding the tool support 18 to stay on the desired cutting plane.

With reference to FIG. 30B, when the position of the saw blade (TCP) is spaced from the reference location associated with bone (RL) with a second distance parameter (DP2), the instrument is controlled such that a motion parameter has a lower magnitude, such as a magnitude of zero is utilized or the movement of the tool support relative to the hand-held portion is otherwise stopped. This is because the kerf has been sufficiently established. In this instance, the guide constraint force value is reduced or inactive and the joint centering constraint force value is also reduced and/or disabled. Alternately, the joint centering constraint may be re-set to hold this fixed relative pose between the tool support 18 and hand-held portion 16.

Once the tool 20 establishes the kerf, the instrument controller 28 may set the value of the motion parameter to a lower magnitude or zero and/or control the state of the virtual constraints, to stop or reduce the actuators 21, 22, 23 from adjusting the tool support 18 relative to the hand-held portion 16. Once the tool 20 has established a cut path within the bone, the tool 20 may flex and move off course a small amount (e.g. skive), pushing back onto the hand-held portion 16 as the control system attempts to adjust for the error. The user may perceive this force as a push-back, since a saw blade is not typically designed to remove hard bone in the direction necessary to adjust pitch and/or roll, for example, once embedded into bone. The sense of "push-back" or "fighting" the hand-held portion is created by the instrument controller 28 controlling the actuators 21, 22, 23 while the tool 20 is in the cutting slot 290. Thus, the only movement that is caused by controlling the actuators to move towards the desired plane is movement of the hand-held portion 16. This means that the instrument controller 28 may cause forces to be applied to the hand-held portion 16, which are then transferred to a user's hand. These forces may result in fatigue and/or discomfort during the cutting process. By changing the motion parameter, the tool 20 may provide less resistance further in the cut. A user may find that by setting the motion parameter value to 0 or by otherwise stopping the movement of the hand-held portion relative to the tool support allows the cut to be finished without struggling against the hand-held portion 16 when the tool 20 is within the cutting slot 290, the cutting slot 290 serving as a natural cut guide (See FIGS. 30A-30B). More particularly, the instrument controller 28 may actively change values of the motion parameter relating to force, velocity, acceleration, or other states of each of the virtual constraints, so that the further the tool 20 enters into the target anatomy, the actuators 21, 22, 23 adjust towards the target plane with a relatively lower force, velocity and/or acceleration than when the cut was first initiated, eventually stopping actuator movement when the tool 20 is mid cut, utilizing the path cut into the bone as the guide. In some examples, an external force/torque sensor may allow the user's applied force to be considered in the virtual simulation. In such cases, the stiffness of the guide constraint may be reduced once the saw blade is sufficiently into the bone and the kerf is established. With reduced guide stiffness and sensing of the user applied force, the constraint solver may find an equilibrium in which the user is able to balance out the guide forces with a small magnitude of applied force. This may give the user haptic feedback indicating to the user that the tool 20 is not perfectly aligned on plane, but at a magnitude such that it does not create fatigue or cause the hand-held portion 16 to push back excessively to the point that the joint limits of the actuators 21, 22, 23 are exhausted.

One exemplary way to control the motion parameter of the tool support is by changing the state of the of the virtual constraints as mentioned above. For example, changing the state of the one or more virtual constraints may include activating the one or more of the virtual constraints, deactivating one or more of the virtual constraints, or changing the tuning parameter of one or more of the virtual constraints (i.e., increasing or decreasing the tuning parameters of the virtual constraint). The joint limit constraints may remain active when the guide constraints or the joint centering constraints are inactive. In other words, by changing the states of the virtual constraints, the tool support 18 may move with a greater force, velocity and/or acceleration when the cut is first begun (high stiffness for the guide constraints), then the force, velocity and/or acceleration after the tool 20 has progressed a threshold distance into bone relative to the reference location (low stiffness for the guide constraint constraints). While stopping the actuators 21, 22, 23 from adjusting the tool support 18 was described in terms of setting the motion parameter to zero, it should be appreciated that the actuators 21, 22, 23 may be stopped with other suitable control logic, such as by stopping the motion control aspect of the algorithm or otherwise freezing the position of the plurality of actuators 21, 22, 23. As described above, the states of the virtual constraints may be controlled based on monitoring any suitable variable, such as the state of the tool, such as the saw blade, relative to a reference location on the patient, such as bone. Alternatively, the states of the virtual constraints may be controlled based on the state of the tool relative to a virtual object, such as the target plane. FIG. 11 illustrates processes carried out to execute the guide, such as when the tool 20 comprises the saw blade 380. In this version, the behavior controller 186 comprises the guide handler which may be synonymous with the constraint generator 384, the constraint solver 189, and the virtual simulator 388. The behavior control 186 further comprises the boundary handler 389 to optionally generate virtual boundary constraints based on the one or more virtual boundaries 184 generated by the boundary generator 182. The guide handler/constraint generator 384, constraint solver 189, virtual simulator 388, and boundary handler 389 each comprise executable software stored in a non-transitory memory of any one or more of the aforementioned controllers and implemented by the control system 60.

In addition, in another exemplary configuration, based on the magnitude of sensed external force, either from a force/torque sensor or derived via actuator motor currents, the control system may trigger the joint centering mode. This allows the control system to detect 'fighting' and go into 'fixed handle' mode when detected. Such a method would also typically be utilized in conjunction with drive motor boundary control, to ensure that the saw blade stays sufficiently on plane when the handle is fixed (and hopefully being guided by the kerf) to allow the cut to continue. If the boundary gets violated (due to the saw blade drifting too far off plane), either feedback could be given to the user through a suitable indicator or the drive motor parameter may be adjusted (e.g., the drive motor may be turned off).

The guide constraint may be used to align a drill bit or bur and/or tap for a screw, anchor, or other fastener when other types of tools are coupled to the tool platform. The guide constraint may be used to align an impactor with a desired trajectory for impacting an acetabular cup implant to seat the acetabular cup implant into a prepared acetabulum. The guide constraint may be used to align tools used to seat other types of implants. The guide constraint may be used for aligning/guiding tools for placing k-wires, cannula, trocars, retractors, and the like.

Input devices, such as on the various user interfaces UI may be employed to switch/activate the various modes of operation of the instrument 14. For example, the UI of the tool 20 may have an input device (button, touch sensor, gesture input, foot pedal, trigger, etc.) that can be actuated to activate the one or more virtual constraints so that the constraint force $F_c$ comprises components of force and torque associated with moving the tool. The control system 60 may be configured to automatically change states of the virtual constraints in certain situations. The control system 60 may also first prompt the user before automatically continuing in another mode, such as by providing selectable prompts on one or more of the displays 38 to continue in the selected mode.

Further, it is contemplated that the instrument controller 28, the user, or both may switch the instrument 14 between modes and behaviors manually through an input device, automatically based on navigation data, actuator data, drive motor data, or a combination thereof. In some cases, the user may determine that the instrument should be held in a particular pose (the tool support relative to the hand-held portion) and override the instrument controller with an input device.

In some configurations, the surface of an anatomical feature to be cut (e.g. surface of a bone) may serve as a reference point, a virtual boundary, or both causing the instrument controller 28 to change operation modes or behavior of: (i) the instrument 14; (ii) one or more actuators 21, 22, 23; (iii) guidance array 200; (iv) one or more visual indicators 201, 202, 203; (v) or a combination thereof.

In some examples, the instrument controller 28 may utilize one or more inputs to determine one or more outputs. The one or more inputs may include a pose of the bone determined by a patient tracker 54, 56, such as the reference location, the tool center point TCP of the tool 20 or pose of the TCP coordinate system by a tool tracker 52 on the tool support 18, the pose of the hand-held portion 16, a commanded pose of the tool 20, a distance parameter, actuator information (such as a commanded or measured position and/or pose, a current position and/or pose, a past position and/or pose, etc.), an input signal from a footswitch, trigger, or touch-screen, or a combination thereof. The one or more outputs of the instrument controller 28 may include changing a motor parameter of the drive motor M, adjusting a motion parameter (e.g. changing the state or tuning parameter of a constraint) of the tool support 18, including changing force, acceleration or velocity, may turn off the boundary control, hold or freeze the tool 20 and tool support 18 relative to the hand-held portion 16, activate a homing mode, or a combination thereof. Any suitable combination of inputs may be utilized with any suitable output.

The current state of the tool 20 and/or current state of one or more actuators relative to the target state and/or relative to the surgical site or relative to the commanded position may be output by the navigation system 32 and represented on the displays 38 via graphical representations of the tool 20, tool support 18, hand-held portion 16, actuators 21, 22, 23, target state, virtual boundaries 184, and/or the surgical site, e.g., the femur F, tibia T, pelvis, vertebral body, or other anatomy. These graphical representations may update in real-time so that the user is able to visualize their movement relative to the target state, virtual boundaries 184, anatomy, etc. For example, the graphical representations of the tool 20 and anatomy may move on the displays 38 in real-time with actual movement of the tool 20 by the tool support 18 and actual movement of the anatomy.

It should be understood that the combination of position and orientation of an object is referred to as the pose of the object. Throughout this disclosure, it is contemplated that the term pose may be replaced by position and/or orientation in one or more degrees of freedom and vice-versa to achieve suitable alternatives of the concepts described herein. In other words, any use of the term pose can be replaced with position and any use of the term position may be replaced with pose.

The methods in accordance with the present teachings is for example a computer implemented method. For example, all the steps or merely some of the steps (i.e. less than the total number of steps) of the method in accordance with the present teachings can be executed by a computer (for example, at least one computer). A configuration of the computer implemented method is a use of the computer for performing a data processing method. Further, in the present teachings, the methods disclosed herein comprise executing, on at least one processor of at least one computer (for example at least one computer being part of the navigation system), the following exemplary steps which are executed by the at least one processor.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating or determining steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term computer includes a server resource. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the present teachings. The cloud computer is for example an elastic compute cloud (EC2) as provided by Amazon Web Services™. A computer for example comprises interfaces in order to receive or output data and/or perform an analogue-to-digital conversion. For example, the present teachings may not involve or in particular comprise or encompass an invasive step which would represent a substantial physical interference with the body requiring professional medical expertise to be carried out and entailing a substantial health risk even when carried out with the required professional care and expertise. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is a virtual reality device or an augmented reality device (also referred to as virtual reality glasses or augmented reality glasses) Another example of a display device would be a standard computer monitor comprising for example a liquid crystal display operatively coupled to the computer for receiving display control data from the computer for generating signals used to display image information content on the display device.

The present teachings also relate to a computer program comprising instructions which, when on the program is executed by a computer, cause the computer to carry out the method or methods, for example, the steps of the method or methods, described herein and/or to a computer-readable storage medium (for example, a non-transitory computer-readable storage medium) on which the program is stored and/or to a computer comprising said program storage medium and/or to a (physical, for example electrical, for example technically generated) signal wave, for example a digital signal wave, such as an electromagnetic carrier wave carrying information which represents the program, for example the aforementioned program, which for example comprises code means which are adapted to perform any or all of the method steps described herein. The signal wave is in one example a data carrier signal carrying the aforementioned computer program. The present teachings also relate to a computer comprising at least one processor and/or the aforementioned computer-readable storage medium and for example a memory, wherein the program is executed by the processor.

Within the framework of the present teachings, computer program elements can be embodied by hardware and/or software (this includes firmware, resident software, microcode, etc.). Within the framework of the present teachings, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction executing system. Such a system can be a computer; a computer can be a data processing device comprising means for executing the computer program elements and/or the program in accordance with the present teachings, for example a data processing device comprising a digital processor (central processing unit or CPU) which executes the computer program elements, and optionally a volatile memory (for example a random access memory or RAM) for storing data used for and/or produced by executing the computer program elements. Within the framework of the present teachings, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet.

In this application, including the definitions below, the term "controller" may be replaced with the term "circuit." The term "controller" may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The controller(s) may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are the BLUETOOTH wireless networking standard from the Bluetooth Special Interest Group and IEEE Standard 802.15.4.

The controller may communicate with other controllers using the interface circuit(s). Although the controller may be depicted in the present disclosure as logically communicating directly with other controllers, in various configurations the controller may actually communicate via a communications system. The communications system includes physical and/or virtual networking equipment such as hubs, switches, routers, and gateways. In some configurations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various configurations, the functionality of the controller may be distributed among multiple controllers that are connected via the communications system. For example, multiple controllers may implement the same functionality distributed by a load balancing system. In a further example, the functionality of the controller may be split between a server (also known as remote, or cloud) controller and a client (or, user) controller.

Some or all hardware features of a controller may be defined using a language for hardware description, such as IEEE Standard 1364-2005 (commonly called "Verilog") and IEEE Standard 10182-2008 (commonly called "VHDL"). The hardware description language may be used to manufacture and/or program a hardware circuit. In some configurations, some or all features of a controller may be defined by a language, such as IEEE 1666-2005 (commonly called "SystemC"), that encompasses both code, as described below, and hardware description.

The various controller programs may be stored on a memory circuit. The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective C, Swift, Haskell, Go, SQL, R, Lisp, Java®, Fortran, Perl, Pascal, Curl, OCaml, JavaScript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SENSORLINK, and Python®.

CLAUSES

I. A computer-implemented medical program or product of controlling movement of a hand-held medical robotic system for use with a tool, the method, program, or product comprising instructions, which, when the program is executed by a computer, cause the computer to complete the following steps: determining a target pose of the tool a known coordinate system; determining a pose of the hand-held portion in the known coordinate system; determining a guide constraint based on the target pose of the tool and the pose of the hand-held portion; calculating a constraint force adapted to move a virtual tool toward the target pose based on the guide constraint; simulating dynamics of the virtual tool in a virtual simulation based on an input from the constraint force, and to output a commanded pose based on the virtual simulation; and determining a commanded joint position of each of a plurality of actuators based on the commanded pose. The clause of I, further comprising controlling each of plurality of actuators based on the commanded joint position of each of the plurality of actuators; OR tracking a portion of patient anatomy with a patient tracker in the known coordinate system, the known coordinate system defined relative to the patient tracker OR further comprises determining a position of each of the actuators of the plurality of actuators, and determining a pose of the tool, and the step of determining the pose of the hand-held portion is based on the pose of the tool and the position of each of the actuators of the plurality of actuators OR wherein the step of determining a position of each of the plurality of actuators is further defined as measuring a position of the each of the plurality of actuators with an encoder coupled to each of the plurality of actuators OR comprising determining a pose of a tracker coupled to the tool support in the known coordinate system, and determining the pose of the tool based on the pose of the tracker coupled to the tool support OR further comprising determining a pose of a tracker coupled to the hand-held portion in the known coordinate system; and determine the pose of the hand-held portion based on the pose of the tracker coupled to the hand-held portion OR wherein the step of determining the target pose of the tool is further defined as defining the target pose in at least three degrees of freedom OR wherein the target pose comprises a target coordinate system and the tool comprises a guided coordinate system, the constraint force is adapted to move the guided coordinate system towards the target coordinate system OR further comprising determining in the known coordinate system, a pose of the tool and wherein the guide constraint has a value for a tuning parameter, said method comprising changing the value of the tuning parameter based on a relationship between the target pose of the tool and the pose of the tool OR wherein the step of simulating dynamics is further defined as calculating the constraint force based on the guide constraint and an external force value OR further comprising planning a pose of an implant in the known coordinate system, and wherein the target pose of the tool is based on the planned pose of the implant OR further comprising determining a joint centering constraint; and controlling the plurality of actuators based on the joint centering constraint OR further comprising calculating a constraint force adapted to move the virtual tool towards the target pose based on the guide constraint and based on the joint centering constraint; and simulating dynamics of the virtual tool in the virtual simulation based on the constraint force and to output a commanded pose, and wherein controlling the plurality of actuators to move towards the target pose of the tool is further defined as commanding the plurality of actuators to align the tool based on the commanded pose OR wherein the guide constraint has a first value for a tuning parameter and the joint centering constraint has a second value for the tuning parameter, the first value being different than the second value so that a resulting constraint force is adapted to align the tool more strongly as a result of the guide constraint as compared to the joint centering constraint OR where the commanded pose is a relationship between the hand-held portion and the tool OR further comprising determining a commanded joint velocity for each of the plurality of actuators based on the commanded pose, and controlling each of the plurality of actuators based on the commanded joint velocity of each of the plurality of actuators.

II. A computer-implemented medical program or product of controlling movement of a hand-held medical robotic system for use with a tool, the method, program, or product comprising instructions, which, when the program is executed by a computer, cause the computer to complete the following steps: determining, in the known coordinate system, a target pose of the tool; determining a position of each of the plurality of actuators; determining a pose of the hand-held portion based on the position of each of the plurality of actuators; determining a commanded pose of the tool based on the pose of the hand-held portion, and the target pose of the tool; and determining a commanded joint position of each of the plurality of actuators based on the commanded pose.

III. A computer-implemented medical program or product of controlling movement of a hand-held medical robotic system for use with a tool, the method, program, or product comprising instructions, which, when the program is executed by a computer, cause the computer to complete the following steps: determining a target pose of the tool in a known coordinate system; determining a pose of the hand-held portion in the known coordinate system; determining a commanded pose based on the target pose of the tool and the pose of the hand-held portion; determining a commanded joint position of each of a plurality of actuators based on the commanded pose; and controlling a tool drive motor based on the commanded joint position of at least one actuator, a measured position of at least one actuator, a previous commanded position of at least one actuator, a previous measured position of at least one actuator, or combinations thereof.

IV. The clause of III, further comprising controlling each of the plurality of actuators based on the commanded joint position for each actuator; OR wherein the step of controlling the tool drive motor is defined as controlling the tool drive motor based on the previous commanded position of the at least one actuator, or combinations thereof OR wherein the step of controlling the tool drive motor is further defined as comparing the commanded joint position for a first actuator of the plurality of actuators and a first motor override limit for the first actuator OR wherein the first motor override limit includes an upper threshold and a lower threshold OR wherein the step of controlling the tool drive motor is further defined as controlling the tool drive motor based on the commanded joint position for a second actuator of the plurality of actuators and a second motor override limit for the second actuator OR wherein the step of controlling the tool drive motor comprises controlling a motor parameter of the tool drive motor at a first value and a second value, wherein the first value is different than the second value, the controller operable to change operation from the first value to the second value based on the commanded joint position and the first motor override limit for the first actuator OR wherein controlling the tool drive motor based on the commanded joint position, a measured position of at least one actuator, a previous commanded position of at least one actuator, a previous measured position of at least one actuator, or combinations thereof is further defined as causing the tool drive motor to stop OR determining a commanded joint velocity for each of the plurality of actuators based on the commanded pose, and controlling each of the plurality of actuators based on the commanded joint velocity of each of the plurality of actuators OR combinations thereof.

V. A computer-implemented medical program or product of controlling movement of a hand-held medical robotic system for use with a tool, the method, program, or product comprising instructions, which, when the program is executed by a computer, cause the computer to complete the following steps: determining a target pose of the tool in a known coordinate system; determining a pose of the hand-held portion in the known coordinate system; controlling the tool drive motor based on a measured position of at least one actuator, a previous measured position of at least one actuator, or combinations thereof.

VI. A computer-implemented medical program or product of controlling movement of a hand-held medical robotic system for use with a tool, the method, program, or product comprising instructions, which, when the program is executed by a computer, cause the computer to complete the following steps: determining a target pose of the tool in a known coordinate system; determining a state of the tool in the known coordinate system; determining a value of a tuning parameter based on a state of the tool; generating a guide constraint based on the target pose of the tool and the pose of the hand-held portion and based on the value of the tuning parameter; calculating a constraint force adapted to move a virtual tool based on the guide constraint; and simulating dynamics of the virtual tool in a virtual simulation based on the constraint force, and to output a commanded pose based on the virtual simulation.

VII. The clause of VII, further comprising controlling each of plurality of actuators based on the commanded pose OR wherein the state of the tool is a previous commanded pose.

VIII. A computer-implemented medical program or product of controlling movement of a hand-held medical robotic system for use with a tool, the method, program, or product comprising instructions, which, when the program is executed by a computer, cause the computer to complete the following steps: determining a target pose of the tool in a known coordinate system; determining a position and/or orientation of a reference coordinate system relative to the known coordinate system; determining a state of the tool in the known coordinate system; determining a state of a first constraint based on a relationship between the state of the tool and the reference coordinate system; determining a state of a second constraint based on a relationship between the state of the tool and the reference coordinate system, with the first constraint being different than the second constraint; calculating a constraint force adapted to move a virtual tool based on the state of the first constraint and/or the state of the second constraint; and simulating dynamics of the virtual tool in a virtual simulation based on the constraint force, and to output a commanded pose based on the virtual simulation.

IX. The clause of VIII, further comprising controlling each of plurality of actuators based on the commanded pose OR wherein the state of the first constraint is selected from a group comprising: an active state of the first constraint, an inactive state of the first constraint, the first constraint having a first value of a tuning parameter, and the first constraint having a second value of the tuning parameter; and wherein the state of the second constraint is selected from the group comprising: an active state of the second constraint, an inactive state of the second constraint, the second constraint having a third value of a tuning parameter, and the second constraint having a fourth value of the tuning parameter OR wherein the first constraint is a guide constraint, and the second constraint is a joint centering constraint OR wherein the first state of the tool and the second state of the tool comprises a position, an orientation, or a pose in the known coordinate system OR wherein the state of the tool is further defined as a first state of the tool at a first time and second state of the tool at a second time, wherein the first state of the tool is different from the second state of the tool and the first time is different than the second time, wherein the state of the first constraint is inactive at the first state of the tool and is active at second state of the tool, and wherein the state of the second constraint is active at the first state of the tool and is inactive at the second state of the tool OR wherein the state of the tool is further defined as a first state of the tool at a first time and second state of the tool at a second time, wherein the first state of the tool is different from the second state of the tool and the first time is different than the second time, wherein the state of the first constraint is having the first value of the tuning parameter at the first state of the tool and having the second value of the tuning parameter at second state of the tool, and wherein the state of the second constraint is having the third value of the tuning parameter at the first state of the tool and having the fourth value of the tuning parameter at the second state of the tool OR further comprising determining a first distance parameter based on the first state of the tool and the reference coordinate system, determining a second distance parameter based on the second state of the tool and the reference coordinate system, and wherein the first and second distance parameter is selected from a group including a direction and a magnitude, and wherein determining the state of a first constraint based on a relationship between the first state of the tool and the reference coordinate system is further defined as determining the first state of the first constraint based on the first distance parameter and wherein determining the second state of the first constraint based on a relationship between the second state of the tool and the reference coordinate system is further defined as determining a determining the second state of the first constraint based on the second distance parameter OR wherein determining the state of a second constraint based on a relationship between the first state of the tool and the reference coordinate system is further defined as determining the first state of the second constraint based on the first distance parameter and wherein determining the second state of the second constraint based on a relationship between the second state of the tool and the reference coordinate system is further defined as determining the second state of the second constraint based on the second distance parameter OR wherein the first distance parameter and the second distance parameter are each selected from a direction away from bone, and a direction into bone OR wherein reference coordinate system is defined relative to a patient tracker OR wherein the reference coordinate system is based on the target pose of the tool OR further comprising receiving a user input signal, and changing the state of the first constraint and/or the second constraint based on the user input signal OR wherein the first and second values of the tuning parameters are defined by a function OR the function is based on a distance and/or angle of the tool to the reference coordinate system in at least one degree of freedom OR wherein the state of the first constraint and/or the state of the second constraint are defined by a function OR wherein the function is based on a distance and/or angle of the tool to the reference coordinate system in at least one degree of freedom OR wherein the state of the first constraint and/or the state of the second constraint are defined by a look-up table OR combinations thereof.

X. A computer-implemented medical program or product of controlling movement of a hand-held medical robotic system for use with a tool, the method, program, or product comprising instructions, which, when the program is executed by a computer, cause the computer to complete the following steps: determining a target pose of the surgical tool in at least one degree of freedom in a known coordinate system; determining a position and/or orientation of a reference coordinate system relative to the known coordinate system; determining a state of the surgical tool in the known coordinate system; determining a state of a first constraint based on a relationship between the state of the surgical tool and the reference coordinate system; and determining a state of a second constraint based on a relationship between the state of the surgical tool and the reference coordinate system, with the first constraint being different than the second constraint.

XI A computer-implemented medical program or product of controlling movement of a hand-held medical robotic system for use with a tool, the method, program, or product comprising instructions, which, when the program is executed by a computer, cause the computer to complete the following steps: determining, in a known coordinate system, a pose of the tool, a pose of the hand-held portion, a boundary, and a target pose of the tool; determining a guide constraint based on the target pose of the tool and the pose of the hand-held portion; controlling the tool drive motor based on the boundary and the pose of the tool.

XII. The clause of XI, further comprising controlling the plurality of actuators to align towards the target pose of the tool based on the guide constraint OR wherein the step of determining the target pose of the tool is further defined as defining the target pose in at least three degrees of freedom, wherein the target pose is a target plane or axis OR further comprising calculating a constraint force adapted to move a virtual representation of a virtual tool towards the target pose based on the guide constraint; and simulating dynamics of the virtual tool in a virtual simulation based on the constraint force and to output a commanded pose, and wherein controlling the plurality of actuators to move towards the target pose of the tool is further defined as commanding the plurality of actuators to align the tool based on the commanded pose OR further comprising determining a commanded joint position of each of the plurality of actuators based on the commanded pose; and controlling each of plurality of actuators based on the commanded joint position of each of the plurality of actuators OR wherein the target pose comprises a target coordinate system and the tool comprises a guided coordinate system, the method including controlling the plurality of actuators to move the guided coordinate system towards the target coordinate system OR wherein the guide constraint has a value for a tuning parameter, said method comprising changing the value of the tuning parameter based on a relationship between the target pose of the tool and the pose of the tool OR the step of simulating dynamics is further defined as calculating the constraint force based on the guide constraint and an external force value OR further comprising planning a pose of an implant in the known coordinate system, and wherein the target pose of the tool is based on the planned pose of the implant OR wherein the boundary is based on the planned pose of the implant OR wherein controlling the tool drive motor comprises controlling a speed of the tool drive motor based on the boundary and the pose of the tool OR further comprising determining a distance parameter with respect a portion of the tool and the boundary, and controlling the tool drive motor is further defined as controlling the speed of the tool drive motor based on the distance parameter OR wherein the distance parameter has a magnitude and a direction OR further comprising preventing actuation of the tool drive motor based on the boundary and the pose of the tool OR wherein controlling the tool drive motor comprises controlling a motor parameter of the tool drive motor at a first value and a second value, wherein the first value is different than the second value, the controller operable to change operation from the first value to the second value based on the boundary and based on the pose of the tool, OR wherein the motor parameter is selected from a group comprising speed, torque, operation time, current, acceleration, or combinations thereof OR wherein the boundary is an object defined in the known coordinate system, wherein the object comprises a mesh, a point, a plane, a plurality of planes, a geometric primitive such line parallel to a planned axis, and combinations thereof OR wherein the boundary is a geometric primitive selected from the group comprising a sphere or a rectangular prism OR further comprising determining a joint centering constraint; and controlling the plurality of actuators based on the joint centering constraint OR further comprising calculating a constraint force adapted to move the virtual tool based on the guide constraint and based on the joint centering constraint; and simulating dynamics of the virtual tool in a virtual simulation based on the constraint force and to output a commanded pose, and wherein controlling the plurality of actuators to move is further defined as commanding the plurality of actuators to align the tool based on the commanded pose OR wherein determining the pose of the hand-held portion comprises determining a position of each of the actuators of the plurality of actuators, and determining a pose of the tool, and determining the pose of the hand-held portion based on the pose of the tool and the position of each of the actuators of the plurality of actuators OR further comprising determining a pose of a tracker coupled to the tool support, and determine the pose of the tool based on the pose of the tracker coupled to the tool support OR further comprising tracking a portion of patient anatomy with a patient tracker, the known coordinate system defined relative to the patient tracker OR wherein the step of determining a position of each of the plurality of actuators is further defined as measuring a position of the each of the plurality of actuators with an encoder coupled to each of the plurality of actuators OR wherein the method further comprises determining a pose of a tracker coupled to the hand-held portion; and determining the pose of the hand-held portion is based on the pose of the tracker coupled to the hand-held portion OR wherein the commanded pose is a relationship between the hand-held portion and the tool OR combinations thereof.

XIII A computer-implemented medical program or product of controlling movement of a hand-held medical robotic system for use with a tool, the method, program, or product comprising instructions, which, when the program is executed by a computer, cause the computer to complete the following steps: determining, in a known coordinate system, a pose of the tool, a boundary mesh, and a target pose of the tool; controlling the plurality of actuators to align the tool towards the target pose of the tool; and controlling the tool drive motor based on the boundary mesh and the pose of the tool.

XIV. A computer-implemented medical program or product of controlling movement of a hand-held medical robotic system for use with a tool, the method, program, or product comprising instructions, which, when the program is executed by a computer, cause the computer to complete the following steps: determining, in a known coordinate system, a pose of the tool, a pose of the hand-held portion, a target pose of the tool, and a boundary; controlling the plurality of actuators to align the tool in a plurality of controlled degrees of freedom based on the target pose of the tool and the pose of the hand-held portion; and controlling the tool drive motor based on the boundary and the pose of the tool in the at least one uncontrolled degree of freedom.

XV. A computer-implemented medical method, program or product of controlling movement of a hand-held medical robotic system for use with a tool, the method, program, or product comprising instructions, which, when the program is executed by a computer, cause the computer to complete the following steps: determining, in a known coordinate system, a pose of the tool, a pose of the hand-held portion, a target pose of the tool, and a boundary; controlling the plurality of actuators to position the tool in a plurality of controlled degrees of freedom based on the target pose of the tool and the pose of the hand-held portion; and controlling the tool drive motor based on the boundary and the pose of the tool in the at least one uncontrolled degree of freedom.

XVI A computer-implemented medical method, program or product of controlling movement of a hand-held medical robotic system for use with a tool, the method, program, or product comprising instructions, which, when the program is executed by a computer, cause the computer to complete the following steps: controlling movement of the plurality of actuators towards a first centering position for each of the plurality of actuators; controlling movement of the plurality of actuators towards a second centering position, the second centering position being different than the first centering position for at least one actuator of the plurality of actuators; and switching automatically between controlling towards the first centering position and the second centering position.

XVII The clause of XVI, wherein the switching is based on a state of the tool relative to a target state in a known coordinate system OR further comprising planning a pose of an implant in a known coordinate system, and wherein the target state of the tool is based on the planned pose of the implant OR wherein the state of the tool comprises a position of the tool, an orientation of the tool, or a pose of the tool OR wherein determining, in the known coordinate system, the state of the tool relative to the target state of the tool includes determining a location of a plane or axis defined by the tool relative to a plurality of cutting planes or planned trajectories in the known coordinate system OR wherein determining, in the known coordinate system, a state of the tool relative to the target states of the tool for the plurality of cutting planes or planned trajectories includes determining angles between a current orientation of the tool and a plurality of target orientations of the tool, determining distances between a current position of the tool and a plurality of target positions of the tool, or determining both the angles and the distances, and determining the one of the plurality of cutting planes or planned trajectories selected by the user based on the values of the angles, values of the distances, or both the values of the angles and the values of the distances OR combinations thereof.

XVIII. A computer-implemented medical method, program or product of controlling movement of a hand-held medical robotic system for use with a tool, the method, program, or product comprising instructions, which, when the program is executed by a computer, cause the computer to complete the following steps: controlling movement of the plurality of actuators towards a first centering position for each of the plurality of actuators; receiving a user input signal indicative of a desire to change centering positions; and based on receipt of the user input signal, controlling movement of the plurality of actuators towards a second centering position for each of the plurality of actuators, the second centering position being different than the first centering position for at least one actuator of the plurality of actuators.

XIX The clause of XVIII, wherein the first centering position of a first actuator of the plurality of actuators is located at a substantially median point of the first actuator, and the second centering position is between the first centering position of the first actuator and a joint threshold of the first actuator or wherein the first centering position of a second actuator of the plurality of actuators is the same as the second centering position for the second actuator or wherein the user input signal is based on an input to a user input device, wherein the user input device is selected from a group comprising a trigger on the instrument, a touchscreen, a foot pedal, a mobile device, and combinations thereof OR wherein the user input signal is based on a position and/or orientation of the tool, OR combinations thereof.

XX A computer-implemented medical method, program or product of controlling movement of a hand-held medical robotic system for use with a tool, the method, program, or product comprising instructions, which, when the program is executed by a computer, cause the computer to complete the following steps: determining a target pose of the tool in a known coordinate system; determining a pose of the hand-held portion in the known coordinate system; generating a guide constraint based on the target pose of the tool and the pose of the hand-held portion; generating a joint centering constraint based on a position of at least one of the plurality of actuators and a centering position for at least one actuator of the plurality of actuators; calculating a constraint force adapted to move a virtual tool based on the guide constraint and the joint centering constraint; simulating dynamics of the virtual tool in a virtual simulation based on the constraint force, and to output a commanded pose based on the virtual simulation; and determining a commanded joint position of each of the plurality of actuators based on the commanded pose.

XXI The clause of XVII, further comprising controlling each of plurality of actuators based on the commanded joint position OR wherein the position of the at least one of the plurality of actuators comprises a measured position of the at least one actuator, a previous commanded position of the at least one actuator, a previous measured position of the at least one actuator, or combinations thereof OR wherein the position of the at least one of the plurality of actuators comprises a previous commanded position of the at least one actuator OR the method further comprising determining an external force value applied between the tool or the tool support and the hand-held portion; and wherein the step of calculating the constraint force is further based on the external force value applied to the tool OR wherein the joint centering constraints has a first value for a tuning parameter, and the guide constraint having a second value for a tuning parameter, the tuning parameters causing the respective constraints to have an increased effect on the constraint force, the tuning parameter of the joint centering constraint being less than the tuning parameter of the guide constraint OR wherein the tuning parameter of the guide constraint or the joint centering constraint affects a stiffness or a damping of the respective constraint OR generating a joint limit constraint based on the position of at least one of the plurality of actuators and a joint limit, and the step of calculating a constraint force is further defined as calculating the constraint force based on the guide constraint, the joint centering constraint, and the joint limit constraint OR wherein the joint centering constraints has a first value for a tuning parameter, the guide constraint having a second value for a tuning parameter, and joint limit constraint having a third value for a tuning parameter, the tuning parameters causing the respective constraints to have an increased effect on the constraint force, the tuning parameter of the joint limit constraint being greater than the tuning parameter of the guide constraint and the tuning parameter of the joint centering constraint OR further comprising determining a pose of the tool in the known coordinate system, and computing the guide constraint based on a relationship between the target pose of the tool and the pose of the tool OR wherein the guide constraint has a value for a tuning parameter, said method comprising changing the value of the tuning parameter of the guide constraint based on a relationship between the target pose of the tool and the pose of the tool OR further comprising determining a commanded joint velocity for each of the plurality of actuators based on the commanded pose, and controlling each of the plurality of actuators based on the commanded joint velocity of each of the plurality of actuators OR combinations thereof.

XXII A computer-implemented medical method, program or product of controlling movement of a hand-held medical robotic system for use with a tool, the method, program, or product comprising instructions, which, when the program is executed by a computer, cause the computer to complete the following steps: determining a target pose of the tool in a known coordinate system; determining a pose of the hand-held portion in the known coordinate system; generating a guide constraint based on the target pose of the tool and the pose of the hand-held portion; and generating a joint centering constraint based on a position of at least one of the plurality of actuators and a centering position for at least one actuator of the plurality of actuators.

XXIII A computer-implemented medical method, program or product of controlling movement of a hand-held medical robotic system for use with a tool, the method, program, or product comprising instructions, which, when the program is executed by a computer, cause the computer to complete the following steps: sensing an amount of current supplied to one or more of the plurality of actuators; estimating an amount of external force applied between the tool support and the hand-held portion based on the output of the one or more current sensors calculating a constraint force adapted to move a virtual tool towards the target pose based on the estimated amount of external force; simulating dynamics of the virtual tool in a virtual simulation based on the constraint force and to output a commanded pose; determining a commanded joint position and/or commanded joint angle of each of the plurality of actuators based on the commanded pose.

XXIV. A computer-implemented medical method of controlling movement of a hand-held medical robotic system for use with a tool, the method comprising the steps of: determining a joint limit constraint based on a position of at least one of the plurality of actuators and a joint limit; determining a workspace limit constraint based on a pose of the tool and a predetermined Cartesian space; calculating a constraint force adapted to move a virtual tool based on the joint limit constraint and the workspace constraint; simulating dynamics of the virtual tool in a virtual simulation based on the constraint force and to output a commanded pose; and determining a commanded joint position of each of the plurality of actuators based on the commanded pose.

XXV. The clause of XXIV, further comprising controlling each of plurality of actuators based on the commanded joint position or wherein the position of the at least one of the plurality of actuators comprises a measured position of at least one actuator, a previous commanded position of the at least one actuator, a previous measured position of at least one actuator, or combinations thereof OR wherein the pose of the tool is defined relative to the hand-held portion OR wherein the predetermined Cartesian space is a volume defined in Cartesian space, a plurality of limits in one or more degrees of freedom, a plurality of orientations, or combinations thereof OR further comprising limiting the roll of the tool support relative to the hand-held portion using the workspace constraint and the joint limit constraint more than pitch and/or elevation OR wherein the roll is more limited than pitch and/or elevation relative to what the tool support is mechanically capable of OR wherein a range of motion of the tool support relative to the hand-held portion is greater in pitch than in roll OR wherein a range of motion of the tool support relative to the hand-held portion is greater in elevation than in roll OR wherein the predetermined Cartesian space is asymmetrical in shape OR further comprising determining a guide constraint based on a target pose of the tool and a pose of the hand-held portion; and wherein the step of calculating the constraint force is further based on the guide constraint OR further comprising determining a commanded joint velocity for each of the plurality of actuators based on the commanded pose, and controlling each of the plurality of actuators based on the commanded joint velocity of each of the plurality of actuators OR combinations thereof.

XXVI. A computer-implemented medical method of controlling movement of a hand-held medical robotic system for use with a tool, the method comprising the steps of: determining a pose of the tool in a known coordinate system; determining a pose of the hand-held portion in the known coordinate system; determining a joint limit based on a position of at least one of the plurality of actuators; determining a workspace limit based on the pose of the tool and a predetermined Cartesian space; and controlling each of plurality of actuators based on the target pose of the tool, the joint limit, and the workspace limit.

XXVII. A hand-held medical robotic system for use with a saw blade/tool, the system comprising: an instrument comprising; a hand-held portion to be held by a user; a blade/tool support coupled to the hand-held portion to support the saw blade/tool, the blade/tool support comprising a saw/tool drive motor; an actuator assembly operatively interconnecting the blade/tool support and the hand-held portion to move the blade/tool support in a plurality of degrees of freedom relative to the hand-held portion to align the blade/tool, the actuator assembly including a plurality of actuators; a localizer; a control system coupled to the localizer, the plurality of actuators and the saw/tool drive motor, the control system configured to determine, in a known coordinate system, a pose of the saw blade/tool, a pose of the hand-held portion, a boundary, and a target pose of the saw blade/tool; the control system comprising: a guide handler to determine a guide constraint based on the target pose of the saw blade/tool and the pose of the hand-held portion; the control system being configured to control the plurality of actuators to align the saw blade/tool towards the target pose based on the guide constraint; and control the saw/tool drive motor based on the boundary and the pose of the saw blade/tool.

XXVIII The system of clause XXVII, wherein the target pose is defined in at least two degrees of freedom.

XXIX. The system of any one of clauses XXVII or XXVIII, wherein the hand-held instrument includes a constraint assembly having a passive linkage operatively interconnecting the blade support and the hand-held portion, the passive linkage being coupled to the blade/tool support and the hand-held portion in a manner to constrain movement of the blade/tool support relative to the hand-held portion in three degrees of freedom.

XXX. The system of any one of clauses XXVII-XXIX, wherein the instrument weighs less than 6 lbs and the instrument is capable of moving in four degrees of freedom.

XXXI. The system of any one of clauses XXVII-XXX, wherein the control system further comprises a constraint solver to calculate a constraint force adapted to move a virtual saw blade/tool towards the target pose based on the guide constraint; and wherein the control system further comprises a virtual simulator to simulate dynamics of the virtual saw blade/tool in a virtual simulation based on the constraint force and to output a commanded pose, and wherein control system is further defined to control the plurality of actuators to align the saw blade/tool based on the commanded pose.

XXXII. The system of any one of clauses XXVII-XXXI, wherein the boundary is an object defined in the known coordinate system, wherein the object comprises a mesh, a point, a plane, a plurality of planes, a geometric primitive such as a line perpendicular to a planned trajectory, and combinations thereof.

XXXIII. The system of any one of clauses XXVII-XXXII, wherein the actuator assembly is configured to align the saw bladetool in fewer than four controlled degrees of freedom.

XXXIV. The system of clause XXXIII, wherein the fewer than four controlled degrees of freedom comprise pitch, roll, and elevation.

XXXV. The system of any one of clauses XXVII-XXXIV, further comprising a passive arm coupled to the instrument or wherein each at least two of plurality of actuators are connected to the tool support and the hand-held portion.

XXXVI. A method of controlling movement of a hand-held medical robotic system for use with a saw blade, the robotic system including a localizer, and a hand-held instrument having a hand-held portion to be held by a user and a blade support movably coupled to the hand-held portion to support the saw blade, an actuator assembly operatively interconnecting the blade support and the hand-held portion, the actuator assembly including a plurality of actuators, the blade support including a saw drive motor, the method comprising the steps of: determining, in a known coordinate system, a pose of the saw blade, a pose of the hand-held portion, a boundary, and a target pose of the saw blade; determining a guide constraint based on the target pose of the saw blade and the pose of the hand-held portion; controlling the plurality of actuators to align towards the target pose of the saw blade based on the guide constraint; and controlling the saw drive motor based on the boundary and the pose of the saw blade.

XXXVII. The method of clause XXXVI, wherein the step of determining the target pose of the saw blade is further defined as defining the target pose in at least three degrees of freedom, wherein the target pose is a target plane.

XXXVIII. The method of clause XXXVII, further comprising calculating a constraint force adapted to move a virtual representation of a virtual saw blade towards the target pose based on the guide constraint; and simulating dynamics of the virtual saw blade in a virtual simulation based on the constraint force and to output a commanded pose, and wherein controlling the plurality of actuators to move towards the target pose of the saw blade is further defined as commanding the plurality of actuators to align the saw blade based on the commanded pose.

XXXIX. The method of clause XXXVIII, further comprising determining a commanded joint position of each of the plurality of actuators based on the commanded pose; and controlling each of plurality of actuators based on the commanded joint position of each of the plurality of actuators.

XL. The method of any one of clauses XXXVI-XXXIX, wherein the target pose comprises a target coordinate system and the saw blade comprises a guided coordinate system, the method including controlling the plurality of actuators to move the guided coordinate system towards the target coordinate system.

XLI. The method of any one of clauses XXXVIII-XL, wherein the guide constraint has a value for a tuning parameter, said method comprising changing the value of the tuning parameter based on a relationship between the target pose of the saw blade and the pose of the saw blade.

XLII. The method of any one of clauses XXXVIII-XLI, wherein the step of simulating dynamics is further defined as calculating the constraint force based on the guide constraint and an external force value.

XLIII. The method of any one of clauses XXXVI-XLI, further comprising planning a pose of an implant in the known coordinate system, and wherein the target pose of the saw blade is based on the planned pose of the implant.

XLIV. The method of clause XLIII, wherein the boundary is based on the planned pose of the implant.

XLV. The method of any one of clauses XXXVI-XLIV, wherein controlling the saw drive motor comprises controlling a speed of the saw drive motor based on the boundary and the pose of the saw blade.

XLVI. The method of clause XLV, further comprising determining a distance parameter with respect a portion of the saw blade and the boundary, and controlling the saw drive motor is further defined as controlling the speed of the saw drive motor based on the distance parameter.

XLVII. The method of clause XLVI, wherein the distance parameter has a magnitude and a direction.

XLVIII. The method of any one of clauses XXXVI-XLVII, further comprising preventing actuation of the saw drive motor based on the boundary and the pose of the saw blade.

XLIX. The method of any one of clauses XXXVI-XLVIII, wherein controlling the saw drive motor comprises controlling a motor parameter of the saw drive motor at a first value and a second value, wherein the first value is different than the second value, the controller operable to change operation from the first value to the second value based on the boundary and based on the pose of the saw blade.

L. The method of clause XLIX, wherein the motor parameter is selected from a group comprising speed, torque, operation time, current, acceleration, or combinations thereof.

LI. The method of any one of clauses XXXVI-L, wherein the boundary is an object defined in the known coordinate system, wherein the object comprises a mesh, a point, a plane, a plurality of planes, a geometric primitive, and combinations thereof.

LII. The method of clause LI, wherein the boundary is a geometric primitive selected from the group comprising a sphere or a rectangular prism.

LIII. The method of any one of clauses XXXVIII-LII, further comprising determining a joint centering constraint; and controlling the plurality of actuators based on the joint centering constraint.

LIV. The method of clause LIII, further comprising calculating a constraint force adapted to move the virtual saw blade based on the guide constraint and based on the joint centering constraint; and simulating dynamics of the virtual saw blade in a virtual simulation based on the constraint force and to output a commanded pose, and wherein controlling the plurality of actuators to move is further defined as commanding the plurality of actuators to align the saw blade based on the commanded pose.

LV. The method of any one of clauses XXXVII-LIV, wherein determining the pose of the hand-held portion comprises determining a position of each of the actuators of the plurality of actuators, and determining a pose of the saw blade, and determining the pose of the hand-held portion based on the pose of the saw blade and the position of each of the actuators of the plurality of actuators.

LVI. The method of clause LV, further comprising determining a pose of a tracker coupled to the blade support, and determine the pose of the saw blade based on the pose of the tracker coupled to the blade support.

LVII. The method of clause LVI, further comprising tracking a portion of patient anatomy with a patient tracker, the known coordinate system defined relative to the patient tracker.

LVIII. The method of clause LV, wherein the step of determining a position of each of the plurality of actuators is further defined as measuring a position of the each of the plurality of actuators with an encoder coupled to each of the plurality of actuators.

LIX. The method of any one of clauses XXXVII-LVIII, wherein the method further comprises determining a pose of a tracker coupled to the hand-held portion; and determining the pose of the hand-held portion is based on the pose of the tracker coupled to the hand-held portion.

LX. The method of any one of clauses XXXVIII-LVIII, wherein the commanded pose is a relationship between the hand-held portion and the saw blade.

LXI. A method of controlling movement of a hand-held medical robotic system for use with a saw blade, the robotic system including a localizer, and a hand-held instrument having a hand-held portion to be held by a user and a blade support movably coupled to the hand-held portion to support the saw blade, an actuator assembly operatively interconnecting the blade support and the hand-held portion, the actuator assembly including a plurality of actuators, the blade support including a saw drive motor, the method comprising the steps of: determining, in a known coordinate system, a pose of the saw blade, a boundary mesh, and a target pose of the saw blade; controlling the plurality of actuators to align the saw blade towards the target pose of the saw blade; and controlling the saw drive motor based on the boundary mesh and the pose of the saw blade.

LXII. A hand-held medical robotic system for use with a saw blade, the system comprising: an instrument comprising; a hand-held portion to be held by a user and a blade support coupled to the hand-held portion, the blade support comprising a saw drive motor to drive motion of the saw blade; an actuator assembly operatively interconnecting the blade support and the hand-held portion to move the blade support to align the saw blade in a plurality of controlled degrees of freedom relative to the hand-held portion to align the saw blade, the actuator assembly being incapable of repositioning the saw blade in at least one uncontrolled degree of freedom, the actuator assembly including a plurality of actuators; a localizer; and a control system coupled to the plurality of actuators, the saw drive motor, and the localizer, the control system configured to: determine, in a known coordinate system, a pose of the saw blade, a pose of the hand-held portion, a target pose of the saw blade, and a boundary, and control the plurality of actuators to align the saw blade in the plurality of controlled degrees of freedom based on the pose of the hand-held portion and the target pose of the saw blade; and control the saw drive motor based on the boundary and the pose of the saw blade in the at least one uncontrolled degree of freedom.

LXIII The system of clause LXII, wherein the target pose is a target plane defined in at least three degrees of freedom.

LXIV. The system of clause LXIII, wherein the actuator assembly is configured to align the saw blade in fewer than four controlled degrees of freedom.

LXV. The system of clause LXIV, wherein the fewer than four controlled degrees of freedom comprise pitch, roll, and elevation.

LXVI. The system of any one of clauses LXII-LXVI, wherein the at least one uncontrolled degree of freedom comprises translation in x, translation in y, yaw, or combinations thereof, wherein x is substantially parallel to a longitudinal axis of the blade support.

LXVII. The system of any one of clauses LXII-LXVI, wherein the hand-held instrument includes a constraint assembly having a passive linkage operatively interconnecting the blade support and the hand-held portion, the passive linkage being coupled to the blade support and the hand-held portion in a manner to constrain movement of the blade support relative to the hand-held portion in three degrees of freedom.

LXVIII. The system of any one of clauses LXVI-LXVII, wherein the instrument weighs less than 6 lbs.

LXIX. The system of any one of clauses LXVII-LXVIII, wherein the boundary is a boundary mesh, wherein controlling the saw drive motor comprises controlling a motor parameter of the saw drive motor at a first value and a second value, wherein the first value is different than the second value, the controller operable to change operation from the first value to the second value based on the boundary mesh and based on the pose of the saw blade.

LXX. The system of clause LXIX, wherein the motor parameter is selected from a group comprising speed, torque, current, acceleration, or combinations thereof.

LXXI. The system of any one of clauses LXIX-LXX, further comprising determining a distance parameter with respect a portion of the saw blade and the boundary, wherein controlling the saw drive motor is based on the distance parameter.

LXXII. The system of clause LXXI, wherein the boundary is an object defined in the known coordinate system, wherein the object comprises a mesh, a point, a plane, a plurality of planes, a geometric primitive, and combinations thereof.

LXXIII The system of any one of clauses LXVI-LXXII, wherein the control system is configured to determine a position of each of the actuators of the plurality of actuators, and determine the pose of the hand-held portion based on the pose of the saw blade and the position of each of the actuators of the plurality of actuators.

LXXIV. The system of any one of clauses LXVI-LXXIII, wherein the control system is configured to determine a pose of a tracker coupled to the blade support in the known coordinate system, and determine the pose of the saw blade based on the pose of the tracker coupled to the blade support in the known coordinate system.

LXXV. The system of any one of clauses LXVI-LXXIV, wherein the control system is configured to determine a pose of a tracker coupled to the hand-held portion in the known coordinate system; and determine the pose of the hand-held portion based on the pose of the tracker coupled to the hand-held portion in the known coordinate system.

LXXVI. The system of clause LXXV, further comprising tracking a portion of patient anatomy with a patient tracker, the known coordinate system defined relative to the patient tracker.

LXXVII. The system of any one of clauses LXII-LXXVI, wherein the control system is configured to determine the boundary based on a planned pose of an implant.

LXXVIII. The system of any one of clauses LXII-LXXVII, further comprising a passive arm coupled to the instrument or wherein each at least two of plurality of actuators are connected to the blade support and the hand-held portion.

LXXIX. A hand-held medical robotic system for use with a tool, the system comprising: an instrument comprising; a hand-held portion to be held by a user and a tool support coupled to the hand-held portion, the tool support comprising a tool drive motor to drive motion of the tool; an actuator assembly operatively interconnecting the tool support and the hand-held portion to move the tool support to move the tool in a plurality of controlled degrees of freedom relative to the hand-held portion to place the tool at a desired pose, the actuator assembly being incapable of repositioning the tool in at least one uncontrolled degree of freedom, the actuator assembly including a plurality of actuators; a localizer; and a control system coupled to the plurality of actuators and the localizer, the control system configured to: determine, in a known coordinate system, a pose of the hand-held portion, a target pose of the tool, and a boundary; control the plurality of actuators to position the tool in the plurality of controlled degrees of freedom based on the pose of the hand-held portion and the target pose of the tool; and control the tool drive motor based on the boundary and the pose of the tool in the at least one uncontrolled degree of freedom.

LXXX. The system of clause LXXIX, further comprising a passive arm coupled to the instrument or wherein each at least two of plurality of actuators are connected to the blade support and the hand-held portion or when the boundary is a line or plane parallel to a planned trajectory.

LXXXI. A method of controlling a hand-held medical robotic system for use with a saw blade, the robotic system including a localizer, and a hand-held instrument having a hand-held portion to be held by a user and a blade support movably coupled to the hand-held portion to support the saw blade, an actuator assembly operatively interconnecting the blade support and the hand-held portion, the actuator assembly including a plurality of actuators, the blade support including a saw drive motor, the actuator assembly being incapable of repositioning the blade support in at least one uncontrolled degree of freedom, the method comprising the steps of: determining, in a known coordinate system, a pose of the saw blade, a pose of the hand-held portion, a target pose of the saw blade, and a boundary; controlling the plurality of actuators to align the saw blade in a plurality of controlled degrees of freedom based on the target pose of the saw blade and the pose of the hand-held portion; and controlling the saw drive motor based on the boundary and the pose of the saw blade in the at least one uncontrolled degree of freedom.

LXXXII. A method of controlling a hand-held medical robotic system for use with a tool, the robotic system including a localizer, and a hand-held instrument having a hand-held portion to be held by a user and a tool support movably coupled to the hand-held portion to support the tool, an actuator assembly operatively interconnecting the tool support and the hand-held portion, the actuator assembly including a plurality of actuators, the tool support including a tool drive motor, the actuator assembly being incapable of repositioning the tool in at least one uncontrolled degree of freedom, the method comprising the steps of: determining, in a known coordinate system, a pose of the tool, a pose of the hand-held portion, a target pose of the tool, and a boundary; controlling the plurality of actuators to position the tool in a plurality of controlled degrees of freedom based on the target pose of the tool and the pose of the hand-held portion; and controlling the tool drive motor based on the boundary and the pose of the tool in the at least one uncontrolled degree of freedom.

LXXXIII A hand-held medical robotic system for use with a saw blade/tool, the system comprising: an instrument comprising; a hand-held portion to be held by a user; a blade/tool support coupled to the hand-held portion to support the saw blade/tool, the blade support comprising a saw/tool drive motor; an actuator assembly operatively interconnecting the blade/tool support and the hand-held portion to move the blade/tool support in a plurality of degrees of freedom relative to the hand-held portion, the actuator assembly including a plurality of actuators; a user input device; a control system coupled to the plurality of actuators, the user input device, and the saw/tool drive motor, the control system configured to: control movement of the plurality of actuators towards a first centering position for each of the plurality of actuators; receiving a user input signal indicative of a desire to change centering positions; and based on receipt of the user input signal, being configured to control movement of the plurality of actuators towards a second centering position for each of the plurality of actuators, the second centering position being different than the first centering position for at least one actuator of the plurality of actuators.

LXXXIV. The system of clause LXXXIII, further comprising a passive arm coupled to the instrument.

LXXXV. A hand-held medical robotic system for use with a saw blade/tool, the system comprising: an instrument comprising; a hand-held portion to be held by a user; a blade/tool support coupled to the hand-held portion to support the saw blade/tool, the blade/tool support comprising a saw/tool drive motor; an actuator assembly operatively interconnecting the blade/tool support and the hand-held portion to move the blade/tool support in a plurality of degrees of freedom relative to the hand-held portion, the actuator assembly including a plurality of actuators; a control system coupled to the plurality of actuators and the saw/tool drive motor, the control system configured to: control movement of the plurality of actuators towards a first centering position for each of the plurality of actuators; control movement of the plurality of actuators towards a second centering position, the second centering position being different than the first centering position for at least one actuator of the plurality of actuators; and switch automatically between controlling the towards the first centering position and the second centering position.

LXXXVI. The system of clause LXXXV, further comprising a passive arm coupled to the instrument or wherein each at least two of plurality of actuators are connected to the blade support and the hand-held portion.

LXXXVII. A method of controlling movement of a hand-held medical robotic system for use with a saw blade/tool, the robotic system including a localizer, and a hand-held instrument having a hand-held portion to be held by a user and a blade/tool support movably coupled to the hand-held portion to support the saw blade/tool, an actuator assembly operatively interconnecting the blade/tool support and the hand-held portion, the actuator assembly including a plurality of actuators, the blade/tool support including a saw drive motor, the method comprising the steps of: controlling movement of the plurality of actuators towards a first centering position for each of the plurality of actuators; controlling movement of the plurality of actuators towards a second centering position, the second centering position being different than the first centering position for at least one actuator of the plurality of actuators; and switching automatically between controlling towards the first centering position and the second centering position.

LXXXVIII. The method of clause LXXXVII, wherein the switching is based on a state of the saw blade/tool relative to a target state in a known coordinate system.

LXXXIX. The method of clause LXXXVIII, further comprising planning a pose of an implant in a known coordinate system, and wherein the target state of the saw blade/tool is based on the planned pose of the implant.

XC. The method of any one of clauses LXXXVIII-LXXXIX, wherein the state of the saw blade/tool comprises a position of the saw blade/tool, an orientation of the saw blade/tool, or a pose of the saw blade/tool.

XCI. The method of clause XC, wherein determining, in the known coordinate system, the state of the saw blade/tool relative to the target state of the saw blade/tool includes determining a location of a plane/axis defined by the saw blade/tool relative to a plurality of cutting planes/trajectories in the known coordinate system.

XCII. The method of clause XCI, wherein determining, in the known coordinate system, a state of the saw blade/tool relative to the target states of the saw blade/tool for the plurality of cutting planes/trajectories includes determining angles between a current orientation of the saw blade/tool and a plurality of target orientations of the saw blade/tool, determining distances between a current position of the saw blade/tool and a plurality of target positions of the saw blade/tool, or determining both the angles and the distances, and determining the one of the plurality of the plurality of cutting planes/trajectories selected by the user based on the values of the angles, values of the distances, or both the values of the angles and the values of the distances.

XCIII. A method of controlling movement of a hand-held medical robotic system for use with a tool, the robotic system including a hand-held instrument having a hand-held portion to be held by a user and a tool support movably coupled to the hand-held portion to support the tool, an actuator assembly operatively interconnecting the tool support and the hand-held portion, the actuator assembly including a plurality of actuators, the method comprising the steps of: controlling movement of the plurality of actuators towards a first centering position for each of the plurality of actuators; controlling movement of the plurality of actuators towards a second centering position, the second centering position being different than the first centering position for at least one actuator of the plurality of actuators; and switching automatically between controlling the towards the first centering position and the second centering position.

XCIV. A method of controlling movement of a hand-held medical robotic system for use with a saw blade/tool, the robotic system including a localizer, and a hand-held instrument having a hand-held portion to be held by a user and a blade/tool support movably coupled to the hand-held portion to support the saw blade/tool, an actuator assembly operatively interconnecting the blade/tool support and the hand-held portion, the actuator assembly including a plurality of actuators, the blade/tool support including a saw/tool drive motor, the method comprising the steps of: controlling movement of the plurality of actuators towards a first centering position for each of the plurality of actuators; receiving a user input signal indicative of a desire to change centering positions; and based on receipt of the user input signal, controlling movement of the plurality of actuators towards a second centering position for each of the plurality of actuators, the second centering position being different than the first centering position for at least one actuator of the plurality of actuators.

XCV. The method of clause XCIV, wherein the first centering position of a first actuator of the plurality of actuators is located at a substantially median point of the first actuator, and the second centering position is between the first centering position of the first actuator and a joint threshold of the first actuator.

XCVI. The method of clause XCV, wherein the first centering position of a second actuator of the plurality of actuators is the same as the second centering position for the second actuator.

XCVII. The method of any one of clauses XCIV-XCVI, wherein the user input signal is based on an input to a user input device, wherein the user input device is selected from a group comprising a trigger on the instrument, a touchscreen, a foot pedal, a mobile device, and combinations thereof.

XCVIII. The method of any one of clauses XCIV-XCVII, wherein the user input signal is based on a position and/or orientation of the saw blade.

XCIX. A hand-held medical robotic system for use with a saw blade/tool, the system comprising: an instrument comprising; a hand-held portion to be held by a user; a blade/tool support coupled to the hand-held portion to support the saw blade, the blade/tool support comprising a saw/tool drive motor; an actuator assembly operatively interconnecting the blade/tool support and the hand-held portion to move the blade/tool support in a plurality of degrees of freedom relative to the hand-held portion to place the saw blade/tool on a desired plane/trajectory, the actuator assembly including a plurality of actuators; a localizer; a control system coupled to the plurality of actuators, the localizer, and the tool drive motor, the control system configured to determine, in a known coordinate system, a target pose of the saw blade/tool and a pose of the hand-held portion, the control system further comprising: a guide handler to determine a guide constraint based on the target pose of the saw blade/tool and the pose of the hand-held portion; a motion controller to determine a joint centering constraint based on a position of at least one of the plurality of actuators and a centering position for at least one actuator of the plurality of actuators; a constraint solver to calculate a constraint force adapted to move a virtual saw blade/tool based on the guide constraint and the joint centering constraint; and a virtual simulator to simulate dynamics of the virtual saw blade/tool in a virtual simulation based on the constraint force and to output a commanded pose; wherein the control system is configured to: determine a commanded joint position of each of the plurality of actuators based on the commanded pose; and control each of plurality of actuators based on the commanded joint position.

C. The system of clause XCIX, wherein the control system is further configured to determine a commanded joint velocity for each of the plurality of actuators based on the commanded pose, and control each of the plurality of actuators based on the commanded joint velocity of each of the plurality of actuators.

CI. The system of clause C, further comprising a passive arm coupled to the instrument.

CII. A hand-held medical robotic system for use with a saw blade/tool, the system comprising: an instrument comprising; a hand-held portion to be held by a user; a blade/tool support coupled to the hand-held portion to support the saw blade/tool, the blade/tool support comprising a saw/tool drive motor; an actuator assembly operatively interconnecting the blade/tool support and the hand-held portion to move the blade/tool support in a plurality of degrees of freedom relative to the hand-held portion to align the blade/tool, the actuator assembly including a plurality of actuators; a localizer; a control system coupled to the plurality of actuators, the localizer, and the saw/tool drive motor, the control system configured to determine, in a known coordinate system, a target pose of the saw blade/tool and a pose of the hand-held portion, the control system further comprising: a guide handler to determine a guide constraint based on the target pose of the saw blade/tool and the pose of the hand-held portion; a motion controller to determine a joint centering constraint based on a position of at least one of the plurality of actuators and a centering position for at least one actuator of the plurality of actuators; a constraint solver to calculate a constraint force adapted to move a virtual saw blade/tool based on the guide constraint and the joint centering constraint; and a virtual simulator to simulate dynamics of the virtual saw blade/tool in a virtual simulation based on the constraint force and to output a commanded pose; wherein the control system is configured to determine a commanded joint position and/or commanded joint angle of each of the plurality of actuators based on the commanded pose; and control each of plurality of actuators based on the commanded joint position and/or commanded joint angle.

CIII. The system of clause CII, wherein the control system is further configured to determine a commanded joint velocity for each of the plurality of actuators based on the commanded pose, and control each of the plurality of actuators based on the commanded joint velocity of each of the plurality of actuators.

CIV. A method of controlling movement of a hand-held medical robotic system for use with a saw blade/tool, the robotic system including a localizer, and a hand-held instrument having a hand-held portion to be held by a user and a blade/tool support movably coupled to the hand-held portion to support the saw blade/tool, an actuator assembly operatively interconnecting the blade/tool support and the hand-held portion, the actuator assembly including a plurality of actuators, the blade/tool support including a saw/tool drive motor, the method comprising the steps of: determining a target pose of the saw blade/tool in a known coordinate system; determining a pose of the hand-held portion in the known coordinate system; generating a guide constraint based on the target pose of the saw blade/tool and the pose of the hand-held portion; generating a joint centering constraint based on a position of at least one of the plurality of actuators and a centering position for at least one actuator of the plurality of actuators; calculating a constraint force adapted to move a virtual saw blade/tool based on the guide constraint and the joint centering constraint; simulating dynamics of the virtual saw blade/tool in a virtual simulation based on the constraint force, and to output a commanded pose based on the virtual simulation; determining a commanded joint position of each of the plurality of actuators based on the commanded pose; and controlling each of plurality of actuators based on the commanded joint position.

CV. The method of clause CIV, wherein the position of the at least one of the plurality of actuators comprises a measured position of the at least one actuator, a previous commanded position of the at least one actuator, a previous measured position of the at least one actuator, or combinations thereof.

CVI. The method of any one of clauses CIV-CV, wherein the position of the at least one of the plurality of actuators comprises a previous commanded position of the at least one actuator.

CVII. The method of any one of clauses CIV-CVI, the method further comprising determining an external force value applied between the saw blade or the blade support and the hand-held portion; and wherein the step of calculating the constraint force is further based on the external force value applied to the saw blade.

CVIII. The method of any one of clauses CIV-CVII, wherein the joint centering constraints has a first value for a tuning parameter, and the guide constraint having a second value for a tuning parameter, the tuning parameters causing the respective constraints to have an increased effect on the constraint force, the tuning parameter of the joint centering constraint being less than the tuning parameter of the guide constraint.

CIX. The method of clause CVIII, wherein the tuning parameter of the guide constraint or the joint centering constraint affects a stiffness or a damping of the respective constraint.

CX. The method of any one of clauses CIV-CIX, the method further comprising generating a joint limit constraint based on the position of at least one of the plurality of actuators and a joint limit, and the step of calculating a constraint force is further defined as calculating the constraint force based on the guide constraint, the joint centering constraint, and the joint limit constraint.

CXI. The method of clause CX, wherein the joint centering constraints has a first value for a tuning parameter, the guide constraint having a second value for a tuning parameter, and joint limit constraint having a third value for a tuning parameter, the tuning parameters causing the respective constraints to have an increased effect on the constraint force, the tuning parameter of the joint limit constraint being greater than the tuning parameter of the guide constraint and the tuning parameter of the joint centering constraint.

CXII. The method of any one of clauses CIV-CXI, further comprising determining a pose of the saw blade in the known coordinate system, and computing the guide constraint based on a relationship between the target pose of the saw blade and the pose of the saw blade.

CXIII. The method of clause CXII, wherein the guide constraint has a value for a tuning parameter, said method comprising changing the value of the tuning parameter of the guide constraint based on a relationship between the target pose of the saw blade and the pose of the saw blade.

CXIV. The method of any one of clauses CIV-CXIII, further comprising determining a commanded joint velocity for each of the plurality of actuators based on the commanded pose, and controlling each of the plurality of actuators based on the commanded joint velocity of each of the plurality of actuators.

CXV. A method of controlling movement of a hand-held medical robotic system for use with a saw blade/tool, the robotic system including a localizer, and a hand-held instrument having a hand-held portion to be held by a user and a blade/tool support movably coupled to the hand-held portion to support the saw blade/tool, an actuator assembly operatively interconnecting the blade/tool support and the hand-held portion, the actuator assembly including a plurality of actuators, the blade/tool support including a saw/tool drive motor, the method comprising the steps of: determining a target pose of the saw blade/tool in a known coordinate system; determining a pose of the hand-held portion in the known coordinate system; generating a guide constraint based on the target pose of the saw blade/tool and the pose of the hand-held portion; generating a joint centering constraint based on a position of at least one of the plurality of actuators and a centering position for at least one actuator of the plurality of actuators; and controlling each of plurality of actuators based on the guide constraint and the joint centering constraint.

CXVI. A hand-held medical robotic system for use with a tool, the system comprising: an instrument comprising; a hand-held portion to be held by a user; a tool support coupled to the hand-held portion to support the tool, the tool support comprising a tool drive motor; an actuator assembly operatively interconnecting the tool support and the hand-held portion to move the tool support in a plurality of degrees of freedom relative to the hand-held portion to align the tool, the actuator assembly including a plurality of actuators; a localizer; a control system coupled to the plurality of actuators, the localizer, and the tool drive motor, the control system configured to determine, in a known coordinate system, a target pose of the tool and a pose of the hand-held portion; one or more current sensors configured to detect an amount of current supplied to each of the plurality of actuators; the control system comprising: a force estimator configured to estimate an amount of external force applied between the tool support and the hand-held portion based on the output of the one or more current sensors; a constraint solver to calculate a constraint force adapted to move a virtual tool towards the target pose based on the estimated amount of external force; a virtual simulator to simulate dynamics of the virtual tool in a virtual simulation based on the constraint force and to output a commanded pose; the control system further configured to: determine a commanded joint position and/or commanded joint angle of each of the plurality of actuators based on the commanded pose; and controlling each of plurality of actuators based on the commanded joint position or commanded joint angle.

CXVII. A method for controlling movement of a hand-held medical robotic system for use with a surgical tool, the robotic system including a localizer, and a hand-held instrument having a hand-held portion to be held by a user and a tool support movably coupled to the hand-held portion to support the surgical tool, an actuator assembly operatively interconnecting the tool support and the hand-held portion, the actuator assembly including a plurality of actuators, the tool support including a tool drive motor, the method comprising the steps of: sensing an amount of current supplied to one or more of the plurality of actuators; estimating an amount of external force applied between the tool support and the hand-held portion based on the output of the one or more current sensors calculating a constraint force adapted to move a virtual tool towards the target pose based on the estimated amount of external force; simulating dynamics of the virtual tool in a virtual simulation based on the constraint force and to output a commanded pose; determining a commanded joint position and/or commanded joint angle of each of the plurality of actuators based on the commanded pose; and controlling each of plurality of actuators based on the commanded joint position and/or commanded joint angle.

CXVIII. A hand-held medical robotic system for use with a tool, the system comprising: an instrument comprising; a hand-held portion to be held by a user; a tool support coupled to the hand-held portion to support the tool, the tool support comprising a tool drive motor; an actuator assembly operatively interconnecting the tool support and the hand-held portion to move the tool support in a plurality of degrees of freedom relative to the hand-held portion to align the tool, the actuator assembly including a plurality of actuators; a localizer; a control system coupled to the plurality of actuators, the localizer, and the tool drive motor, the control system comprising: a motion controller to determine a joint limit constraint based on a position of at least one of the plurality of actuators and a joint threshold, and to determine a workspace limit constraint based on a pose of the tool and a predetermined Cartesian space; a constraint solver to calculate a constraint force adapted to move a virtual saw blade based on the joint limit constraint and the workspace constraint; and a virtual simulator to simulate dynamics of the virtual saw blade in a virtual simulation based on the constraint force and to output a commanded pose; wherein the control system is configured to determine a commanded joint position and/or commanded joint angle of each of the plurality of actuators based on the commanded pose; and control each of plurality of actuators based on the commanded joint position and/or commanded joint angle.

CXIX. The system of clause CXVIII, wherein the control system is further configured to determine a commanded joint velocity for each of the plurality of actuators based on the commanded pose, and control each of the plurality of actuators based on the commanded joint velocity of each of the plurality of actuators.

CXX. The system of clause CXVIII, further comprising a passive arm coupled to the instrument.

CXXI. A hand-held medical robotic system for use with a saw blade/tool, the system comprising: an instrument comprising; a hand-held portion to be held by a user; a blade/tool support coupled to the hand-held portion to support the saw blade, the blade/tool support comprising a saw/tool drive motor; an actuator assembly operatively interconnecting the blade/tool support and the hand-held portion to move the blade/tool support in a plurality of degrees of freedom relative to the hand-held portion to align the saw blade/tool, the actuator assembly including a plurality of actuators; a localizer; a control system coupled to the plurality of actuators, the localizer, and the saw drive motor/tool, the control system configured to determine, in a known coordinate system, a target pose of the saw blade/tool in at least one degree of freedom and a pose of the hand-held portion; and determine a joint limit based on a position of at least one of the plurality of actuators and a joint threshold, determine a workspace limit based on the pose of the saw blade/tool and a predetermined Cartesian space, and control each of plurality of actuators based on the target pose of the blade/tool, the joint limit, and the workspace limit.

CXXII. A method of controlling movement of a hand-held medical robotic system for use with a saw blade/tool, the robotic system including a hand-held instrument having a hand-held portion to be held by a user and a blade/tool support movably coupled to the hand-held portion to support the saw blade/tool, an actuator assembly operatively interconnecting the blade support and the hand-held portion for moving the blade/tool support in a plurality of degrees of freedom, the actuator assembly including a plurality of actuators, the blade/tool support including a saw/tool drive motor, the method comprising the steps of: determining a joint limit constraint based on a position of at least one of the plurality of actuators and a joint limit; determining a workspace limit constraint based on a pose of the saw blade/tool and a predetermined Cartesian space; calculating a constraint force adapted to move a virtual saw blade/tool based on the joint limit constraint and the workspace constraint; simulating dynamics of the virtual saw blade/tool in a virtual simulation based on the constraint force and to output a commanded pose; determining a commanded joint position of each of the plurality of actuators based on the commanded pose; and controlling each of plurality of actuators based on the commanded joint position.

CXXIII. The method of clause CXXII, wherein the position of the at least one of the plurality of actuators comprises a measured position of at least one actuator, a previous commanded position of the at least one actuator, a previous measured position of at least one actuator, or combinations thereof.

CXXIV. The method of any one of clauses CXXII-CXXIII, wherein the pose of the saw blade is defined relative to the hand-held portion.

CXXV. The method of any one of clauses CXXII-CXXIV, wherein the predetermined Cartesian space is a volume defined in Cartesian space, a plurality of limits in one or more degrees of freedom, a plurality of orientations, or combinations thereof.

CXXVI. The method of any one of clauses CXXII-CXXV, further comprising limiting the roll of the blade support relative to the hand-held portion using the workspace constraint and the joint limit constraint more than pitch and/or elevation.

CXXVII. The method of any one of clauses CXXII-CXXVI, wherein the roll is more limited than pitch and/or elevation relative to what the blade support is mechanically capable of.

CXXVIII. The method of any one of clauses CXXII-CXXVII, wherein a range of motion of the blade support relative to the hand-held portion is greater in pitch than in roll.

CXXIX. The method of any one of clauses CXXII-CXXVII, wherein a range of motion of the blade support relative to the hand-held portion is greater in elevation than in roll.

CXXX. The method of any one of clauses CXXII-CXXIX, wherein the predetermined Cartesian space is asymmetrical in shape.

CXXXI. The method of any one of clauses CCXXIII-CXXXI, further comprising determining a guide constraint based on a target pose of the saw blade and a pose of the hand-held portion; and wherein the step of calculating the constraint force is further based on the guide constraint.

CXXXII. The method of any one of clauses CXXII-CXXXI, further comprising determining a commanded joint velocity for each of the plurality of actuators based on the commanded pose, and controlling each of the plurality of actuators based on the commanded joint velocity of each of the plurality of actuators.

CXXIX A method of controlling movement of a hand-held medical robotic system for use with a saw blade or other tool, the robotic system including a localizer, and a hand-held instrument having a hand-held portion to be held by a user and a blade/tool support movably coupled to the hand-held portion to support the saw blade or tool, an actuator assembly operatively interconnecting the blade/tool support and the hand-held portion for moving the blade/tool support in a plurality of degrees of freedom, the actuator assembly including a plurality of actuators, the blade/tool support including a saw/tool drive motor; the method comprising the steps of: determining a pose of the saw blade/tool in a known coordinate system; determining a pose of the hand-held portion in the known coordinate system; determining a joint limit based on a position of at least one of the plurality of actuators; determining a workspace limit based on the pose of the saw blade/tool and a predetermined Cartesian space; and controlling each of plurality of actuators based on the target pose of the saw blade/tool, the joint limit, and the workspace limit.

CXXX. A hand-held medical robotic system for use with a tool, the system comprising: an instrument comprising; a hand-held portion to be held by a user; a tool support coupled to the hand-held portion to support the tool, the tool support comprising a tool drive motor; an actuator assembly operatively interconnecting the tool support and the hand-held portion to move the tool support in a plurality of degrees of freedom relative to the hand-held portion to align the tool, the actuator assembly including a plurality of actuators; a localizer; a control system coupled to the plurality of actuators, the localizer, and the tool drive motor, the control system configured to determine, in a known coordinate system, a target pose of the tool and a pose of the hand-held portion; a constraint solver to calculate a constraint force adapted to move a virtual tool towards the target pose based on an external force; a virtual simulator to simulate dynamics of the virtual tool in a virtual simulation based on the constraint force and to output a commanded pose; the control system further configured to: determine a commanded joint position and/or commanded joint angle of each of the plurality of actuators based on the commanded pose; and controlling each of plurality of actuators based on the commanded joint position or commanded joint angle.

CXXXI. A method for controlling movement of a hand-held medical robotic system for use with a surgical tool, the robotic system including a localizer, and a hand-held instrument having a hand-held portion to be held by a user and a tool support movably coupled to the hand-held portion to support the surgical tool, an actuator assembly operatively interconnecting the tool support and the hand-held portion, the actuator assembly including a plurality of actuators, the tool support including a tool drive motor, the method comprising the steps of: estimating an amount of external force applied between the tool support and the hand-held portion; calculating a constraint force adapted to move a virtual tool towards the target pose based on the estimated amount of external force; simulating dynamics of the virtual tool in a virtual simulation based on the constraint force and to output a commanded pose; determining a commanded joint position and/or commanded joint angle of each of the plurality of actuators based on the commanded pose; and controlling each of the plurality of actuators based on the commanded joint position and/or commanded joint angle.

Several embodiments have been described in the foregoing description. However, the embodiments discussed herein are not intended to be exhaustive or limit the present teachings to any particular form. The terminology, which has been used, is intended to be in the nature of words of description rather than of limitation. Many modifications and variations are possible in light of the above teachings and the presentation teachings may be practiced otherwise than as specifically described.

What is claimed is:

1. A hand-held medical robotic system for use with a saw blade, the system comprising:

an instrument comprising;

a hand-held portion to be held by a user and a blade support coupled to the hand-held portion, the blade support comprising a saw drive motor to drive motion of the saw blade;

an actuator assembly operatively interconnecting the blade support and the hand-held portion to move the blade support to align the saw blade in a plurality of controlled degrees of freedom relative to the hand-held portion to align the saw blade, the actuator assembly being incapable of repositioning the saw blade in at least one uncontrolled degree of freedom, the actuator assembly including a plurality of actuators;

a localizer; and a control system coupled to the plurality of actuators, the saw drive motor, and the localizer, the control system configured to:

determine, in a known coordinate system, a pose of the saw blade, a pose of the hand-held portion, a target pose of the saw blade, and a boundary, and control the plurality of actuators to align the saw blade in the plurality of controlled degrees of freedom based on the pose of the hand-held portion and the target pose of the saw blade; and control the saw drive motor based on the boundary and the pose of the saw blade in the at least one uncontrolled degree of freedom;

wherein the target pose is a target plane defined in at least three degrees of freedom.

2. The system of claim 1, wherein the actuator assembly is configured to align the saw blade in fewer than four controlled degrees of freedom.

3. The system of claim 2, wherein the fewer than four controlled degrees of freedom comprise pitch, roll, and elevation.

4. The system of claim 3, wherein the at least one uncontrolled degree of freedom comprises translation in x, translation in y, yaw, or combinations thereof, wherein x is substantially parallel to a longitudinal axis of the blade support.

5. The system of claim 1, wherein the hand-held portion includes a constraint assembly having a passive linkage operatively interconnecting the blade support and the hand-held portion, the passive linkage being coupled to the blade support and the hand-held portion in a manner to constrain movement of the blade support relative to the hand-held portion in three degrees of freedom.

6. The system of claim 1, wherein the instrument weighs less than 6 lbs.

7. The system of claim 1, wherein the boundary is a boundary mesh, wherein controlling the saw drive motor comprises controlling a motor parameter of the saw drive motor at a first value and a second value, wherein the first value is different than the second value, the control system operable to change operation from the first value to the second value based on the boundary mesh and based on the pose of the saw blade.

8. The system of claim 7, wherein the motor parameter is selected from a group comprising speed, torque, current, acceleration, or combinations thereof.

9. The system of claim 1, wherein the control system is configured to determine a distance parameter based on a position of a portion of the saw blade and the boundary, wherein the control system is configured to control the drive motor based on the distance parameter.

10. The system of claim 1, wherein the boundary is one dimensional, two dimensional or three dimensional.

11. A hand-held medical robotic system for use with a saw blade, the system comprising:

an instrument comprising;

a hand-held portion to be held by a user and a blade support coupled to the hand-held portion, the blade support comprising a saw drive motor to drive motion of the saw blade;

an actuator assembly operatively interconnecting the blade support and the hand-held portion to move the blade support to align the saw blade in a plurality of controlled degrees of freedom relative to the hand-held portion to align the saw blade with a target pose, the actuator assembly including a plurality of actuators;

a localizer; and a control system coupled to the plurality of actuators, the saw drive motor, and the localizer, the control system configured to:

determine, in a known coordinate system, a state of the saw blade, a target pose of the saw blade, and a boundary;

control the plurality of actuators to align the saw blade in the plurality of controlled degrees of freedom with a target pose; and control the saw drive motor based on the state of the saw blade and the boundary; and determine a distance parameter based on a position of a portion of the saw blade and the boundary, wherein the control system is configured to control the drive motor based on the distance parameter.

12. The system of claim 11, wherein the boundary is a plane or a two-dimensional or three-dimensional shape.

13. The system of claim 12, wherein the target pose is a target plane, and wherein the boundary is perpendicular to the target plane.

14. The system of claim 13, wherein the target pose is the target plane, and wherein the boundary is parallel to the target plane.

15. The system of claim 14, wherein the target pose is defined in at least three degrees of freedom.

16. The system of claim 15, wherein the target plane is based on a planned pose of an implant.

17. The system of claim 16, wherein the control system is configured to determine a distance parameter based on a position of a portion of the saw blade and the boundary, wherein the control system is configured to control the drive motor based on the distance parameter.

18. A hand-held medical robotic system for use with a saw blade, the system comprising:

an instrument comprising;

a hand-held portion to be held by a user and a blade support coupled to the hand-held portion, the blade support comprising a saw drive motor to drive motion of the saw blade;

an actuator assembly operatively interconnecting the blade support and the hand-held portion to move the blade support to align the saw blade in a plurality of controlled degrees of freedom relative to the hand-held portion to align the saw blade with a target pose, the actuator assembly including a plurality of actuators;

a localizer; and a control system coupled to the plurality of actuators, the saw drive motor, and the localizer, the control system configured to:

determine, in a known coordinate system, a state of the saw blade, and a boundary, and control the plurality of actuators to align the saw blade in the plurality of controlled degrees of freedom with the boundary; and control the saw drive motor based on the state of the saw blade and the boundary; and wherein the boundary is a boundary mesh, wherein controlling the saw drive motor comprises controlling a motor parameter of the saw drive motor at a first value and a second value, wherein the first value is different than the second value, the controller operable to change operation from the first value to the second value based on the boundary mesh and based on the pose of the saw blade.

19. The system of claim 18, wherein the motor parameter is selected from a group comprising speed, torque, current, acceleration, or combinations thereof.

* * * * *